US011083729B2

(12) United States Patent
Ouk et al.

(10) Patent No.: US 11,083,729 B2
(45) Date of Patent: Aug. 10, 2021

(54) METHODS OF TREATING CANCER WITH SMALL MOLECULE NF-κB INHIBITORS

(71) Applicant: ImmuneTarget, Inc., Medina, WA (US)

(72) Inventors: Samedy Ouk, San Diego, CA (US); Hsiou-Chi Liou, New York, NY (US)

(73) Assignee: ImmuneTarget, Inc., Medina, WA (US)

( * ) Notice: Subject to any disclaimer, the term of this patent is extended or adjusted under 35 U.S.C. 154(b) by 0 days.

(21) Appl. No.: 16/020,688

(22) Filed: Jun. 27, 2018

(65) Prior Publication Data

US 2019/0000851 A1    Jan. 3, 2019

Related U.S. Application Data

(60) Provisional application No. 62/525,650, filed on Jun. 27, 2017.

(51) Int. Cl.
*A61P 35/00* (2006.01)
*A61K 31/352* (2006.01)
*A61K 31/519* (2006.01)
*C07D 491/052* (2006.01)

(52) U.S. Cl.
CPC ........... *A61K 31/519* (2013.01); *A61P 35/00* (2018.01); *C07D 491/052* (2013.01)

(58) Field of Classification Search
CPC ...... A61K 31/519; A61K 31/352; A61P 35/00
See application file for complete search history.

(56) References Cited

U.S. PATENT DOCUMENTS

| | | | |
|---|---|---|---|
| 4,272,535 A | 6/1981 | Blythin et al. | |
| 7,498,336 B2 | 3/2009 | Weissman et al. | |
| 7,498,366 B2 * | 3/2009 | Taguchi | B60C 1/0025 524/487 |
| 10,226,464 B2 * | 3/2019 | Ouk | A61P 35/00 |
| 2007/0074233 A1 | 3/2007 | Moriya | |
| 2019/0142836 A1 | 5/2019 | Ouk et al. | |

FOREIGN PATENT DOCUMENTS

| | | |
|---|---|---|
| JP | 2884170 B2 * | 4/1999 |
| WO | 2004073615 A2 | 9/2004 |
| WO | 2007146375 A2 | 12/2007 |
| WO | 2008014266 A2 | 1/2008 |
| WO | 2008014266 A3 | 1/2008 |
| WO | 2008014266 A9 | 1/2008 |
| WO | 2017117355 A1 | 7/2017 |

OTHER PUBLICATIONS

Zeligs et al., (Clin Cancer Res. vol. 22 pp. 4302-4308 Published 2016) (Year: 2016).*
Churakov (Chem Rev. vol. 104 pp. 2601-2615 published 2004) (Year: 2004).*
Hala M. Aly et al: "Efficient one-pot preparation of novel fused chromeno[2,3-d]pyrimidine and pyrano[2,3-d] pyrimidine derivatives", European Journal of Medicinal Chemistry, vol. 47, 2012, pp. 18-23.
David J. Blythin et al: "Simple synthetic route to "oxa-deazaflavins" (2H[1]-benzopyrano[2,3-d]ppimidine-2,4(3H)-diones)", Heterocycles, vol. 16, No. 2, 1981, p. 203.
Rebecca L. Chan et al: "The chemistry of an electron-deficient 5-deazaflavin. 8-Cyano-10-methyl-5-Deazaisoalloxazine", Journal of the American Chemical Society, vol. 99, No. 20, 1977, pp. 6721-6730.
Xiaoxue Dou et al: "Synthesis and biological evaluation of novel pyrimido[4,5-b]quinoline-2,4-dione derivatives as MDM2 ubiquitin ligase inhibitors", Medicinal Chemistry, vol. 9, No. 4, 2013, pp. 581-587.
Tetsuji Kawamoto et al: "Synthesis and evaluation of nitro 5-deazaflavins as novel bioreductive antitumor agents", Bioorganic & Medicinal Chemistry Letters, vol. 5, No. 18, 1995, pp. 2109-2114.
Kenya Mori et al: "Novel synthesis of pyrimido[4,5-b]quinoline-2(3H),4(10H)-dion es (5-deazaflavins)", Journal of the Chemical Society, Chemical Communications., No. 17, 1978, p. 764.
V. Pande et al: "NF—[kappa] B in human disease: current inhibitors and prospects for de nova structure based design of inhibitors", Current Medicinal Chemistry, vol. 12, No. 3, 2005, pp. 357-374.
Fumio Yoneda et al: "Synthesis and properties of 1-benzothiopyrano[2,3-d]pyrimidine-2,4(3H)-dione (5-deaza-10-thiaflavin)", Tetrahedron Letters, vol. 19, No. 31, 1978, pp. 2803-2806.
Fumio Yoneda et al: "Syntheses of 5-deazaflavines", Journal of the Chemical Society, Perkin Transactions 1, No. 16, 1976, pp. 1805-1808.
International Search Report and Written Opinion of the International Searching Authority, PCT/US2016/069124, dated Feb. 28, 2017.
Stephen Berge: "Pharmaceutical Salts", Journal of Pharmaceutical Sciences, vol. 66, No. 1, 1977, pp. 1-20.
Arora, S. et al: "An undesired effect of chemotherapy: gemcitabine promotes pancreatic cancer cell invasiveness through reactive oxygen species-dependent, nuclear factor κB- and hypoxia-inducible factor 1α-mediated up-regulation of CXCR4", J. Biol. Chem., vol. 288, 2013, pp. 21197-21207.
Barbie, D.A., et al: "Systematic RNA interference reveals that oncogenic KRAS-driven cancers require TBK1", Nature, vol. 462, 2009, pp. 108-112.

(Continued)

*Primary Examiner* — Theodore R. Howell
*Assistant Examiner* — George W Kosturko
(74) *Attorney, Agent, or Firm* — Proskauer Rose LLP

(57) ABSTRACT

The present invention provides, inter alia, compounds capable of inhibiting NF-κB. Pharmaceutical compositions containing and methods of using the compounds are also provided herein. Also provided are methods and kits for treating cancer and solid tumors in a subject, as well as methods and kits for inducing cancer cell death and apoptosis of a cancer cell, all utilizing the NF-κB inhibitors described herein.

17 Claims, 99 Drawing Sheets

(89 of 99 Drawing Sheet(s) Filed in Color)

(56) References Cited

OTHER PUBLICATIONS

Blakely, C.M., et al: "NF-κB activating complex engaged in response to EGFR oncogene inhibition drives tumor cell survival and residual disease in lung cancer", vol. 11(1), 2015, pp. 98-110.

Giopanou, I., et al: "Comprehensive Evaluation of Nuclear Factor-κB Expression Patterns in Non-Small Cell Lung Cancer", vol. 10(7), 2015, pp. 1-17.

Jiang, N. et al: "Triptolide reverses the Taxol resistance of lung adenocarcinoma by inhibiting the NF-κB signaling pathway and the expression of NF-κB-regulated drug-resistant genes", vol. 13(1), 2015, pp. 153-159.

Ouyang, L. et al: "Programmed cell death pathways in cancer: a review of apoptosis, autophagy and programmed necrosis", vol. 45, 2012, pp. 487-498.

Tait, SWG et al: "Die another way—non-apoptotic mechanisms of cell death", vol. 127, 2014, pp. 2135-2144.

Takeuchi, S. et al: "Chemotherapy-Derived Inflammatory Responses Accelerate the Formation of Immunosuppressive Myeloid Cells in the Tissue Microenvironment of Human Pancreatic Cancer", Cancer Research vol. 75(13), 2015, pp. 2629-2640.

Wang, W., et al: "The Nuclear Factor-kB RelA Transcription Factor Is Constitutively Activated in Human Pancreatic Adenocarcinoma Cells", vol. 5, 1999, pp. 119-127.

Xie, Y. et al: "Ferroptosis: process and function. Cell Death and Differentiation", vol. 23, 2016, pp. 369-379.

Gerbino, P.: "Remington: The Science and Practice of Pharmacy, 21st Edition", 2006, vol. 70(3) Article 71, p. 3.

Daniluk, J.: "An NF-κB pathway-mediated positive feedback loop amplifies Ras activity to pathological levels in mice", 2012, vol. 122(4), pp. 1519-1528.

Wu, D. et al: "NF-κB Expression and Outcomes in Solid Tumors: A Systematic Review and Meta-Analysis", 2015, vol. 94 (40), pp. 1-12.

Rotili, D. et al: "Benzodeazaoxaflavins as Sirtuin Inhibitors with Antiproliferative Properties in Cancer Stem Cells", 2012, vol. 55(18), pp. 8193-8197.

Rotili, D. et al: "Identification of Tri- and Tetracyclic Pyrimidinediones as Sirtuin Inhibitors", 2010, vol. 5(5), pp. 674-677.

Marchand, C. et al: "Deazaflavin Inhibitors of Tyrosyl-DNA Phosphodiesterase 2 (TDP2) Specific for the Human Enzyme and Active against Cellular TDP2", May 2016, vol. 11(7), pp. 1925-1933.

Dickens, M. et al: "5-Deazaflavin derivatives as inhibitors of p53 ubiquitination by HDM2", 2013, vol. 21, pp. 6868-6877.

Bryn, S.: Solid-State Chemistry of Drugs, 2nd Ed. (1999), Ch. 11—Hydrates and Solvates, 233-47.

Rouhi, A.M.: Chem. & Eng. News, (2003), 81(8), 32-35.

Morissette, S.: Adv. Drug Delivery Rev. 2004, 56, 275-300.

Chen, Z.: Nat Cell Biol. Aug. 2005; 7(8): 758-65.

International Search Report and Written Opinion of the International Searching Authority, PCT/US2018/039815, dated Oct. 15, 2018.

Ramos, "NF-kB in Human Disease: Current Inhibitors and Prospects for De Novo Structure Based Design of Inhibitors", Current Medicinal Chemistry, 12, pp. 357-374 (2005).

Schuliga, "NF-kappaB Signaling in Chronic Inflammatory Airway Disease", Biomolecules, 5, pp. 1266-1283 (2015).

U.S. Appl. No. 16/859,745, filed Apr. 27, 2020, Ouk et al.

\* cited by examiner

Figs. 1A-1D
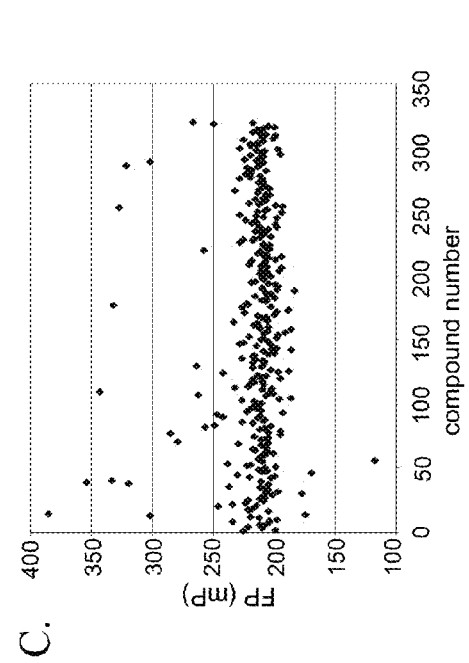
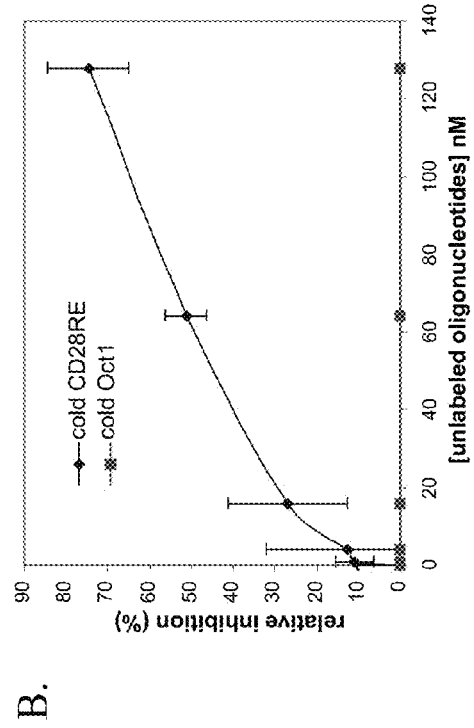
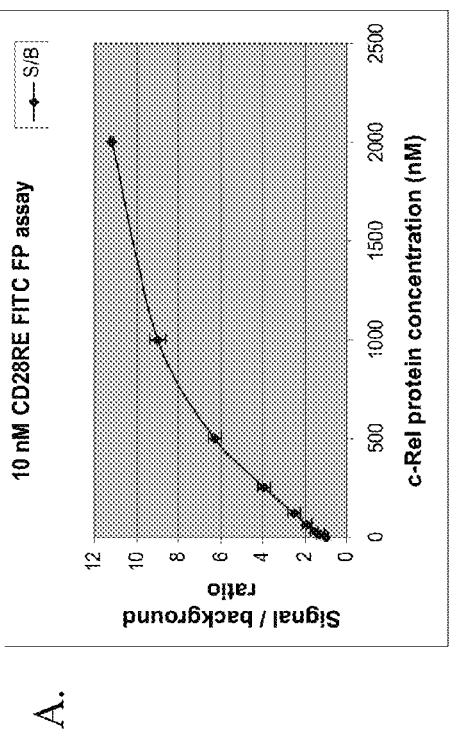
FP assay optimization. A. c-Rel(281) at 2-fold dilutions (2000 to 15.625 nM) were mixed with CD28RE-FITC (10, 3.3, 1.1, 0.33, 0.11 nM) in the FP buffer for 30 minutes. mP values were used to calculate Signal/Background ratio. Only the data for 10nM and 0.33nM are shown here. B. Cold competition with specific (CD28RE) and non-specific (Oct1) oligo. C. Distribution of FP signals in a representative 384-well plate. Z' value for the plate is 0.83.

Fig. 3A

| IV administration | | 5 mg/kg | | | | | | | | | | | |
|---|---|---|---|---|---|---|---|---|---|---|---|---|---|
| Animal | No. of pts used for t₁/₂ | t₁/₂ (hr) | C₀ (ng/mL) | AUC_last (hr*ng/mL) | AUC_inf (hr*ng/mL) | AUC_Extr (%) | V_c (L/kg) | V_ss (L/kg) | CL (mL/min/kg) | MRT (hr) | Last time point for AUC_last (hr) | Time points for T1/2 (hr) | Rsq |
| Mouse 1 | 3 | 0.504 | 1213 | 886 | 889 | 0.330 | 4.09 | 2.70 | 93.7 | 0.491 | 4 | 0.5, 2, 4 | 0.973 |
| Mouse 2 | 3 | 1.67 | 2652 | 989 | 992 | 0.278 | 12.2 | 2.00 | 84.0 | 0.397 | 8 | 2, 4, 8 | 0.984 |
| Mouse 3 | 3 | 0.486 | 1516 | 834 | 836 | 0.242 | 4.19 | 2.45 | 99.7 | 0.409 | 4 | 0.5, 2, 4 | 0.991 |
| N | 3 | 3 | 3 | 3 | 3 | 3 | 3 | 3 | 3 | 3 | | | |
| Mean | | 0.888 | 2128 | 903 | 905 | 0.285 | 6.82 | 2.40 | 92.5 | 0.432 | | | |
| SD | | 0.680 | 1329 | 79 | 79 | 0.047 | 4.64 | 0.38 | 7.9 | 0.051 | | | |
| CV% | | 76.6 | 62.4 | 8.75 | 8.70 | 16.6 | 68.0 | 15.8 | 8.50 | 11.8 | | | |

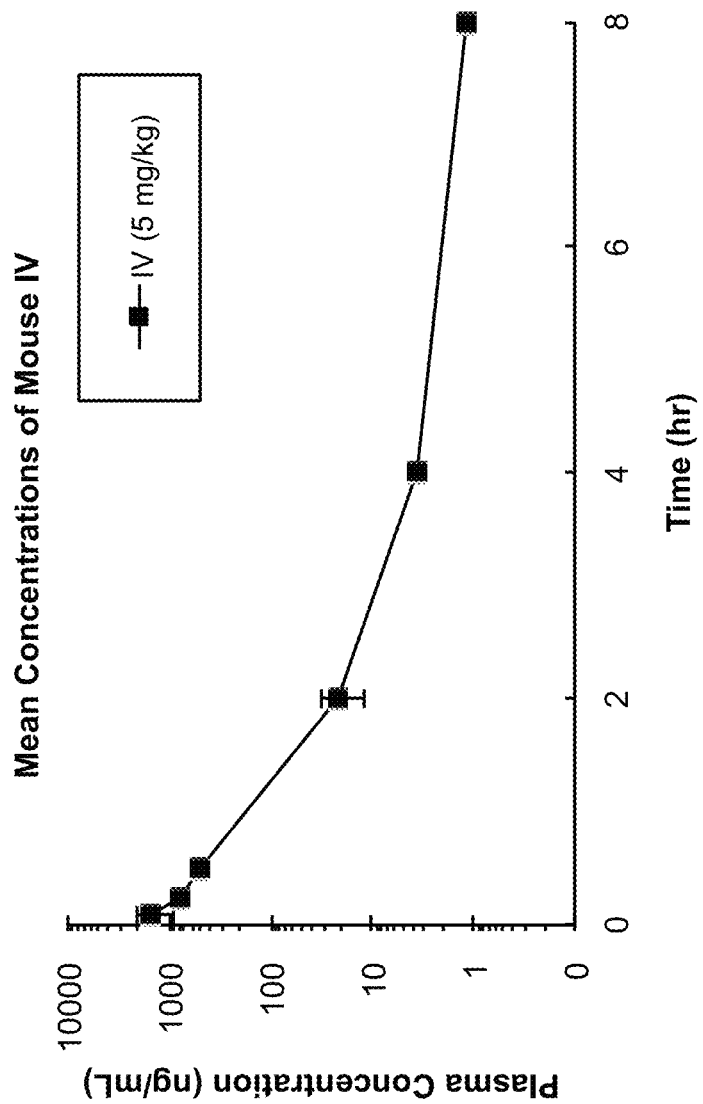

Fig. 4A

IV administration: 5 mg/kg

| Animal | No. of pts used for t₁/₂ | t₁/₂ (hr) | C₀ (ng/mL) | AUC$_{inf}$ (hr*ng/mL) | AUC$_{last}$ (hr*ng/mL) | AUC Extr (%) | V$_c$ (L/kg) | V$_{ss}$ (L/kg) | CL (mL/min/kg) | MRT (hr) | Last time point for AUClast (hr) | Time points for T1/2 (hr) | Rsq |
|---|---|---|---|---|---|---|---|---|---|---|---|---|---|
| Mouse 4 | 4 | 2.21 | 4248 | 4593 | 4997 | 8.28 | 1.18 | 2.61 | 16.7 | 2.632 | 8 | 0.5, 2, 4, 8 | 0.927 |
| Mouse 5 | 4 | 2.78 | 2796 | 4945 | 5874 | 15.8 | 1.41 | 3.21 | 14.2 | 3.777 | 8 | 0.5, 2, 4, 8 | 0.846 |
| Mouse 6 | 4 | 2.37 | 3057 | 5222 | 5814 | 10.2 | 2.94 | 2.60 | 14.3 | 3.094 | 8 | 0.5, 2, 4, 8 | 0.963 |
| N | 3 | 3 | 3 | 3 | 3 | 3 | 3 | 3 | 3 | 3 | | | |
| Mean | | 2.45 | 3367 | 4917 | 5562 | 11.4 | 3.18 | 2.84 | 15.1 | 3.17 | | | |
| SD | | 0.29 | 846 | 320 | 490 | 3.9 | 0.23 | 0.33 | 1.40 | 0.58 | | | |
| CV% | | 12.0 | 27.3 | 6.51 | 8.81 | 34.4 | 7.38 | 11.6 | 9.27 | 18.2 | | | |

Fig. 5A

IV administration — 5 mg/kg

| Animal | No. of pts used for t₁/₂ | t₁/₂ (hr) | C₀ (ng/mL) | AUC_last (hr*ng/mL) | AUC_inf (hr*ng/mL) | AUC Extr (%) | V_z (L/kg) | V_ss (L/kg) | CL (mL/min/kg) | MRT (hr) | Last time point for AUC_last (hr) | Time points for T1/2 (hr) | Rsq |
|---|---|---|---|---|---|---|---|---|---|---|---|---|---|
| Mouse 7 | 3 | 0.827 | 4525 | 4312 | 4318 | 0.101 | 1.38 | 1.12 | 19.3 | 0.903 | 8 | 2, 4, 8 | 0.926 |
| Mouse 8 | 3 | 0.852 | 2652 | 1808 | 1808 | 0.111 | 3.40 | 2.44 | 46.1 | 0.881 | 8 | 2, 4, 8 | 0.948 |
| Mouse 9 | 3 | 0.949 | 3239 | 1596 | 1598 | 0.126 | 4.39 | 2.12 | 52.2 | 0.680 | 8 | 2, 4, 8 | 0.948 |
| N | 3 | 3 | 3 | 3 | 3 | 3 | 3 | 3 | 3 | 3 | | | |
| Mean | | 0.876 | 3472 | 2571 | 2574 | 0.113 | 3.02 | 1.89 | 39.2 | 0.842 | | | |
| SD | | 0.065 | 958 | 1511 | 1512 | 0.012 | 1.49 | 0.69 | 17.5 | 0.146 | | | |
| CV% | | 7.37 | 27.6 | 58.8 | 58.8 | 11.0 | 49.2 | 36.4 | 44.61 | 17.4 | | | |

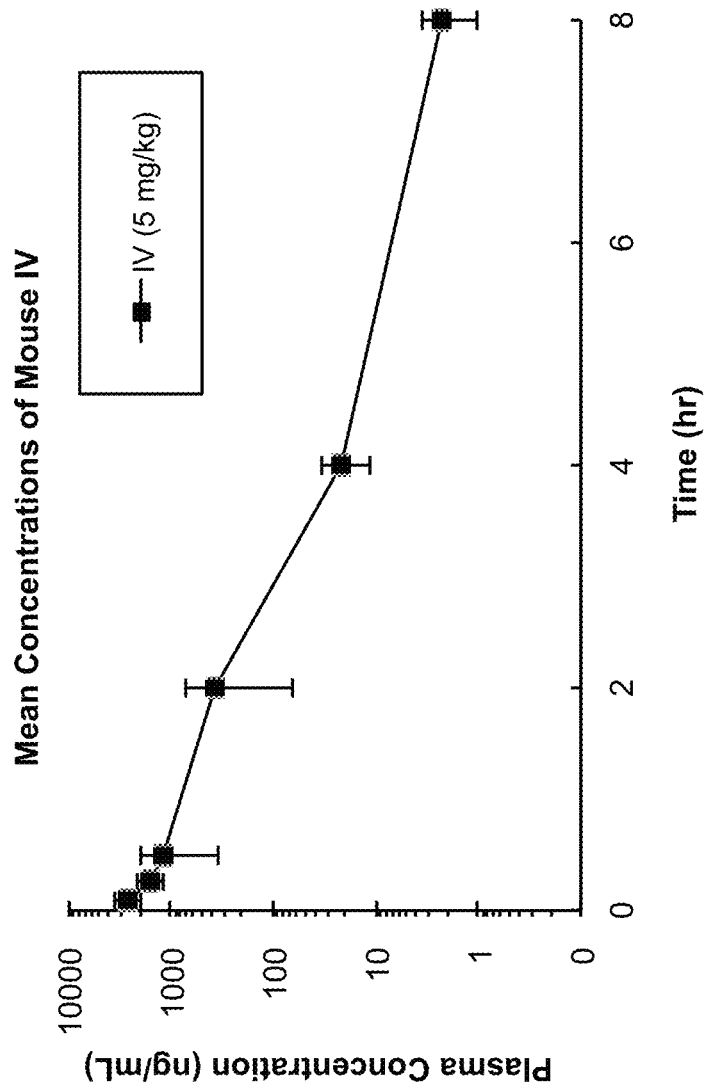

Fig. 6A

IV administration — 5 mg/kg

| Animal | No. of pts used for t1/2 | t1/2 (hr) | C0 (ng/mL) | AUClast (hr*ng/mL) | AUCinf (hr*ng/mL) | AUCExtr (%) | Vz (L/kg) | Vss (L/kg) | CL (mL/min/kg) | MRT (hr) | Last time point for AUClast (hr) | Time points for T1/2 (hr) | Rsq |
|---|---|---|---|---|---|---|---|---|---|---|---|---|---|
| Mouse 4 | 3 | 3.10 | 18433 | 5676 | 5905 | 5.17 | 3.73 | 1.16 | 13.9 | 1.39 | 8 | 24.0 | 0.799 |
| Mouse 5 | 3 | 3.10 | 16093 | 5837 | 5994 | 2.62 | 2.52 | 0.984 | 13.9 | 1.18 | 8 | 24.0 | 0.908 |
| Mouse 6 | 3 | 2.95 | 9183 | 4640 | 5008 | 7.34 | 4.26 | 2.10 | 16.6 | 2.11 | 8 | 24.0 | 0.995 |
| N | 3 | 3 | 3 | 3 | 3 | 3 | 3 | 3 | 3 | 3 | | | |
| Mean | | 2.71 | 14833 | 5384 | 5602 | 5.04 | 3.50 | 1.41 | 14.8 | 1.55 | | | |
| SD | | 0.54 | 4952 | 649 | 507 | 2.36 | 0.88 | 0.61 | 1.6 | 0.50 | | | |
| CV% | | 10.0 | 33.4 | 12.1 | 10.0 | 46.8 | 25.3 | 43.1 | 10.6 | 31.0 | | | |

Fig. 7A

IV administration — 5 mg/kg

| Animal | No. of pts used for t₁/₂ | t₁/₂ (hr) | C₀ (ng/mL) | AUC$_{last}$ (hr*ng/mL) | AUC$_{inf}$ (hr*ng/mL) | AUC Extr (%) | V$_z$ (L/kg) | V$_{ss}$ (L/kg) | CL (mL/min/kg) | MRT (hr) | Last time point for AUC$_{last}$ (hr) | Time points for T1/2 (hr) | Rsq |
|---|---|---|---|---|---|---|---|---|---|---|---|---|---|
| Mouse 10 | 3 | 2.19 | 26182 | 10197 | 10620 | 3.99 | 1.49 | 0.728 | 7.85 | 1.57 | 8 | 2,4,8 | 0.979 |
| Mouse 11 | 3 | 2.12 | 10813 | 10642 | 10949 | 2.72 | 1.45 | 0.714 | 7.61 | 1.56 | 8 | 2,4,8 | 0.975 |
| Mouse 12 | 3 | 2.19 | 24756 | 11995 | 12459 | 3.81 | 1.27 | 0.662 | 6.71 | 1.54 | 8 | 2,4,8 | 0.989 |
| N | 3 | 3 | 3 | 3 | 3 | 3 | 3 | 3 | 3 | 3 | | | |
| Mean | | 2.17 | 22584 | 10898 | 11333 | 3.84 | 1.39 | 0.698 | 7.39 | 1.56 | | | |
| SD | | 0.04 | 5048 | 951 | 963 | 0.13 | 0.11 | 0.063 | 0.60 | 0.02 | | | |
| CV% | | 1.74 | 22.4 | 8.55 | 8.50 | 3.49 | 7.87 | 9.20 | 8.16 | 1.09 | | | |

Fig. 8A

IV administration — 5 mg/kg

| Animal | No. of pts used for t½ | t½ (hr) | C₀ (ng/mL) | AUC_last (hr*ng/mL) | AUC_inf (hr*ng/mL) | AUC Extr (%) | V_c (L/kg) | V_ss (L/kg) | CL (mL/min/kg) | MRT (hr) | Last time point for AUClast (hr) | Time points for T1/2 (hr) | Rsq |
|---|---|---|---|---|---|---|---|---|---|---|---|---|---|
| Mouse 7 | 3 | 2.33 | 12228 | 8149 | 8708 | 6.42 | 1.93 | 1.22 | 9.57 | 2.13 | 8 | 24, 8 | 0.988 |
| Mouse 8 | 3 | 1.84 | 14538 | 10579 | 10946 | 3.30 | 1.21 | 0.775 | 7.62 | 1.69 | 8 | 24, 8 | 0.988 |
| Mouse 9 | 3 | 2.11 | 16059 | 8725 | 9193 | 4.77 | 1.66 | 1.11 | 9.08 | 2.04 | 8 | 24, 8 | 1.00 |
| N | 3 | 3 | 3 | 3 | 3 | 3 | 3 | 3 | 3 | 3 | | | |
| Mean | | 2.10 | 14242 | 9101 | 9614 | 4.83 | 1.60 | 1.03 | 8.75 | 1.95 | | | |
| SD | | 0.25 | 1579.7 | 1365 | 1174 | 1.56 | 0.36 | 0.23 | 1.03 | 0.23 | | | |
| CV% | | 11.8 | 11.1 | 13.81 | 12.21 | 33.3 | 22.67 | 22.7 | 11.58 | 11.9 | | | |

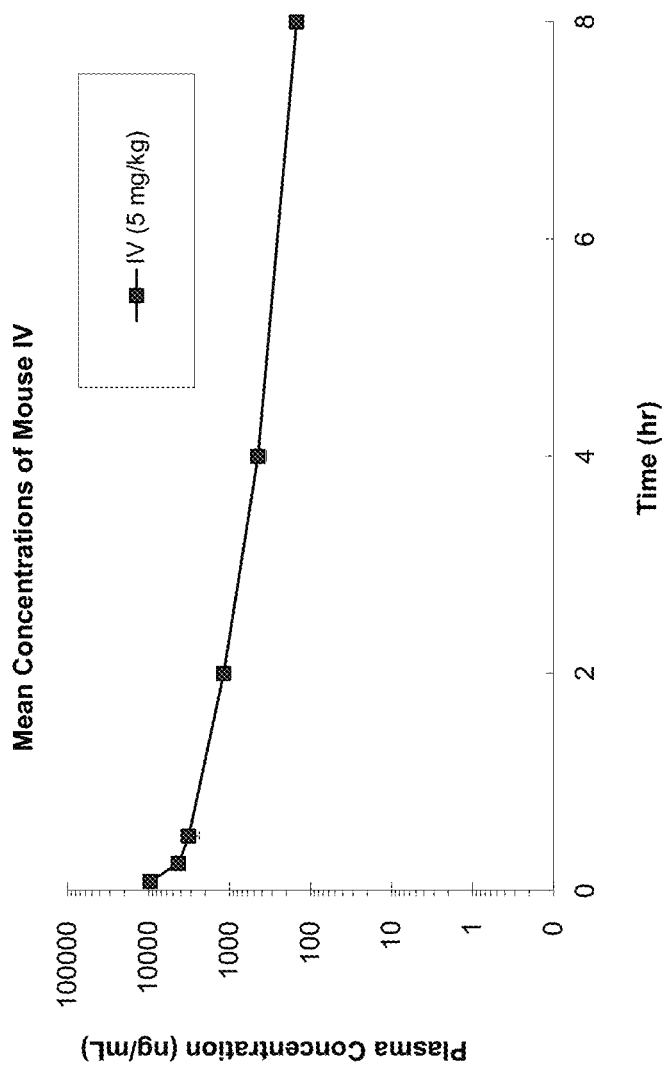

Fig. 9

| Cell | Passage | Characteristics | 24h and 48h - Doublicate readout | | | | | | |
|---|---|---|---|---|---|---|---|---|---|
| | | | Vehicle | | IT-852 (Neg. Ctl) | | IT-848 | | Erlotinib |
| | | | ATP assay | PARP assay | ATP assay | PARP assay | ATP assay | PARP assay | ATP assay | PARP assay |
| NCI-H1975 | Cell line | Erlotinib Resistant | 4% GDM-12 in PBS | | 1, 2, 4, 8 uM | | 1, 2, 4, 8 uM | | 1, 5, 10, 20 uM | 0.01, 0.1, 1, 5 uM |
| HCC827 | Cell line | Erlotinib Sensitive | | | | | | | | |
| Adeno 76yo M | p3 | Patient derived | | | | | | | | |
| Adeno 72yo F | p9 | Patient derived | | | | | | | | |
| SCC | p4 | Patient derived | | | | | | | | |

Fig. 10

50 % Growth Inhibition (IG50) and PARP activity inhibition at 24 hours time point (uM)

| Cell | Passage | Characteristics | Vehicle | | IT-852 (Neg. Ctl) | | IT-848 | | Erlotinib | |
|---|---|---|---|---|---|---|---|---|---|---|
| | | | ATP assay | PARP assay | ATP assay | PARP assay | ATP assay | PARP assay | ATP assay | PARP assay |
| NCI-H1975 | Cell line | Erlotinib Resistant | NA | NA | >8 | >8 | >8 | Not clear | >20 | >20 |
| HCC827 | Cell line | Erlotinib Sensitive | NA | NA | >8 | >8 | 4 | Not clear | >5 | Not seen |
| Adeno 76yo M | p3 | Patient derived | NA | NA | >8 | >8 | >8 | 2 | >5 | Not seen |
| Adeno 72yo F | p9 | Patient derived | NA | NA | >8 | >8 | >8 | 6 | >5 | Not seen |
| SCC | p4 | Patient derived | NA | NA | >8 | >8 | >8 | 4 | >5 | Not seen |

Fig. 11

| | | 50% Growth Inhibition (IG50) and PARP activity inhibition at 48 hours time point (uM) | | | | | | | |
|---|---|---|---|---|---|---|---|---|---|
| | | Vehicle | | IT-852 (Neg. Ctl) | | IT-848 | | Erlotinib | |
| Cell | Passage | Characteristics | ATP assay | PARP assay | ATP assay | PARP assay | ATP assay | PARP assay | ATP assay | PARP assay |
| NCI-H1975 | Cell line | Erlotinib Resistant | NA | NA | >8 | >8 | 6 | 4 | >20 | >20 |
| HCC827 | Cell line | Erlotinib Sensitive | NA | NA | >8 | >8 | 2 | 4 | 0.01 | 0.01 to 0.1 |
| Adeno 76yo M | p3 | Patient derived | NA | NA | >8 | >8 | 3 | 2 | >5 | >5 |
| Adeno 72yo F | p9 | Patient derived | NA | NA | >8 | >8 | 8 | 4 | >5 | >5 |
| SCC | p4 | Patient derived | NA | NA | >8 | >8 | 4 | 3 | >5 | >5 |

Fig. 14

| Cell line | Type | Biomarker | Drug Sensitive/Resistant status |
|---|---|---|---|
| HCC827 | ADC | EGFR (Del 19) | Erlotinib sensitive |
| PC9 | ADC | EGFR (Del 19) | Cisplatin sensitive, TKIs sensitive |
| H1975 | ADC | EGFR (L858R/T790M) | Erlotinib resistant |
| H1650 | ADC (bronchoalveolar) | EGFR (Del 19) | Resistant to 1st, 2nd and 3rd generation TKIs |
| H2228 | ADC | EML4-ALK fusion | Crizotinib, Alectinib sensitive |
| H1437 | ADC | EGFR (WT) | |
| H2030 | ADC (lymphonode metastesis) | Kras-mutation | |
| H23 | ADC (alveolar basal epithelial) | Kras-mutation (myc +; src +; abl +; erb +; ras +; sis −) | |
| A549 | ADC | Kras-mutation (MEK inhibitor resistant) | Erlotinib sensitive; Alectinib insensitive |
| H522 | ADC | TP53 mutation, Kras(WT), EGFR(WT), ALK(WT) | |
| H460 | LCC | Kras-mutation + gainfuction p110 alpha of PI3K | |
| H1581 | LCC | FGFR amplified | |
| DMS114 | SCC | FGFR amplified | |
| SKMES-1 | SqCC | p53 mutant | |
| NL20 | Fibroblast (healthy) | | |

Fig. 16A

PLC/PRF/5

| IT-848+Sorafenib inhibition% | | Sorafenib | | | |
|---|---|---|---|---|---|
| | | | 1 µM | 2 µM | 4 µM |
| | | | 2 µM | | |
| | | | 4 µM | | |

| | IT848 | | |
|---|---|---|---|
| | 2 µM | 3 µM | 4 µM |
| | 90.604 | 94.954 | 100.619 |
| | 87.569 | 93.917 | 93.897 |
| | 70.726 | 69.564 | 68.190 |

| IT-845+Sorafenib inhibition% | | Sorafenib | | | |
|---|---|---|---|---|---|
| | | | 1 µM | 2 µM | 4 µM |
| | | | 2 µM | | |
| | | | 4 µM | | |

| | IT845 | | |
|---|---|---|---|
| | 2 µM | 3 µM | 4 µM |
| | 112.008 | 112.873 | 111.596 |
| | 100.581 | 108.177 | 113.190 |
| | 80.597 | 81.106 | 80.405 |

Fig. 16B

HUH-7

| IT-848+Sorafenib inhibition% | | IT848 | | |
|---|---|---|---|---|
| | | 2 µM | 3 µM | 4 µM |
| Sorafenib | 1 µM | 85.471 | 86.123 | 84.310 |
| | 2 µM | 85.246 | 81.616 | 79.922 |
| | 4 µM | 62.741 | 66.630 | 66.994 |

| IT-845+Sorafenib inhibition% | | IT845 | | |
|---|---|---|---|---|
| | | 2 µM | 3 µM | 4 µM |
| Sorafenib | 1 µM | 85.327 | 85.761 | 70.153 |
| | 2 µM | 77.167 | 74.532 | 68.367 |
| | 4 µM | 60.095 | 61.162 | 55.161 |

Fig. 16C

HepG2

| IT-848+Sorafenib inhibition% | | IT848 | | |
|---|---|---|---|---|
| | | 2 μM | 3 μM | 4 μM |
| Sorafenib | 1 μM | 90.625 | 105.099 | 102.075 |
| | 2 μM | 86.096 | 92.213 | 97.005 |
| | 4 μM | 73.127 | 73.064 | 72.187 |

| IT-845+Sorafenib inhibition% | | IT845 | | |
|---|---|---|---|---|
| | | 2 μM | 3 μM | 4 μM |
| Sorafenib | 1 μM | 97.898 | 106.652 | 84.311 |
| | 2 μM | 94.166 | 92.669 | 77.833 |
| | 4 μM | 78.237 | 71.024 | 59.641 |

Fig. 16D

Hep3B

| IT-848+Sorafenib inhibition% | | IT848 | | |
|---|---|---|---|---|
| Sorafenib | | 2 μM | 3 μM | 4 μM |
| | 1 μM | 100.578 | 116.563 | 113.720 |
| | 2 μM | 101.901 | 105.726 | 88.941 |
| | 4 μM | 76.594 | 75.648 | 67.703 |

| IT-845+Sorafenib inhibition% | | IT845 | | |
|---|---|---|---|---|
| Sorafenib | | 2 μM | 3 μM | 4 μM |
| | 1 μM | 103.928 | 94.419 | 72.838 |
| | 2 μM | 90.787 | 92.739 | 59.369 |
| | 4 μM | 77.562 | 73.173 | 50.199 |

METHODS OF TREATING CANCER WITH SMALL MOLECULE NF-κB INHIBITORS

CROSS-REFERENCE TO RELATED APPLICATIONS

The present invention claims benefit to U.S. provisional application Ser. No. 62/525,650 filed Jun. 27, 2017, the entire contents of which are incorporated by reference.

FIELD OF INVENTION

The present invention provides, inter alia, compounds and pharmaceutical compositions capable of inhibiting NF-κB, as well methods of using said compounds and compositions.

BACKGROUND OF THE INVENTION

NF-κB/Rel

NF-κB/Rel (nuclear factor kappa B) is a family of transcription factors that includes p50/p105 (NF-κB1), p52/p100 (NF-κB2), p65 (RelA), c-Rel, and RelB. These molecules can homo- or heterodimerize, and are generally sequestered in the cytoplasm by their inhibitors, IκBs. Upon activation, IκBs are degraded by the 26s proteasome and NF-κB dimers migrate into the nucleus to perform transcriptional activity.

NF-κB (p50/p65) and c-Rel are regulated by the canonical IKK α/β/γ kinase complex pathway, whereas RelB and p52 (NF-κB2) are regulated by an alternative pathway via the IKKα/NIK complex. Despite this similarity, each NF-κB family member is distinct with regard to tissue expression pattern, response to receptor signals, and target gene specificity. These differences are evident from the non-redundant phenotypes exhibited by individual NF-κB/Rel knockout mice. Therefore, therapeutics targeted to different NF-κB/Rel members are likely to have different biological effects and toxicity profiles.

Many receptors and stimuli can activate NF-κB/Rel, including TCR/BCR, TNF receptor superfamily (e.g. CD40, TNFR1, TNFR2, BAFF, APRIL, RANK), IL-1/TLR receptors, and Nod-like receptors, as well as activating oncogenes (e.g. Src, Ras, LMP-1, Tax, v-FLIP), reactive oxygen radicals, radiation, and chemotherapeutic agents. In response to these stimuli, NF-κB/Rel regulates the expression of cytokines, chemokines, and molecules that play a role in adhesion, the cell cycle, apoptosis, and angiogenesis. As such, NF-κB/Rel transcription factors are important therapeutic targets for many human disorders, including inflammation, autoimmune diseases, and cancer, and small molecule inhibitors of NF-κB/Rel may be useful as therapeutics for these disorders.

Lung Cancers

Lung cancer is the leading cause of cancer mortality in the US (approximately 160,000 deaths) and the world (nearly 1.7 million deaths). The incidence rate remains the third-highest (222,500 cases in the US in 2016), behind breast and prostate cancer.

Chemotherapeutic platinum-based agents, usually in combination with other drugs, are the most commonly prescribed drugs for a majority of lung cancer patients, including both small cell and non-small cell lung cancer (NSCLC) patients. Thus far, twenty drugs have been approved to manage lung cancers, including chemotherapy agents (e.g. carboplatin, gemcitabine, paclitaxel), targeted agents (e.g. EGFR inhibitors, such as gefitinib, erlotinib, afatinib, and osimetinib, and ALK inhibitors, such as crizotinib, ceritinib, and alectinib), monoclonal antibodies (e.g. anti-VEGF antibodies, such as bevacizumab, and anti-EGFR antibodies, such as necitumumab), and immunotherapy agents (e.g. anti-PD-1 antibodies, such as nivolumab and pembrolizumab, and anti-PD-L1 antibodies, such as atezolizumab). Despite the emergence of new therapies, lung cancer mortality remains very high and the five-year survival rate is low (approximately 18%) due to rapid development of drug resistance.

NF-κB overactivation has been identified in human cancers, including, but not limited to, myelomas, leukemias, lymphomas, lung cancers, gastric and colorectal cancers, liver cancers, esophageal and head and neck carcinomas, breast cancers, ovarian cancers, and prostate cancers.

NF-κB signaling is required for cancer cell growth, proliferation, metastasis, anti-apoptosis mechanisms, and drug resistance. NF-κB signaling is also required for development of the tumor microenvironment, which involves activation of myeloid-derived suppressor cells (MDSC) to prevent cytotoxic T-cell activity against tumor cells and activation of stromal cell and nurse-like cells to support tumor cell survival.

A comprehensive analysis of the NF-κB expression profile of 77 well-documented NSCLC primary tumor samples indicated that RelA, RelB, and p50 are generally overexpressed. Further findings correlated RelA expression with intensity of inflammation infiltration and RelB expression with tumor proliferation. (Giopanou et al., 2015).

Attempts to inhibit NF-κB directly or indirectly have been demonstrated. For example, the direct and covalently-binding NF-κB inhibitor, PS1086, used in combination with the EGFR inhibitor erlotinib, overcomes erlotinib resistance in a mouse xenograft model of non-small cell lung adenocarcinoma. (Blakely et al., 2015). The naturally-occurring NF-κB inhibitor, triptolide, reverses taxol resistance of lung adenocarcinoma by inhibiting the NF-κB signaling pathway and expression of NF-κB-regulated drug-resistant genes. (Jiang et al., 2016).

Pancreas Cancers

With an estimated 54,000 new cases in the US every year, resulting in 43,000 deaths, pancreas cancer is the deadliest cancer. Pancreas cancer accounts for 3% of all cancers but 7% of total cancer deaths. The disease is aggressive and early diagnosis is rare. For all stages of pancreas cancers, one- and five-year survival rates have stagnated at 20% and 7%, respectively. At present, gemcitabine+erlotinib and FOLFIRINOX (folic acid+5-fluorouracil+irinotecan+oxaliplatin) are the commonly accepted treatment regimens, though they offer dismal benefits.

There is strong evidence linking NF-κB to pancreas cancer's aggressiveness and rapid development of drug resistance. First, constitutively activated RelA, a subunit of NF-κB, was detected in 16 out of 24 pancreatic adenocarcinoma (PDAC) patient samples (67%) and 9 out of 11 PDAC cell lines (82%), while RelA is not activated in normal pancreas tissue. (Wang et al., 1999).

Second, nearly all PDAC tumors (detected in 95% of PDAC patients) have K-Ras mutation. K-Ras mutation is a significant driver of cancers and usually is a marker of a cancer's aggressiveness. But K-Ras mutation alone might not be enough to cause cancer. Apparently, K-Ras mutation in combination with chronic inflammation is the cause. K-Ras mutation perpetuates an inflammation even through the NF-κB pathway. (Barbie et al., 2009; Daniluk et al., 2012).

Third, PDAC cells, through activation of the NF-κB pathway, express GM-CSF to turn monocytes into myeloid-derived suppressor cells (MDSC), which suppress T-cells from fighting PDAC. (Takeuchi et al., 2015).

Finally, chemotherapy fails to deliver durable or strong effects because the chemotherapy agent (gemcitabine) quickly activates the NF-κB pathway through reactive oxygen species (ROS). This NF-κB pathway leads to overexpression of CXCR-4 on the cell surface, thus promoting PDAC metastasis. Consequently, while treating PDAC with gemcitabine might slightly delay tumor growth, gemcitabine may simultaneously induce the tumor to be more invasive. (Arora et al., 2013).

Other Solid Tumors

In a meta-analysis of data from 44 clinical studies with a total of 4,418 solid tumor patients, NF-κB overexpression was associated with worse overall survival (OS) at 3, 5, and 10 years. NF-κB expression was associated with poor 3-year OS in both tumor and lymph node, and at all metastasis stages. Among the tumor types, NF-κB was associated with worse 3-year OS of colorectal cancer and esophageal carcinoma and worse 5-year OS of colorectal cancer, esophageal carcinoma and non-small cell lung cancer. Furthermore, expression of NF-κB is associated with worse survival in most solid tumors irrespective of NF-κB localization (nuclear or cytosol). This study suggesting that NF-κB could be a potential drug target for a broad variety of solid tumors. (Wu et al., 2015).

Given the role of NF-κB in pathogenesis, survival, metastasis, and treatment resistance of cancers, NF-κB inhibitors of the present invention could be effective cancer treatments, particularly for the cancers associated with overexpression, upregulation, overactivation, or constitutive activation of NF-κB.

SUMMARY OF THE INVENTION

The present invention relates to compounds capable of inhibiting NF-kB/Rel.

One embodiment of the present invention is a compound. The compound has a structure of formula (I)

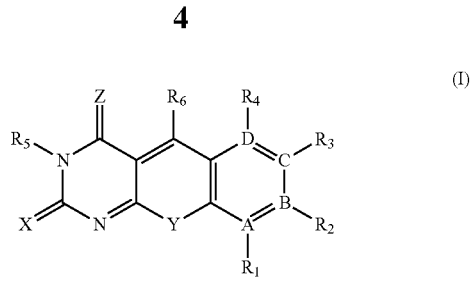

wherein:

A, B, C, and D are independently selected from the group consisting of carbon and nitrogen;

X, Y, and Z are independently selected from the group consisting of oxygen, sulfur, and $NR^a$;

$R_1$, $R_2$, $R_3$, and $R_4$ are independently selected from the group consisting of no atom, hydrogen, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —$OR^a$(C=O)$R^b$, —O(C=O)$R^a$, —O(C=O)$OR^a$, —O(C=O)$NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —S(C=O)$R^a$, —S(C=O)$OR^a$, —S(C=O)$NR^aR^b$;

$R_5$ is selected from the group consisting of hydrogen, $C_{1-9}$ alkyl, $C_{2-9}$ alkenyl, $C_{2-9}$ alkynyl, aryl, heterocyclic, —$R^aCO$, —$R^aNHCO$, and —$R^aOCO$; and $R_6$, $R^a$, $R^b$, and $R^c$ are independently selected from the group consisting of hydrogen, hydroxyl, amine, $C_{1-9}$ alkyl, $C_{2-9}$ alkenyl, $C_{2-9}$ alkynyl, aryl, and heterocyclic, or is a crystalline form, hydrate, or pharmaceutically acceptable salt thereof.

Another embodiment of the present invention is a compound. The compound is selected from the group consisting of the compounds in Table 1, and crystalline forms, hydrates, or pharmaceutically acceptable salts thereof.

TABLE 1

| Designation | Structure |
| --- | --- |
| IT-806 | ![structure] |
| IT-807 | ![structure] |
| IT-809 | ![structure] |

TABLE 1-continued

| Designation | Structure |
|---|---|
| IT-810 | 7-bromo-9-methoxy-chromeno-pyrimidine-2,4-dione |
| IT-814 | 7-chloro-9-ethoxy-chromeno-pyrimidine-2,4-dione |
| IT-817 | 8-methoxy-chromeno-pyrimidine-2,4-dione |
| IT-854 | 7-chloro-9-methoxy-2-thioxo-chromeno-pyrimidin-4-one |
| IT-861 | 8-methoxy-2-thioxo-chromeno-pyrimidin-4-one |
| IT-804 | chromeno-pyrimidine-2,4-dione |
| IT-818 | 7-methoxy-chromeno-pyrimidine-2,4-dione |
| IT-819 | 8-hydroxy-chromeno-pyrimidine-2,4-dione |
| IT-820 | 8-methyl-chromeno-pyrimidine-2,4-dione |

TABLE 1-continued

| Designation | Structure |
|---|---|
| IT-821 | (structure: chromeno-pyrimidine-2,4-dione with 7-OEt) |
| IT-822 | (structure: chromeno-pyrimidine-2,4-dione with 5-OMe, 7-OMe) |
| IT-862 | (structure: 2-thioxo-chromeno-pyrimidin-4-one with 7-OMe) |
| IT-863 | (structure: 2-thioxo-chromeno-pyrimidin-4-one with 7-OH) |
| IT-864 | (structure: 2-thioxo-chromeno-pyrimidin-4-one with 7-Me) |
| IT-865 | (structure: 2-thioxo-chromeno-pyrimidin-4-one with 5-OMe, 7-OMe) |
| IT-823 | (structure: chromeno-pyrimidine-2,4-dione with 7-OnPr) |
| IT-826 | (structure: chromeno-pyrimidine-2,4-dione with 6-Cl, 7-OnPr) |
| IT-825 | (structure: chromeno-pyrimidine-2,4-dione with 7-OC$_6$H$_{13}$) |

TABLE 1-continued
| Designation | Structure |
|---|---|
| IT-827 | 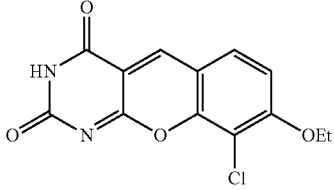 [SMILES: CCOc1ccc2cc3c(=O)[nH]c(=O)nc-3oc2c1Cl] |
| IT-824 | 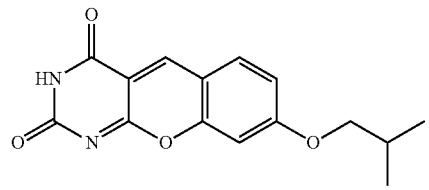 [SMILES: CC(C)COc1ccc2cc3c(=O)[nH]c(=O)nc-3oc2c1] |
| IT-828 | 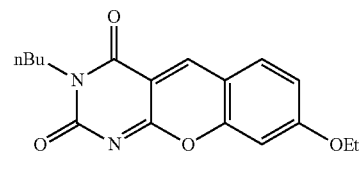 |
| IT-829 | 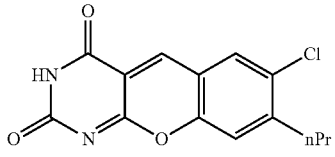 |
| IT-830 | 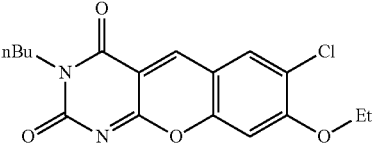 |
| IT-831 | 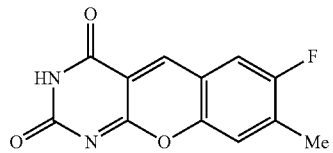 [SMILES: Cc1cc2oc3nc(=O)[nH]c(=O)c-3cc2cc1F] |
| IT-832 | 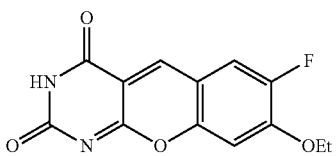 [SMILES: CCOc1cc2oc3nc(=O)[nH]c(=O)c-3cc2cc1F] |
| IT-833 | 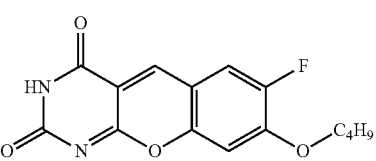 |
| IT-834 | 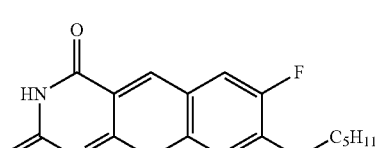 |

TABLE 1-continued

| Designation | Structure |
|---|---|
| IT-835 | (structure: pyrimidochromene with 7-F, 8-OC₆H₁₃) |
| IT-836 | (structure: pyrimidochromene with 7-F, 8-OC₇H₁₅) |
| IT-837 | (structure: pyrimidochromene with 7-F, 8-O-isopentyl) |
| IT-838 | (structure: pyrimidochromene with 7-F, 8-O-CH₂C(CH₃)₃ neopentyl-like) |
| IT-839 | (structure: pyrimidochromene with 7-F, 8-O-isohexyl) |
| IT-840 | (structure: pyrimidochromene with 7-F, 8-O-neopentyl) |
| IT-841 | (structure: pyrimidochromene with 7-Cl, 8-OC₆H₁₃) |
| IT-842 | (structure: pyrimidochromene with 7-Cl, 8-O-isobutyl) |
| IT-843 | (structure: pyrimidochromene with 9-Cl, 8-OC₅H₁₁) |

TABLE 1-continued
| Designation | Structure |
|---|---|
| IT-844 | 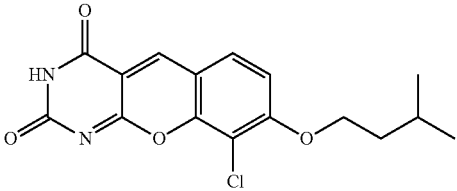 [SMILES: CC(C)CCOc1ccc2cc3c(=O)[nH]c(=O)nc-3oc2c1Cl] |
| IT-845 | 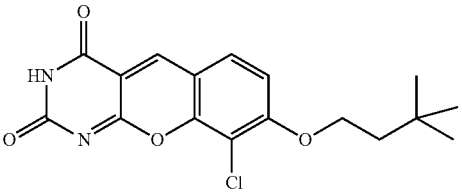 [SMILES: CC(C)(C)CCOc1ccc2cc3c(=O)[nH]c(=O)nc-3oc2c1Cl] |
| IT-846 | 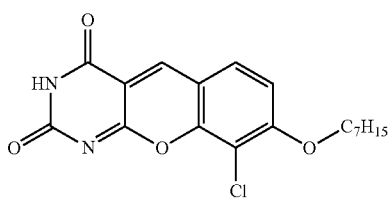 |
| IT-847 | 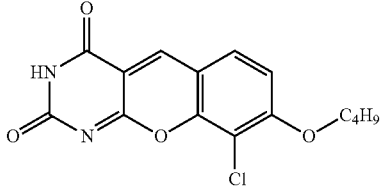 |
| IT-848 | 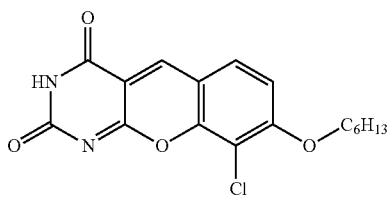 |
| IT-849 | 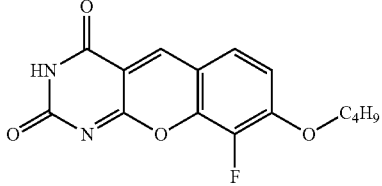 |
| IT-850 | 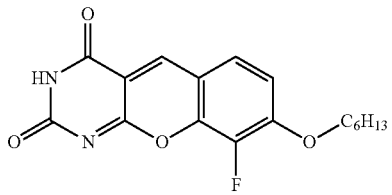 |

TABLE 1-continued

| Designation | Structure |
|---|---|
| IT-851 | pyrimidine-chromene fused tricyclic core with 8-F and 7-O-isohexyl (OCH2CH2CH2CH(CH3)2) substituents |
| IT-852 | pyrimidine-chromene fused tricyclic core with 8-F and 7-O-isobutyl substituents |
| IT-872 | pyrimidine-thiochromene fused tricyclic core with 7-OEt substituent |
| IT-882 | pyrimidine-chromene fused tricyclic core with 7-O-C$_4$H$_9$ substituent |
| IT-883 | pyrimidine-chromene fused tricyclic core with 7-O-(CH$_2$)$_4$-OC(O)CH$_3$ substituent |
| IT-853 | pyrimidine-chromene fused tricyclic core with 8-F and 7-O-C$_7$H$_{15}$ substituents |
| IT-855 | pyrimidine-chromene fused tricyclic core with 8-Cl and 7-O-C$_5$H$_{10}$-COOH substituents |
| IT-856 | pyrimidine-chromene fused tricyclic core with 8-Cl and 7-O-C$_4$H$_8$-COOH substituents |

TABLE 1-continued

| Designation | Structure |
|---|---|
| IT-857 | Chromeno-pyrimidinedione with Cl and O(CH2)3COOH substituents |
| IT-858 | Chromeno-pyrimidinedione with Cl and OCH2COOH substituents |
| IT-859 | Chromeno-pyrimidinedione with Cl and O-C4H8-C(O)OMe substituents |
| IT-866 | Chromeno-pyrimidinedione with Cl and O(CH2)6OAc substituents |
| IT-867 | Chromeno-pyrimidinedione with Cl and O(CH2)3OAc substituents |
| IT-868 | Chromeno-pyrimidinedione with Cl and O(CH2)4OAc substituents |
| IT-875 | Chromeno-pyrimidinedione with OCH2CH2OCH2CH2OMe substituent |
| IT-876 | Chromeno-pyrimidinedione with Cl and OCH2CH2OCH2CH2OMe substituents |

TABLE 1-continued
| Designation | Structure |
|---|---|
| IT-884 | 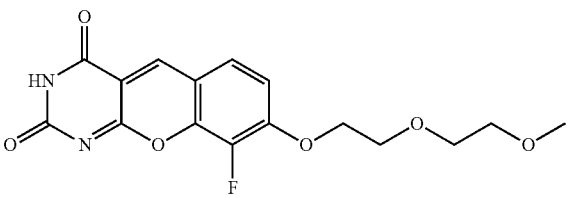 [SMILES: COCCOCCOc1ccc2cc3c(=O)[nH]c(=O)nc-3oc2c1F] |
| IT-885 | 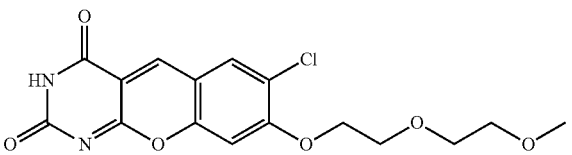 [SMILES: COCCOCCOc1cc2oc3nc(=O)[nH]c(=O)c-3cc2cc1Cl] |
| IT-886 | 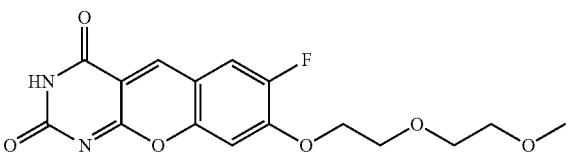 [SMILES: COCCOCCOc1cc2oc3nc(=O)[nH]c(=O)c-3cc2cc1F] |
| IT-877 | 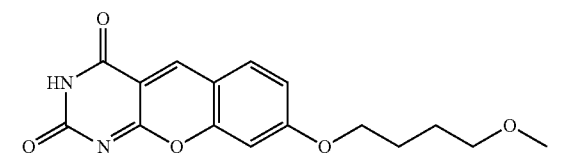 [SMILES: COCCCCOc1ccc2cc3c(=O)[nH]c(=O)nc-3oc2c1] |
| IT-878 | 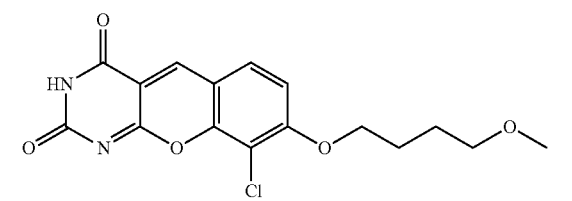 |
| IT-887 | 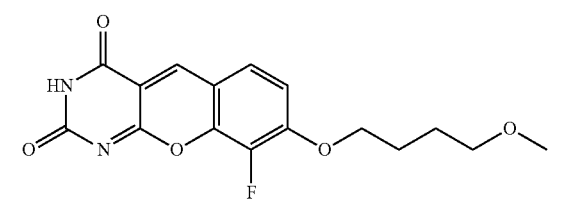 [SMILES: COCCCCOc1ccc2cc3c(=O)[nH]c(=O)nc-3oc2c1F] |
| IT-888 | 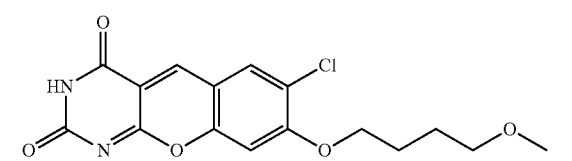 [SMILES: COCCCCOc1cc2oc3nc(=O)[nH]c(=O)c-3cc2cc1Cl] |
| IT-889 | 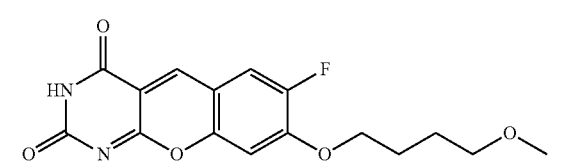 |
| IT-890 | 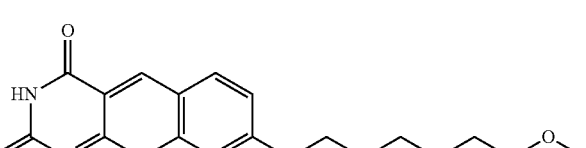 |

TABLE 1-continued

| Designation | Structure |
|---|---|
| IT-879 | 8-chloro-7-(3-(2-methoxyethoxy)propoxy)-2H-chromeno[2,3-d]pyrimidine-2,4(3H)-dione |
| IT-891 | 8-fluoro-7-(3-(2-methoxyethoxy)propoxy)-2H-chromeno[2,3-d]pyrimidine-2,4(3H)-dione |
| IT-892 | 6-chloro-7-(3-(2-methoxyethoxy)propoxy)-2H-chromeno[2,3-d]pyrimidine-2,4(3H)-dione |
| IT-880 | 6-fluoro-7-(3-(2-methoxyethoxy)propoxy)-2H-chromeno[2,3-d]pyrimidine-2,4(3H)-dione |
| IT-893 | 8-chloro-7-(O-$C_5H_{10}$-C(O)NH$_2$)-2H-chromeno[2,3-d]pyrimidine-2,4(3H)-dione |
| IT-894 | 8-chloro-7-(O-$C_4H_8$-C(O)NH$_2$)-2H-chromeno[2,3-d]pyrimidine-2,4(3H)-dione |
| IT-895 | 8-chloro-7-(4-amino-4-oxobutoxy)-2H-chromeno[2,3-d]pyrimidine-2,4(3H)-dione |
| IT-896 | 8-chloro-7-(2-carboxyethoxy)-2H-chromeno[2,3-d]pyrimidine-2,4(3H)-dione |

TABLE 1-continued

| Designation | Structure |
|---|---|
| IT-897 | Chromeno-pyrimidinedione with 8-Cl, 7-O-CH₂CH₂C(O)NH₂ substituent |
| IT-898 | Chromeno-pyrimidinedione with 8-Cl, 7-O-CH₂C(O)NH₂ substituent |
| IT-899 | Chromeno-pyrimidinedione with 8-Cl, 7-O-C₃H₆-C(O)OMe substituent |
| IT-701 | Chromeno-pyrimidinedione with 8-Cl, 7-O-C₅H₁₀-C(O)OMe substituent |
| IT-702 | Chromeno-pyrimidinedione with 8-Cl, 7-O-(CH₂)₆-OH substituent |
| IT-703 | Chromeno-pyrimidinedione with 8-Cl, 7-O-(CH₂)₅-OAc substituent |
| IT-704 | Chromeno-pyrimidinedione with 8-Cl, 7-O-(CH₂)₅-OH substituent |

TABLE 1-continued

| Designation | Structure |
|---|---|
| IT-705 | 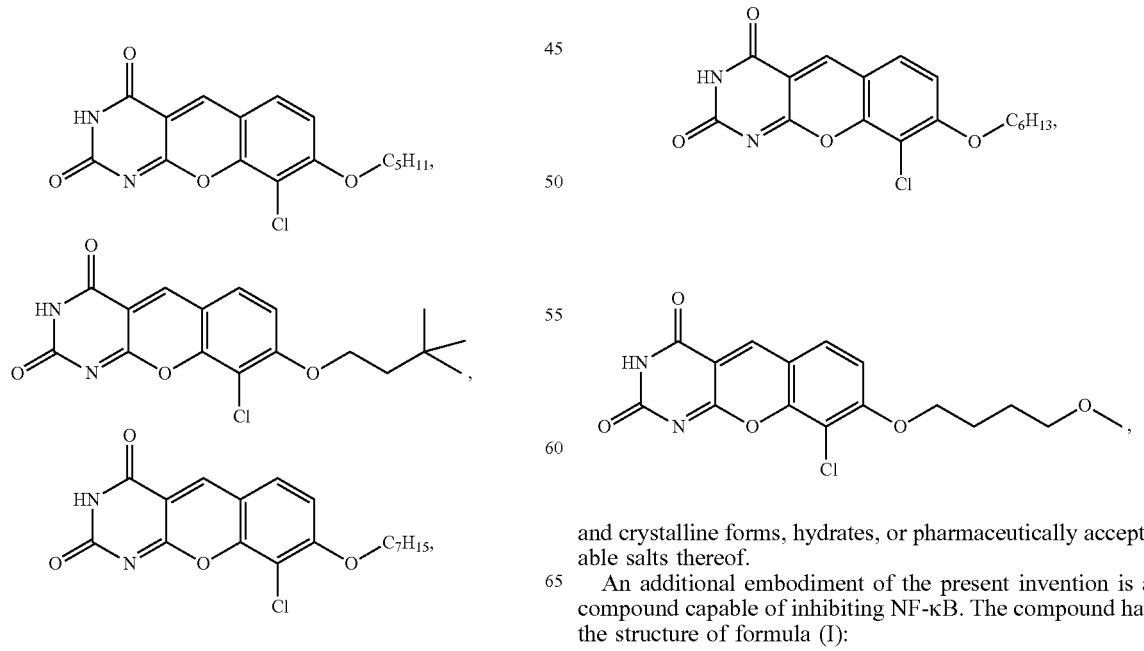 |
| IT-706 | 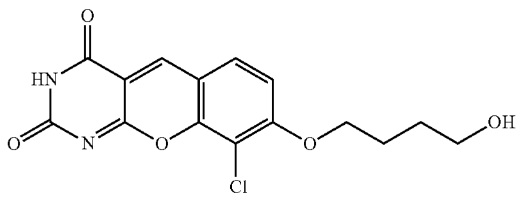 [SMILES: O=c1nc2oc3c(Cl)c(OCCCCO)ccc3cc-2c(=O)[nH]1] |
| IT-707 | 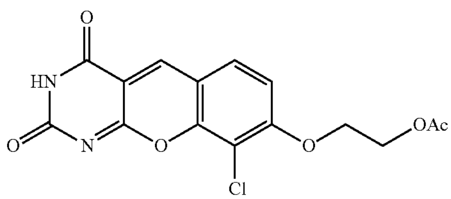 [SMILES: CC(=O)OCCOc1ccc2cc3c(=O)[nH]c(=O)nc-3oc2c1Cl] |
| IT-708 | 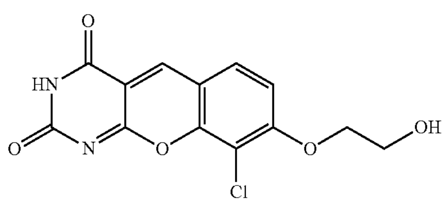 [SMILES: O=c1nc2oc3c(Cl)c(OCCO)ccc3cc-2c(=O)[nH]1] |

A further embodiment of the present invention is a compound. The compound is selected from the group consisting of:

and crystalline forms, hydrates, or pharmaceutically acceptable salts thereof.

An additional embodiment of the present invention is a compound capable of inhibiting NF-κB. The compound has the structure of formula (I):

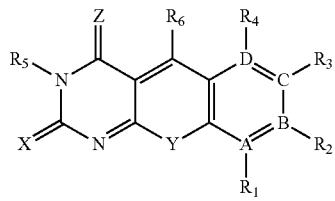

wherein:
A, B, C, and D are independently selected from the group consisting of carbon and nitrogen;
X, Y, and Z are independently selected from the group consisting of oxygen, sulfur, and NR$^a$;
R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;
R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and
R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or is a crystalline form, hydrate, or pharmaceutically acceptable salt thereof.

A further embodiment of the present invention is a compound capable of inhibiting NF-κB. The compound is selected from the group consisting of the compounds in Table 1, and crystalline forms, hydrates, or pharmaceutically acceptable salts thereof.

An additional embodiment of the present invention is a compound capable of inhibiting NF-κB. The compound is selected from the group consisting of:

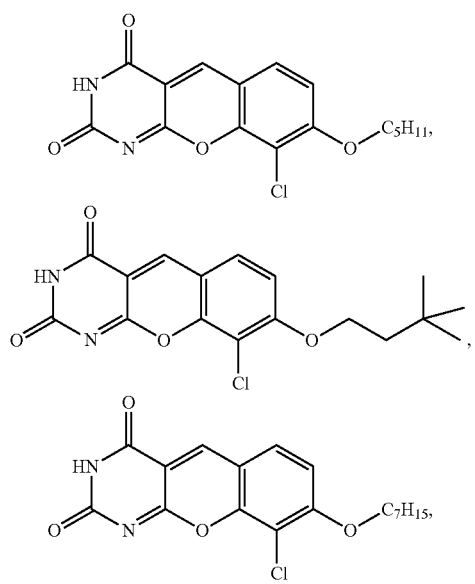

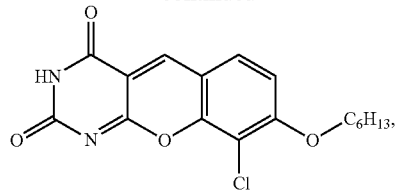

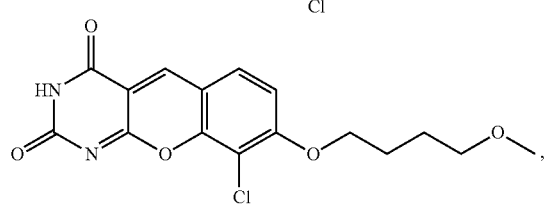

and crystalline forms, hydrates, or pharmaceutically acceptable salts thereof.

Another embodiment of the present invention is a pharmaceutical composition. The pharmaceutical composition comprises a pharmaceutically acceptable carrier and any of the compounds disclosed herein.

A further embodiment of the present invention is a method of inhibiting NF-κB in a cell. The method comprises contacting the cell with any of the compounds disclosed herein.

An additional embodiment of the present invention is a method for treating cancer in a subject. The method comprises administering to the subject an effective amount of a compound having the structure of formula (I):

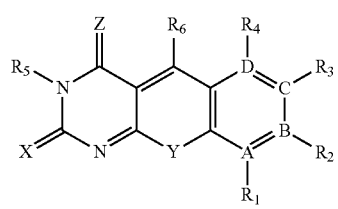

wherein:
A, B, C, and D are independently selected from the group consisting of carbon and nitrogen;
X, Y, and Z are independently selected from the group consisting of oxygen, sulfur, and NR$^a$;
R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;
R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and
R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof.

Another embodiment of the present invention is a method for treating cancer in a subject. The method comprises administering to the subject an effective amount of a compound selected from the group consisting of the compounds in Table 1, and crystalline forms, hydrates, or pharmaceutically acceptable salts thereof.

A further embodiment of the present invention is a method for treating cancer in a subject. The method comprises administering to the subject an effective amount of a compound selected from the group consisting of:

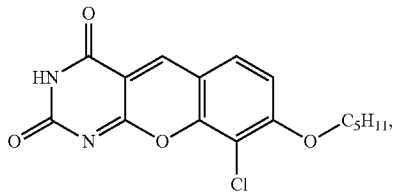

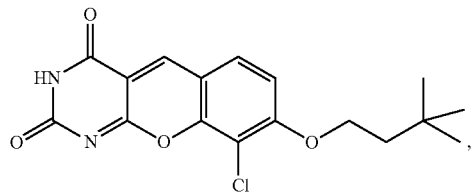

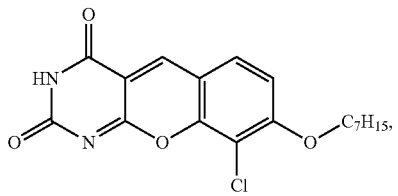

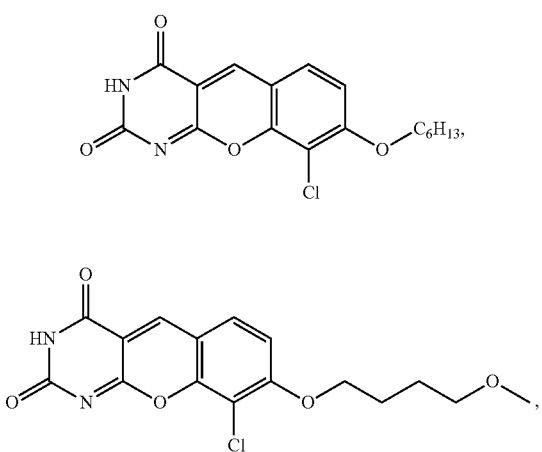

and crystalline forms, hydrates, or pharmaceutically acceptable salts thereof.

An additional embodiment of the present invention is a method for treating a solid tumor in a subject. The method comprises administering to the subject an effective amount of a compound having the structure of formula (I):

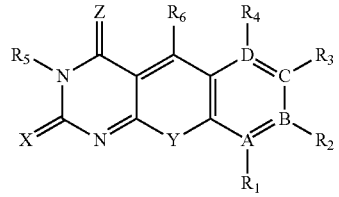

wherein:
A, B, C, and D are independently selected from the group consisting of carbon and nitrogen;
X, Y, and Z are independently selected from the group consisting of oxygen, sulfur, and NR$^a$;
R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;
R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and
R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic,
or a crystalline form, hydrate, or pharmaceutically acceptable salt thereof.

Another embodiment of the present invention is a method for treating a solid tumor in a subject. The method comprises administering to the subject an effective amount of a compound selected from the group consisting of the compounds in Table 1, and crystalline forms, hydrates, or pharmaceutically acceptable salts thereof.

A further embodiment of the present invention is a method for treating a solid tumor in a subject. The method comprises administering to the subject an effective amount of a compound selected from the group consisting of:

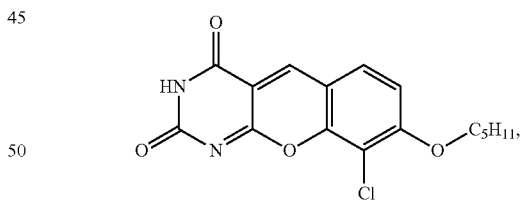

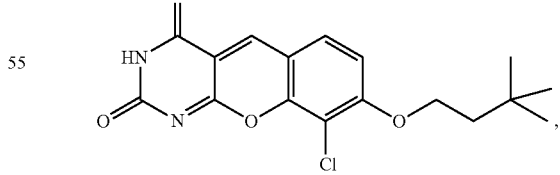

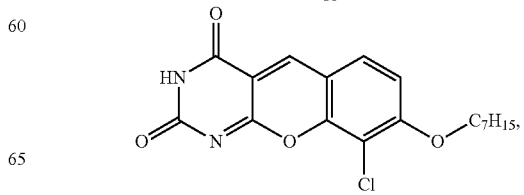

-continued

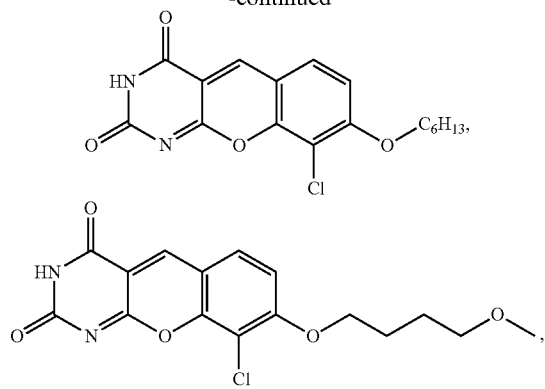

and crystalline forms, hydrates, or pharmaceutically acceptable salts thereof.

An additional embodiment of the present invention is a method for inducing cancer cell death. The method comprises contacting a cancer cell with an effective amount of a compound having the structure of formula (I):

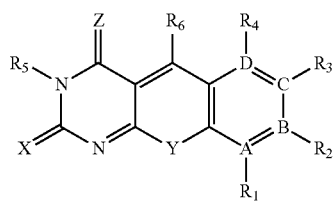

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —$OR^a(C=O)R^b$—$O(C=O)R^a$, —$O(C=O)OR^a$, —$O(C=O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C=O)R^a$, —$S(C=O)OR^a$, —$S(C=O)NR^aR^b$;
$R_5$ is selected from the group consisting of hydrogen, $C_{1-9}$ alkyl, $C_{2-9}$ alkenyl, $C_{2-9}$ alkynyl, aryl, heterocyclic, —$R^aCO$, —$R^aNHCO$, and —$R^aOCO$; and
$R_6$, $R^a$, $R^b$, and $R^c$ are independently selected from the group consisting of hydrogen, hydroxyl, amine, $C_{1-9}$ alkyl, $C_{2-9}$ alkenyl, $C_{2-9}$ alkynyl, aryl, and heterocyclic,
or a crystalline form, hydrate, or pharmaceutically acceptable salt thereof.

Another embodiment of the present invention is a method for inducing cancer cell death. The method comprises contacting a cancer cell with an effective amount of a compound selected from the group consisting of the compounds in Table 1, and crystalline forms, hydrates, or pharmaceutically acceptable salts thereof.

A further embodiment of the present invention is a method for inducing cancer cell death. The method comprises contacting a cancer cell with an effective amount of a compound selected from the group consisting of:

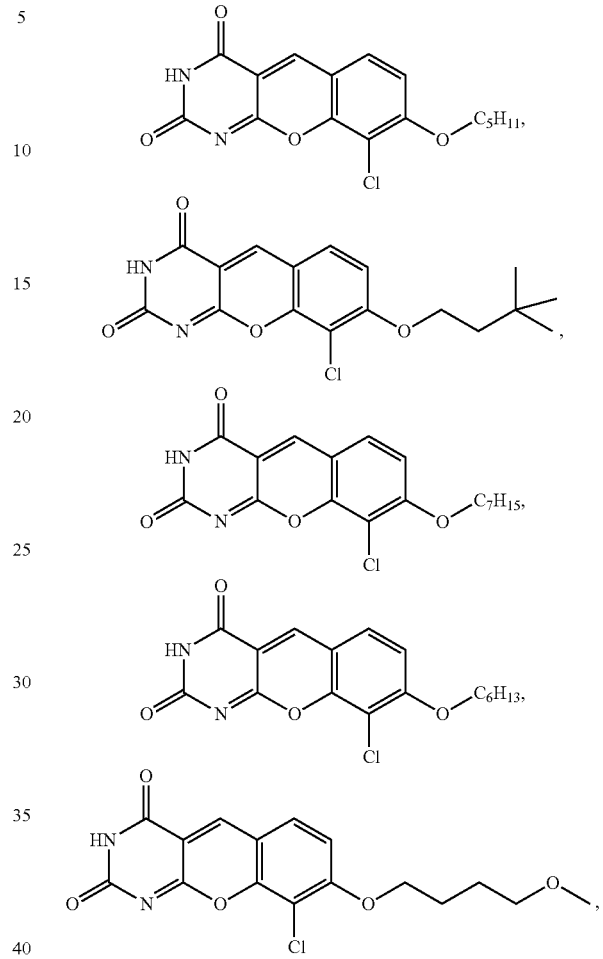

and crystalline forms, hydrates, or pharmaceutically acceptable salts thereof.

An additional embodiment of the present invention is a method for inducing apoptosis of a cancer cell, comprising contacting the cancer cell with an effective amount of a compound having the structure of formula (I):

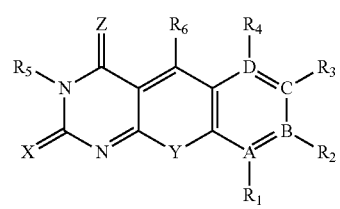

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{2-9}$ alkenyl, $C_{2-9}$ alkynyl, aryl, heterocyclic, —OH, —$OR^a$, —OR$^a$OR$^b$, —OR$^a$OR$^b$OR$^c$, —OR$^a$(C=O)R$^b$ —O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;

R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and R$_6$, R$^a$, R$^b$, and R are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof.

Another embodiment of the present invention is a method for inducing apoptosis of a cancer cell. The method comprises contacting the cancer cell with an effective amount of a compound selected from the group consisting of the compounds in Table 1, and crystalline forms, hydrates, or pharmaceutically acceptable salts thereof.

A further embodiment of the present invention is a method for inducing apoptosis of a cancer cell. The method comprises contacting the cancer cell with an effective amount of a compound selected from the group consisting of:

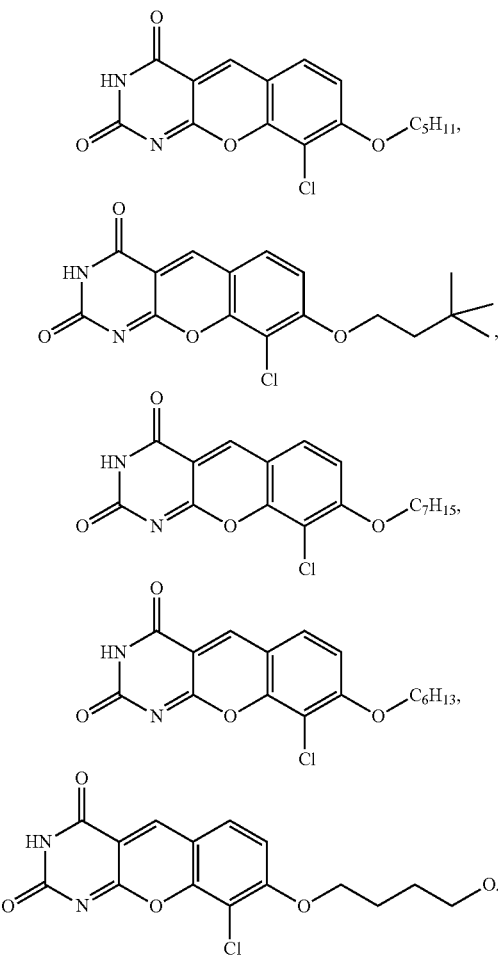

and crystalline forms, hydrates, or pharmaceutically acceptable salts thereof.

An additional embodiment of the present invention is a kit for treating cancer in a subject. The kit comprises a compound having the structure of formula (I):

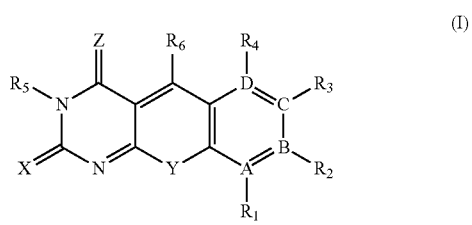

wherein:

A, B, C, and D are independently selected from the group consisting of carbon and nitrogen;

X, Y, and Z are independently selected from the group consisting of oxygen, sulfur, and NR$^a$;

R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$, —O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;

R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof, packaged together with instructions for its use.

Another embodiment of the present invention is a kit for treating cancer in a subject. The kit comprises a compound selected from the group consisting of the compounds in Table 1, and crystalline forms, hydrates, or pharmaceutically acceptable salts thereof.

A further embodiment of the present invention is a kit for treating cancer in a subject. The kit comprises a compound selected from the group consisting of:

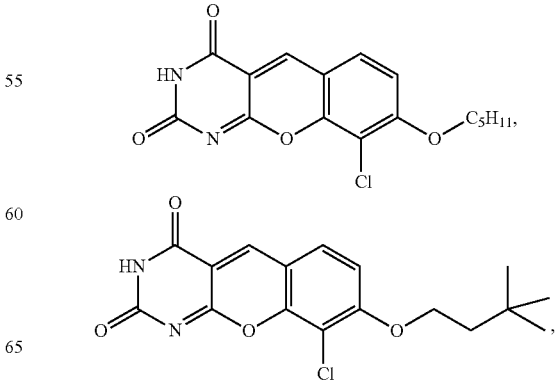

-continued

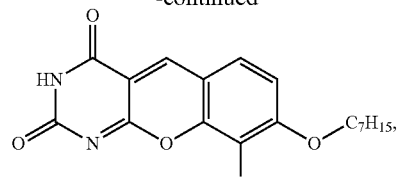

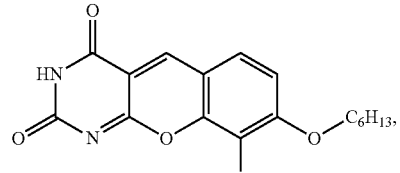

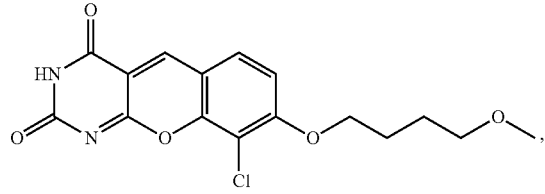

and crystalline forms, hydrates, or pharmaceutically acceptable salts thereof,
packaged together with instructions for its use.

An additional embodiment of the present invention is a kit for treating a solid tumor in a subject. The kit comprises a compound having the structure of formula (I):

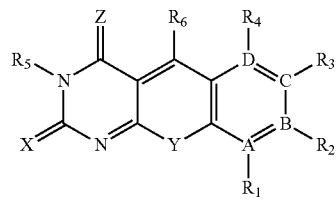

wherein:
A, B, C, and D are independently selected from the group consisting of carbon and nitrogen;
X, Y, and Z are independently selected from the group consisting of oxygen, sulfur, and NR$^a$;
R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;
R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and
R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic,
or a crystalline form, hydrate, or pharmaceutically acceptable salt thereof,
packaged together with instructions for its use.

Another embodiment of the present invention is a kit for treating a solid tumor in a subject. The kit comprises a compound selected from the group consisting of the compounds in Table 1, and crystalline forms, hydrates, or pharmaceutically acceptable salts thereof.

A further embodiment of the present invention is a kit for treating a solid tumor in a subject. The kit comprises a compound selected from the group consisting of:

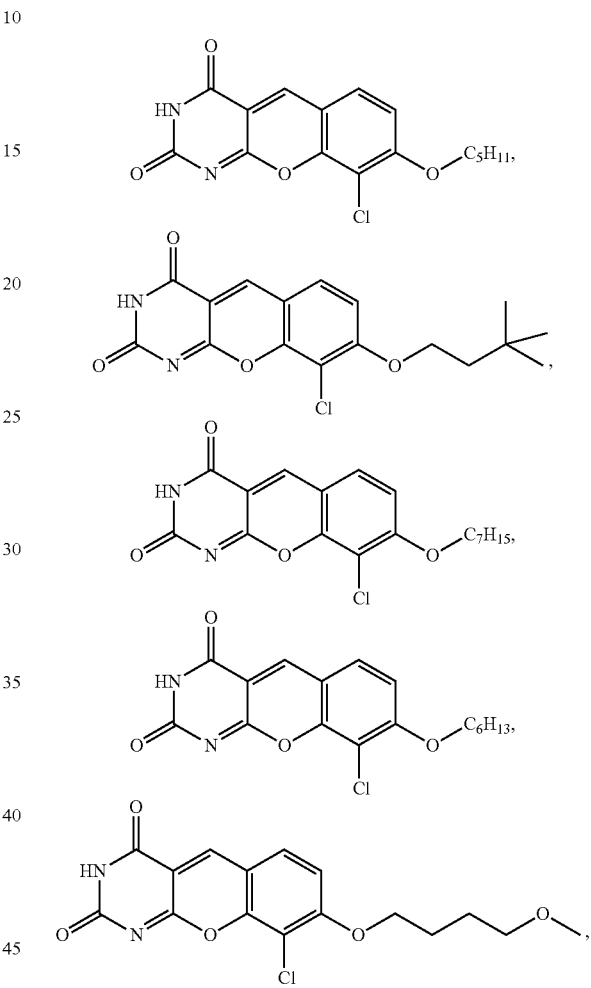

and crystalline forms, hydrates, or pharmaceutically acceptable salts thereof,
packaged together with instructions for its use.

An additional embodiment of the present invention is a kit for inducing cancer cell death. The kit comprises a compound having the structure of formula (I):

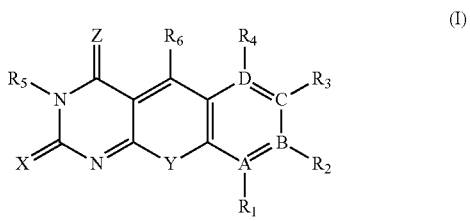

wherein:

A, B, C, and D are independently selected from the group consisting of carbon and nitrogen;

X, Y, and Z are independently selected from the group consisting of oxygen, sulfur, and NR$^a$;

R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;

R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof, packaged together with instructions for its use.

Another embodiment of the present invention is a kit for inducing cancer cell death. The kit comprises a compound selected from the group consisting of the compounds in Table 1, and crystalline forms, hydrates, or pharmaceutically acceptable salts thereof.

A further embodiment of the present invention is a kit for inducing cancer cell death. The kit comprises a compound selected from the group consisting of:

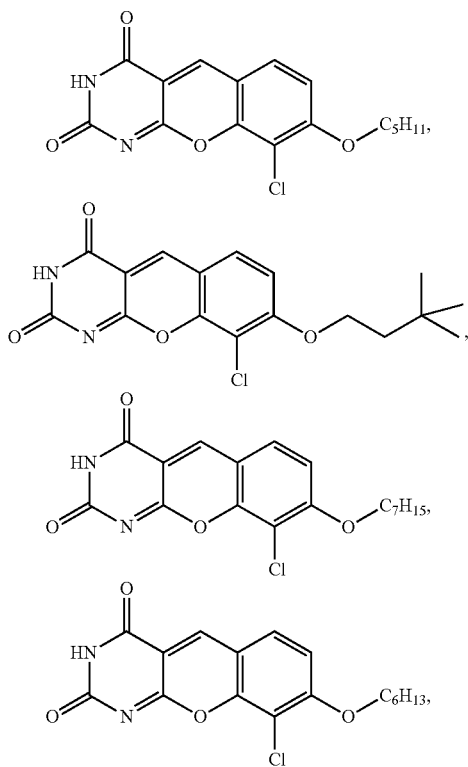

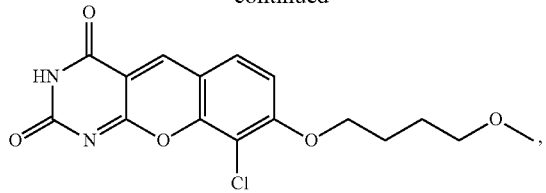

and crystalline forms, hydrates, or pharmaceutically acceptable salts thereof, packaged together with instructions for its use.

An additional embodiment of the present invention is a kit for inducing apoptosis of a cancer cell. The kit comprises a compound having the structure of formula (I):

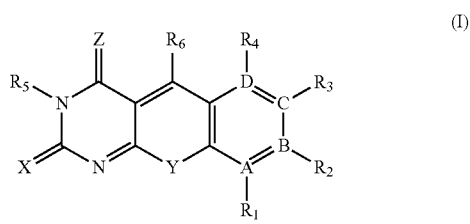

wherein:

A, B, C, and D are independently selected from the group consisting of carbon and nitrogen;

X, Y, and Z are independently selected from the group consisting of oxygen, sulfur, and NR$^a$;

R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;

R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof, packaged together with instructions for its use.

Another embodiment of the present invention is a kit for inducing apoptosis of a cancer cell. The kit comprises a compound selected from the group consisting of the compounds in Table 1, and crystalline forms, hydrates, or pharmaceutically acceptable salts thereof.

A further embodiment of the present invention is a kit for inducing apoptosis of a cancer cell. The kit comprises a compound selected from the group consisting of:

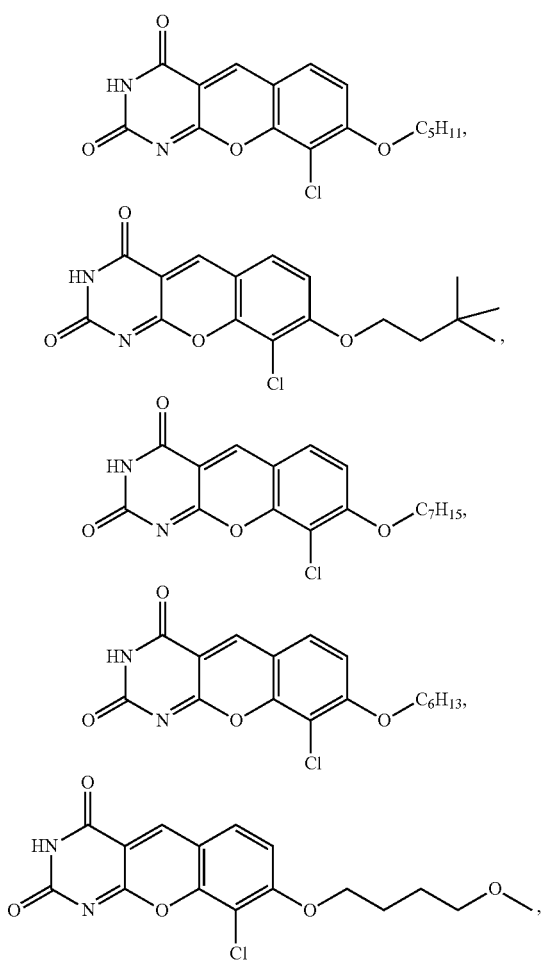

and crystalline forms, hydrates, or pharmaceutically acceptable salts thereof,
packaged together with instructions for its use.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows a line graph of results from 10 nM CD28RE FITC fluorescence polarization assays. FIG. 1B shows a line graph of cold competition with specific (CD28RE) and non-specific (Oct1) oligo. FIG. 1C is a dot plot showing distribution of fluorescence polarization signals in a representative 384-well plate. FIG. 1D shows a line graph of results from 0.33 nM CD28RE FITC fluorescence polarization assays.

FIG. 3A is a table showing pharmacokinetic data for compound 13. FIG. 3B is a line graph showing mean plasma concentration of intravenous compound 13 in mice over time.

FIG. 4A is a table showing pharmacokinetic data for compound 20.

FIG. 5A is a table showing pharmacokinetic data for compound 26. FIG. 5B is a line graph showing mean plasma concentration of intravenous compound 26 in mice over time.

FIG. 6A is a table showing pharmacokinetic data for compound 42.

FIG. 7A is a table showing pharmacokinetic data for compound 44.

FIG. 8A is a table showing pharmacokinetic data for compound 46. FIG. 8B is a line graph showing mean plasma concentration of intravenous compound 46 in mice over time.

FIG. 9 is a chart showing the experimental design for determining the potency of NF-κB inhibitors of the present invention on NSCLC.

FIG. 10 is a chart showing 50% growth inhibition (IG50) of various cell lines and patient-derived samples exposed to NF-κB inhibitors of the present invention 24 hours post-treatment.

FIG. 11 is a chart showing 50% growth inhibition (IG50 of various cell lines and patient-derived samples exposed to NF-κB inhibitors of the present invention 48 hours post-treatment.

FIG. 14 is a chart listing lung cancer cell lines with their respective cell type, characteristic biomarker, and drug sensitive/resistant status.

FIG. 15A: HCC827 cells treated with IT-848; FIG. 15B: HCC827 cells treated with IT-852; FIG. 15C: PC9 cells treated with IT-852; FIG. 15D: H1975 cells treated with IT-852; FIG. 15E: H1437 cells treated with IT-848; FIG. 15F: H1437 cells treated with IT-852; FIG. 15G: H23 cells treated with IT-848; FIG. 15H: H23 cells treated with IT-852; FIG. 15I: A549 cells treated with IT-848; FIG. 15J: H522 cells treated with IT-852; FIG. 15K: H460 cells treated with IT-852; FIG. 15L: H1581 cells treated with IT-852.

FIGS. 16A-16D are tables showing growth inhibition of various hepatocellular carcinoma (HCC) cell lines treated with a combination of either IT-845 or IT-848 and sorafenib at the concentrations shown. FIG. 16A: PLC/PRF/5 cells; FIG. 16B: HUH-7 cells; FIG. 16C: HepG2 cells; FIG. 16D: Hep3B cells.

FIGS. 17A-17O are histograms showing the percentage cell viability for various cell types treated with vehicle, IT-845, IT-848, sorafenib, or combinations thereof. FIGS. 17A-17C: HCC-01 cells; FIGS. 17M-17O: HCC-05 cells. FIGS. 17A, 17D, 17G, 17J, 17M: monotherapy with IT-845, IT-848, or sorafenib; FIGS. 17B, 17E, 17H, 17K, 17N: IT-845 in combination with sorafenib; FIGS. 17C, 17F, 17I, 17L, 17O: IT-848 in combination with sorafenib.

FIGS. 18A-18C: HCC-06 cells; FIGS. 18M-18O: HCC-10 cells. FIGS. 18A, 18D, 18G, 18J, 18M: monotherapy with IT-845, IT-848, or sorafenib; FIGS. 18B, 18E, 18H, 18K, 18N: IT-845 in combination with sorafenib; FIGS. 18C, 18F, 18I, 18L, 18O: IT-848 in combination with sorafenib.

FIGS. 19A-19C: Normal human hepatocytes; FIGS. 19D-19F: normal human Kupffer cells; FIGS. 19G-19I: normal human hepatic stellate cells. FIGS. 19A, 19D, 19G: monotherapy with IT-845, IT-848, sorafenib, or erlotinib; FIGS. 19B, 19E, 19H: IT-845 in combination with sorafenib or erlotinib; FIGS. 19C, 19F, 19I: IT-848 in combination with sorafenib or erlotinib.

FIGS. 20A-20C: NSCLC-01 cells; FIGS. 20Y-20AA: NSCLC-09 cells; FIGS. 20AB-20AD: NSCLC-10 cells. FIGS. 20A, 20D, 20G, 20J, 20M, 20P, 20S, 20V, 20Y, 20AB: monotherapy with IT-845, IT-848, or erlotinib; FIGS. 20B, 20E, 20H, 20K, 20N, 20Q, 20T, 20W, 20Z, 20AC: IT-845 in combination with erlotinib; FIGS. 20C, 20F, 20I, 20L, 20O, 20R, 20U, 20X, 20AA, 20AD: IT-848 in combination with erlotinib.

DETAILED DESCRIPTION OF THE INVENTION

Figure 2:
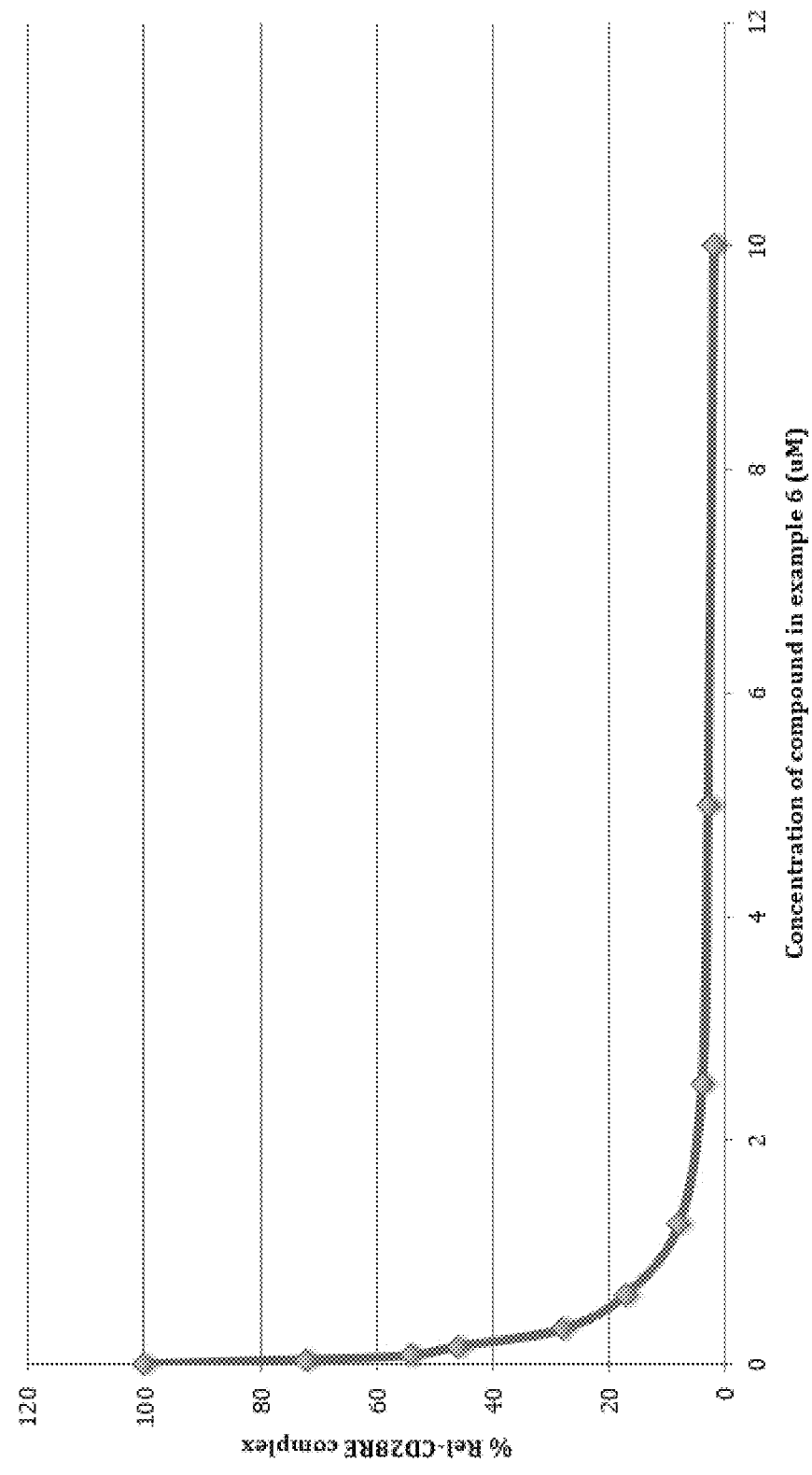
FIG. 2 is a line graph showing Rel/NF-κB inhibition by compound 6 by EMSA.
Figure 4B:
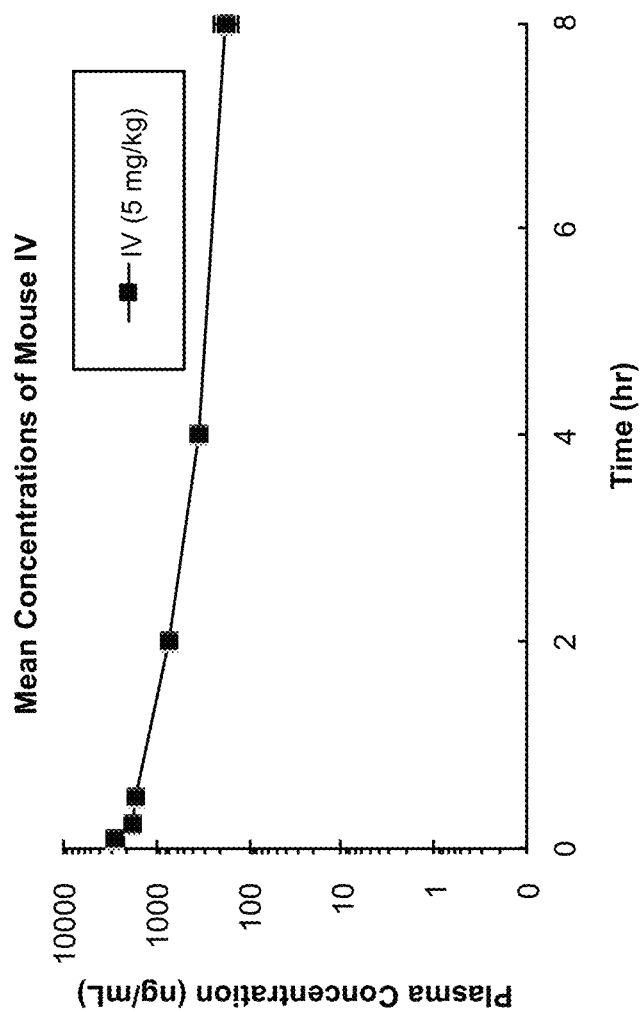
FIG. 4B is a line graph showing mean plasma concentration of intravenous compound 20 in mice over time.
Figure 6B:
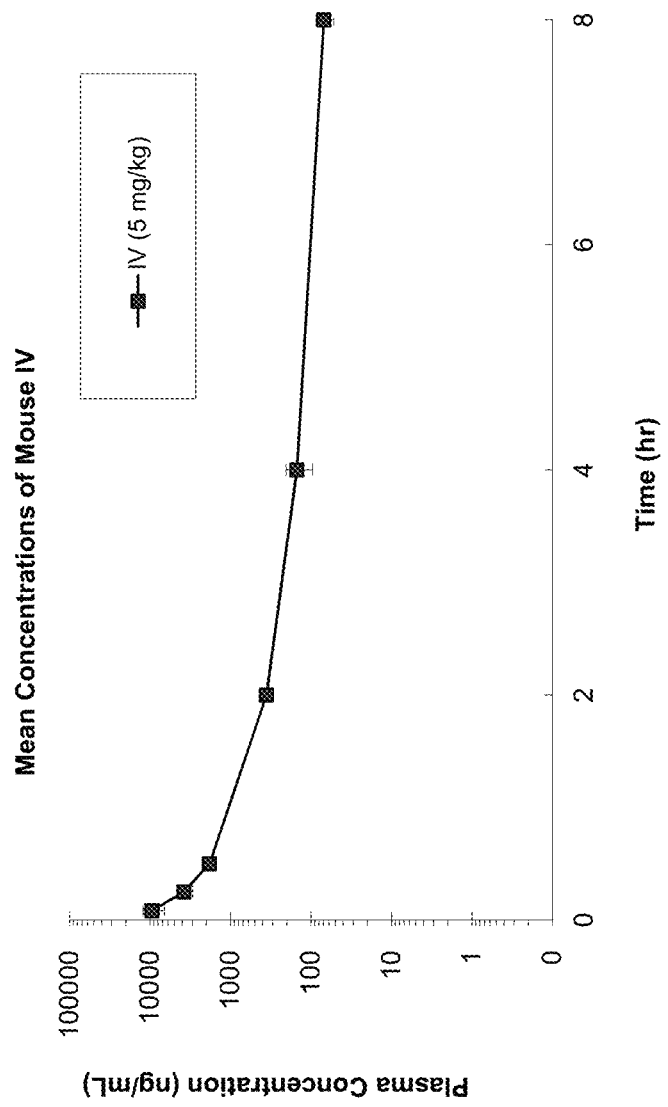
FIG. 6B is a line graph showing mean plasma concentration of intravenous compound 42 in mice over time.
Figure 7B:
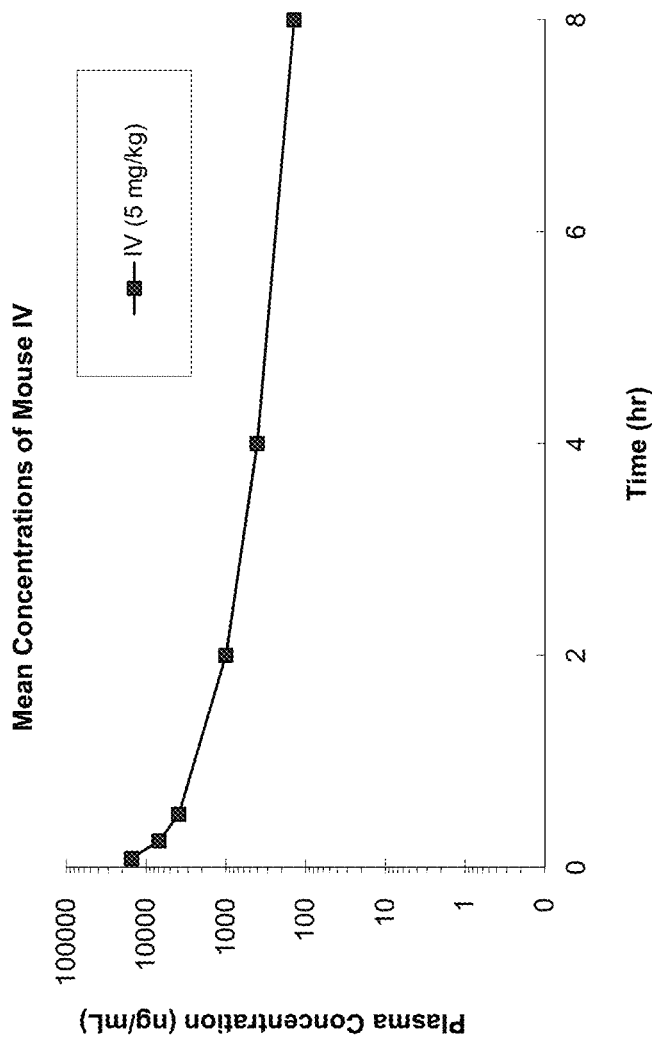
FIG. 7B is a line graph showing mean plasma concentration of intravenous compound 44 in mice over time.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The term "about" generally indicates within +0.5%, 1%, 2%, 5%, or up to +10% of the indicated value. For example, an amount of "about 10 wt %" generally indicates, in its broadest sense, 10 wt %±10%, which indicates 9.0-11.0 wt %. The term "about" may alternatively indicate a variation or average in a physical characteristic of a group.

One embodiment of the present invention is a compound. The compound has the structure of formula (I):

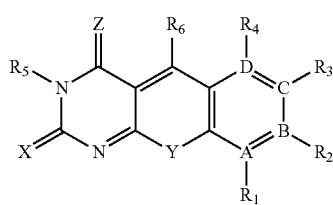

(I)

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —$OR^a(C=O)R^b$, —$O(C=O)R^a$, —$O(C=O)OR^a$, —$O(C=O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C=O)R^a$, —$S(C=O)OR^a$, —$S(C=O)NR^aR^b$;
$R_5$ is selected from the group consisting of hydrogen, $C_{1-9}$ alkyl, $C_{2-9}$ alkenyl, $C_{2-9}$ alkynyl, aryl, heterocyclic, —$R^aCO$, —$R^aNHCO$, and —$R^aOCO$; and
$R_6$, $R^a$, $R^b$, and $R^c$ are independently selected from the group consisting of hydrogen, hydroxyl, amine, $C_{1-9}$ alkyl, $C_{2-9}$ alkenyl, $C_{2-9}$ alkynyl, aryl, and heterocyclic, or is a crystalline form, hydrate, or pharmaceutically acceptable salt thereof.

As used herein, the term "compound" refers to two or more atoms that are connected by one or more chemical bonds. In the present invention, "chemical bonds" and "bonds" are interchangeable and include, but are not limited to, covalent bonds, ionic bonds, hydrogen bonds, and van der Waals interactions. Covalent bonds of the present invention include single, double, and triple bonds. Compounds of the present invention include, but are not limited to, organic molecules. Atoms that comprise the compounds of the present invention are "linked" if they are connected by a chemical bond of the present invention.

Organic compounds of the present invention include linear, branched, and cyclic hydrocarbons with or without functional groups. The term "$C_{x-y}$" when used in conjunction with a chemical moiety, such as, alkyl, alkenyl, alkynyl or alkoxy is meant to include groups that contain from x to y carbons in the chain. For example, the term "$C_{x-y}$ alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. The terms "$C_{x-y}$ alkenyl" and "$C_{x-y}$ alkynyl" refer to substituted or unsubstituted unsaturated aliphatic groups analogous in length and possible substitution to the alkyls described above, but containing at least one double or triple bond respectively.

The term "independently selected" and grammatical variations thereof mean that, in a chemical structure of the present invention, (e.g., formula I), if more than one atom in the structure can be selected from a list of elements, those atoms may or may not be of the same element. Similarly, if more than one chemical moiety in the structure can be selected from a list of chemical moieties, those moieties may or may not be the same.

In one aspect of this embodiment,
X, Y, and Z are independently selected from the group consisting of oxygen and sulfur;
$R_1$ is selected from the group consisting of —H, —F, —Cl, —OMe, and —OEt;
$R_2$ is selected from the group consisting of —H, —$CH_3$, —OH, —OMe, —OEt, -Me, -Et, -nPr, —O-nPr, —OEtnPr, —$OC_4H_9$, —$OC_5H_{11}$, —$OC_6H_{13}$, —$OC_7H_{15}$, —O-isobutyl, —O-isopentyl, —$OC_nH_{2n}OMe$, —$OC_nH_{2n}OC_mH_{2m}OMe$, —$OC_nH_{2n}OH$, —OC$_n$H$_{2n}$OC$_m$H$_{2m}$OH, OC$_n$H$_{2n}$OEt,
—OC$_n$H$_{2n}$OC$_m$H$_{2m}$OEt, —O—C$_n$H$_{2n}$COOH,
—O—C$_n$H$_{2n}$CONH2, —O—C$_n$H$_{2n}$CONHMe,

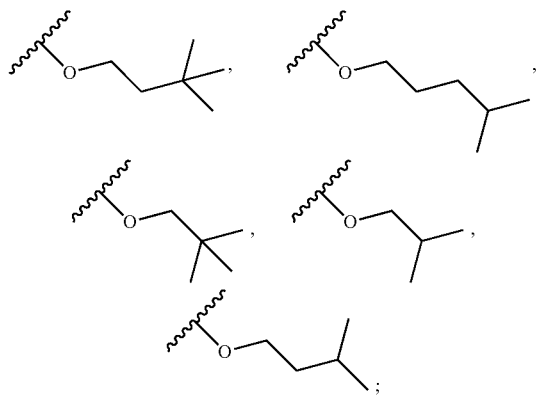

R$_3$ is selected from the group consisting of —H, —Cl, —Br, —F, and —OMe;
R$_4$ is selected from the group consisting of —H and —OMe;
R$_5$ is selected from the group consisting of —H, -Me, -Et, —Pr, -iPr, -Ph, iBu and -nBu; R$_6$ is selected from the group consisting of —H and —CH$_3$;
m is 2, 3, 4 or 5; and, n is 2, 3, 4, or 5.

In another aspect of this embodiment,
X, Y, and Z are independently selected from the group consisting of oxygen and sulfur; and
R$_6$ is hydrogen.

Preferably,
Z is oxygen;
R$_1$ and R$_3$ are selected from the group consisting of hydrogen, halogen, —CN, and —CF$_3$;
R$_2$ is selected from the group consisting of C$_{1-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe, and —OH;
R$_4$ is selected from the group consisting of hydrogen, C$_{1-9}$ alkoxy and —OH;
m is 2, 3, 4 or 5; and n is 2, 3, 4, or 5.

More preferably,
X and Y are oxygen; and
R$_4$ is hydrogen.

In an exemplary aspect of this embodiment, the compound is selected from the group consisting of:

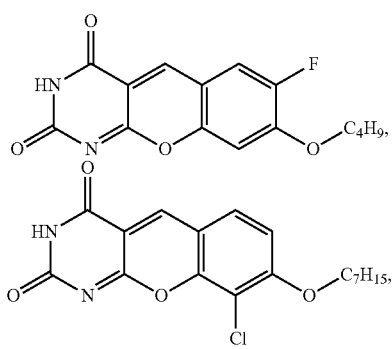

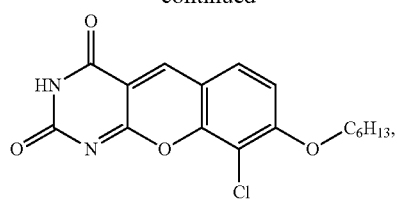

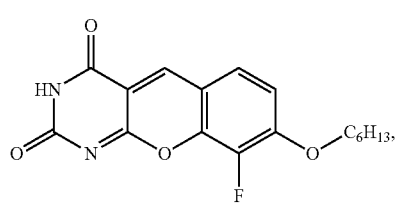

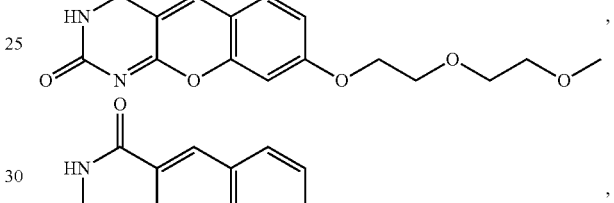

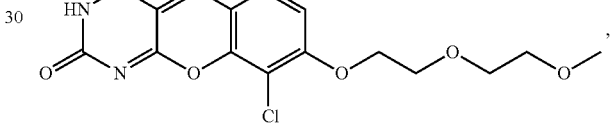

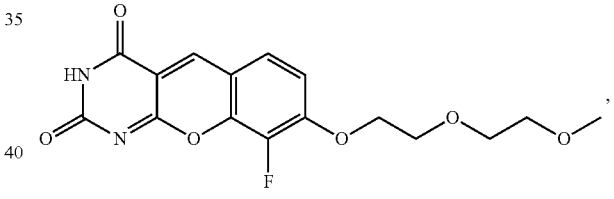

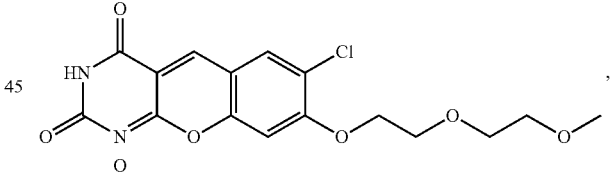

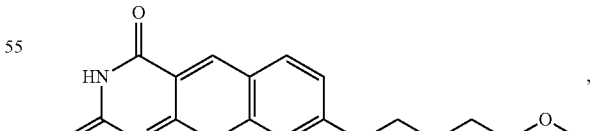

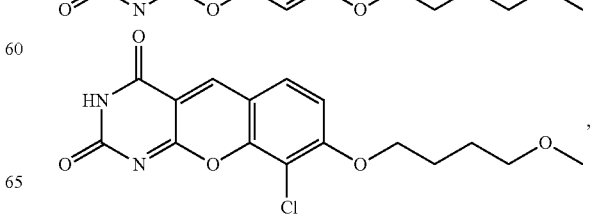

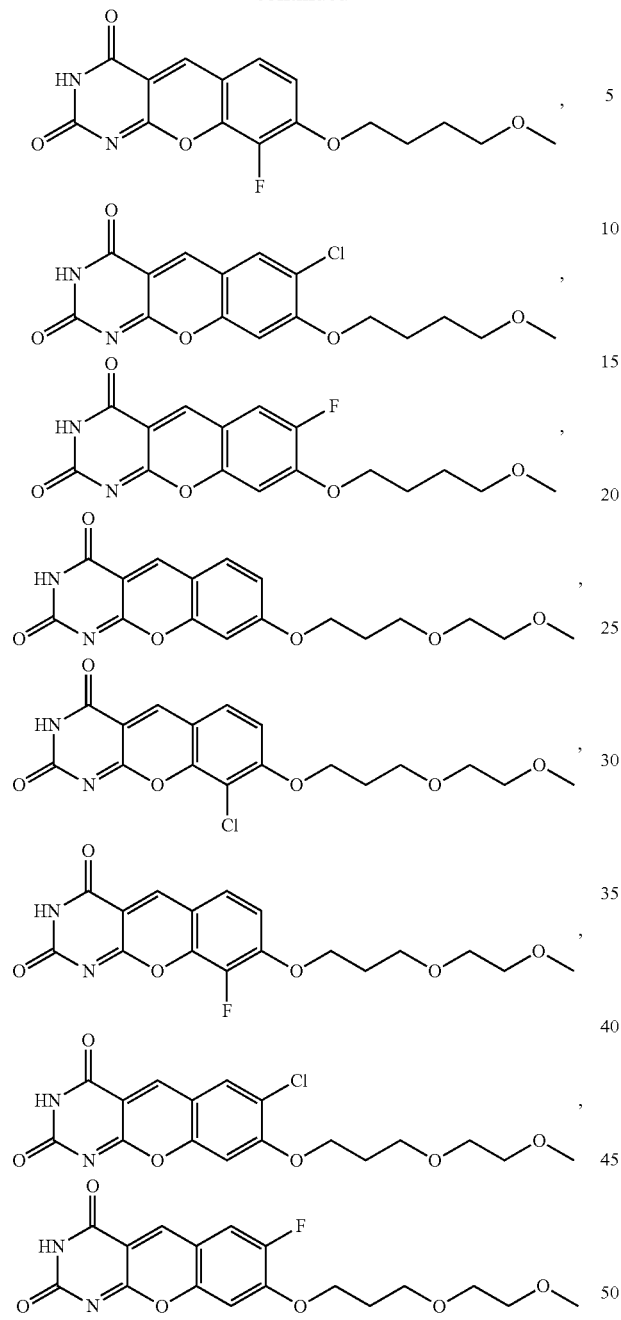

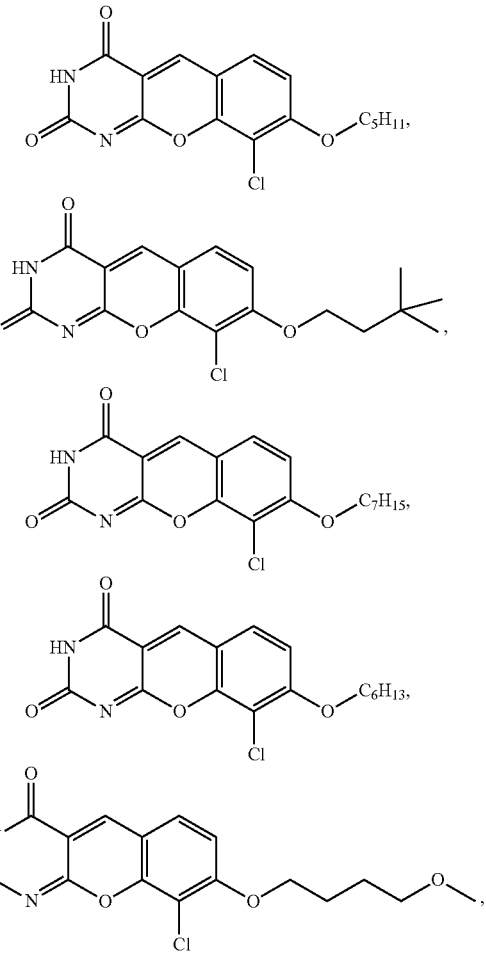

In an additional aspect of this embodiment, $R_1$ and $R_2$ are linked by at least one bond.

In a further aspect of this embodiment, $R_2$ and $R_3$ are linked by at least one bond.

The compound according to claim 1, wherein $R_3$ and $R_4$ are linked by at least one bond.

Another embodiment of the present invention is a compound. The compound is selected from the group consisting of the compounds in Table 1, and crystalline forms, hydrates, or pharmaceutically acceptable salts thereof.

A further embodiment of the present invention is a compound. The compound is selected from the group consisting of:

and crystalline forms, hydrates, or pharmaceutically acceptable salts thereof.

An additional embodiment of the present invention is a compound capable of inhibiting NF-κB. The compound has the structure of formula (I):

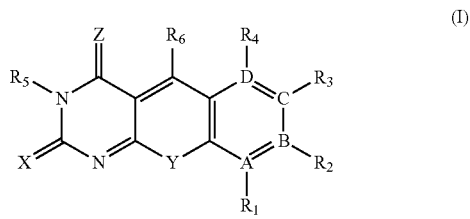

wherein:
A, B, C, and D are independently selected from the group consisting of carbon and nitrogen;
X, Y, and Z are independently selected from the group consisting of oxygen, sulfur, and $NR^a$;
$R_1$, $R_2$, $R_3$, and $R_4$ are independently selected from the group consisting of no atom, hydrogen, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —O(C=O)$R^a$, —O(C=O)$OR^a$, —O(C=O)$NR^aR^b$, cyano, nitro, $CF_3$, $CHF_2$, $CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —CSR$^a$, —CSOR$^a$, —CSNR$^a$R$^b$, —CSNHCSN-R$^a$R$^b$, —SH, —SR$^a$, —S(C=O)R$^a$, —S(C=O)OR$^a$, —S(C=O)NR$^a$R$^b$;

R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or is a crystalline form, hydrate, or pharmaceutically acceptable salt thereof.

In the present invention, the compound capable of inhibiting NF-κB may function as a direct or indirect NF-κB/Rel inhibitor. A direct NF-κB/Rel inhibitor is a compound that binds to or interacts with NF-κB/Rel directly and inhibits its DNA binding and transcriptional function. An indirect NF-κB/Rel inhibitor is a compound that binds to or interacts with a compound other than NF-κB/Rel, thereby generating a downstream inhibitory effect on NF-κB/Rel activity.

In one aspect of this embodiment,

X, Y, and Z are independently selected from the group consisting of oxygen and sulfur;

R$_1$ is selected from the group consisting of —H, —F, —Cl, —OMe, and —OEt;

R$_2$ is selected from the group consisting of —H, —CH$_3$, —OH, —OMe, —OEt, -Et, -nPr, —O-nPr, —OEtnPr, —OC$_4$H$_9$, —OC$_5$H$_{11}$, —OC$_6$H$_{13}$, —OC$_7$H$_{15}$, —O-isobutyl, —O-isopentyl, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe, R$_3$ is selected from the group consisting of —H, —Cl, —Br, —F, and —OMe;

R$_4$ is selected from the group consisting of —H and —OMe;
R$_5$ is selected from the group consisting of —H, -Me, and -nBu;
R$_6$ is selected from the group consisting of —H and —CH$_3$;
m is 2, 3, 4 or 5; and n is 2, 3, 4, or 5.

In another aspect of this embodiment,

X, Y, and Z are independently selected from the group consisting of oxygen and sulfur; and R$_6$ is hydrogen.

Preferably,

Z is oxygen;

R$_1$ and R$_3$ are selected from the group consisting of hydrogen, halogen, —CN, and —CF$_3$;

R$_2$ is selected from the group consisting of C$_{1-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, and —OH;

R$_4$ is selected from the group consisting of hydrogen, C$_{1-9}$ alkoxy and —OH;

m is 2, 3, 4 or 5; and n is 2, 3, 4, or 5.

More preferably,

X and Y are oxygen; and

R$_4$ is hydrogen.

In an exemplary aspect of this embodiment, the compound is selected from the group consisting of:

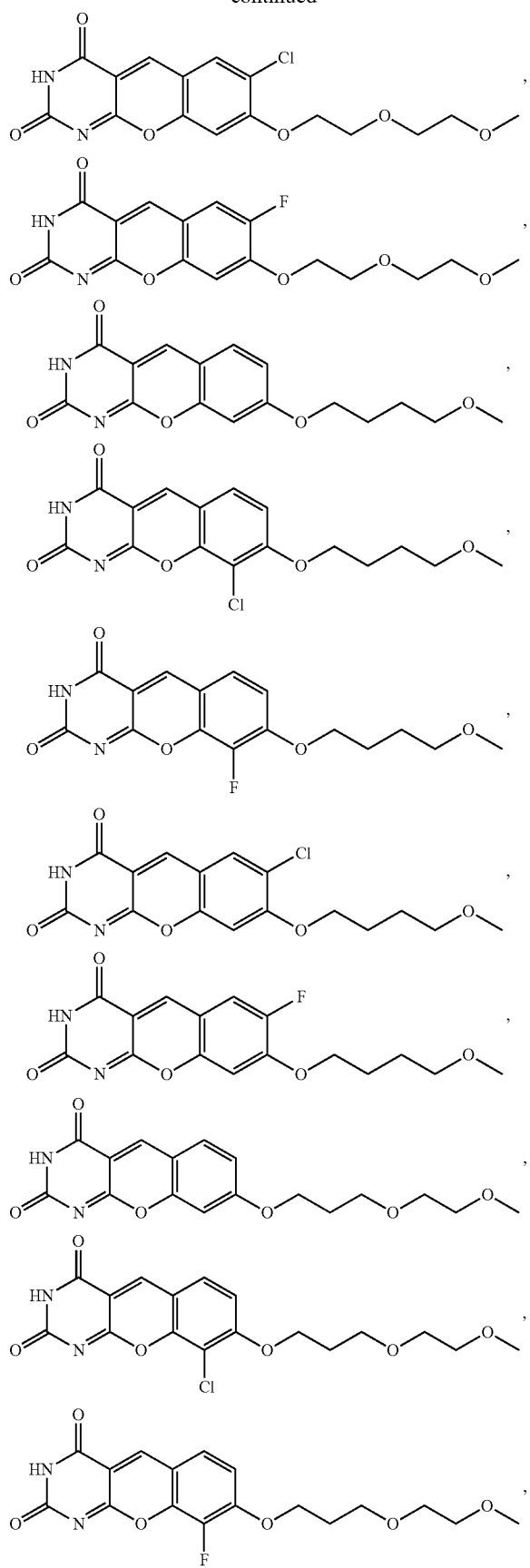

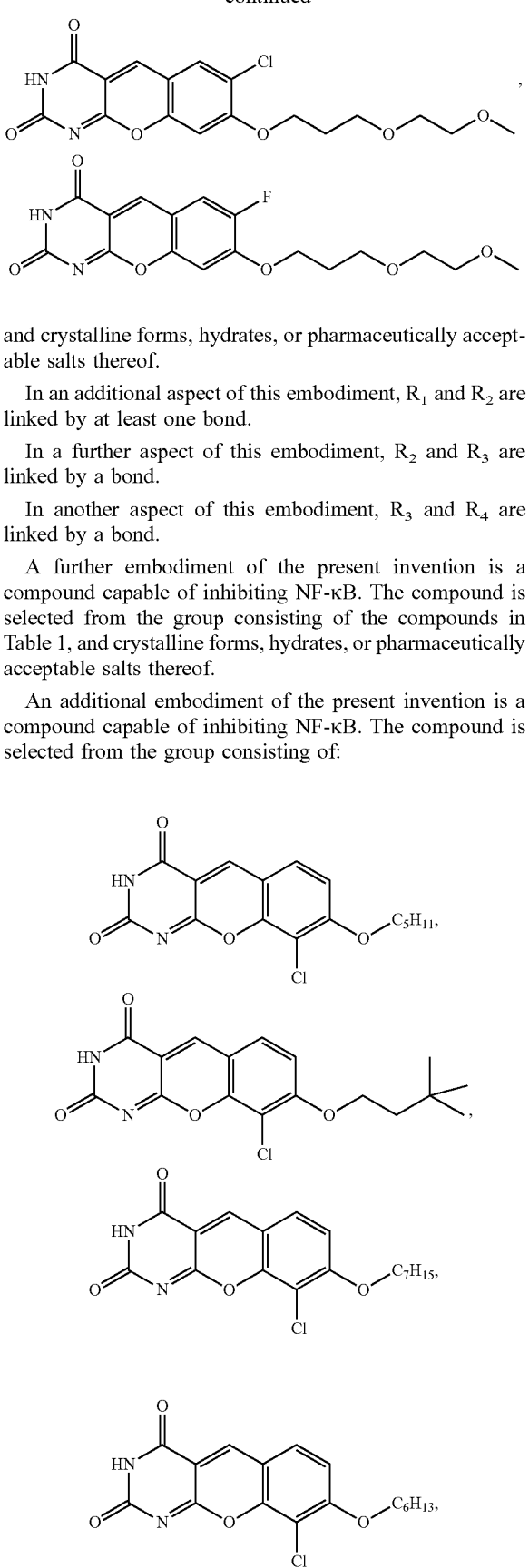

and crystalline forms, hydrates, or pharmaceutically acceptable salts thereof.

In an additional aspect of this embodiment, $R_1$ and $R_2$ are linked by at least one bond.

In a further aspect of this embodiment, $R_2$ and $R_3$ are linked by a bond.

In another aspect of this embodiment, $R_3$ and $R_4$ are linked by a bond.

A further embodiment of the present invention is a compound capable of inhibiting NF-κB. The compound is selected from the group consisting of the compounds in Table 1, and crystalline forms, hydrates, or pharmaceutically acceptable salts thereof.

An additional embodiment of the present invention is a compound capable of inhibiting NF-κB. The compound is selected from the group consisting of:

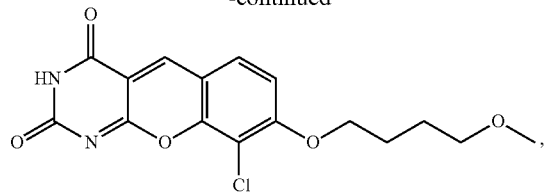

and crystalline forms, hydrates, or pharmaceutically acceptable salts thereof.

R1 and R2, R2 and R3, and R3 and R4, can be joined to form a ring, aromatic or not. The ring can be a hydrocarbon ring or a heterocyclic ring.

Another embodiment of the present invention is a pharmaceutical composition. The pharmaceutical composition comprises a pharmaceutically acceptable carrier and any of the compounds disclosed herein. The pharmaceutical composition may also include any number of other auxiliary agents used in the art, e.g., buffering agents, stabilizing agents, emulsifying agents, pH adjusting agents, surfactants, and flavorants.

A further embodiment of the present invention is a method of inhibiting NF-κB in a cell. The method comprises contacting the cell with any of the compounds disclosed herein.

As used herein, the term "contacting" means bringing a compound of the present invention into close proximity to the cells of the present invention. This may be accomplished using conventional techniques of drug delivery to mammals (e.g., tail vein injection, intravenous injection, peroral administration) or in the in vitro situation by, e.g., providing a compound of the present invention to a culture media to which the cells of the present invention are exposed.

Cells of the present invention include any cell type, cancerous or non-cancerous, in vitro or in vivo, that expresses NF-κB or any NF-κB family member. Cells of the present invention include, but are not limited to, human, monkey, ape, hamster, rat, or mouse cells. In some embodiments, cells of the present invention include, but are not limited to, CHO (e.g., CHO K1, DXB-11 CHO, Veggie-CHO), COS (e.g., COS-7), retinal cells, Vero, CV1, kidney (e.g., HEK293, 293 EBNA, MSR293, MDCK, HaK, BHK), HeLa, HepG2, WI38, MRc 5, Col0205, HB 8065, HL-60, (e.g., BHK21), Jurkat, Daudi, A431 (epidermal), CV-1, U937, 3T3, L cells, C127 cells, SP2/0, NS-0, MMT 060562, Sertoli cells, BRL 3A cells, HT1080 cells, myeloma cells, tumor cells, and any cell line derived from any of the aforementioned cells.

An additional embodiment of the present invention is a method for treating cancer in a subject. The method comprises administering to the subject an effective amount of a compound having the structure of formula (I):

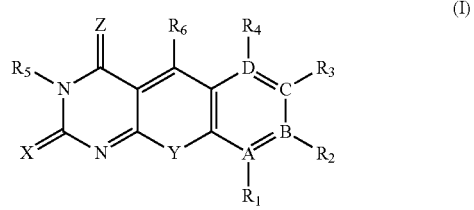

wherein:
A, B, C, and D are independently selected from the group consisting of carbon and nitrogen;
X, Y, and Z are independently selected from the group consisting of oxygen, sulfur, and NR$^a$;
R$_1$, R$_2$, R$_3$, and R$_4$ are independently selected from the group consisting of no atom, hydrogen, halogen, C$_{1-9}$ alkyl, C$_{2-9}$ alkenyl, C$_{2-9}$ alkynyl, aryl, heterocyclic, —OH, —OR$^a$, —OR$^a$OR$^b$, —OR$^a$OR$^b$OR$^c$, —OR$^a$(C=O)R$^b$—O(C=O)R$^a$, —O(C=O)OR$^a$, —O(C=O)NR$^a$R$^b$, cyano, nitro, —CF$_3$, —CHF$_2$, —CH$_2$F, —CHO, —COOH, —COR$^a$, —COOR$^a$, —CONR$^a$R$^b$, —CONHCONR$^a$R$^b$, —NR$^a$R$^b$, —NHCOR$^a$, —NR$^b$COR$^a$, —CSOH, —CSR$^a$, —CSOR$^a$, —CSNR$^a$R$^b$, —CSNHCSNR$^a$R$^b$, —SH, —SR$^a$, —S(C=O)R$^a$, —S(C=O)OR$^a$, —S(C=O)NR$^a$R$^b$;
R$_5$ is selected from the group consisting of hydrogen, C$_{1-9}$ alkyl, C$_{2-9}$ alkenyl, C$_{2-9}$ alkynyl, aryl, heterocyclic, —R$^a$CO, —R$^a$NHCO, and —R$^a$OCO; and
R$_6$, R$^a$, R$^b$, and R$^c$ are independently selected from the group consisting of hydrogen, hydroxyl, amine, C$_{1-9}$ alkyl, C$_{2-9}$ alkenyl, C$_{2-9}$ alkynyl, aryl, and heterocyclic, or a crystalline form, hydrate, or pharmaceutically acceptable salt thereof.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

Cancers include both solid and hematologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

The NF-κB inhibitors of the present invention or compositions containing the same of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the NF-κB inhibitors or compositions containing same of the present invention may be administered in conjunction with other treatments. The NF-κB inhibitors or the compositions of the present invention may be encapsulated or otherwise protected against gastric or other secretions, if desired.

In the present invention, an "effective amount" or a "therapeutically effective amount" of the NF-κB inhibitors of the present invention, including the compositions containing same, as well as chemotherapeutic agents and targeted therapeutic agents of the present invention is an amount of such inhibitor, composition, or agent that is sufficient to induce beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent or composition according to the invention will be that amount of the agent or composition, which is the lowest dose effective to produce the desired effect. The effective dose of an agent or composition of the present invention may be administered as two, three, four, five, six or more sub-doses, administered separately at appropriate intervals throughout the day.

In one aspect of this embodiment,
X, Y, and Z are independently selected from the group consisting of oxygen and sulfur;
$R_1$ is selected from the group consisting of —H, —F, —Cl, —OMe, and —OEt;
$R_2$ is selected from the group consisting of —H, —CH$_3$, —OH, —OMe, —OEt, -Me, -Et, -nPr, —O-nPr, —OEtnPr, —OC$_4$H$_9$, —OC$_5$H$_{11}$, —OC$_6$H$_{13}$, —OC$_7$H$_{15}$, —O-isobutyl, —O-isopentyl, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, —OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe,

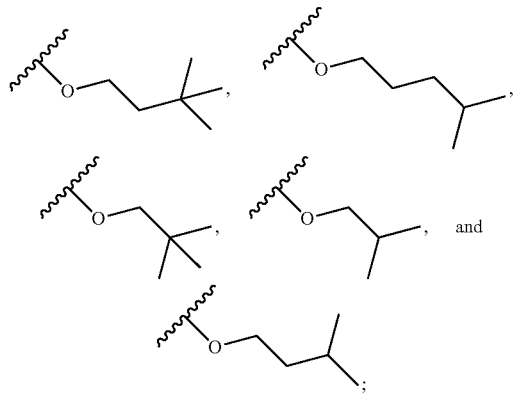

$R_3$ is selected from the group consisting of —H, —Cl, —Br, —F, and —OMe;
$R_4$ is selected from the group consisting of —H and —OMe;
$R_5$ is selected from the group consisting of —H, -Me, -Et, —Pr, -iPr, -Ph, -iBu, and -nBu;
$R_6$ is selected from the group consisting of —H and —CH$_3$,
m is 2, 3, 4 or 5; and
n is 2, 3, 4, or 5.

In another aspect of this embodiment,
X, Y, and Z are independently selected from the group consisting of oxygen and sulfur; and
$R_6$ is hydrogen.
Preferably,
Z is oxygen;
$R_1$ and $R_3$ are selected from the group consisting of hydrogen, halogen, —CN, and —CF$_3$;
$R_2$ is selected from the group consisting of $C_{1-9}$ alkoxy, —OC$_n$H$_{2n}$OMe, —OC$_n$H$_{2n}$OC$_m$H$_{2m}$OMe, —OC$_n$H$_{2n}$OH, —OC$_n$H$_{2n}$OC$_m$H$_{2m}$OH, OC$_n$H$_{2n}$OEt, —OC$_n$H$_{2n}$OC$_m$H$_{2m}$OEt, —O—C$_n$H$_{2n}$COOH, —O—C$_n$H$_{2n}$CONH2, —O—C$_n$H$_{2n}$CONHMe, and —OH;
m is 2, 3, 4 or 5;
n is 2, 3, 4, or 5; and
$R_4$ is selected from the group consisting of hydrogen, $C_{1-9}$ alkoxy and —OH.

or a crystalline form, hydrate, or pharmaceutically acceptable salt thereof.

More preferably, X and Y are oxygen; and $R_4$ is hydrogen.

In a preferred aspect of this embodiment, the compound is selected from the group consisting of:

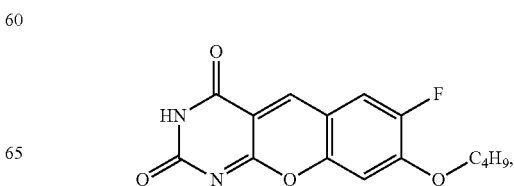

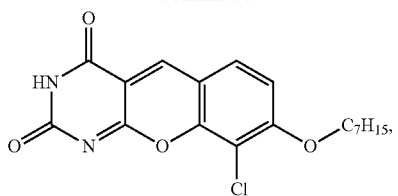

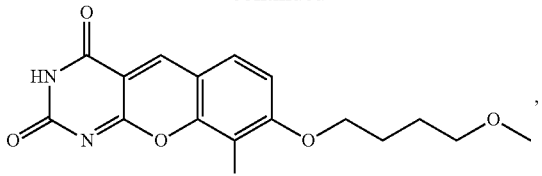

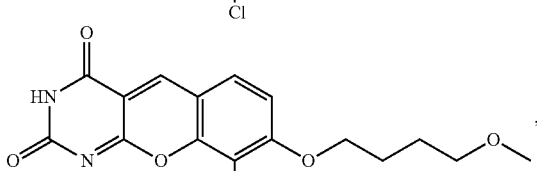

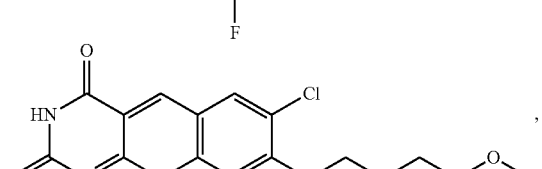

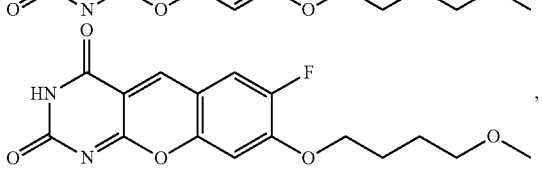

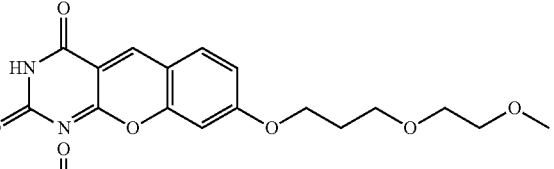

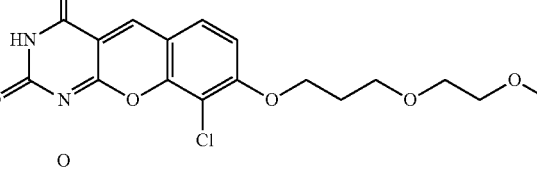

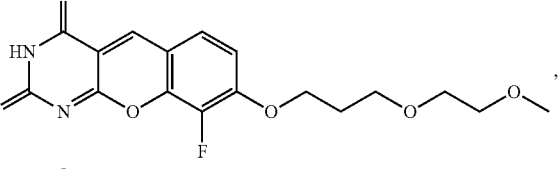

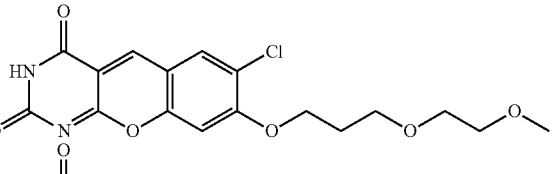

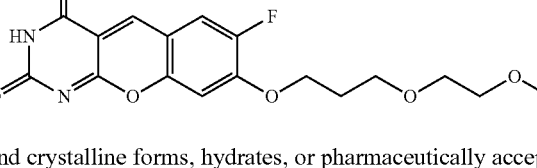

and crystalline forms, hydrates, or pharmaceutically acceptable salts thereof.

In another aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

Lung cancers include, but are not limited to, non-small cell lung cancer (NSCLC), small cell lung cancer, mesothelioma, and carcinoid tumors. NSCLCs include, but are not limited to, adenocarcinoma, adenocarcinoma in situ, bronchioalveolar carcinoma, minimally invasive adenocarcinoma, squamous cell carcinoma, large cell carcinoma, and large cell neuroendocrine tumors.

Lung cancers of the present invention may also include lung cancers with particular genetic characteristics or drug response profiles. For example, lung cancers of the present invention include, but are not limited to, EGFR inhibitor-sensitive and EGFR inhibitor-resistant lung cancers. EGFR inhibitor-sensitive lung cancers include, but are not limited to, erlotinib-sensitive lung cancers. EGFR inhibitor-resistant lung cancers include, but are not limited to, erlotinib-resistant lung cancers.

Liver cancers of the present invention include, but are not limited to, hepatocellular carcinomas.

In an additional aspect of this embodiment, the subject is a mammal.

Preferably, the mammal is selected from the group consisting of humans, primates, farm animals, domestic animals, and laboratory animals.

More preferably, the mammal is a human.

In another aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

Another embodiment of the present invention is a method for treating cancer in a subject. The method comprises administering to the subject an effective amount of a compound selected from the group consisting of the compounds in Table 1, and crystalline forms, hydrates, or pharmaceutically acceptable salts thereof.

In one aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

In another aspect of this embodiment, the subject is a mammal.

Preferably, the mammal is selected from the group consisting of humans, primates, farm animals, domestic animals, and laboratory animals.

More preferably, the mammal is a human.

In a further aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

A further embodiment of the present invention is a method for treating cancer in a subject. The method comprises administering to the subject an effective amount of a compound selected from the group consisting of:

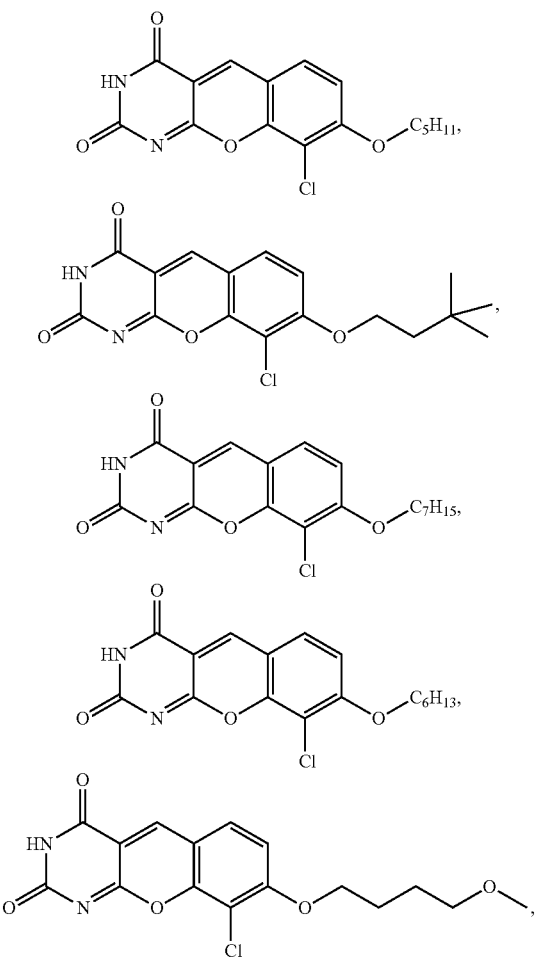

and crystalline forms, hydrates, or pharmaceutically acceptable salts thereof.

In one aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

In another aspect of this embodiment, the subject is a mammal.

Preferably, the mammal is selected from the group consisting of humans, primates, farm animals, domestic animals, and laboratory animals.

More preferably, the mammal is a human.

In a further aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

An additional embodiment of the present invention is a method for treating a solid tumor in a subject. The method comprising administering to the subject an effective amount of a compound having the structure of formula (I):

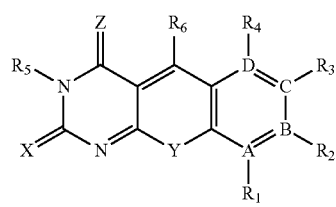

(I)

wherein:
A, B, C, and D are independently selected from the group consisting of carbon and nitrogen;
X, Y, and Z are independently selected from the group consisting of oxygen, sulfur, and NRa;
R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;
R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and
R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic,
or a crystalline form, hydrate, or pharmaceutically acceptable salt thereof.

Non-limiting examples of solid tumors include both benign and malignant tumors, as well as tumors of the solid cancers listed above. Preferably, the solid tumor is an esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, or thymus tumor.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

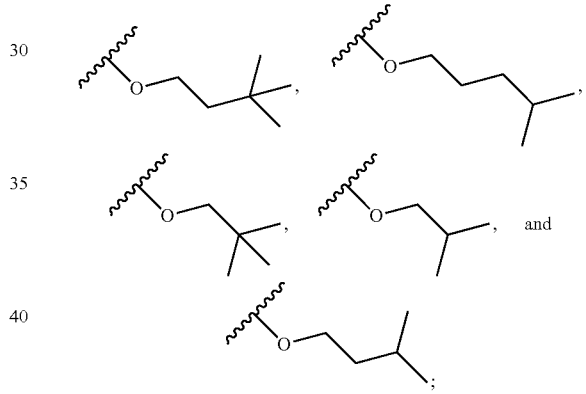

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,
X, Y, and Z are independently selected from the group consisting of oxygen and sulfur; and
R6 is hydrogen,
or a crystalline form, hydrate, or pharmaceutically acceptable salt thereof.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;

m is 2, 3, 4 or 5;
n is 2, 3, 4, or 5; and
R4 is selected from the group consisting of hydrogen, $C_{1-9}$ alkoxy and —OH.
More preferably,
X and Y are oxygen; and
R4 is hydrogen.
In a preferred aspect of this embodiment, the compound is selected from the group consisting of:
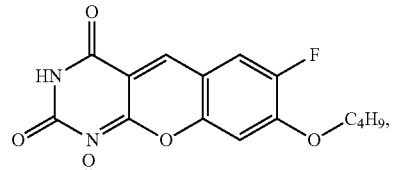
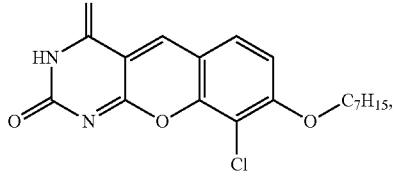
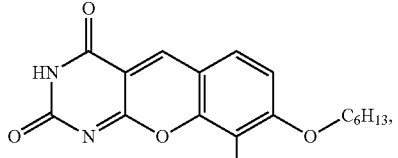
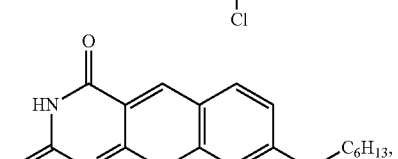
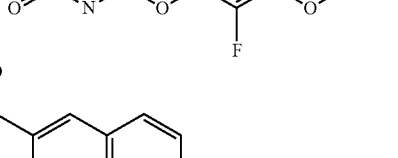
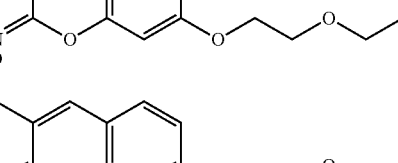
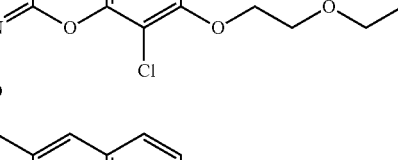
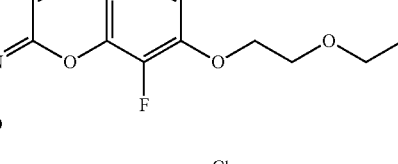
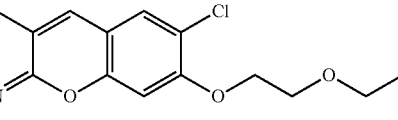
-continued
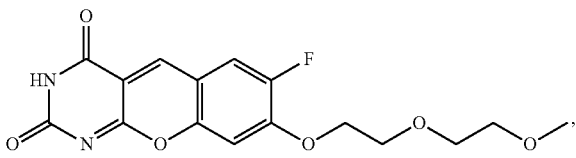
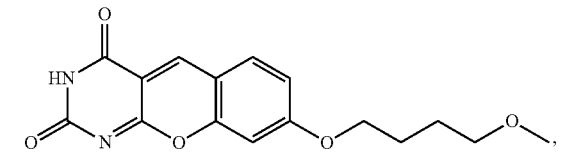
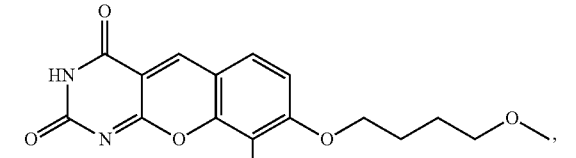
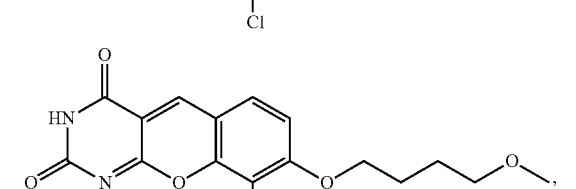
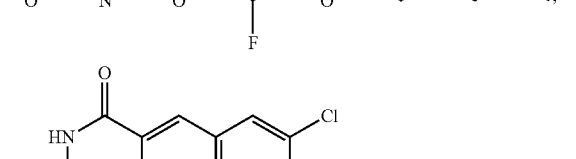
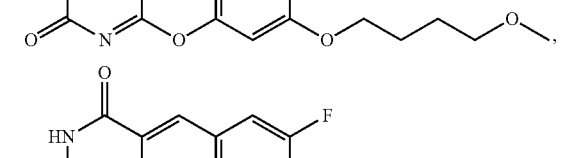
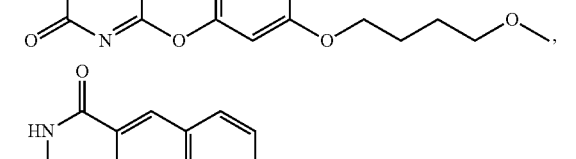
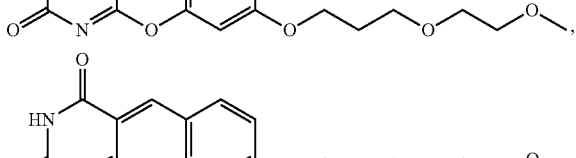
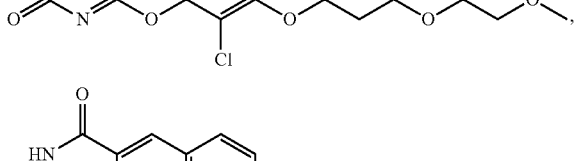
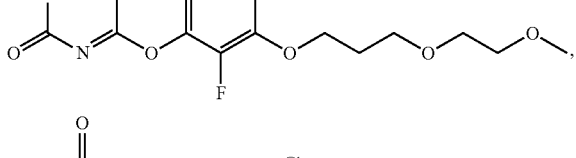

-continued

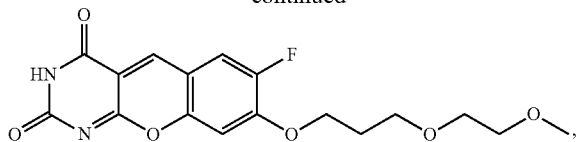

and crystalline forms, hydrates, or pharmaceutically acceptable salts thereof.

In a further aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

Liver tumors of the present invention include, but are not limited to, hepatocellular carcinomas.

Lung tumors include tumors that arise in connection with the lung cancers listed above, including, for example, non-small cell lung cancer (NSCLC) such as adenocarcinoma, adenocarcinoma in situ, bronchioalveolar carcinoma, minimally invasive adenocarcinoma, squamous cell carcinoma, large cell carcinoma, and large cell neuroendocrine tumors, as well as small cell lung cancer, mesothelioma, and carcinoid tumors.

Lung tumors of the present invention may also include lung tumors with particular genetic characteristics or drug response profiles. For example, lung tumors of the present invention include, but are not limited to, EGFR inhibitor-sensitive and EGFR inhibitor-resistant lung tumors. EGFR inhibitor-sensitive lung tumors include, but are not limited to, erlotinib-sensitive lung tumors. EGFR inhibitor-resistant lung tumors include, but are not limited to, erlotinib-resistant lung tumors.

In an additional aspect of this embodiment, the subject is a mammal.

Preferably, the mammal is selected from the group consisting of humans, primates, farm animals, domestic animals, and laboratory animals.

More preferably, the mammal is a human.

In another aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

Another embodiment of the present invention is a method for treating a solid tumor in a subject. The method comprises administering to the subject an effective amount of a compound selected from the group consisting of the compounds in Table 1, and crystalline forms, hydrates, or pharmaceutically acceptable salts thereof.

In one aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

In another aspect of this embodiment, the subject is a mammal.

Preferably, the mammal is selected from the group consisting of humans, primates, farm animals, domestic animals, and laboratory animals.

More preferably, the mammal is a human.

In a further aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

A further embodiment of the present invention is a method for treating a solid tumor in a subject. The method comprises administering to the subject an effective amount of a compound selected from the group consisting of:

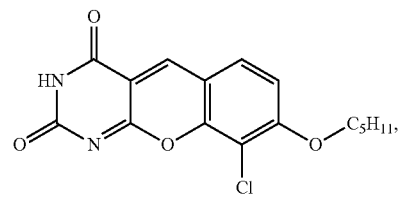

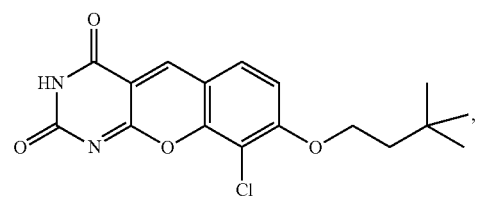

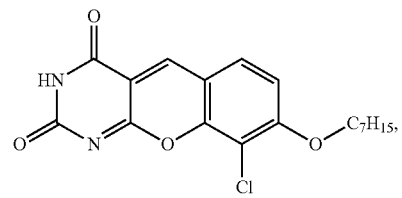

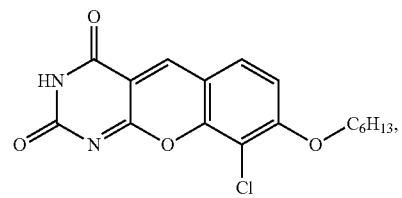

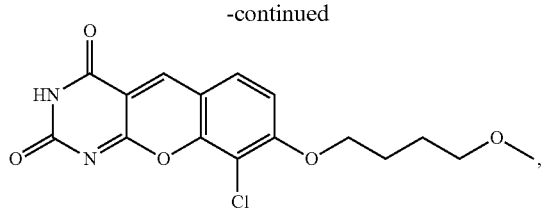

and crystalline forms, hydrates, or pharmaceutically acceptable salts thereof.

In one aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

In another aspect of this embodiment, the subject is a mammal.

Preferably, the mammal is selected from the group consisting of humans, primates, farm animals, domestic animals, and laboratory animals.

More preferably, the mammal is a human.

In a further aspect of this embodiment, the effective amount is selected from the group consisting of about 1 μM, about 2 μM, about 4 μM, and about 8 μM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises administering to the subject an effective amount of a chemotherapeutic agent or targeted therapeutic agent.

An additional embodiment of the present invention is a method for inducing cancer cell death. The method comprises contacting a cancer cell with an effective amount of a compound having the structure of formula (I):

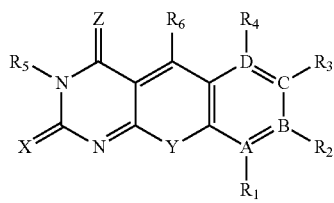

wherein:
A, B, C, and D are independently selected from the group consisting of carbon and nitrogen;
X, Y, and Z are independently selected from the group consisting of oxygen, sulfur, and NRa;
R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;

R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic, or a crystalline form, hydrate, or pharmaceutically acceptable salt thereof.

As used herein, the terms "induce," "inducing," "induced," and grammatical variations thereof mean to bring about, cause, produce, effect, or otherwise give rise to a given outcome, such as, for example, cancer cell death or apoptosis of a cancer cell.

Cancer cell death may result from a number of mechanisms, including, but not limited to, apoptosis, necroptosis, pyroptosis, ferroptosis, autophagic cell death, and caspase-independent cell death. Such cell death mechanisms, among others, are known to those of skill in the art, and are reviewed in, for example, Ouyang et al., 2012, Tait et al., 2014, and Xie et al., 2016.

Cancer cells of the present invention may be, for example, primary or immortalized cells. Non-limiting examples of cancer cells include cells derived from any of the cancers listed above, including, for example, esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

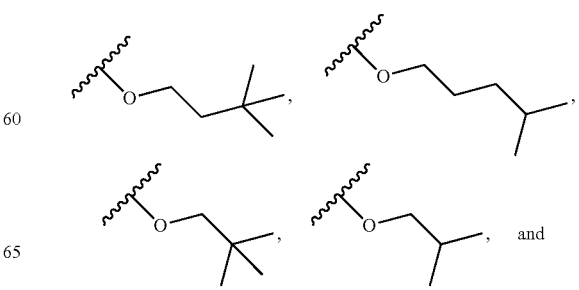

-continued

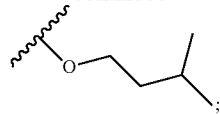

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,

X, Y, and Z are independently selected from the group consisting of oxygen and sulfur; and
R6 is hydrogen.

Preferably,

Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,

X and Y are oxygen; and
R4 is hydrogen,
or a crystalline form, hydrate, or pharmaceutically acceptable salt thereof.

In a preferred aspect of this embodiment, the compound is selected from the group consisting of:

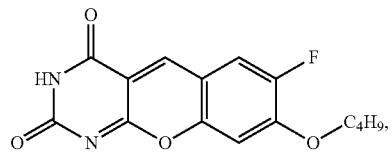

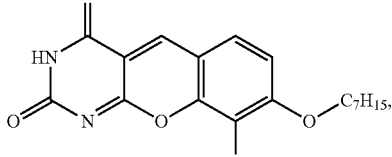

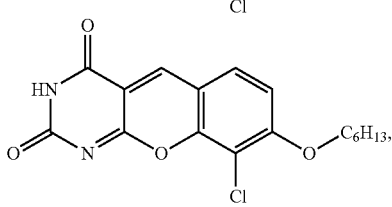

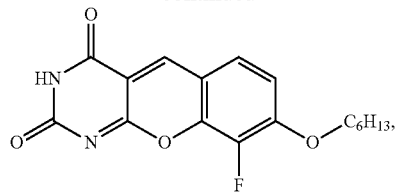

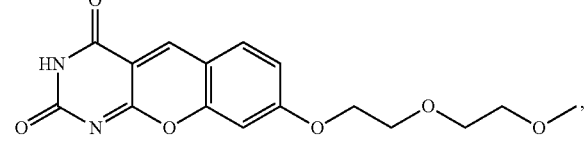

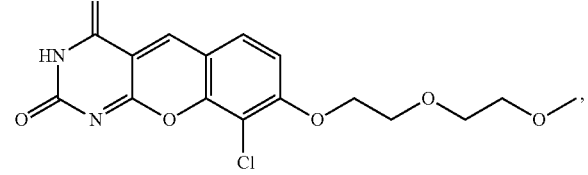

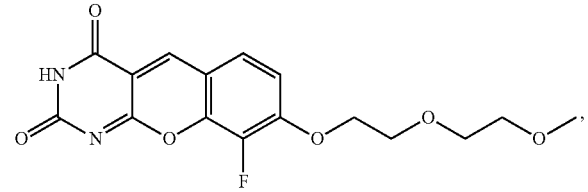

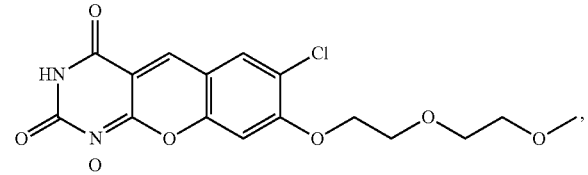

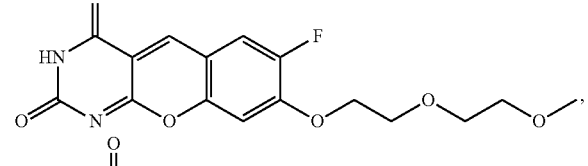

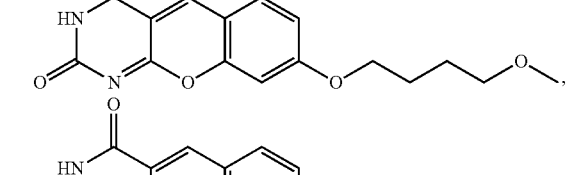

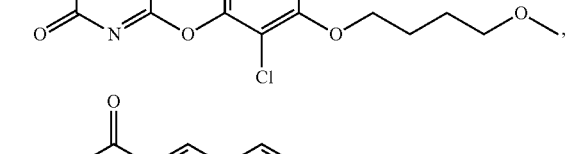

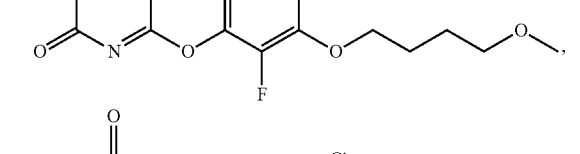

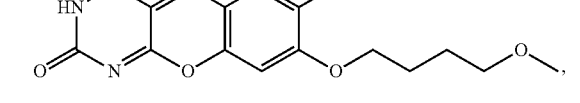

-continued

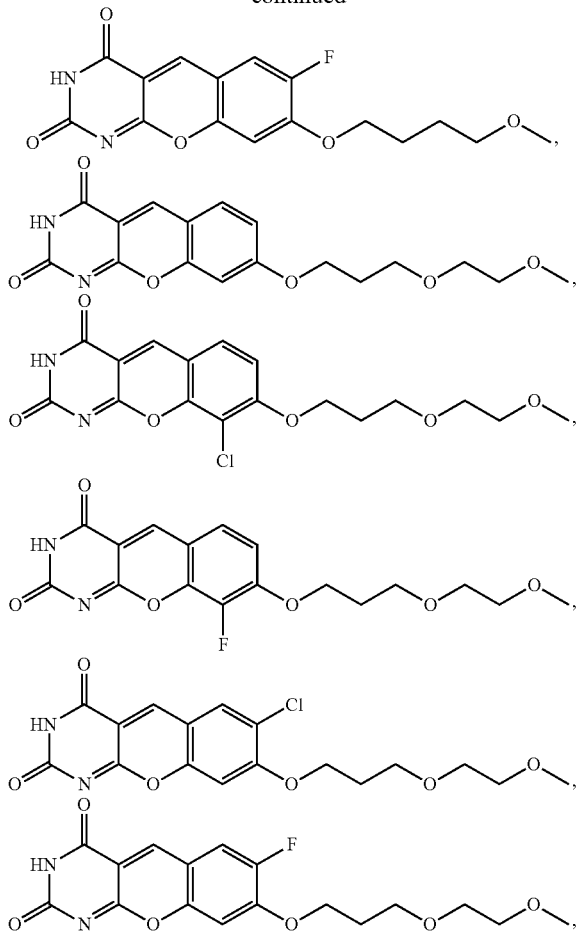

and crystalline forms, hydrates, or pharmaceutically acceptable salts thereof.

In a further aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

Non-limiting examples of liver cancer cells include, but are not limited to, hepatocellular carcinoma cells.

Non-limiting examples of lung cancer cells include, for example, HCC827, PC9, H1975, H1650, H2228, H1437, H2030, H23, A549, H522, H460, H1581, DMS114, and SKMES-1.

More preferably, the lung cancer cell is selected from the group consisting of H1975 and HCC827.

In an additional aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

Another embodiment of the present invention is a method for inducing cancer cell death. The method comprises contacting a cancer cell with an effective amount of a compound selected from the group consisting of the compounds in Table 1, and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

More preferably, the lung cancer cell is selected from the group consisting of H1975 and HCC827.

In another aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

A further embodiment of the present invention is a method for inducing cancer cell death. The method comprises contacting a cancer cell with an effective amount of a compound selected from the group consisting of:

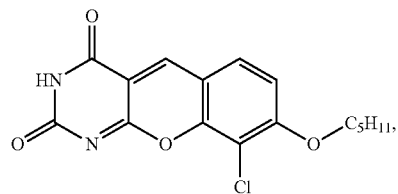

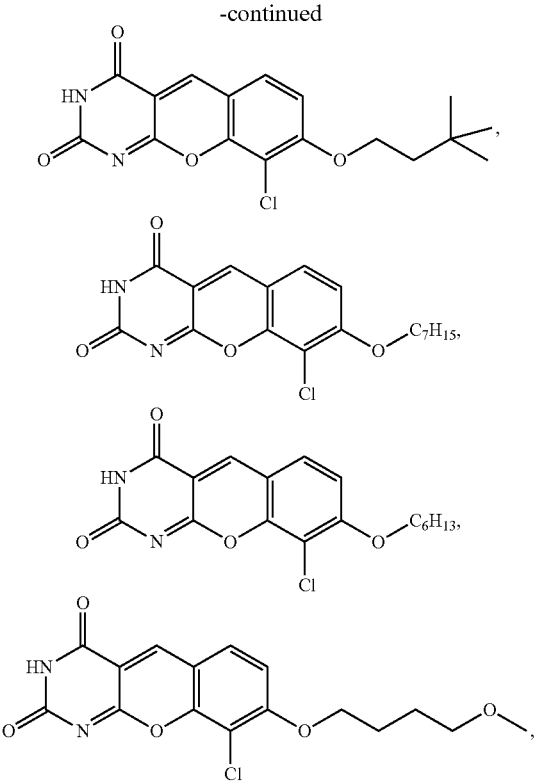

and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

More preferably, the lung cancer cell is selected from the group consisting of H1975 and HCC827.

In another aspect of this embodiment, the effective amount is selected from the group consisting of about 1 μM, about 2 μM, about 4 μM, and about 8 μM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

An additional embodiment of the present invention is a method for inducing apoptosis of a cancer cell. The method comprises contacting the cancer cell with an effective amount of a compound having the structure of formula (I):

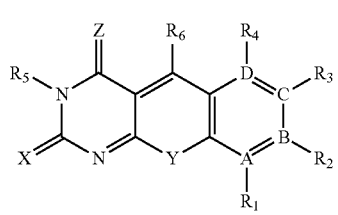

(I)

wherein:
A, B, C, and D are independently selected from the group consisting of carbon and nitrogen;
X, Y, and Z are independently selected from the group consisting of oxygen, sulfur, and NRa;
R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;
R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and
R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic,
or a crystalline form, hydrate, or pharmaceutically acceptable salt thereof.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

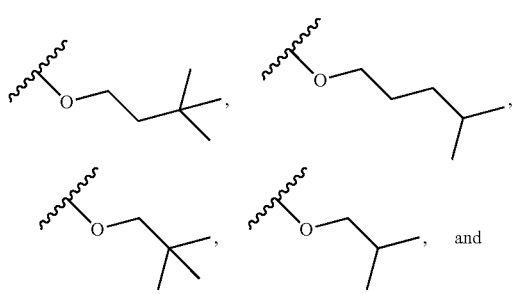

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,
X, Y, and Z are independently selected from the group consisting of oxygen and sulfur; and
R6 is hydrogen.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,
X and Y are oxygen; and
R4 is hydrogen.

In a preferred aspect of this embodiment, the compound is selected from the group consisting of:

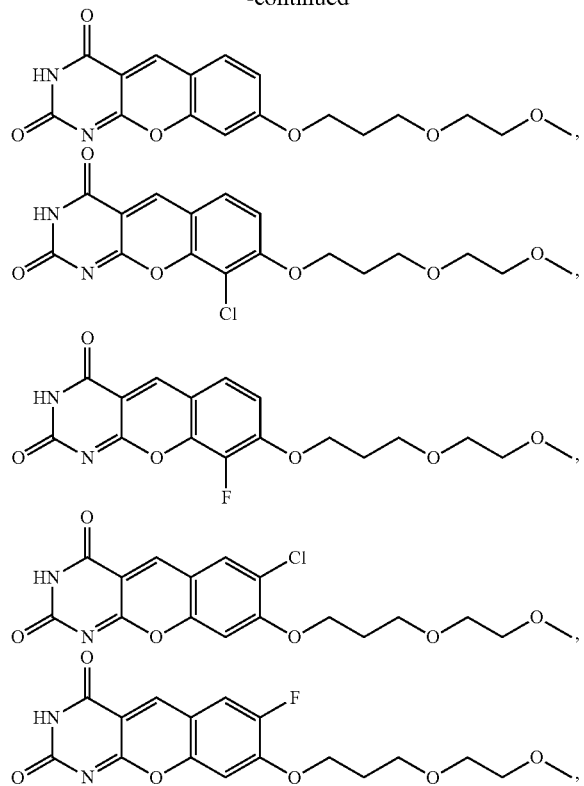

and crystalline forms, hydrates, or pharmaceutically acceptable salts thereof.

In a further aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

More preferably, the lung cancer cell is selected from the group consisting of H1975 and HCC827.

In an additional aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

Another embodiment of the present invention is a method for inducing apoptosis of a cancer cell. The method comprises contacting the cancer cell with an effective amount of a compound selected from the group consisting of the compounds in Table 1, and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

More preferably, the lung cancer cell is selected from the group consisting of H1975 and HCC827.

In another aspect of this embodiment, the effective amount is selected from the group consisting of about 1 µM, about 2 µM, about 4 µM, and about 8 µM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

A further embodiment of the present invention is a method for inducing apoptosis of a cancer cell. The method comprises contacting the cancer cell with an effective amount of a compound selected from the group consisting of:

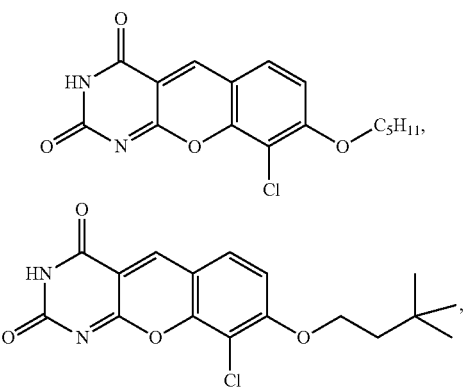

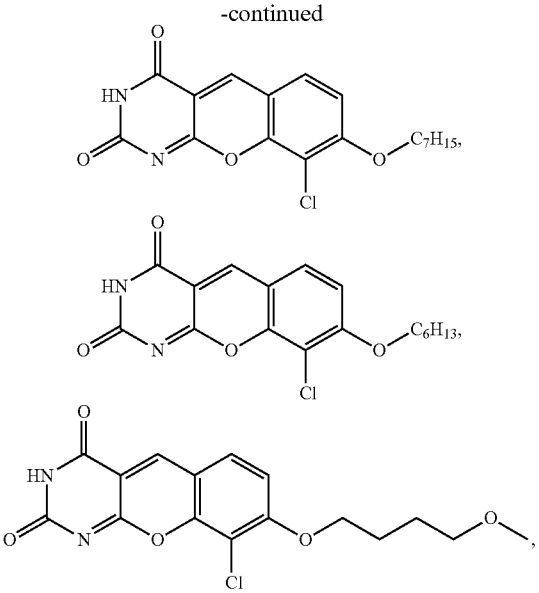

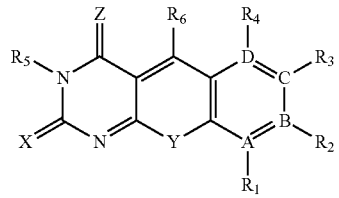

and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is a lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell lung cancer (NSCLC) cell, and liver cancer cell.

More preferably, the lung cancer cell is selected from the group consisting of H1975 and HCC827.

In another aspect of this embodiment, the effective amount is selected from the group consisting of about 1 μM, about 2 μM, about 4 μM, and about 8 μM.

In an additional aspect of this embodiment, the effective amount is about 0.01 mg/kg to about 50 mg/kg. Preferably, the effective amount is about 0.1 mg/kg to about 25 mg/kg. More preferably, the effective amount is about 0.1 mg/kg to about 10 mg/kg.

In another aspect of this embodiment, the method further comprises contacting the cancer cell with an effective amount of a chemotherapeutic agent or targeted therapeutic agent.

An additional embodiment of the present invention is a kit for treating cancer in a subject. The kit comprises a compound having the structure of formula (I):

wherein:
A, B, C, and D are independently selected from the group consisting of carbon and nitrogen;
X, Y, and Z are independently selected from the group consisting of oxygen, sulfur, and NRa;
R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;
R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and
R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic,
or a crystalline form, hydrate, or pharmaceutically acceptable salt thereof,
packaged together with instructions for its use.

The kits may also include suitable storage containers, e.g., ampules, vials, tubes, etc., for each NF-κB inhibitor of the present invention (which may e.g., may be in the form of pharmaceutical compositions) and other reagents, e.g., buffers, balanced salt solutions, etc., for use in administering the NF-κB inhibitors to subjects. The NF-κB inhibitors of the invention and other reagents may be present in the kits in any convenient form, such as, e.g., in a solution or in a powder form. The kits may further include a packaging container, optionally having one or more partitions for housing the NF-κB inhibitors or pharmaceutical compositions of the present invention and other optional reagents.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

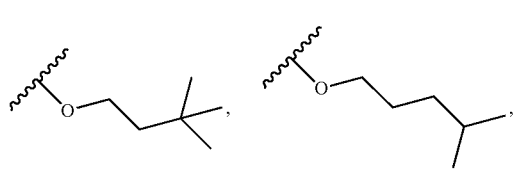

-continued

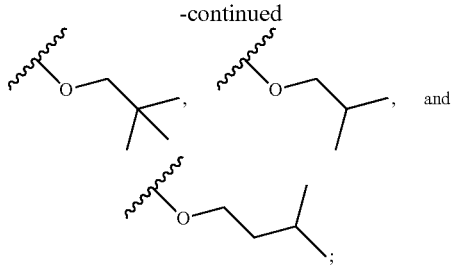

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,
X, Y, and Z are independently selected from the group consisting of oxygen and sulfur; and
R6 is hydrogen,
or a crystalline form, hydrate, or pharmaceutically acceptable salt thereof.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,
X and Y are oxygen; and
$R_4$ is hydrogen.

In a preferred aspect of this embodiment, the compound is selected from the group consisting of:

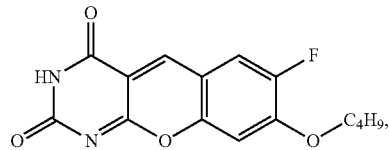

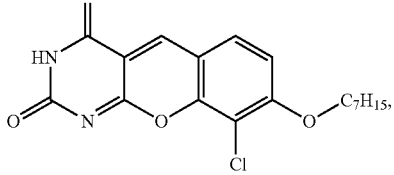

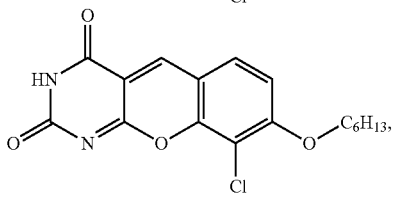

-continued

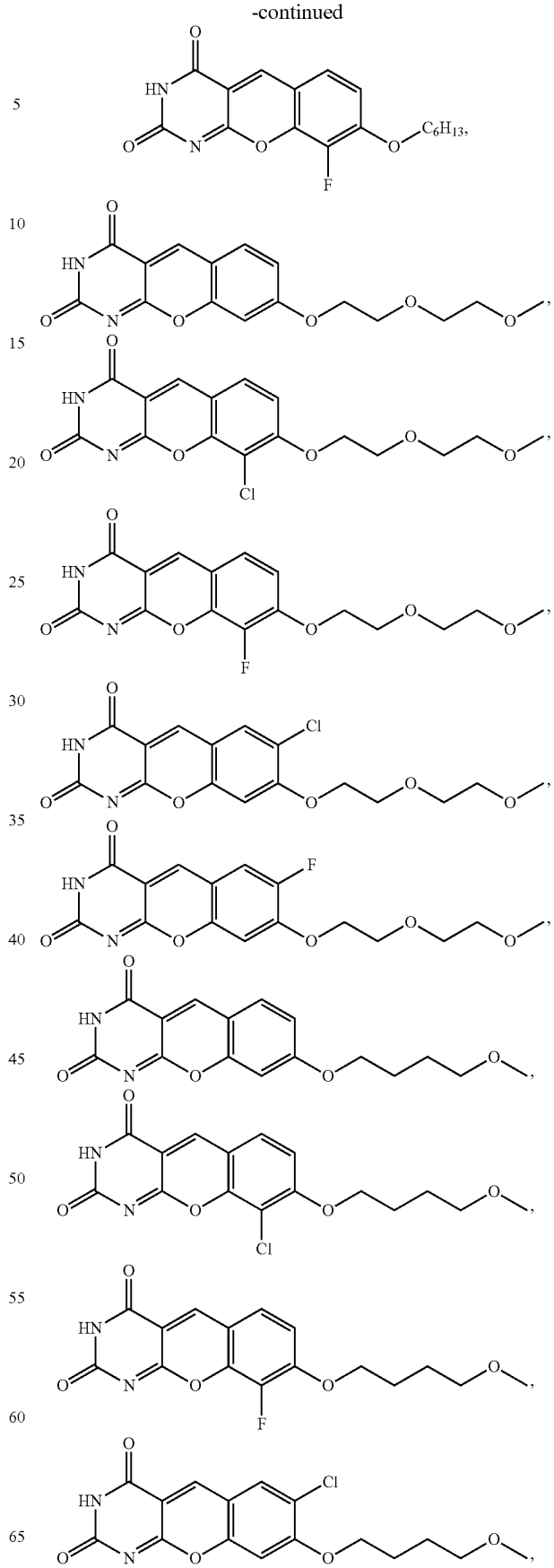

-continued

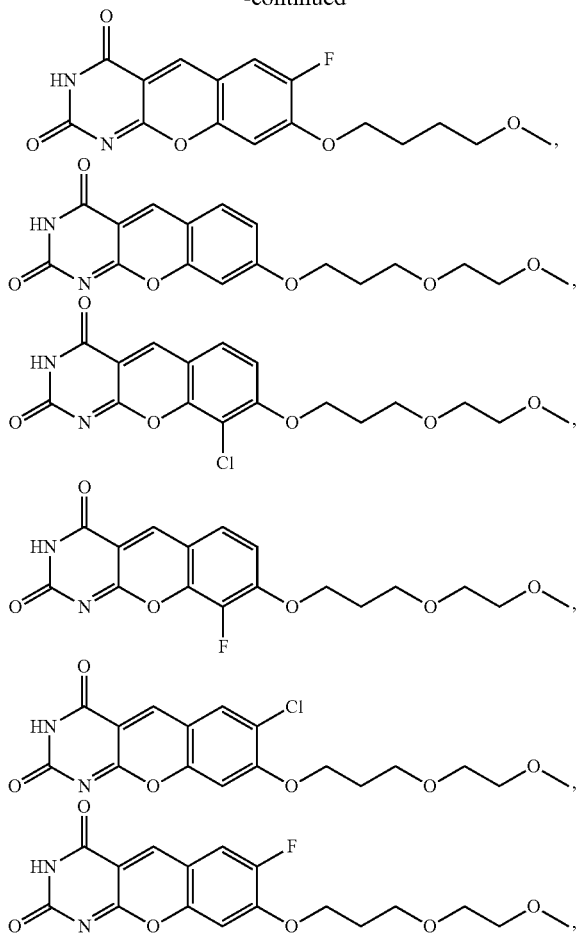

and crystalline forms, hydrates, or pharmaceutically acceptable salts thereof.

In another aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

In an additional aspect of this embodiment, the subject is a mammal.

Preferably, the mammal is selected from the group consisting of humans, primates, farm animals, domestic animals, and laboratory animals.

More preferably, the mammal is a human.

Another embodiment of the present invention is a kit for treating cancer in a subject. The kit comprises a compound selected from the group consisting of the compounds in Table 1, and crystalline forms, hydrates, or pharmaceutically acceptable salts thereof.

In another aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

In another aspect of this embodiment, the subject is a mammal.

Preferably, the mammal is selected from the group consisting of humans, primates, farm animals, domestic animals, and laboratory animals.

More preferably, the mammal is a human.

A further embodiment of the present invention is a kit for treating cancer in a subject. The kit comprises a compound selected from the group consisting of:

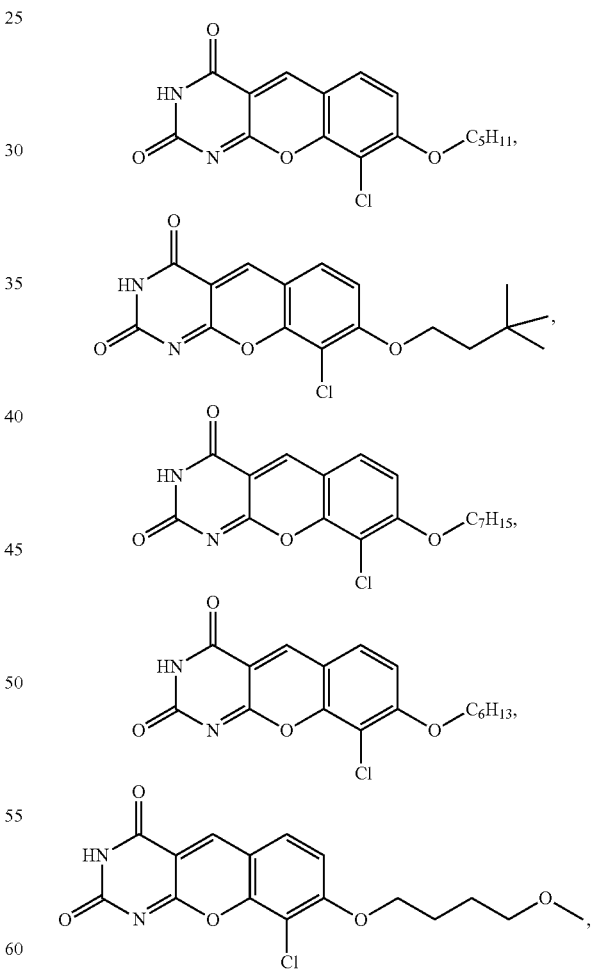

and crystalline forms, hydrates, or pharmaceutically acceptable salts thereof,
packaged together with instructions for its use.

In another aspect of this embodiment, the cancer is selected from the group consisting of esophageal cancer, stomach cancer, small intestinal cancer, colon cancer, rectal cancer, anal cancer, liver cancer, intrahepatic bile duct cancer, gallbladder cancer, pancreatic cancer, larynx cancer, lung cancer, bronchus cancer, bone cancer, skin cancer, melanoma, breast cancer, uterine cervix cancer, uterine corpus cancer, ovarian cancer, vulva cancer, vaginal cancer, prostate cancer, testis cancer, urinary bladder cancer, kidney cancer, brain cancer, nervous system cancer, thyroid cancer, and thymus cancer.

Preferably, the cancer is selected from the group consisting of lung cancer, pancreatic cancer, liver cancer, colorectal cancer, gastric cancer, and breast cancer.

More preferably, the cancer is lung cancer or liver cancer.

In another aspect of this embodiment, the subject is a mammal.

Preferably, the mammal is selected from the group consisting of humans, primates, farm animals, domestic animals, and laboratory animals.

More preferably, the mammal is a human.

An additional embodiment of the present invention is a kit for treating a solid tumor in a subject. The kit comprises a compound having the structure of formula (I):

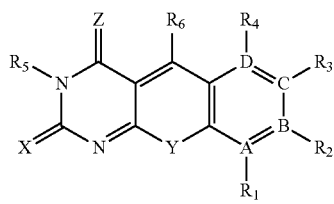
(I)

wherein:
A, B, C, and D are independently selected from the group consisting of carbon and nitrogen;
X, Y, and Z are independently selected from the group consisting of oxygen, sulfur, and NRa;
R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;
R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and
R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic,
or a crystalline form, hydrate, or pharmaceutically acceptable salt thereof,
packaged together with instructions for its use.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH₃, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

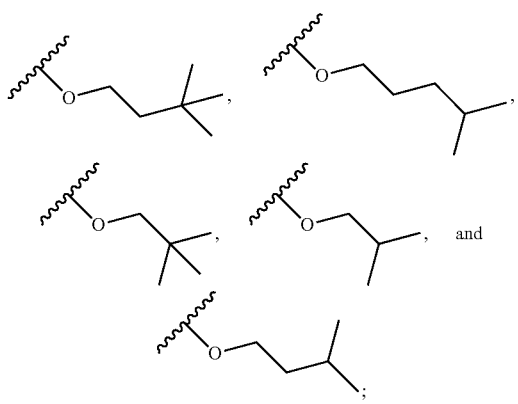

and

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,
X, Y, and Z are independently selected from the group consisting of oxygen and sulfur; and
R6 is hydrogen.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,
X and Y are oxygen; and
R4 is hydrogen.

In a preferred aspect of this embodiment, the compound is selected from the group consisting of:

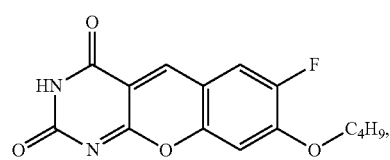

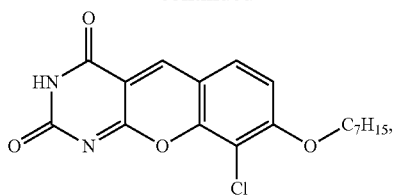
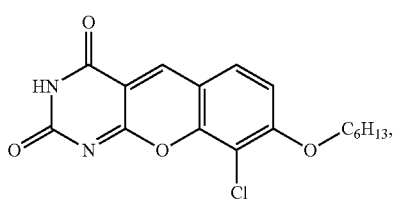
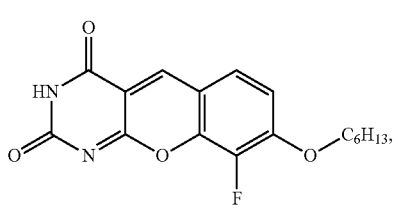
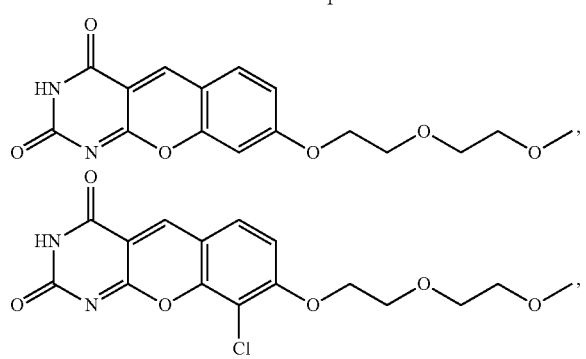
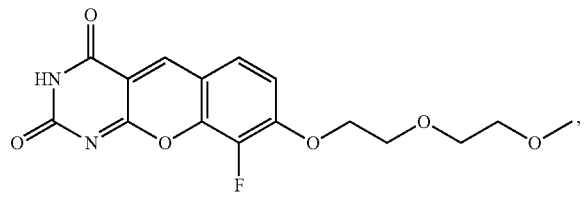
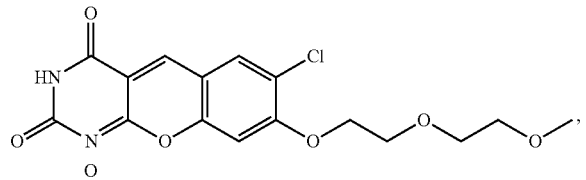
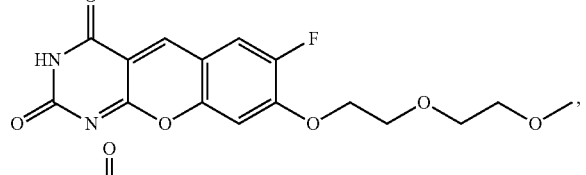
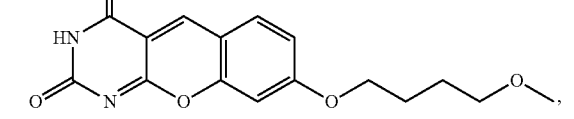
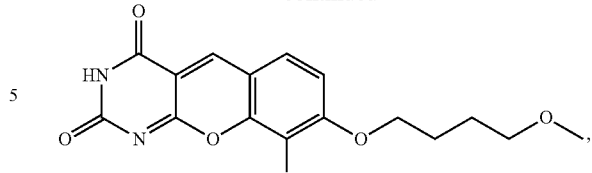
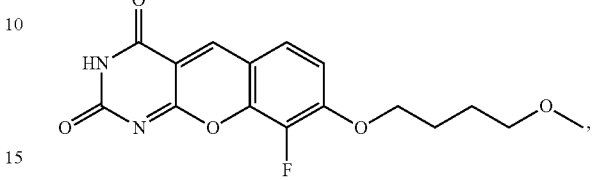
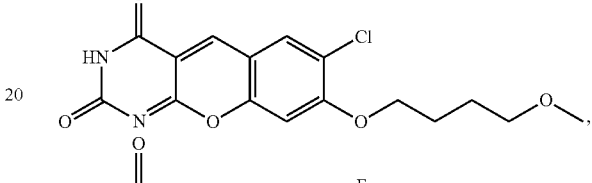
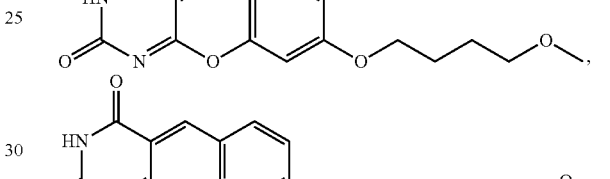
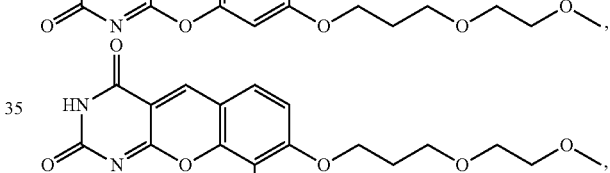
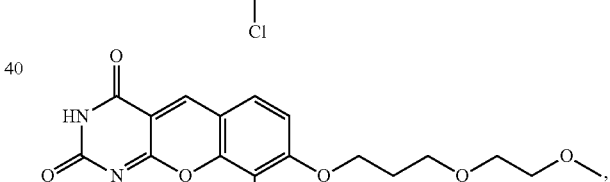
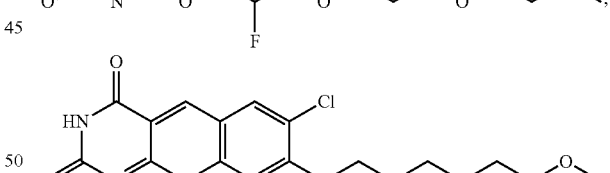
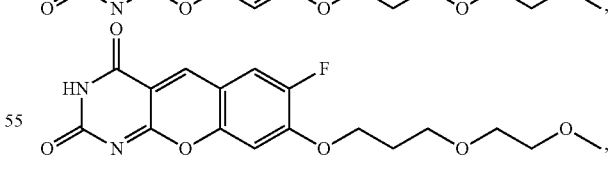
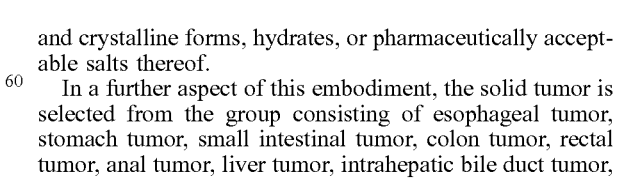

and crystalline forms, hydrates, or pharmaceutically acceptable salts thereof.

In a further aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

In an additional aspect of this embodiment, the subject is a mammal.

Preferably, the mammal is selected from the group consisting of humans, primates, farm animals, domestic animals, and laboratory animals.

More preferably, the mammal is a human.

Another embodiment of the present invention is a kit for treating a solid tumor in a subject. The kit comprises a compound selected from the group consisting of the compounds in Table 1, and crystalline forms, hydrates, or pharmaceutically acceptable salts thereof.

In one aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

In another aspect of this embodiment, the subject is a mammal.

Preferably, the mammal is selected from the group consisting of humans, primates, farm animals, domestic animals, and laboratory animals.

More preferably, the mammal is a human.

A further embodiment of the present invention is a kit for treating a solid tumor in a subject. The kit comprises a compound selected from the group consisting of:

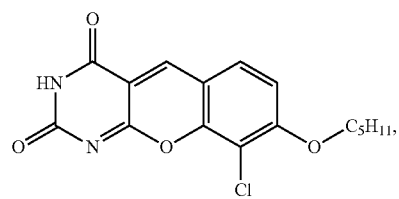

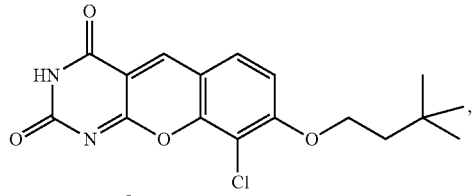

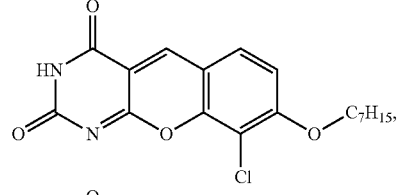

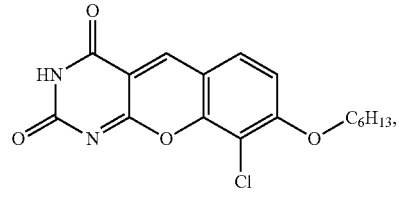

-continued

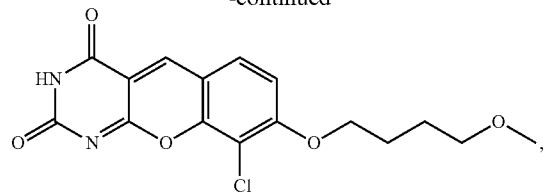

and crystalline forms, hydrates, or pharmaceutically acceptable salts thereof,
packaged together with instructions for its use.

In one aspect of this embodiment, the solid tumor is selected from the group consisting of esophageal tumor, stomach tumor, small intestinal tumor, colon tumor, rectal tumor, anal tumor, liver tumor, intrahepatic bile duct tumor, gallbladder tumor, pancreatic tumor, larynx tumor, lung tumor, bronchus tumor, bone tumor, skin tumor, melanoma, breast tumor, uterine cervix tumor, uterine corpus tumor, ovarian tumor, vulva tumor, vaginal tumor, prostate tumor, testis tumor, urinary bladder tumor, kidney tumor, brain tumor, nervous system tumor, thyroid tumor, and thymus tumor.

Preferably, the solid tumor is a lung tumor or liver tumor.

In another aspect of this embodiment, the subject is a mammal.

Preferably, the mammal is selected from the group consisting of humans, primates, farm animals, domestic animals, and laboratory animals.

More preferably, the mammal is a human.

An additional embodiment of the present invention is a kit for inducing cancer cell death. The kit comprises a compound having the structure of formula (I):

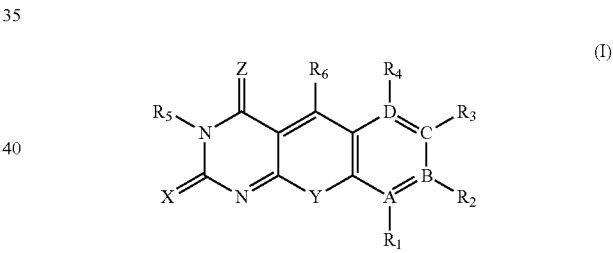

wherein:

A, B, C, and D are independently selected from the group consisting of carbon and nitrogen;

X, Y, and Z are independently selected from the group consisting of oxygen, sulfur, and NRa;

R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;

R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic, or a crystalline form, hydrate, or pharmaceutically acceptable salt thereof,
packaged together with instructions for its use.

In one aspect of this embodiment,
X, Y, and Z are independently selected from the group consisting of oxygen and sulfur;
R1 is selected from the group consisting of —H, —F, —Cl, —OMe, and —OEt;
R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

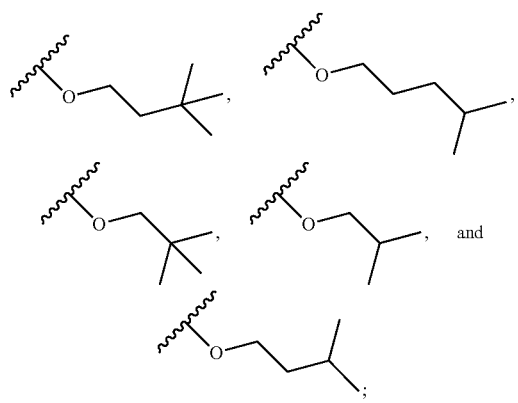

R3 is selected from the group consisting of —H, —Cl, —Br, —F, and —OMe;
R4 is selected from the group consisting of —H and —OMe;
R5 is selected from the group consisting of —H, -Me, -Et, —Pr, -iPr, -Ph, -iBu, and -nBu; and
R6 is selected from the group consisting of —H and —CH3,
m is 2, 3, 4 or 5; and,
n is 2, 3, 4, or 5.

In another aspect of this embodiment,
X, Y, and Z are independently selected from the group consisting of oxygen and sulfur; and
R6 is hydrogen.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,
X and Y are oxygen; and
R4 is hydrogen,
or a crystalline form, hydrate, or pharmaceutically acceptable salt thereof.

In a preferred aspect of this embodiment, the compound is selected from the group consisting of:

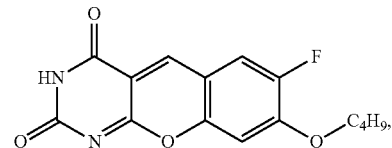

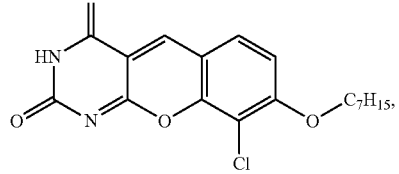

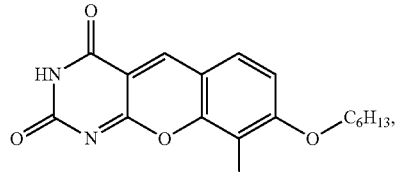

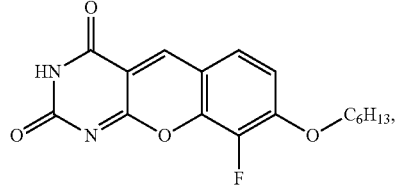

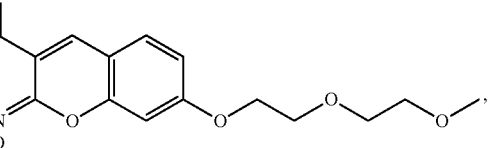

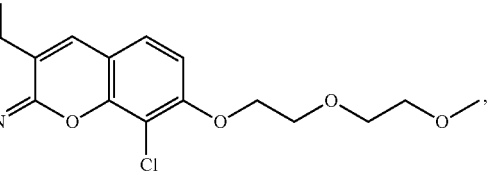

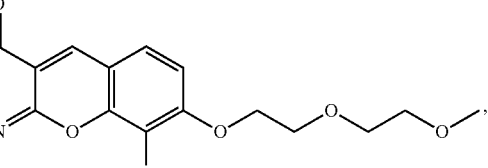

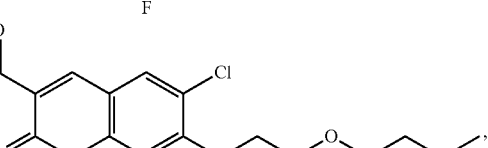

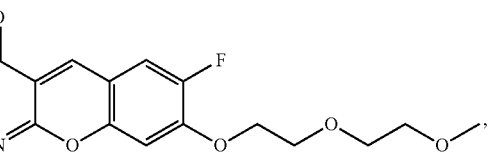

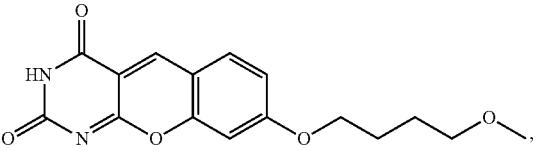

-continued

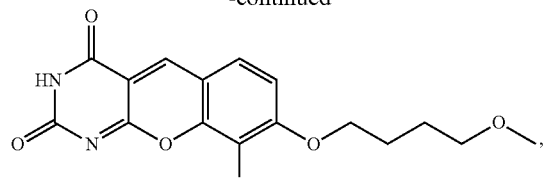
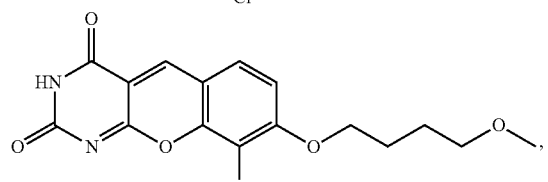
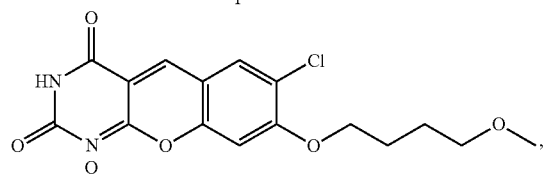
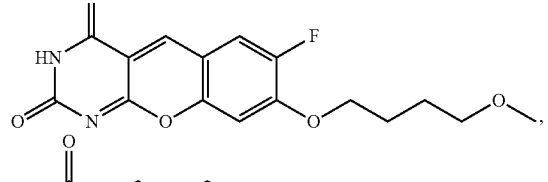
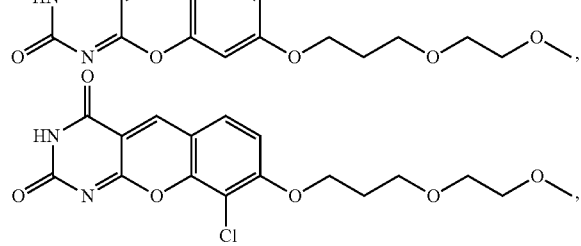
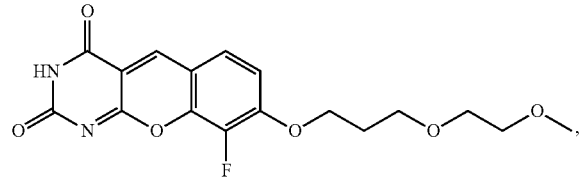
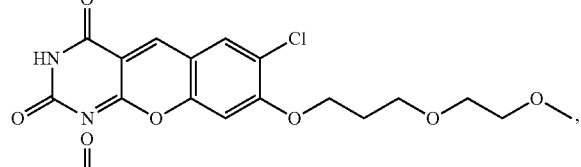
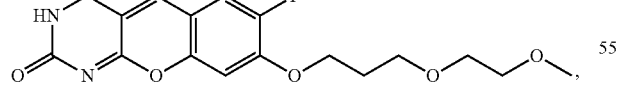

and crystalline forms, hydrates, or pharmaceutically acceptable salts thereof.

In a further aspect of this embodiment, in the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

Another embodiment of the present invention is a kit for inducing cancer cell death. The kit comprises a compound selected from the group consisting of the compounds in Table 1, and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

A further embodiment of the present invention is a kit for inducing cancer cell death. The kit comprises a compound selected from the group consisting of:

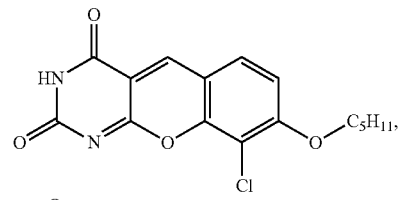
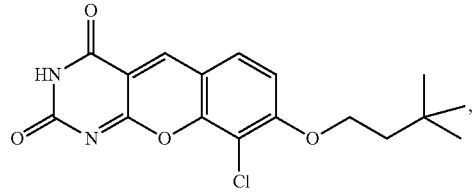

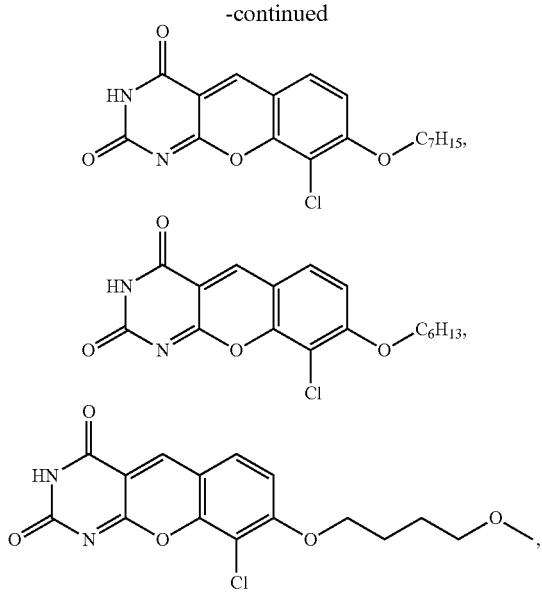

and crystalline forms, hydrates, or pharmaceutically acceptable salts thereof,
packaged together with instructions for its use.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

An additional embodiment of the present invention is a kit for inducing apoptosis of a cancer cell. The kit comprises a compound having the structure of formula (I):

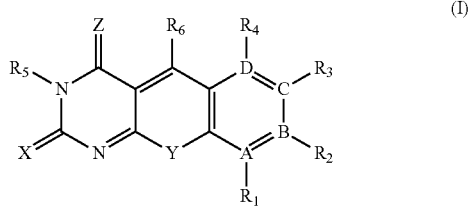

wherein:

A, B, C, and D are independently selected from the group consisting of carbon and nitrogen;

X, Y, and Z are independently selected from the group consisting of oxygen, sulfur, and NRa;

R1, R2, R3, and R4 are independently selected from the group consisting of no atom, hydrogen, halogen, $C_{1-9}$ alkyl, $C_{2-9}$ alkenyl, $C_{2-9}$ alkynyl, aryl, heterocyclic, —OH, —ORa, —ORaORb, —ORaORbORc, —ORa(C=O)Rb —O(C=O)Ra, —O(C=O)ORa, —O(C=O)NRaRb, cyano, nitro, —CF3, —CHF2, —CH2F, —CHO, —COOH, —CORa, —COORa, —CONRaRb, —CONHCONRaRb, —NRaRb, —NHCORa, —NRbCORa, —CSOH, —CSRa, —CSORa, —CSNRaRb, —CSNHCSNRaRb, —SH, —SRa, —S(C=O)Ra, —S(C=O)ORa, —S(C=O)NRaRb;

R5 is selected from the group consisting of hydrogen, $C_{1-9}$ alkyl, $C_{2-9}$ alkenyl, $C_{2-9}$ alkynyl, aryl, heterocyclic, —RaCO, —RaNHCO, and —RaOCO; and R6, Ra, Rb, and Rc are independently selected from the group consisting of hydrogen, hydroxyl, amine, $C_{1-9}$ alkyl, $C_{2-9}$ alkenyl, $C_{2-9}$ alkynyl, aryl, and heterocyclic, or a crystalline form, hydrate, or pharmaceutically acceptable salt thereof, packaged together with instructions for its use.

In one aspect of this embodiment,

X, Y, and Z are independently selected from the group consisting of oxygen and sulfur;

R1 is selected from the group consisting of —H, —F, —Cl, —OMe, and —OEt;

R2 is selected from the group consisting of —H, —CH3, —OH, —OMe, —OEt, -Me, -Et, -nPr, —O-nPr, —OEtnPr, —OC4H9, —OC5H11, —OC6H13, —OC7H15, —O-isobutyl, —O-isopentyl, —OCnH2nOMe, —OCnH2nOCmH2mOMe, —OCnH2nOH, —OCnH2nOCmH2mOH, —OCnH2nOEt, —OCnH2nOCmH2mOEt, —O-CnH2nCOOH, —O-CnH2nCONH2, —O-CnH2nCONHMe,

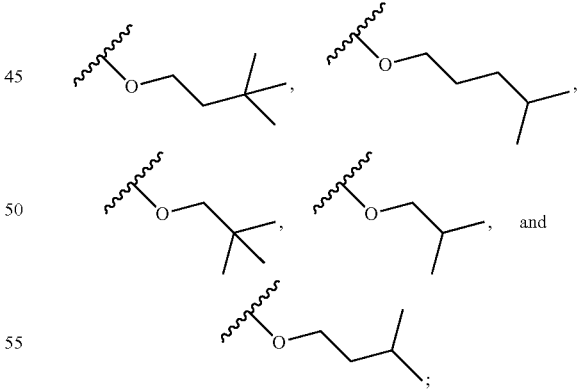

R3 is selected from the group consisting of —H, —Cl, —Br, —F, and —OMe;

R4 is selected from the group consisting of —H and —OMe;

R5 is selected from the group consisting of —H, -Me, -Et, —Pr, -iPr, -Ph, -iBu, and -nBu; and R6 is selected from the group consisting of —H and —CH3, m is 2, 3, 4 or 5; and, n is 2, 3, 4, or 5.

In another aspect of this embodiment,
X, Y, and Z are independently selected from the group consisting of oxygen and sulfur; and
R6 is hydrogen.

Preferably,
Z is oxygen;
R1 and R3 are selected from the group consisting of hydrogen, halogen, —CN, and —CF3;
R2 is selected from the group consisting of $C_{1-9}$ alkoxy, —OCnH2nOMe, —OCnH2nOCmH2mOMe, —OCnH2nOH, —OCnH2nOCmH2mOH, OCnH2nOEt, —OCnH2nOCmH2mOEt, —O-CnH2nCOOH, —O-CnH2nCONH2, —O-CnH2nCONHMe, and —OH;
m is 2, 3, 4 or 5;
n is 2, 3, 4, or 5; and
R4 is selected from the group consisting of hydrogen, $C_{1-9}$ alkoxy and —OH.

More preferably,
X and Y are oxygen; and
R4 is hydrogen.

In a preferred embodiment of this invention, the compound is selected from the group consisting of:

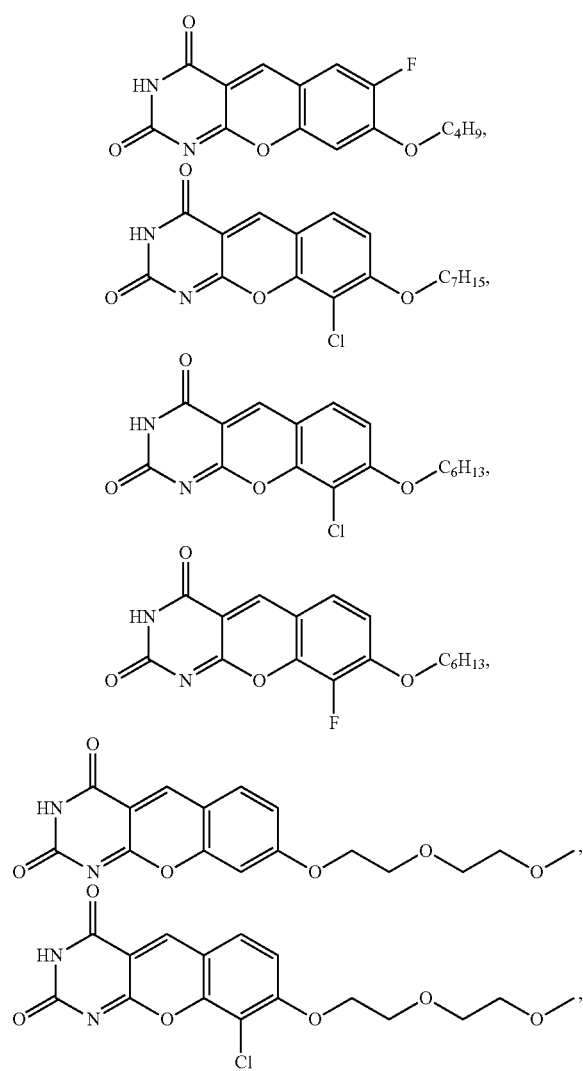

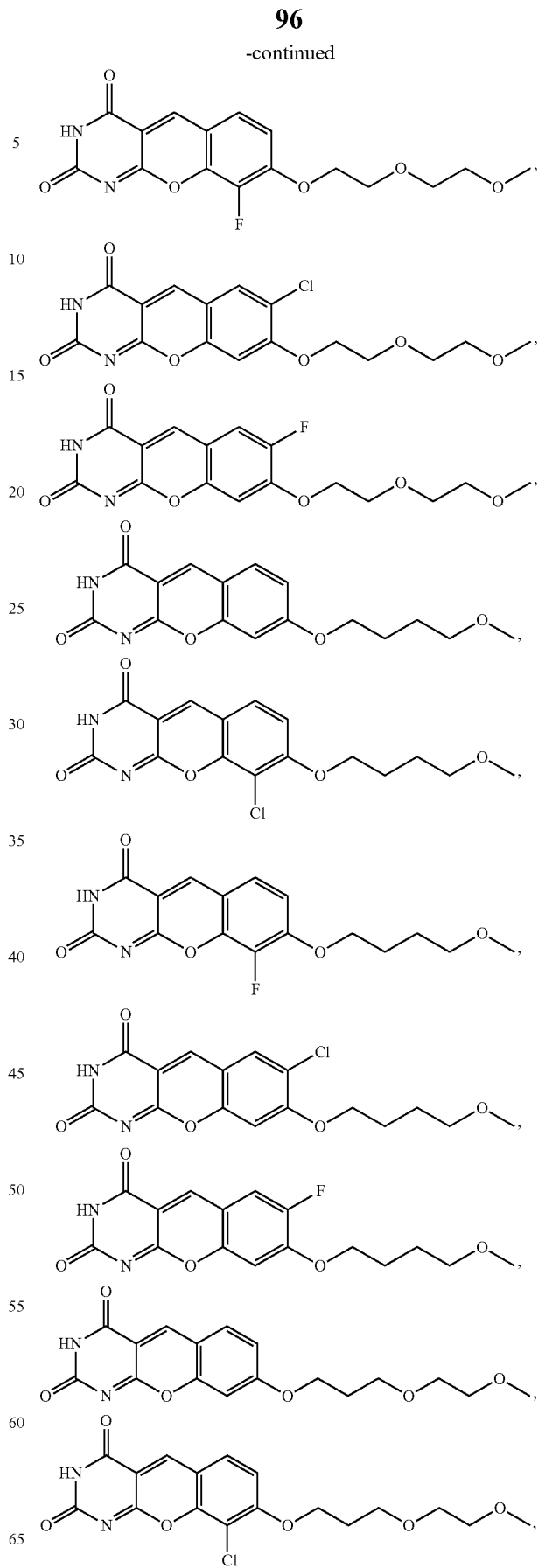

-continued

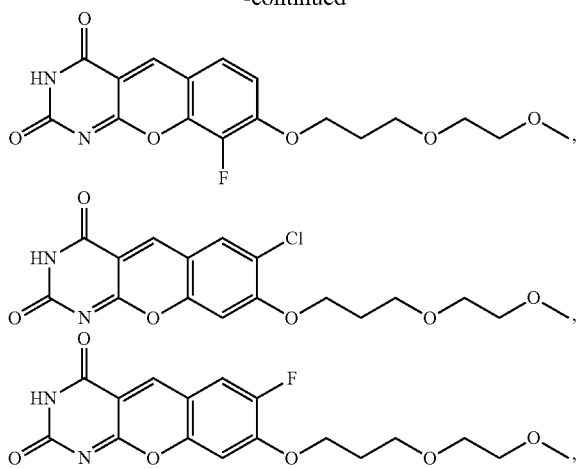

and crystalline forms, hydrates, or pharmaceutically acceptable salts thereof.

In a further aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

Another embodiment of the present invention is a kit for inducing apoptosis of a cancer cell. The kit comprises a compound selected from the group consisting of the compounds in Table 1, and crystalline forms, hydrates, or pharmaceutically acceptable salts thereof.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

A further embodiment of the present invention is a kit for inducing apoptosis of a cancer cell. The kit comprises a compound selected from the group consisting of:

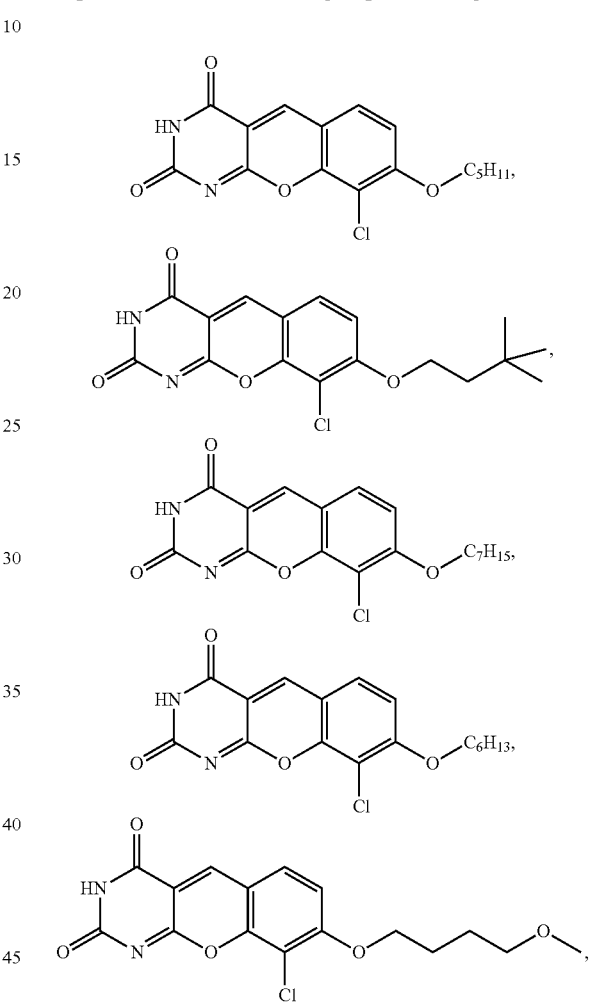

and crystalline forms, hydrates, or pharmaceutically acceptable salts thereof,
packaged together with instructions for its use.

In one aspect of this embodiment, the cancer cell is selected from the group consisting of esophageal cancer cell, stomach cancer cell, small intestinal cancer cell, colon cancer cell, rectal cancer cell, anal cancer cell, liver cancer cell, intrahepatic bile duct cancer cell, gallbladder cancer cell, pancreatic cancer cell, larynx cancer cell, lung cancer cell, bronchus cancer cell, bone cancer cell, skin cancer cell, melanoma cell, breast cancer cell, uterine cervix cancer cell, uterine corpus cancer cell, ovarian cancer cell, vulva cancer cell, vaginal cancer cell, prostate cancer cell, testis cancer cell, urinary bladder cancer cell, kidney cancer cell, brain cancer cell, nervous system cancer cell, thyroid cancer cell, and thymus cancer cell.

Preferably, the cancer cell is selected from the group consisting of lung cancer cell, pancreatic cancer cell, liver cancer cell, colorectal cancer cell, gastric cancer cell, and breast cancer cell.

More preferably, the cancer cell is selected from the group consisting of lung cancer cell, non-small cell lung cancer (NSCLC) cell, drug-resistant non-small cell cancer (NSCLC) cell, and liver cancer cell.

More preferably, the lung cancer cell is selected from the group consisting of H1975 and HCC827.

It is to be understood that the methods of the present invention may involve administration of the compounds listed above or crystalline forms, hydrates, or pharmaceutically acceptable salts thereof. Likewise, the kits of the present invention may include the compounds listed above or crystalline forms, hydrates, or pharmaceutically acceptable salts thereof.

Definitions

The term "aliphatic", as used herein, means a group composed of carbon and hydrogen atoms that does not contain aromatic rings. Accordingly, aliphatic groups include alkyl, alkenyl, alkynyl, and carbocyclyl groups.

The term "alkyl" means the radical of saturated aliphatic groups that does not have a ring structure, including straight chain alkyl groups, and branched chain alkyl groups. Alkyl groups of the present invention have at least one and up to twenty carbon atoms and can be optionally substituted with one or more heteroatoms selected from halogen, nitrogen, oxygen, and sulfur.

The term "alkyl" also refers to cyclic hydrocarbon rings having at least three, and up to twenty, carbon atoms, optionally substituted with one or more heteroatoms selected from halogen, nitrogen, oxygen, and sulfur. The cyclic hydrocarbon ring can be monocyclic, bicyclic, polycyclic or bridge cyclic. Examples of alkyl groups include, but are not limited to, methyl, ethyl, propyl, isopropyl, butyl, isobutyl, pentyl, neopentyl, cyclopropyl, cyclobutyl, 2-chlorobutyl, 3-fluoropentyl, 4-hydroxybutyl, 3-methoxypropyl, 2-methoxypropyl, 2-methylbutyl, 3-methylbutyl (isopentyl), 2-chloro-4-hydroxybutyl, 5-aminohexyl, 2,2-difluorocyclobutyl, 1,3-difluorocyclohexyl, 3-thiolhexyl, and the like.

The term "alkenyl" refers to a straight or branched hydrocarbon chain having at least three, and up to twenty, carbon atoms with at least one double bond (—C=C—), optionally substituted with one or more heteroatoms selected from halogen, nitrogen, oxygen, and sulfur.

The term "alkenyl" also refers to cyclic hydrocarbon rings having at least three, and up to twenty, carbon atoms with at least one double bond (—C=C—), optionally substituted with one or more heteroatoms selected from halogen, nitrogen, oxygen, and sulfur. Examples of alkenyl groups include, but are not limited to, ethenyl, chlorovinyl, propenyl, propenylene, allyl, 1,4-butandienyl, 1,2-cyclobutenyl, and the like.

The term "alkynyl" refers to a straight or branched hydrocarbon chain having at least three, and up to twenty, carbon atoms with at least one triple bond, with or without one or more double bond, and optionally substituted with one or more heteroatoms selected from halogen, nitrogen, oxygen, and sulfur. The term "alkenyl" also refers to cyclic hydrocarbon rings with at least one triple bond with or without one or more double bond (—C≡C—) and optionally substituted with one or more heteroatoms selected from halogen, nitrogen, oxygen, and sulfur. Examples of alkynyl groups include, but are not limited to, ethynyl, propynyl, butynyl, 3-methylbutynyl, and the like.

The term "aryl" refers to monocyclic, bicyclic or polycyclic aromatic hydrocarbon ring structures optionally substituted with one or more heteroatoms selected from halogen, nitrogen, oxygen, and sulfur, and/or optionally substituted with one or more alkyl, alkenyl or alkynyl groups. Examples of aryl groups include, but are not limited to, phenyl, naphthyl, hydroxyl phenyl, chlorophenyl, 2-chloro-4-fluorophenyl, methylphenyl, cyanonaphthyl, and the like.

The term "heterocyclic" refers to saturated or unsaturated mono- or poly-carbocyclic structures in which at least one carbon atom of at least one of the rings is replaced by nitrogen, sulfur, phosphorus, or oxygen. The term "heterocyclic" is intended to encompass fully saturated and unsaturated ring systems as well as partially unsaturated ring systems, including all possible isomeric forms of the heterocycle (for example, pyrrolyl comprises 1H-pyrrolyl and 2H-pyrrolyl).

Examples of a monocyclic heterocycle (e.g., a 4-, 5-, or 6-membered ring) or a bicyclic (e.g., a 5/6, 5/5, 6/6 system) saturated heterocycle include, but are not limited to, tetrahydrofuranyl, pyrrolidinyl, tetrahydrothienyl, dihydrooxazolyl, piperidinyl, hexahydropyrimidinyl, dioxanyl, morpholinyl, dithianyl, thiomorpholinyl, piperazinyl and the like.

Examples of a partially saturated monocyclic, bicyclic or tricyclic heterocycle include, but are not limited to, pyrrolinyl, imidazolinyl, pyrazolinyl, 2,3-dihydrobenzofuranyl, 1,3-benzodioxolanyl, 2,3dihydro-1,4-benzodioxinyl, indolinyl and the like.

Examples of an aromatic monocyclic, bicyclic or tricyclic heterocycle include, but are not limited to, pyrrolyl, furanyl, thienyl, imidazolyl, oxazolyl, isoxazolyl, thiazolyl, isothiazolyl, pyrazolyl, 1,2,3-triazolyl, 1,2,5-thiadiazolyl, 1,2,3-thiadiazolyl, 1,2,3-oxadiazolyl, 1,2,5-oxadiazolyl, pyridinyl, pyrimidinyl, pyrazinyl, pyridazinyl, triazinyl, benzofuranyl, isobenzofuranyl, benzothienyl, isobenzothienyl, indolizinyl, indolyl, isoindoly, benzoxazolyl, benzimidazolyl, indazolyl, benzisoxazolyl, benzisothiazolyl, benzopyrazolyl, benzoxadiazolyl, benzothiadiazolyl, benzotriazolyl, quinolinyl, isoquinolinyl, cinnolinyl, quinolizinyl, phthalazinyl, quinoxalinyl, quinazolinyl, naphthyridinyl, pteridinyl, pyrrolopyridinyl, thienopyridinyl, furanopyridinyl, isothiazolopyridinyl, thiazolopyridinyl, isoxazolopyridinyl, oxazolopyridinyl, pyrazolopyridinyl, imidazopyridinyl, pyrrolopyrazinyl, thienopyrazinyl, furanopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furanopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furanopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridinyl, thiadiazolopyridinyl, triazolopyridinyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl and the like.

The term "carbonyl" includes, but is not limited to, CHO (aldehyde group), COOH (carboxylic acid), $COR^a$ (ketone), $COOR^a$ (carboxylic ester), $CONR^aR^b$ (amide), $CONHCONR^aR^b$ (imide), $R^aCOX$ (acyl halide), and $R^aCOOCOR^b$ (acid anhydride).

The term "halogen" includes, but is not limited to, fluorine, chlorine, bromine, iodine, and astatine.

In the present invention, the term "crystalline form" means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage.

Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term "hydrate", as used herein, means a solid or a semi-solid form of a chemical compound containing water in a molecular complex. The water is generally in a stoichiometric amount with respect to the chemical compound.

As used herein, "pharmaceutically acceptable salts" refer to derivatives of the compounds disclosed herein wherein the compounds are modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2''-nitrilotris(ethanol)), trometh-amine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminum, calcium, lithium, magnesium, potassium, sodium, zinc and the like. (Pharmaceutical salts, Berge, S. M. et al., J. Pharm. Sci., (1977), 66, 1-19).

The pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

The compositions of the invention comprise one or more active ingredients in admixture with one or more pharmaceutically acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate;

(10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

Any formulation of the invention may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The methods of the present invention may further comprise administering to the subject at least one additional agent. Likewise, the kits of the present invention may further comprise at least one additional agent. In the methods and kits of the present invention, the additional agent may be selected from the group consisting of an antibody or fragment thereof, a cytotoxic agent, including, but not limited to, chemotherapeutic agents, a targeted agent, including, but not limited to, targeted therapeutic agents, a toxin, a radionuclide, an immunomodulator, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')2, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Non-limiting examples of antibodies that may be used in the present invention include rituximab (Rituxan), cetuximab (Erbitux), bevacizumab (Avastin), necitumumab, nivolumab, pembrolizumab, and atezolizumab.

Cytotoxic agents according to the present invention include, but are not limited to, DNA damaging agents, antimetabolites, anti-microtubule agents, and antibiotic agents.

DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof.

Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof.

Anti-microtubule agents include without limitation vinca alkaloids, paclitaxel (Taxol®), docetaxel (Taxotere®), and ixabepilone (Ixempra®).

Antibiotic agents include without limitation include actinomycin, anthracyclines, valrubicin, epirubicin, bleomycin, plicamycin, mitomycin, pharmaceutically acceptable salts thereof, prodrugs, and combinations thereof.

Targeted agents of the present invention include, but are not limited to, EGFR inhibitors, such as gefitinib, erlotinib, afatinib, and osimetinib, as well as ALK inhibitors, such as crizotinib, ceritinib, and alectinib. Targeted agents of the present invention also include, for example, sorafenib.

In the present invention, the term "toxin" means an antigenic poison or venom of plant or animal origin. An example is diphtheria toxin or portions thereof.

In the present invention, the term "radionuclide" means a radioactive substance administered to the subject, e.g., intravenously or orally, after which it penetrates via the subject's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG). Additional immunomodulators of the present invention include, but are not limited to, immune checkpoint inhibitors. Immune checkpoint inhibitors of the present invention include, but are not limited to, antibodies against, and antagonists of, CTLA-4, PD-1, PD-L1, LAG3, IDO1, and the like.

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an anti-angiogenesis agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

The following examples are provided to further illustrate the methods of the present invention. These examples are illustrative only and are not intended to limit the scope of the invention in any way.

EXAMPLES

Example 1

General Synthesis Scheme

The NF-κB inhibitors of the present invention can be synthesized by any of the suitable methods known in the art, or as further described below.

Scheme 1.1

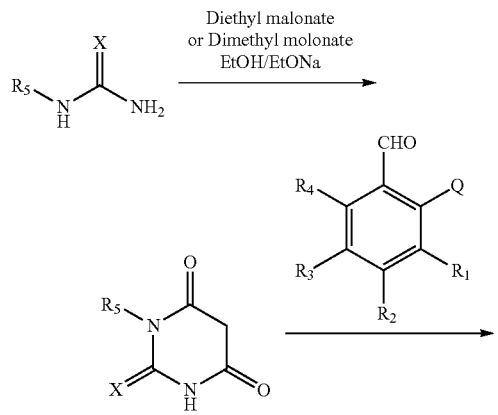

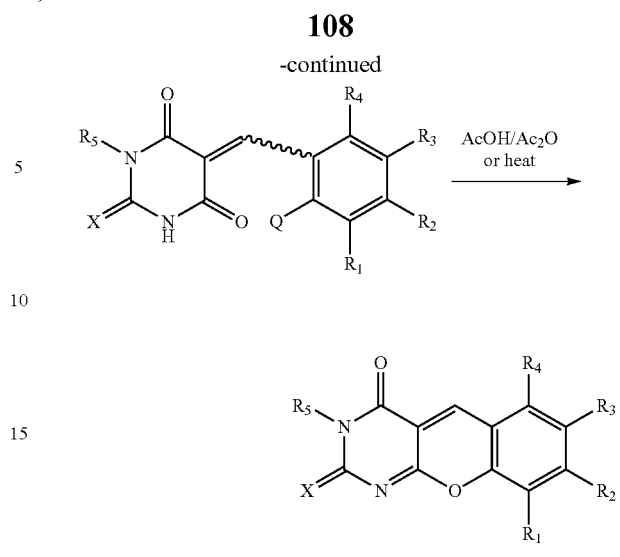

X = O, S, NH$_2$, NHR$_6$
Q = OH, OAc, Halogen (F, Cl, Br)

Scheme 1.2

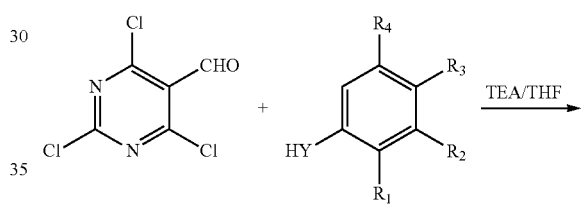

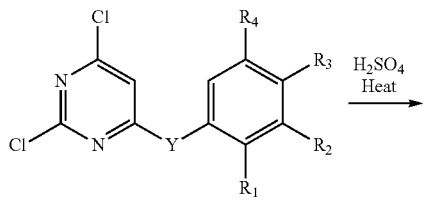

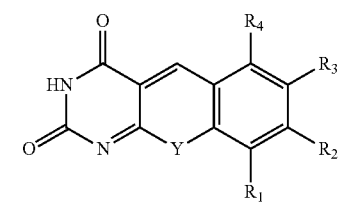

YH = OH, SH, RNH

Scheme 1.3

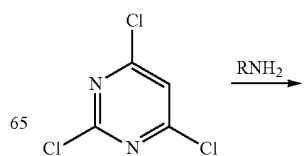

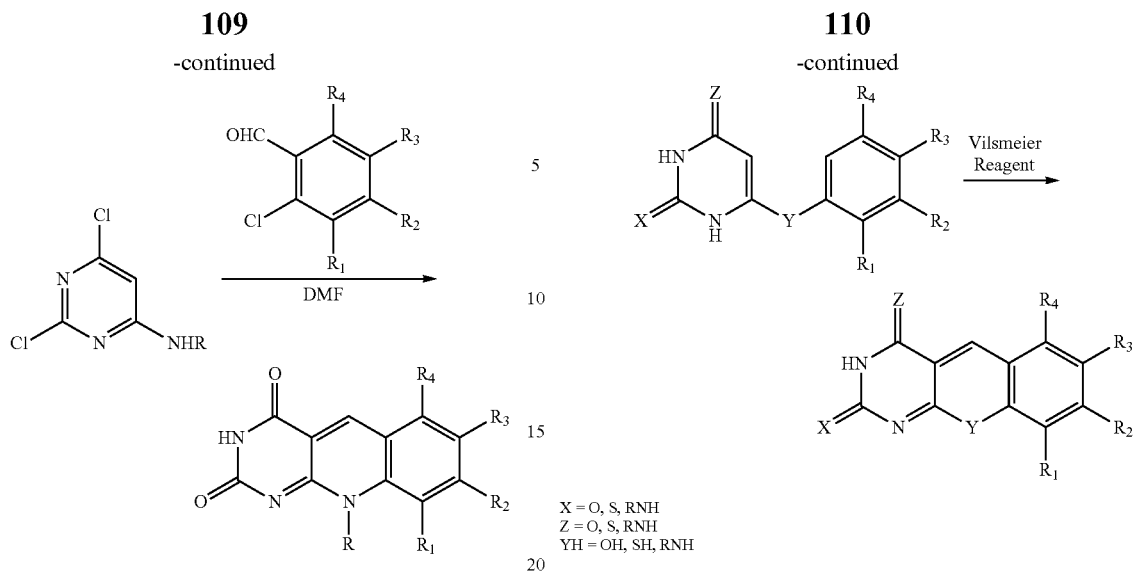
Scheme 1.4
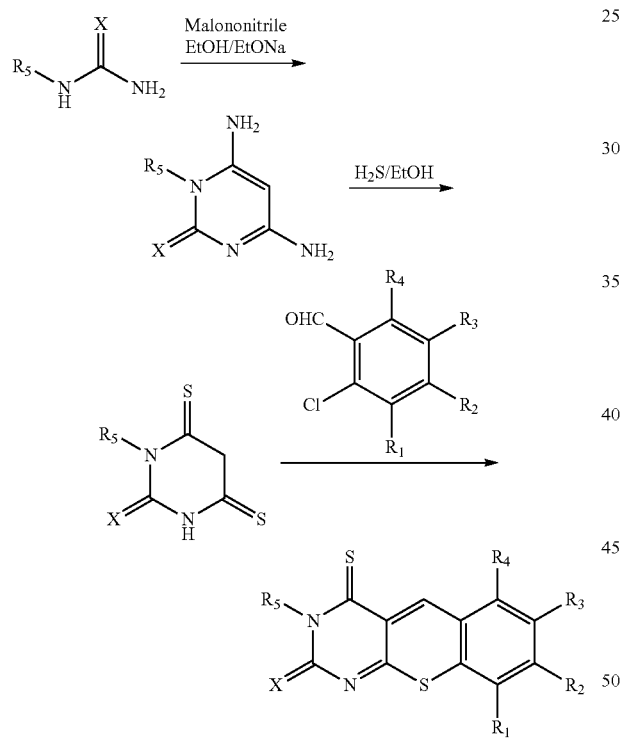
Scheme 1.5
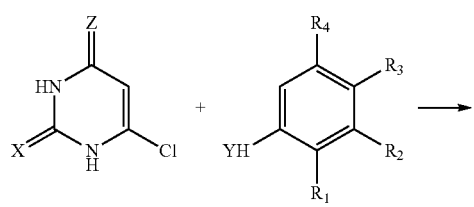
Scheme 2.1
Scheme 2.2
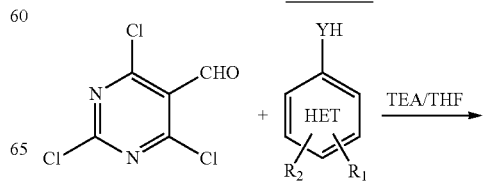

-continued

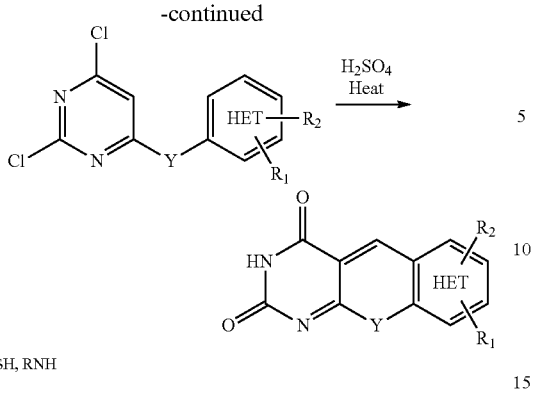

YH = OH, SH, RNH

Scheme 2.3

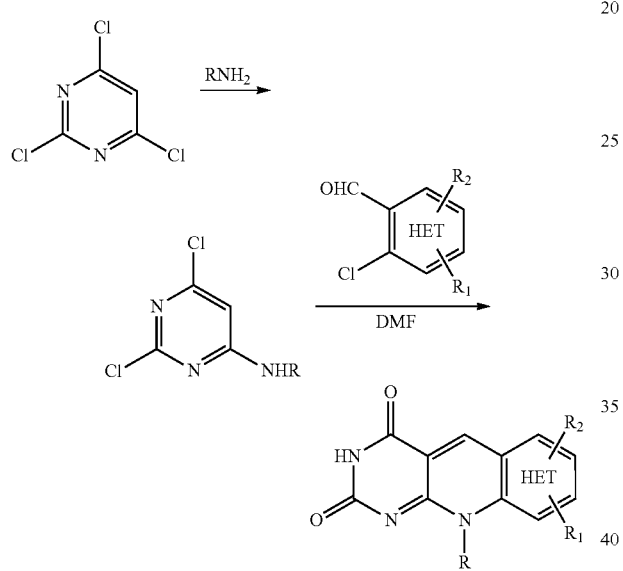

Example 2

Compound-Specific Synthesis Protocols

Preparation of 9-methoxy-2H-chromeno[2,3-d]pyrimidine-2,4(3H)-dione

Step 1: Preparation of Compound 1a, 5-(2-hydroxy-3-methoxybenzylidene)pyrimidine-2,4,6(1H,3H,5H)-trione, 1a In a round bottom flask, a mixture of O-vanillin (1.52 g, 10.0 mmol) and barbituric acid (1.28 g, 10.0 mmol) in ethanol (20 ml) was stirred and heated to 30° C. overnight. The reaction mixture was cooled to room temperature. Subsequently, the reaction mixture was filtered. Solid yellow cake was collected and vacuum dried at 40° C. to 50° C. to yield desired product 1a, (2.20 g, 8.4 mmol, 84%).

Step 2: Preparation of 9-methoxy-2H-chromeno[2,3-d]pyrimidine-2,4(3H)-dione

In a scintillation vial, a suspension of compound 1a, (500 mg, 1.9 mmol) in a mixture of acetic acid (15 ml) and acetic anhydride (2 ml) was stirred and heated to 80° C. After 10 minutes at 80° C., the mixture turned homogeneous. The mixture was stirred at 80° C. for 3 hours. The mixture was cooled to room temperature and stirred overnight. Precipitation occurred during overnight stirring. Yellow solid was filtered, washed with water and vacuum dried at 40° C. to 50° C. to yield compound 1 (355 mg, 1.45 mmol, 77%).

Preparation of 9-ethoxy-2H-chromeno[2,3-d]pyrimidine-2,4(3H)-dione

Step 1: Preparation of compound 2a, 5-(3-ethoxy-2-hydroxybenzylidene)pyrimidine-2,4,6(1H,3H,5H)-trione, 2a In a scintillation vial, a mixture of 3-ethoxysalicyladehide (0.332 g, 2.0 mmol) and barbituric acid (0.256 g, 2.0 mmol) in ethanol (10 ml) was stirred and heated to 40° C. overnight. The reaction mixture was cooled to room temperature. Subsequently, the reaction mixture was filtered. Solid yellow cake was collected and vacuum dried at 40° C. to 50° C. to yield desired product 2a, (0.37 g, 1.3 mmol, 67%).

Step 2: Preparation of 9-ethoxy-2H-chromeno[2,3-d]pyrimidine-2,4(3H)-dione

In a scintillation vial, a suspension of compound 2a, (138 mg, 0.5 mmol) in a mixture of acetic acid (4.5 ml) and acetic anhydride (0.5 ml) was stirred and heated to 80° C. After 10 minutes at 80° C., the mixture turned homogeneous and remained homogeneous during the heating. The mixture was stirred at 80° C. for 1 hour. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 2 (62 mg, 0.24 mmol, 48%).

Preparation of 7-chloro-9-methoxy-2H-chromeno[2,3-d]pyrimidine-2,4(3H)-dione

Step 1: Preparation of 5-(5-chloro-2-hydroxy-3-methoxybenzylidene)pyrimidine-2,4,6(1H,3H,5H)-trione, 3a In a scintillation vial, a mixture of 5-chloro-2-hydroxy-3-methoxybenzaldehyde (0.374 g, 2.0 mmol) and barbituric acid (0.256 g, 2.0 mmol) in a mixture of ethanol (10 ml) and water (5 ml) was stirred and heated to 25° C. for 2 hours. The reaction mixture was cooled to room temperature. Subsequently, the reaction mixture was filtered. Solid yellow cake was collected and vacuum dried at 40° C. to 50° C. to yield desired product 3a, (0.51 g, 1.7 mmol, 86%).

Step 2: Preparation of 7-chloro-9-methoxy-2H-chromeno[2,3-d]pyrimidine-2,4(3H)-dione In a scintillation vial, a suspension of compound 3a, (148 mg, 0.5 mmol) in a mixture of acetic acid (4.5 ml) and acetic anhydride (0.5 ml) was stirred and heated to 80° C. for 1.5 hour. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 3 (98 mg, 0.35 mmol, 70%).

Preparation of 7-bromo-9-methoxy-2H-chromeno[2,3-d]pyrimidine-2,4(3H)-dione

Step 1: Preparation of 5-(5-bromo-2-hydroxy-3-methoxybenzylidene)pyrimidine-2,4,6(1H,3H,5H)-trione, 4a A solution of 5-bromo-2-hydroxy-3-methoxybenzaldehyde (0.462 g, 2.0 mmol) in ethanol (40 ml) was added to a solution of barbituric acid (0.256 g, 2.0 mmol) in water (40 ml). The mixture was stirred at room temperature for 2 days. Subsequently, the reaction mixture was filtered. Orange solid cake was collected and vacuum dried at 40° C. to 50° C. to yield desired product 4a, (0.46 g, 1.34 mmol, 67%).

Step 2: Preparation of 7-bromo-9-methoxy-2H-chromeno[2,3-d]pyrimidine-2,4(3H)-dione In a scintillation vial, a suspension of compound 4a, (170 mg, 0.5 mmol) in a mixture of acetic acid (4.5 ml) and acetic anhydride (0.5 ml) was stirred and heated to 80° C. for 30 hours. The mixture was cooled to room temperature. Acetic acid and acetic anhydride were removed from the reaction mixture by $N_2$ stream blowing to cause precipitation. Yellow solid was filtered, washed with water and vacuum dried at 40° C. to 50° C. to yield compound 4 (145 mg, 0.45 mmol, 90%).

Preparation of 7-chloro-9-methoxy-2H-chromeno[2,3-d]pyrimidine-2,4(3H)-dione

Step 1: Preparation of 5-chloro-3-ethoxy-2-hydroxybenzaldehyde, 5a

In a round bottom flask, N-chlorosuccinimide (8.68 g, 65 mmol) was added to a solution of 3-ethoxysalicylaldehyde (8.30 g, 50 mmol) in THF (100 ml). The mixture was stirred at room temperature for 5 hours. The reaction was quenched with water (100 ml) and extracted with ethyl acetate (150 ml). The organic layer was washed successively with saturated $NaHCO_3$ aq, HCl aq. (0.5 M, 150 ml) and then with brine (150 ml). Organic layer was concentrated to dryness to yield compound 5a (9.60 g, 48 mmol, 96%) that can be used in the next step without further purification.

Step 2: Preparation of 5-(5-bromo-2-hydroxy-3-methoxybenzylidene)pyrimidine-2,4,6(1H,3H,5H)-trione, 5b In a scintillation vial, a mixture of 5a (0.40 g, 2.0 mmol), barbituric acid (0.256 g, 2.0 mmol), ethanol (7 ml) and water (10 ml) was stirred at room temperature for 2 hours. Subsequently, the reaction mixture was filtered. Solid yellow cake was collected and vacuum dried at 40° C. to 50° C. to yield desired product 5b, (0.558 g, 1.88 mmol, 94%).

Step 3: Preparation of 7-chloro-9-methoxy-2H-chromeno[2,3-d]pyrimidine-2,4(3H)-dione In a scintillation vial, a suspension of compound 5b, (100 mg, 0.5 mmol) in a mixture of acetic acid (4.5 ml) and acetic anhydride (0.5 ml) was stirred and heated to 80° C. for 0.5 hour. The mixture turned homogeneous after 10 minutes at 80° C. Precipitation reoccurred after 20 minutes at 80° C. The reaction was stopped after 30 minutes. The mixture was cooled to room temperature. Yellow solid was filtered, washed with water and vacuum dried at 40° C. to 50° C. to yield compound 5 (58 mg, 0.20 mmol, 40%).

Preparation of 8-methoxy-2H-chromeno[2,3-d]pyrimidine-2,4(3H)-dione

Step 1: Preparation of 5-(2-hydroxy-4-methoxybenzylidene)pyrimidine-2,4,6(1H,3H,5H)-trione, 6a In a scintillation vial, a mixture of 2-hydroxy-4-methoxybenzaldehyde (0.456 g, 3.0 mmol), barbituric acid (0.384 g, 3.0 mmol), ethanol (10 ml) and water (5 ml) was stirred at room temperature for 15 hours. Subsequently, the reaction mixture was filtered. Solid yellow cake was collected and vacuum dried at 40° C. to 50° C. to yield desired product 6a, (0.695 g, 2.65 mmol, 88%).

Step 2: Preparation of 8-methoxy-2H-chromeno[2,3-d]pyrimidine-2,4(3H)-dione

In a scintillation vial, a suspension of compound 6a, (278 mg, 1.0 mmol) in a mixture of acetic acid (4.5 ml) and acetic anhydride (0.5 ml) was stirred and heated to 80° C. for 2 hours. The mixture turned homogeneous after 10 minutes at 80° C. The mixture was cooled to room temperature. Yellow solid was filtered, washed with ethanol and then with water and vacuum dried at 40° C. to 50° C. to yield compound 6 (148 mg, 0.60 mmol, 60%).

Preparation of 7-chloro-9-methoxy-2-thioxo-2H-chromeno[2,3-d]pyrimidin-4(3H)-one Step 1: Preparation of 5-(5-chloro-2-hydroxy-3-methoxybenzylidene)-2-thioxodihydropyrimidine-4,6(1H,5H)-dione, 7a In a scintillation vial, a mixture of 5-chloro-2-hydroxy-3-methoxybenzaldehyde (0.374 g, 2.0 mmol), 2-thiobarbituric acid (0.288 g, 3.0 mmol), ethanol (15 ml) and water (5 ml) was stirred at room temperature for 15 hours. Subsequently, the reaction mixture was filtered. Solid orange cake was collected and vacuum dried at 40° C. to 50° C. to yield desired product 7a, (0.47 g, 1.5 mmol, 75%).

Step 2: Preparation of 7-chloro-9-methoxy-2-thioxo-2H-chromeno[2,3-d]pyrimidin-4(3H)-one In a scintillation vial, a suspension of compound 7a, (158 mg, 0.5 mmol) in a mixture of acetic acid (4.5 ml) and acetic anhydride (0.5 ml) was stirred and heated to 80° C. for 2 hours. The mixture was cooled to room temperature. Red solid was filtered, washed with ethanol and then with water and vacuum dried at 40° C. to 50° C. to yield compound 7 (62 mg, 0.21 mmol, 42%).

Preparation of 8-methoxy-2-thioxo-2H-chromeno[2,3-d]pyrimidin-4(3H)-one

Step 1: Preparation of 5-(2-hydroxy-4-methoxybenzylidene)-2-thioxodihydropyrimidine-4,6(1H,5H)-dione, 8a In a scintillation vial, a mixture of 2-hydroxy-4-methoxybenzaldehyde (0.456 g, 3.0 mmol), 2-thiobarbituric acid (0.288 g, 3.0 mmol), ethanol (10 ml) and water (5 ml) was stirred at room temperature for 2 hours. Subsequently, the reaction mixture was filtered. Solid yellow cake was collected and vacuum dried at 40° C. to 50° C. to yield desired product 8a, (0.761 g, 2.73 mmol, 91%).

Step 2: Preparation of 8-methoxy-2-thioxo-2H-chromeno[2,3-d]pyrimidin-4(3H)-one In a scintillation vial, a suspension of compound 8a, (150 mg, 0.54 mmol) in a mixture of acetic acid (4.5 ml) and acetic anhydride (0.5 ml) was stirred and heated to 80° C. for 2 hours. The mixture was cooled to room temperature. Red solid was filtered, and re-suspended in saturated aqueous solution of NaHCO3 for 1 hour. Red solid was filtered again, washed with water and vacuum dried at 40° C. to 50° C. to yield compound 8 (84 mg, 0.32 mmol, 60%).

Preparation of 2H-chromeno[2,3-d]pyrimidine-2,4(3H)-dione

Step 1: Preparation of 5-(2-hydroxybenzylidene)pyrimidine-2,4,6(1H,3H,5H)-trione, 9a In a scintillation vial, a mixture of salicylaldehyde (0.122 g, 1.0 mmol), barbituric acid (0.128 g, 1.0 mmol) and water (10 ml) was stirred at room temperature for 1 hour. Subsequently, the reaction mixture was filtered. Solid yellow cake was collected and vacuum dried at 40° C. to 50° C. to yield desired product 9a, (0.761 g, 2.73 mmol, 91%).

Step 2: Preparation of 2H-chromeno[2,3-d]pyrimidine-2,4(3H)-dione

In a scintillation vial, a suspension of compound 9a, (116 mg, 0.5 mmol) in a mixture of acetic acid (4.5 ml) and acetic anhydride (0.5 ml) was stirred and heated to 80° C. for 2 hours. The mixture was cooled to room temperature. Yellow solid was filtered, washed with water and vacuum dried at 40° C. to 50° C. to yield compound 9 (43 mg, 0.20 mmol, 40%).

Preparation of 7-methoxy-2H-chromeno[2,3-d]pyrimidine-2,4(3H)-dione

Step 1: Preparation of 5-(2-hydroxy-5-methoxybenzylidene)pyrimidine-2,4,6(1H,3H,5H)-trione, 10a In a scintillation vial, a mixture of 2-hydroxy-5-methoxybenzaldehyde (0.304 g, 2.0 mmol), barbituric acid (0.256 g, 2.0 mmol) and water (10 ml) was stirred at room temperature for 3 hours. Subsequently, the reaction mixture was filtered. Solid red cake was collected and vacuum dried at 40° C. to 50° C. to yield desired product 10a, (0.42 g, 1.60 mmol, 80%).

Step 2: Preparation of 7-methoxy-2H-chromeno[2,3-d]pyrimidine-2,4(3H)-dione

In a scintillation vial, a suspension of compound 10a, (131 mg, 0.5 mmol) in a mixture of acetic acid (4.5 ml) and acetic anhydride (0.5 ml) was stirred and heated to 80° C. for 3 hours. The mixture was cooled to room temperature. Yellow solid was filtered, washed with water and vacuum dried at 40° C. to 50° C. to yield compound 10 (110 mg, 0.20 mmol, 90%).

Preparation of 8-hydroxy-2H-chromeno[2,3-d]pyrimidine-2,4(3H)-dione

Step 1: Preparation of 5-(2,4-dihydroxybenzylidene)pyrimidine-2,4,6(1H,3H,5H)-trione, 11a In a scintillation vial, a mixture of 2,4-dihydroxybenzaldehyde (0.276 g, 2.0 mmol), barbituric acid (0.256 g, 2.0 mmol) and ethanol (8 ml) was stirred at room temperature for 15 hours. Subsequently, the reaction mixture was filtered. Solid orange cake was collected and vacuum dried at 40° C. to 50° C. to yield desired product 1a, (0.447 g, 1.8 mmol, 90%).

Step 2: Preparation of 8-hydroxy-2H-chromeno[2,3-d]pyrimidine-2,4(3H)-dione

In a scintillation vial, a suspension of compound 11a, (124 mg, 0.5 mmol) in a mixture of acetic acid (3 ml) and acetic anhydride (1 ml) was stirred and heated to 80° C. for 18 hours. The mixture was cooled to room temperature and stirred overnight. Yellow solid was filtered, washed with water and vacuum dried at 40° C. to 50° C. to yield compound 11 (85 mg, 0.37 mmol, 74%).

Preparation of 8-methyl-2H-chromeno[2,3-d]pyrimidine-2,4(3H)-dione

Step 1: Preparation of 5-(2-hydroxy-4-methylbenzylidene)pyrimidine-2,4,6(1H,3H,5H)-trione, 12a In a scintillation vial, a mixture of 2-hydroxy-4-methylbenzaldehyde (0.272 g, 2.0 mmol), barbituric acid (0.256 g, 2.0 mmol) and water (10 ml) was stirred at room temperature for 3 hours. Subsequently, ethyl acetate (5 ml) was added to the reaction mixture to wash unreacted 2-hydroxy-4-methylbenzaldehyde. The reaction mixture was filtered. Solid yellow cake was collected and vacuum dried at 40° C. to 50° C. to yield desired product 12a, (0.461 g, 1.87 mmol, 94%).

Step 2: Preparation of 8-methyl-2H-chromeno[2,3-d]pyrimidine-2,4(3H)-dione

In a scintillation vial, a suspension of compound 12a, (123 mg, 0.5 mmol) in a mixture of acetic acid (2.5 ml) and acetic anhydride (0.25 ml) was stirred and heated to 80° C. for 5 hours. The mixture was cooled to room temperature and stirred overnight. Yellow solid was filtered, washed with water and vacuum dried at 40° C. to 50° C. to yield compound 12 (100 mg, 0.44 mmol, 88%).

Preparation of 8-ethoxy-2H-chromeno[2,3-d]pyrimidine-2,4(3H)-dione

Step 1: Preparation of 4-ethoxy-2-hydroxybenzaldehyde, 13a

A suspension of 2,4-dihydroxybenzaldehyde (3.04 g, 20 mmol), ethyl bromide (2.29 g, 21 mmol), potassium carbonate (2.90 g, 21 mmol), NaI (2.98 g, 20 mmol) and 18-crown-6 (0.528 g, 2 mmol) in acetone (15 ml) was stirred and heated to 70° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-ethoxy-2-hydroxybenzaldehyde (3.01 g, 18.1 mmol, 90%) and 2,4-diethoxybenzaldehyde (0.134 g, 0.7 mmol, 3.4%).

Step 2: Preparation of 5-(4-ethoxy-2-hydroxybenzylidene)pyrimidine-2,4,6(1H,3H,5H)-trione, 13b In a scintillation vial, a mixture of 2-hydroxy-4-ethoxybenzaldehyde (0.498 g, 3.0 mmol), barbituric acid (0.384 g, 3.0 mmol) and water (10 ml) was stirred at room temperature for 2 hours. The reaction mixture was filtered. Solid yellow cake was collected and vacuum dried at 40° C. to 50° C. to yield desired product 13b, (0.68 g, 2.46 mmol, 82%).

Step 3: Preparation of 8-ethoxy-2H-chromeno[2,3-d]pyrimidine-2,4(3H)-dione

In a scintillation vial, a suspension of compound 13b, (276 mg, 1.0 mmol) in a mixture of acetic acid (5.0 g) and acetic anhydride (0.612 g, 6 mmol) was stirred and heated to 80° C. for 3 hours. Yellow solid was filtered, washed with water and vacuum dried at 40° C. to 50° C. to yield compound 13 (177 mg, 0.68 mmol, 68%).

Preparation of 6,8-dimethoxy-2H-chromeno[2,3-d]pyrimidine-2,4(3H)-dione

Step 1: Preparation of 2,4,6-trimethoxybenzaldehyde, 14a

In a round bottom flask, POCl3 (7.3 ml, 80 mmol) was added to a mixture of 1,3,5-trimethoxybenzene (8.41 g, 50 mmol) in DMF (15 ml). The temperature of reaction mixture was kept below 30° C. by slowly adding POCl3. After addition of POCl3, the mixture was still stirred at room temperature for an addition 1 hour. The reaction mixture was added into a cold saturated NaHCO3 solution. The pH of the solution was adjusted to remain above 7. Precipitation of desired product occurred. The off-white product was filtered and rinsed with NaHCO3 aq., then with HCl aq. 0.5M and then with water. Off-white solid was collected and vacuum dried at room temperature to yield 14a (9.60 g, 48 mmol, 98%).

Step 2: 2-hydroxy-4,6-dimethoxybenzaldehyde, 14b

A solution of 14a (5.88 g, 30 mmol) in dichloromethane (40 ml) in a round bottom flask was cooled to 0° C. (ice+brine bath). To the solution was added BCl3 (45 ml of 1M solution in hexane, 45 mmol). The reaction mixture was allowed to slowly warm to room temperature over 1 hour. After 1.5 hour of reaction, TLC analysis indicated that trace amount of starting material remained. An additional $BCl_3$ (10 ml of 1M solution in hexane, 10 mmol) was added into the mixture. The mixture was stirred at room temperature for an additional 1 hour. Subsequently, the reaction mixture was quenched with HCl aq. 1M (100 ml). The mixture was extracted with ethyl acetate. The organic layer was successively washed with HCl aq. 1M and brine, and then dried over $Mg_2SO_4$. The organic layer was concentrated and chromatographed to yield 14b (5.44 g, 29.8 mmol, 99%).

Step 3: Preparation of 5-(2-hydroxy-4,6-dimethoxybenzylidene)pyrimidine-2,4,6(1H,3H,5H)-trione, 14c In a scintillation vial, a mixture of 4,6-dimethoxysalicylaldehyde (0.364 g, 2.0 mmol), barbituric acid (0.256 g, 2.0 mmol) and water (10 ml) was stirred at room temperature for 4.5 hours. The reaction mixture was filtered. Solid orange cake was collected and vacuum dried at 40° C. to 50° C. to yield a mixture containing 4,6-dimethoxysalicylaldehyde, 5-(2-hydroxy-4,6-dimethoxybenzylidene)pyrimidine-2,4,6(1H,3H,5H)-trione and 5-(6,8-dimethoxy-2,4-dioxo-2,3,4,5-tetrahydro-1H-chromeno[2,3-d]pyrimidin-5-yl)pyrimidine-2,4,6(1H,3H,5H)-trione. The mixture was purified by (1) washed with hot ethyl acetate to remove 4,6-dimethoxysalicylaldehyde; (2) re suspended solid obtained after ethyl acetate wash in NaHCO3 aq. The suspension was filtered to obtain a yellow cake. The yellow cake was vacuum dried at 40° C. to 50° C. to yield desired product 14c, (56 mg, 0.19 mmol, 9.6%).

Step 4: Preparation of 6,8-dimethoxy-2H-chromeno[2,3-d]pyrimidine-2,4(3H)-dione

In a scintillation vial, a suspension of compound 14c, (56 mg, 0.19 mmol) in a mixture of acetic acid (2 ml) and acetic anhydride (0.2 ml) was stirred and heated to 80° C. for 5 hours. Yellow solid was filtered, washed with water and vacuum dried at 40° C. to 50° C. to yield compound 14 (35 mg, 0.13 mmol, 67%).

Preparation of 7-methoxy-2-thioxo-2H-chromeno[2,3-d]pyrimidin-4(3H)-one

Step 1: Preparation of 5-(2-hydroxy-5-methoxybenzylidene)-2-thioxodihydropyrimidine-4,6(1H,5H)-dione, 15a In a scintillation vial, a mixture of 2-hydroxy-5-methoxybenzaldehyde (0.456 g, 3.0 mmol), 2-thiobarbituric acid (0.432 g, 2.0 mmol), ethanol (10 ml) and water (5 ml) was stirred at room temperature for 15 hours. Subsequently, the reaction mixture was filtered. Solid red cake was collected and vacuum dried at 40° C. to 50° C. to yield desired product 15a, (0.716 g, 2.57 mmol, 86%).

Step 2: Preparation of 7-methoxy-2-thioxo-2H-chromeno[2,3-d]pyrimidin-4(3H)-one

In a scintillation vial, a suspension of compound 15a, (139 mg, 0.5 mmol) in a mixture of acetic acid (4.5 ml) and acetic anhydride (0.5 ml) was stirred and heated to 80° C. for 4 hours. The mixture was cooled to room temperature. Bordeaux red solid was filtered, washed with water and vacuum dried at 40° C. to 50° C. to yield compound 15 (85 mg, 0.33 mmol, 65%).

Preparation of 8-hydroxy-2-thioxo-2H-chromeno[2,3-d]pyrimidin-4(3H)-one

Step 1: Preparation of 5-(2,4-dihydroxybenzylidene)-2-thioxodihydropyrimidine-4,6(1H,5H)-dione, 16a In a scintillation vial, a mixture of 2,4-dihydroxybenzaldehyde (0.414 g, 3.0 mmol), 2-thiobarbituric acid (0.432 g, 2.0 mmol), ethanol (10 ml) and water (5 ml) was stirred at room temperature for 5 hours. Subsequently, the reaction mixture was filtered. Solid red cake was collected and vacuum dried at 40° C. to 50° C. to yield desired product 16a, (0.697 g, 2.60 mmol, 88%).

Step 2: Preparation of 8-hydroxy-2-thioxo-2H-chromeno[2,3-d]pyrimidin-4(3H)-one In a scintillation vial, a suspension of compound 16a, (132 mg, 0.5 mmol) in a mixture of acetic acid (4.5 ml) and acetic anhydride (0.5 ml) was stirred and heated to 80° C. for 4 hours. The mixture was cooled to room temperature. Orange solid was filtered, washed with water and vacuum dried at 40° C. to 50° C. to yield compound 16 (115 mg, 0.47 mmol, 93%).

Preparation of 8-methyl-2-thioxo-2H-chromeno[2,3-d]pyrimidin-4(3H)-one

Step 1: Preparation of 5-(2-hydroxy-4-methylbenzylidene)-2-thioxodihydropyrimidine-4,6(1H,5H)-dione, 17a In a scintillation vial, a mixture of 2-hydroxy-4-methoxybenzaldehyde (0.272 g, 3.0 mmol), 2-thiobarbituric acid (0.288 g, 2.0 mmol), and water (10 ml) was stirred at room temperature for 13 hours. Ethyl acetate (5 ml) was added to the reaction mixture to wash unreacted 2-hydroxy-4-methoxybenzaldehyde. Subsequently, the reaction mixture was filtered. Solid yellow cake was collected and vacuum dried at 40° C. to 50° C. to yield desired product 17a, (0.437 g, 1.67 mmol, 83%).

Step 2: Preparation of 8-methyl-2-thioxo-2H-chromeno[2,3-d]pyrimidin-4(3H)-one In a scintillation vial, a suspension of compound 17a, (131 mg, 0.5 mmol) in a mixture of acetic acid (2.5 ml) and acetic anhydride (0.25 ml) was stirred and heated to 80° C. for 7 hours. The mixture was cooled to room temperature. Yellow solid was filtered, washed with NaHCO3 aq., then with water and vacuum dried at 40° C. to 50° C. to yield compound 17 (33 mg, 0.13 mmol, 27%).

Preparation of 6,8-dimethoxy-2-thioxo-2H-chromeno[2,3-d]pyrimidin-4(3H)-one

Step 1, Preparation of 5-(2-hydroxy-4,6-dimethoxybenzylidene)-2-thioxodihydropyrimidine-4,6(1H,5H)-dione, 18a In a scintillation vial, a mixture of 4,6-dimethoxysalicylaldehyde (0.364 g, 2.0 mmol), 2-thiobarbituric acid (0.288 g, 2.0 mmol) and water (15 ml) was stirred and warmed to 50° C. for 30 minutes. The mixture was cooled to room temperature for 15 hours. The reaction mixture was filtered. Solid orange cake was collected and re-suspended in ethyl acetate (20 ml). The suspension was filtered to remove ethyl acetate and unreacted 4,6-dimethoxysalicylaldehyde. The solid orange from ethyl acetate was again re-suspended in saturated NaHCO3 aq. The suspension was filtered and washed with water. The solid orange from saturated NaHCO3 aq. suspension was vacuum dried at 40° C. to 50° C. to yield compound 18a, (0.202 g, 0.65 mmol, 33%).

Step 2: Preparation of 6,8-dimethoxy-2-thioxo-2H-chromeno[2,3-d]pyrimidin-4(3H)-one In a scintillation vial, a suspension of compound 18a, (154 mg, 0.5 mmol) in a mixture of acetic acid (2.7 ml) and acetic anhydride (0.3 ml) was stirred and heated to 80° C. for 4 hours. The mixture was cooled to room temperature. Red solid was filtered, washed with water and vacuum dried at 40° C. to 50° C. to yield compound 18 (85 mg, 0.29 mmol, 58%).

Preparation of 8-propoxy-2H-chromeno[2,3-d]pyrimidine-2,4(3H)-dione

Step 1: Preparation of 4-n-Propoxy-2-hydroxybenzaldehyde, 19a

A suspension of 2,4-dihydroxybenzaldehyde (0.76 g, 5.5 mmol), 1-iodopropane (1.02 g, 6 mmol), potassium carbonate (7.60 g, 5.5 mmol), and 18-crown-6 (0.132 g, 0.5 mmol) in acetone (12 ml) was stirred and heated to 65° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-n-Propoxy-2-hydroxybenzaldehyde, 19a (0.747 g, 3.85 mmol, 77%).

Step 2: Preparation of 5-(2-hydroxy-4-propoxybenzylidene)pyrimidine-2,4,6(1H,3H,5H)-trione, 19b In a round bottom flask, a mixture of 19a (0.66 g, 4.0 mmol), barbituric acid (0.512 g, 4.0 mmol), ethanol (15 ml) and water (20 ml) was stirred at room temperature for 15 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 19b, (0.777 g, 2.68 mmol, 67%).

Step 3: Preparation of 8-propoxy-2H-chromeno[2,3-d]pyrimidine-2,4(3H)-dione In a scintillation vial, a suspension of compound 19b, (145 mg, 0.5 mmol) in a mixture of acetic acid (2.5 g) and acetic anhydride (0.31 g, 3 mmol) was stirred and heated to 80° C. for 15 hours. The mixture was cooled to room temperature. Yellow solid was filtered, washed with water and vacuum dried at 40° C. to 50° C. to yield compound 19 (42 mg, 0.15 mmol, 30%).

Preparation of 7-chloro-8-propoxy-2H-chromeno[2,3-d]pyrimidine-2,4(3H)-dione

Step 1: Preparation of 5-chloro-2,4-dihydroxybenzaldehyde

In a scintillation vial, 2,4-dihydroxybenzaldehyde (1.38 g, 10 mmol) was dissolved in ethyl ether (18 ml). The mixture was placed under N2 atmosphere and cooled to 0° C. To the mixture was added sulfuryl chloride (0.91 ml, 11 mmol). The mixture was kept under N2 atmosphere at 0° C. for 30 minutes. The reaction mixture was poured into ice water and extracted with ethyl acetate (20 ml). Organic layer was washed with brine, concentrated and chromatographed to yield 5-chloro-2,4-dihydroxybenzaldehyde (0.55 g, 3.2 mmol, 32%) and 3-chloro-2,4-dihydroxybenzaldehyde (0.233 g, 1.34 mmol, 13.4%)

Step 2: Preparation of 5-chloro-2-hydroxy-4-propoxybenzaldehyde

A suspension of 5-chloro-2,4-dihydroxybenzaldehyde (0.517 g, 3.0 mmol), 1-iodopropane (0.501 g, 3 mmol), potassium carbonate (0.414 g, 3.0 mmol), and 18-crown-6 (0.079 g, 0.3 mmol) in acetone (10 ml) was stirred and heated to 70° C. for 15 hours. The mixture was cooled to room temperature and quenched with HCl, aq. 1M. The mixture was extracted with ethyl acetate (30 ml). Organic layer was washed with saturated NaHCO3 aq. (30 ml), water (30 ml) and then with brine (30 ml). Organic layer was dried over MgSO4, concentrated and chromatographed to yield 5-chloro-2-hydroxy-4-propoxybenzaldehyde (0.41 g, 1.91 mmol, 63%).

Step 3: Preparation of 5-(5-chloro-2-hydroxy-4-propoxybenzylidene)pyrimidine-2,4,6(1H,3H,5H)-trione, 20a In a round bottom flask, a mixture of 5-chloro-2-hydroxy-4-propoxybenzaldehyde (0.41 g, 1.91 mmol), barbituric acid (0.256 g, 2.0 mmol), ethanol (15 ml) and water (10 ml) was stirred at room temperature for 5 hours. The reaction mixture was concentrated to reduce volume by 30% by evaporation. After ethanol evaporation, water (20 ml) was added to the reaction mixture. The reaction was stirred at room temperature for 30 minutes and then filtered. Solid yellow cake was collected and vacuum dried at 40° C. to 50° C. to yield compound 20a, (0.59 g, 1.82 mmol, 95%).

Step 4: Preparation of 7-chloro-8-propoxy-2H-chromeno[2,3-d]pyrimidine-2,4(3H)-dione In a scintillation vial, a suspension of compound 20a, (162 mg, 0.5 mmol) in a mixture of acetic acid (2.5 g) and acetic anhydride (0.31 g, 3 mmol) was stirred and heated to 80° C. for 6 hours. The mixture was cooled to room temperature. Yellow solid was filtered, washed with water and vacuum dried at 40° C. to 50° C. to yield compound 20 (126 mg, 0.40 mmol, 80%).

Preparation of 8-(n-hexyloxy)-2H-chromeno[2,3-d]pyrimidine-2,4(3H)-dione

Step 1: Preparation of 4-(n-hexyloxy)-2-hydroxybenzaldehyde

A suspension of 2,4-dihydroxybenzaldehyde (0.828 g, 6.0 mmol), 1-iodohexane (1.40 g, 6.6 mmol), potassium carbonate (0.497 g, 3.6 mmol), and 18-crown-6 (0.158 g, 0.6 mmol) in acetone (15 ml) was stirred and heated to 70° C. for 15 hours. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 4-(n-hexyloxy)-2-hydroxybenzaldehyde (0.973 g, 4.38 mmol, 73%).

Step 2: Preparation of 5-(4-(n-hexyloxy)-2-hydroxybenzylidene)pyrimidine-2,4,6(1H,3H,5H)-trione, 21a In a round bottom flask, a mixture of 4-(n-hexyloxy)-2-hydroxybenzaldehyde (0.444 g, 2.0 mmol), barbituric acid (0.256 g, 2.0 mmol), ethanol (15 ml) and water (15 ml) was stirred at room temperature for 3 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 21a, (0.564 g, 1.70 mmol, 85%).

Step 3: Preparation of 8-(n-hexyloxy)-2H-chromeno[2,3-d]pyrimidine-2,4(3H)-dione In a scintillation vial, a suspension of compound 21a, (332 mg, 1.0 mmol) in a mixture of acetic acid (3.0 g) and acetic anhydride (0.51 g, 5 mmol) was stirred and heated to 80° C. for 5 hours. The mixture was cooled to room temperature. Yellow solid was filtered, washed with water and vacuum dried at 40° C. to 50° C. to yield compound 21 (148 mg, 0.46 mmol, 46%).

Preparation of 9-chloro-8-ethoxy-2H-chromeno[2,3-d]pyrimidine-2,4(3H)-dione

Step 1: Preparation of 3-chloro-2,4-dihydroxybenzaldehyde

In a scintillation vial, 2,4-dihydroxybenzaldehyde (1.38 g, 10 mmol) was dissolved in ethyl ether (18 ml). The mixture was placed under N2 atmosphere and cooled to 0° C. To the mixture was added sulfuryl chloride (0.91 ml, 11 mmol). The mixture was kept under N2 atmosphere at 0° C. for 30 minutes. The reaction mixture was poured into ice water and extracted with ethyl acetate (20 ml). Organic layer was washed with brine, concentrated and chromatographed to yield 5-chloro-2,4-dihydroxybenzaldehyde (0.55 g, 3.2 mmol, 32%) and 3-chloro-2,4-dihydroxybenzaldehyde (0.233 g, 1.34 mmol, 13.4%)

Step 2: Preparation of 3-chloro-2-hydroxy-4-ethoxybenzaldehyde

A suspension of 3-chloro-2,4-dihydroxybenzaldehyde (0.465 g, 2.7 mmol), iodoethane (0.421 g, 2.7 mmol), potassium carbonate (0.226 g, 1.62 mmol), and 18-crown-6 (0.071 g, 0.27 mmol) in acetone (10 ml) was stirred and heated to 70° C. for 15 hours. The mixture was cooled to room temperature and quenched with HCl, aq. 1M. The mixture was extracted with ethyl acetate (30 ml). Organic layer was washed with saturated NaHCO3 aq. (30 ml), water (30 ml) and then with brine (30 ml). Organic layer was dried over MgSO4, concentrated and chromatographed to yield 3-chloro-2-hydroxy-4-ethoxybenzaldehyde (0.217 g, 1.08 mmol, 40%) and 3-chloro-2,4-diethoxybenzaldehyde (0.057 g, 0.25 mmol, 9.4%).

Step 3: Preparation of 5-(3-chloro-4-ethoxy-2-hydroxybenzylidene)pyrimidine-2,4,6(1H,3H,5H)-trione, 22a In a round bottom flask, a mixture of 3-chloro-2-hydroxy-4-ethoxybenzaldehyde (0.217 g, 1.08 mmol), barbituric acid (0.139 g, 1.08 mmol), ethanol (10 ml) and water (10 ml) was stirred at room temperature for 10 hours. The reaction mixture was concentrated to reduce volume by 30% by evaporation. After ethanol evaporation, water (20 ml) was added to the reaction mixture. The reaction was stirred at room temperature for 30 minutes and then filtered. Solid yellow cake was collected and vacuum dried at 40° C. to 50° C. to yield compound 22a, (0.30 g, 0.97 mmol, 90%).

Step 4: Preparation of 9-chloro-8-ethoxy-2H-chromeno[2,3-d]pyrimidine-2,4(3H)-dione In a scintillation vial, a suspension of compound 22a, (155 mg, 0.5 mmol) in a mixture of acetic acid (1.5 g) and acetic anhydride (0.306 g, 3 mmol) was stirred and heated to 80° C. for 16 hours. The mixture was cooled to room temperature. Yellow solid was filtered, washed with water and vacuum dried at 40° C. to 50° C. to yield compound 22 (127 mg, 0.40 mmol, 80%).

Preparation of 8-isobutoxy-2H-chromeno[2,3-d]pyrimidine-2,4(3H)-dione

Step 1: Preparation of 2-hydroxy-4-isobutoxybenzaldehyde

A suspension of 2,4-dihydroxybenzaldehyde (0.76 g, 5.5 mmol), 1-iodo-2-methylpropane (1.196 g, 6.5 mmol), potassium carbonate (0.828 g, 6.0 mmol), and 18-crown-6 (0.132 g, 0.5 mmol) in acetone (10 ml) was stirred and heated to 70° C. for 3 days. The mixture was cooled to room temperature and quenched with HCl, aq. 1M. The mixture was extracted with ethyl acetate (50 ml). Organic layer was washed with water (50 ml) twice and then with brine (50 ml). Organic layer was dried over MgSO4, concentrated and chromatographed to yield 2-hydroxy-4-isobutoxybenzaldehyde (0.425 g, 2.2 mmol, 40%).

Step 2: Preparation of 5-(2-hydroxy-4-isobutoxybenzylidene)pyrimidine-2,4,6(1H,3H,5H)-trione, 23a In a round bottom flask, a mixture of 2-hydroxy-4-isobutoxybenzaldehyde (0.388 g, 2.0 mmol), barbituric acid (0.256 g, 2.0 mmol), ethanol (5 ml) and water (10 ml) was stirred at room temperature for 5 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected and vacuum dried at 40° C. to 50° C. to yield compound 23a, (0.563 g, 1.85 mmol, 92%).

Step 3: Preparation of 8-isobutoxy-2H-chromeno[2,3-d]pyrimidine-2,4(3H)-dione

In a scintillation vial, a suspension of compound 23a, (152 mg, 0.5 mmol) in a mixture of acetic acid (1.5 g) and acetic anhydride (0.31 g, 3 mmol) was stirred and heated to 80° C. for 6 hours. The mixture was cooled to room temperature. Yellow solid was filtered, and chromatographed (MeOH:DCM, 5:95) to yield compound 23 (17 mg, 0.06 mmol, 12%).

Preparation of 3-(n-butyl)-8-ethoxy-2H-chromeno[2,3-d]pyrimidine-2,4(3H)-dione

Step 1: Preparation of 1-butylpyrimidine-2,4,6(1H,3H,5H)-trione

In a round bottom flask, dimethyl malonate (6.60 g, 50 mmol) was added to a mixture of n-Butyl urea (5.80 g, 50 mmol) and sodium ethoxide (21% in ethanol, 19.43 g, 60 mmol). Upon the addition of dimethyl malonate, the reaction mixture was placed under nitrogen and heated to reflux. After 1 hour at reflux, the reaction mixture turned a viscous suspension. Ethanol (15 ml) was added into the mixture. The mixture was stirred at reflux for a total reaction time of 18 hours. At the end of the reaction, solid was filtered (crop 1). Filtrate was collected and concentrated to cause precipitation. The second crop of solid was filtered. Combined solid crop 1 and crop 2 was dissolved in water (100 ml) and acidified with HCl, aq. 1M to cause precipitation of desired product. Filtrate residue from crop 2 was concentrate and chromatographed to yield desired product. Combined desired product (7.103 g, 38 mmol, 77%) was vacuum dried.

Step 2: Preparation of 1-butyl-5-(4-ethoxy-2-hydroxybenzylidene)pyrimidine-2,4,6(1H,3H,5H)-trione, 24a In a round bottom flask, a mixture of 2-hydroxy-4-ethoxybenzaldehyde (0.498 g, 3.0 mmol), 1-butylpyrimidine-2,4,6(1H,3H,5H)-trione (0.555 g, 5.0 mmol), ethanol (10 ml) and water (10 ml) was stirred at room temperature for 15 hours. The reaction mixture was concentrated to reduce volume by 30% by evaporation. After ethanol evaporation, water (30 ml) was added to the reaction mixture. The reaction was stirred at room temperature for 30 minutes and then filtered. Solid yellow cake was collected, washed with a mixture of ethyl acetate:hexane (20:80) and vacuum dried at 40° C. to 50° C. to yield compound 24a, (0.7939 g, 1.39 mmol, 80%).

Step 3: Preparation of 3-(n-butyl)-8-ethoxy-2H-chromeno[2,3-d]pyrimidine-2,4(3H)-dione In a scintillation vial, a suspension of compound 24a, (0.498 mg, 0.5 mmol) in a mixture of acetic acid (3.5 g) and acetic anhydride (0.765 g, 7.5 mmol) was stirred and heated to 80° C. for 15 hours. The mixture became homogeneous after 15 minutes at 80° C. The mixture was cooled to room temperature. Yellow solid was filtered, and chromatographed (MeOH:DCM, 5:95) to yield compound 24 (102 mg, 0.32 mmol, 21%).

Preparation of 7-chloro-8-propyl-2H-chromeno[2,3-d]pyrimidine-2,4(3H)-dione

Step 1: Preparation of 4-chloro-3-propylphenol

In a scintillation vial, 3-n-Propylphenol (1.36 g, 10 mmol) was dissolved in ethyl ether (10 ml). The mixture was cooled with ice/brine bath. To the mixture was added sulfuryl chloride (0.91 ml, 11 mmol) over 2 minutes. The mixture remained at −10° C. to 0° C. for an hour. The mixture was quenched with water and extracted with ethyl acetate. The organic layer was concentrated and chromatographed to yield 4-chloro-3-propylphenol (1.156 g, 6.8 mmol, 68%), 2-chloro-3-propylphenol (0.097 g, 0.57 mmol, 5.7%) and 6-chloro-3-propylphenol (0.156 g, 0.92 mmol, 9.2%).

Step 2: Preparation of 5-chloro-2-hydroxy-4-propylbenzaldehyde

In a scintillation vial, a mixture of 4-chloro-3-propylphenol (0.857 g, 5 mmol), magnesium chloride anhydrous (0.712 g, 7.5 mmol), paraformaldehyde (0.90 g, 30 mmol), and triethyl amine (1.01 g, 10 mmol) in acetonitrile anhydrous (10 ml) was heated to 70° C. for 15 hours. The reaction mixture was cooled to room temperature and then filtered. The white cake was washed with HCl aq. 1M (50 ml) and ethyl acetate (80 ml). Filtrate was decanted. Organic layer was separated and washed with brine. Organic layer was concentrate and chromatographed to yield 5-chloro-2-hydroxy-4-propylbenzaldehyde (0.612 g, 3.1 mmol, 61%).

Step 3: Preparation of 5-(5-chloro-2-hydroxy-4-propylbenzylidene)pyrimidine-2,4,6(1H,3H,5H)-trione In a round bottom flask, a mixture of 5-chloro-2-hydroxy-4-propylbenzaldehyde (0.397 g, 2.0 mmol), barbituric acid (0.256 g, 2.0 mmol), ethanol (10 ml) and water (10 ml) was stirred at room temperature for 15 hours. The reaction mixture was concentrated to reduce volume by 30% by evaporation. After ethanol evaporation, water (40 ml) was added to the reaction mixture. The reaction was stirred at room temperature for 30 minutes and then filtered. Solid yellow cake was washed with ethyl acetate:hexane (5:95), collected and vacuum dried at 40° C. to 50° C. to yield compound 25a, (0.41 g, 1.32 mmol, 66%).

Step 4: Preparation of 7-chloro-8-propyl-2H-chromeno[2,3-d]pyrimidine-2,4(3H)-dione In a scintillation vial, a suspension of compound 25a, (0.308 mg, 1.0 mmol) in a mixture of acetic acid (2.5 g) and acetic anhydride (0.612 g, 6.0 mmol) was stirred and heated to 80° C. for 6 hours. The mixture was cooled to room temperature and allowed to sit overnight. Yellow solid was filtered, dried at 40° C. to 50° C. to yield compound 25 (250 mg, 0.86 mmol, 86%).

Preparation of 3-butyl-7-chloro-8-ethoxy-2H-chromeno[2,3-d]pyrimidine-2,4(3H)-dione

Step 1: Preparation of 1-butyl-5-(5-chloro-4-ethoxy-2-hydroxybenzylidene)pyrimidine-2,4,6(1H,3H,5H)-trione, 26a In a round bottom flask, a mixture of 5-chloro-4-ethoxy-2-hydroxybenzaldehyde (0.295 g, 1.475 mmol), barbituric acid (0.192 g, 1.5 mmol), ethanol (20 ml) and water (10 ml) was stirred at room temperature for 3.5 hours. The reaction mixture was concentrated to reduce volume by 30% by evaporation. After ethanol evaporation, water (50 ml) was added to the reaction mixture. The reaction was stirred at room temperature for 30 minutes and then filtered. Solid orange cake was collected and vacuum dried at 40° C. to 50° C. to yield compound 26a, (0.463 g, 1.26 mmol, 85%).

Step 2: Preparation of 3-butyl-7-chloro-8-ethoxy-2H-chromeno[2,3-d]pyrimidine-2,4(3H)-dione, compound 26

In a scintillation vial, a suspension of compound 26a, (0.367 mg, 1.0 mmol) in a mixture of acetic acid (2.5 g) and acetic anhydride (0.51 g, 5.0 mmol) was stirred and heated to 80° C. for 15 hours. The mixture was cooled to room temperature and allowed to sit overnight. Yellow solid was filtered, dried at 40° C. to 50° C. to yield compound 26 (278 mg, 0.80 mmol, 80%).

Preparation of 7-fluoro-8-methyl-2H-chromeno[2,3-d]pyrimidine-2,4(3H)-dione

Step 1: Preparation of 5-fluoro-2-hydroxy-4-methylbenzaldehyde, 27a

In a scintillation vial, a suspension of 4-fluoro-3-methylphenol, (1.26 g, 10.0 mmol), $MgCl_2$ anhydrous (1.42 g, 15 mmol), paraformaldehyde (1.50 g, 50 mmol) and triethylamine (2.02 g, 20 mmol) in acetonitrile anhydrous (15 ml) was stirred and heated to 70° C. for 8 hours. The mixture was cooled to room temperature, quenched with HCl, aq. 1M (20 ml) and extract with ethyl acetate. The organic layer was dried with MgSO4, filtered over silica gel, concentrated and chromatographed to yield compound 27a (1.05 g, 6.8 mmol, 68%).

Step 2: Preparation of 5-(5-fluoro-2-hydroxy-4-methylbenzylidene)pyrimidine-2,4,6(1H,3H,5H)-trione In a round bottom flask, a mixture of 27a (0.308 g, 2.0 mmol), barbituric acid (0.256 g, 2.0 mmol), ethanol (10 ml) and water (10 ml) was stirred at room temperature for 5 hours After 5 hours of reaction, water (50 ml) was added to the reaction mixture. The reaction was stirred at room temperature for 30 minutes and then filtered. Solid yellow cake was collected and vacuum dried at 40° C. to 50° C. to yield compound 27b, (0.3424 g, 1.29 mmol, 65%).

Step 3: Preparation of 7-fluoro-8-methyl-2H-chromeno[2,3-d]pyrimidine-2,4(3H)-dione In a scintillation vial, a suspension of compound 27b, (0.264 mg, 1.0 mmol) in a mixture of acetic acid (4 ml) and acetic anhydride (0.51 g, 5.0 mmol) was stirred and heated to 80° C. for 5 hours. The mixture was cooled to room temperature and allowed to sit overnight. Yellow solid was filtered, dried at 40° C. to 50° C. to yield compound 27 (189 mg, 0.77 mmol, 77%).

Preparation of 8-ethoxy-7-fluoro-2H-chromeno[2,3-d]pyrimidine-2,4(3H)-dione

Step 1: Preparation of 3-ethoxy-4-fluorophenol, 28a

In a scintillation vial, a mixture of 4-fluororesorcinol (0.512 g, 4.0 mmol), K2CO3 (0.607 g, 4.4 mmol), 18-crown-6 (0.106 g, 0.4 mmol), iodoethane (0.686 g, 4.4 mmol) in acetone (5 ml) was heated to 50° C. overnight. The mixture was cooled to room temperature, quenched with HCl aq. 1M (20 ml), extracted with ethyl acetate (30 ml). Organic layer was concentrated and chromatographed to yield 28a (0.349 g, 2.34 mmol, 56%).

Step 2: Preparation of 4-ethoxy-5-fluoro-2-hydroxybenzaldehyde, 28b

In a scintillation vial, a suspension of 28a, (0.68 g, 4.3 mmol), MgCl2 anhydrous (0.613 g, 6.45 mmol), paraformaldehyde (0.774 g, 25.8 mmol) and triethylamine (0.868 g, 8.6 mmol) in acetonitrile anhydrous (10 ml) was stirred and heated to 70° C. for 4 hours. The mixture was cooled to room temperature, quenched with HCl, aq. 1M (20 ml) and extract with ethyl acetate (30 ml). The organic layer was dried with MgSO4, filtered over silica gel, concentrated and chromatographed to yield compound 28b (0.70 g, 3.48 mmol, 81%).

Step 3: Preparation of 5-(4-ethoxy-5-fluoro-2-hydroxybenzylidene)pyrimidine-2,4,6(1H,3H,5H)-trione, 28c In a round bottom flask, a mixture of 28b (0.184 g, 1.0 mmol), barbituric acid (0.128 g, 1.0 mmol), ethanol (10 ml) and water (10 ml) was stirred at room temperature for 6 hours After 6 hours of reaction, water (50 ml) was added to the reaction mixture. The reaction was stirred at room temperature for 30 minutes and then filtered. Solid yellow cake was collected and vacuum dried at 40° C. to 50° C. to yield compound 28c, (0.263 g, 0.89 mmol, 89%).

Step 4: Preparation of 8-ethoxy-7-fluoro-2H-chromeno[2,3-d]pyrimidine-2,4(3H)-dione In a scintillation vial, a suspension of compound 28c, (0.147 mg, 0.5 mmol) in a mixture of acetic acid (2 ml) and acetic anhydride (0.204 g, 2 mmol) was stirred and heated to 80° C. for 4 hours. The mixture was cooled to room temperature and allowed to sit overnight. Yellow solid was filtered, dried at 40° C. to 50° C. to yield compound 28 (130 mg, 0.48 mmol, 96%).

Synthesis of compounds 29 to 36 follow the same protocol described for compound 28.

Synthesis of compounds 37 to 38 follow the same protocol described for compound 20.

Synthesis of compounds 39 to 48 follow the same protocol described for compound 22.

8-ethoxy-2H-thiochromeno[2,3-d]pyrimidine-2,4(3H)-dione

Preparation of 8-ethoxy-2H-thiochromeno[2,3-d]pyrimidine-2,4(3H)-dione

Step 1, Preparation of 2,4-dichloro-6-((3-ethoxyphenyl)thio)pyrimidine-5-carbaldehyde, 49a In a scintillation vial, 2,4,6-trichloropyrimidine carboxaldehyde (0.422 g, 2 mmol) was dissolved in anhydrous THF (5 ml). The mixture was cooled to −30° C. To the cold mixture was added triethyl amine (0.242 g, 2.4 mmol) and 3-ethoxybenzenethiol (0.308 g, 2 mmol). The mixture was maintained at −30° C. for 3 hours. After 3 hours, the mixture was filtered. Cake was rinsed with ethyl ether. Filtrate contains desired product was concentrated. Product was crystallized on siting under nitrogen stream. Yellow pale solid was filtered and dried under vacuum to yield 49a (0.331 g, 1.0 mmol, 50%).

Step 2, Preparation of 8-ethoxy-2H-thiochromeno[2,3-d]pyrimidine-2,4(3H)-dione

In a scintillation vial, compound 49a (0.331 g, 1.0 mmol) was slowly and carefully added to concentrate 98% $H_2SO_4$ (4 ml). The mixture was stirred at room temperature overnight. To the mixture was added EtOAc (25 ml) and water (25 ml). Precipitation occurred. Orange solid was filtered, washed with water and vacuum dried to yield compound 49 (0.137 g, 0.5 mmol, 50%).

Synthesis of compounds 50-52 follow the same protocol described for compound 22.

6-((9-chloro-2,4-dioxo-3,4-dihydro-2H-chromeno[2,3-d]pyrimidin-8-yl)oxy)hexanoic acid Step 1, Preparation of methyl 6-(2-chloro-4-formyl-3-hydroxyphenoxy)hexanoate, 53a In a scintillation vial, a suspension of 3-chloro-2,4-dihydroxybenzaldehyde (0.69 g, 4 mmol), $K_2CO_3$ (0.552 g, 4.0 mmol), 18-crown-6 (0.106 g, 0.4 mmol) and methyl 6-bromohexanoate (0.919 g, 4.4 mmol) in acetone (5 ml) was heated and stirred overnight at 65° C. The reaction mixture was cooled to room temperature, acidified with HCl, aq. 1M and extracted with ethyl acetate (50 ml), twice. Organic layer was washed with water (50 ml) twice and then with brine (50 ml). Organic layer was dried over $MgSO_4$, concentrated and chromatographed to yield compound 53a (0.25 g, 0.83 mmol, 20.7%).

Step 2, Preparation of 6-(2-chloro-4-formyl-3-hydroxyphenoxy)hexanoic acid, 53b

A mixture of compound 53a (0.25 g, 0.83 mmol) in MeOH (3 ml) and NaOH aq. 1M (5 ml) was warmed to 60° C. for 2 hours. The mixture was cooled to room temperature. To the mixture was added HCl, aq. 1M (8 ml) and then extracted with ethyl acetate (20 ml). Organic layer was dried over $MgSO_4$, concentrated and chromatographed to yield compound 53b (0.192 g, 0.67 mmol, 81%).

Step 3, Preparation of 6-(2-chloro-3-hydroxy-4-((2,4,6-trioxotetrahydropyrimidin-5(2H)-ylidene)methyl)phenoxy)hexanoic acid, 53c In a round bottom flask, a mixture of compound 53b (0.192 g, 0.67 mmol), barbituric acid (0.103 g, 0.8 mmol), iPrOH (6 ml) and water (6 ml) was stirred at room temperature for 24 hours. Water (30 ml) was added to the reaction mixture. The reaction was stirred at room temperature for 30 minutes and then filtered. Solid yellow cake was collected and vacuum dried at 40° C. to 50° C. to yield compound 53c, (0.22 g, 0.55 mmol, 83%).

Step 4, Preparation of 6-((9-chloro-2,4-dioxo-3,4-dihydro-2H-chromeno[2,3-d]pyrimidin-8-yl)oxy)hexanoic acid In a scintillation vial, a suspension of compound 53c, (0.22 g, 0.55 mmol) in a mixture of acetic acid (1.62 g) and acetic anhydride (0.283 g) was stirred and heated to 80° C. for 2 days. The mixture was cooled to room temperature and sit for 3 hours. Yellow solid was filtered, washed with water and vacuum dried at 40° C. to 50° C. to yield compound 53 (161 mg, 0.43 mmol, 78%).

Synthesis of compounds 54-59 follow the same protocol described for compound 53.

4-((9-chloro-2,4-dioxo-3,4-dihydro-2H-chromeno[2,3-d]pyrimidin-8-yl)oxy)butyl acetate Step 1, 6-(2-chloro-4-formyl-3-hydroxyphenoxy)butyl acetate, 60a In scintillation vial, a suspension of 3-chloro-2,4-dihydroxybenzaldehyde (0.5175 g, 3 mmol), $KHCO_3$ (0.49 g, 4.9 mmol), NaI (0.45 g, 3 mmol), 18-crown-6 (0.132 g, 0.5 mmol) and methyl 6-bromobutnoate (0.585 g, 3.0 mmol) in acetone (5 ml) was heated and stirred for 4 days at 70° C. The reaction mixture was cooled to room temperature, acidified with HCl, aq. 1M and extracted with ethyl acetate (25 ml). Organic layer was washed with water (25 ml) and then with brine (25 ml). Organic layer was dried over $MgSO_4$, concentrated and chromatographed to yield compound 60a (0.182 g, 0.64 mmol, 21.2%).

Step 2, Preparation of 4-(2-chloro-3-hydroxy-4-((2, 4,6-trioxotetrahydropyrimidin-5(2H)-ylidene) methyl)phenoxy)butyl acetate, 60b In a scintillation vial, a mixture of compound 60a (0.182 g, 0.64 mmol), barbituric acid (0.089 g, 0.7 mmol), iPrOH (3 ml) and water (3 ml) was stirred at room temperature for 24 hours. Water (10 ml) was added to the reaction mixture. The reaction was stirred at room temperature for 10 minutes and then filtered. Solid yellow cake was collected and vacuum dried at 40° C. to 50° C. to yield compound 60b, (0.209 g, 0.53 mmol, 82%).

Step 3, Preparation of 4-((9-chloro-2,4-dioxo-3,4-dihydro-2H-chromeno[2,3-d]pyrimidin-8-yl)oxy) butyl acetate In a scintillation vial, a suspension of compound 60b, (0.209 g, 0.55 mmol) in a mixture of acetic acid (1.65 g) and acetic anhydride (0.281 g) was stirred and heated to 80° C. for 4.5 hours. The mixture was cooled to room temperature and sit for 3 hours. Yellow solid was filtered, dried at 40° C. to 50° C. to yield compound 60 (108 mg, 0.28 mmol, 52%).

8-(2-(2-methoxyethoxy)ethoxy)-2H-chromeno[2,3-d]pyrimidine-2,4(3H)-dione

Step 1, Preparation of 2-hydroxy-4-(2-(2-methoxyethoxy)ethoxy)benzaldehyde, 61a

In a scintillation vial, a suspension of 2,4-dihydroxybenzaldehyde (0.552 g, 4 mmol), K$_2$CO$_3$ (0.552 g, 4.0 mmol), 18-crown-6 (0.106 g, 0.4 mmol) and 1-bromo-2-(2-methoxyethoxy) ethane (90-95% purity, 0.61 g, 3.0 mmol) in acetone (5 ml) was heated and stirred overnight at 80° C. The reaction mixture was cooled to room temperature, acidified with HCl, aq. 1M and extracted with ethyl acetate (25 ml). Organic layer was washed with water (25 ml) and then with brine (25 ml). Organic layer was dried over MgSO$_4$, concentrated and chromatographed to yield compound 61a (0.35 g, 1.46 mmol, 36.4%).

Step 2, Preparation of 5-(2-hydroxy-4-(2-(2-methoxyethoxy)ethoxy)benzylidene)pyrimidine-2,4, 6(1H,3H,5H)-trione, 61b In a scintillation vial, a mixture of compound 61a (0.35 g, 1.46 mmol), barbituric acid (0.224 g, 1.75 mmol), ethanol (10 ml) and water (10 ml) was stirred and warmed to 40 to 50° C. for 15 minutes and them stirred at room temperature overnight. Water (30 ml) was added to the reaction mixture. The reaction was stirred at room temperature for 15 minutes and then filtered. Solid yellow cake was collected and vacuum dried at 40° C. to 50° C. to yield compound 61b, (0.434 g, 1.24 mmol, 85%).

Step 3, Preparation of 8-(2-(2-methoxyethoxy) ethoxy)-2H-chromeno[2,3-d]pyrimidine-2,4(3H)-dione In a scintillation vial, a suspension of compound 61b, (0.263 g, 0.75 mmol) in a mixture of acetic acid (2.25 g) and acetic anhydride (0.383 g) was stirred and heated to 80° C. for 6 hours. The mixture was concentrated to remove ~50% of its volume and then cooled to room temperature and sit for 3 hours. Yellow solid was filtered, dried at 40° C. to 50° C. to yield compound 61 (189 mg, 0.57 mmol, 76%).

Synthesis of compounds of example 62-65 follow the same protocol described for compound 61.

9-chloro-8-(4-methoxybutoxy)-2H-chromeno[2,3-d] pyrimidine-2,4(3H)-dione

Step 1, Preparation of 3-chloro-2-hydroxy-4-(4-methoxybutoxy)benzaldehyde, 66a

In scintillation vial, a suspension of 3-chloro-2,4-dihydroxybenzaldehyde (1.725 g, 10 mmol), K$_2$CO$_3$ (1.38 g, 10 mmol), 18-crown-6 (0.264 g, 1.0 mmol) and 1-bromo-4-methoxybutane (0.835 g, 5.0 mmol) in acetone (10 ml) was heated and stirred overnight at 70° C. The reaction mixture was cooled to room temperature, acidified with HCl, aq. 1M and extracted with ethyl acetate (50 ml). Organic layer was washed with water (50 ml) and then with brine (50 ml). Organic layer was dried over MgSO$_4$, concentrated and chromatographed to yield compound 66a (0.898 g, 3.47 mmol, 34.7%).

Step 2, Preparation of 5-(3-chloro-2-hydroxy-4-(4-methoxybutoxy)benzylidene)pyrimidine-2,4,6(1H, 3H,5H)-trione, 66b In a round bottom flash, a mixture of compound 66a (0.498 g, 1.5 mmol), barbituric acid (0.256 g, 2.0 mmol), ethanol (6 ml) and water (6 ml) was stirred at room temperature overnight. Water (15 ml) was added to the reaction mixture. The reaction was stirred at room temperature for 15 minutes and then filtered. Solid yellow cake was collected and vacuum dried at 40° C. to 50° C. to yield compound 66b, (0.466 g, 1.34 mmol, 89.6%).

Step 3, Preparation of 9-chloro-8-(4-methoxybutoxy)-2H-chromeno[2,3-d]pyrimidine-2,4(3H)-dione In a scintillation vial, a suspension of compound 66b, (0.369 g, 1.0 mmol) in a mixture of acetic acid (2.1 g) and acetic anhydride (0.51 g) was stirred and heated to 80 to 90° C. overnight. The mixture was concentrated to remove ~50% of its volume and then cooled to room temperature and sit for 3 hours. Yellow solid was filtered, dried at 40° C. to 50° C. to yield compound 66 (300 mg, 0.86 mmol, 86%).

Synthesis of compounds of example 67-70 follow the same protocol described for compound 66.

Synthesis of compounds 71-74 follow the same protocol described for compound 75, below.

7-fluoro-8-(3-(2-methoxyethoxy)propoxy)-2H-chromeno[2,3-d]pyrimidine-2,4(3H)-dione Step 1, Preparation of 4-fluoro-3-(3-(2-methoxyethoxy)propoxy)phenol, 75a In scintillation vial, a suspension of 4-fluororesorcinol (1.28 g, 10 mmol), K$_2$CO$_3$ (1.38 g, 10 mmol), 18-crown-6 (0.264 g, 1.0 mmol) and 1-bromo-3-(2-methoxyethoxy) propane (0.985 g, 5.0 mmol) in acetone (10 ml) was heated and stirred overnight at 70° C. The reaction mixture was cooled to room temperature, acidified with HCl, aq. 1M and extracted with ethyl acetate (50 ml). Organic layer was washed with water (50 ml) and then with brine (50 ml). Organic layer was dried over MgSO$_4$, concentrated and chromatographed to yield compound 75a (0.921 g, 3.74 mmol, 37.4%).

Step 2, Preparation of 5-fluoro-2-hydroxy-4-(3-(2-methoxyethoxy)propoxy)benzaldehyde, 75b In a scintillation vial, a suspension of compound 75a, (0.478 g, 1.96 mmol), MgCl$_2$ anhydrous (0.279 g, 2.93 mmol), paraformaldehyde (0.12 g, 4 mmol) and triethylamine (0.296 g, 2.93 mmol) in acetonitrile anhydrous (5 ml) was stirred and heated to 60° C. for 2 hours. The mixture was cooled to room temperature, quenched with HCl, aq. 1M (15 ml) and extract with ethyl acetate. The organic layer was dried with MgSO$_4$, filtered over silica gel, concentrated and chromatographed to yield compound 75b (0.34 g, 1.25 mmol, 64%).

Step 3, Preparation of 5-(5-fluoro-2-hydroxy-4-(3-(2-methoxyethoxy)propoxy)benzylidene)pyrimidine-2,4,6(1H,3H,5H)-trione, 75c In a round bottom flash, a mixture of compound 75b (0.140 g, 0.51 mmol), barbituric acid (0.079 g, 0.62 mmol), ethanol (3 ml) and water (3 ml) was stirred at room temperature overnight. Water (15 ml) was added to the reaction mixture. The reaction was stirred at room temperature for 15 minutes and then filtered. Solid yellow cake was collected and vacuum dried at 40° C. to 50° C. to yield compound 75c, (0.189 g, 0.49 mmol, 97%).

Step 4, Preparation of 7-fluoro-8-(3-(2-methoxyethoxy)propoxy)-2H-chromeno[2,3-d]pyrimidine-2,4(3H)-dione In a scintillation vial, a suspension of compound 75c, (0.172 g, 0.45 mmol) in a mixture of acetic acid (1.58 g) and acetic anhydride (0.226 g) was stirred and heated to 80 to 90° C. for 5 hours. The mixture was concentrated to remove ~50% of its volume and then cooled to room temperature and sit for 3 hours. Yellow solid was filtered, washed with water and vacuum dried at 40° C. to 50° C. to yield compound 75 (144 mg, 0.39 mmol, 88%).

NMR Spectroscopy

NMR spectroscopy was performed using standard Bruker® 400 MHz NMR.

| Cmpd. | Structure | MW | 1H NMR, 400 MHz, DMSO-d6 |
| --- | --- | --- | --- |
| 1 | 8-methoxy-2H-chromeno[2,3-d]pyrimidine-2,4(3H)-dione | 244 | 3.99 (s, 3H), 7.48 (dd, J = 7.92, 7.92 Hz, 1H), 7.58-7.63 (m, 2H), 8.92 (s, 1H), 11.46 (s, 1H) |
| 2 | 8-ethoxy-2H-chromeno[2,3-d]pyrimidine-2,4(3H)-dione | 258 | 1.44 (t, J = 7.00 Hz, 3H), 4.26 (q, J = 7.00 Hz, 2H), 7.46 (dd, J = 7.92, 7.92 Hz, 1H), 7.57-7.63 (m, 2H), 8.92 (s, 1H), 11.47 (s, 1H) |
| 3 | 6-chloro-8-methoxy-2H-chromeno[2,3-d]pyrimidine-2,4(3H)-dione | 279 | 4.02 (s, 3H), 7.65 (d, J = 2.30 Hz, 1H), 7.73 (d, J = 2.30 Hz, 1H), 8.85 (s, 1H), 11.53 (s, 1H) |
| 4 | 6-bromo-8-methoxy-2H-chromeno[2,3-d]pyrimidine-2,4(3H)-dione | 323 | 4.01 (s, 3H), 7.73 (d, J = 2.14 Hz, 1H), 7.87 (d, J = 2.14 Hz, 1H), 8.83 (s, 1H), 11.52 (s, 1H) |
| 5 | 6-chloro-8-ethoxy-2H-chromeno[2,3-d]pyrimidine-2,4(3H)-dione | 293 | 1.43 (t, J = 7.00 Hz, 3H), 4.28 (q, J = 7.00 Hz, 2H), 7.63 (d, J = 2.28 Hz, 1H), 7.72 (d, J = 2.28 Hz, 1H), 8.84 (s, 1H), 11.53 (s, 1H) |

| Cmpd. | Structure | MW | 1H NMR, 400 MHz, DMSO-d6 |
|---|---|---|---|
| 6 | 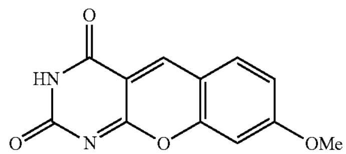 [SMILES: COc1ccc2cc3c(=O)[nH]c(=O)nc-3oc2c1] | 244 | 3.91 (s, 3H), 7.11 (dd, J = 8.88, 2.65 Hz, 1H), 7.28 (d, J = 2.65 Hz, 1H), 7.95 (d, J = 8.88 Hz, 1H), 8.83 (s, 1H), 11.28 (s, 1H) |
| 7 | 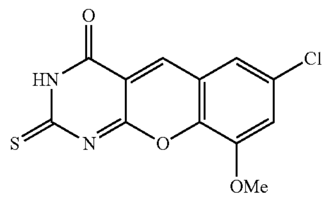 [SMILES: COc1cc(Cl)cc2cc3c(=O)[nH]c(=S)nc-3oc12] | 295 | 4.00 (s, 3H), 7.65 (d, J = 2.30 Hz, 1H), 7.73 (d, J = 2.30 Hz, 1H), 9.01 (s, 1H), 12.63 (s, 1H) |
| 8 | 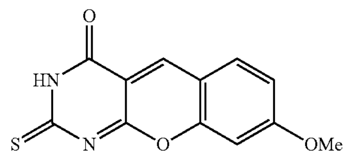 [SMILES: COc1ccc2cc3c(=O)[nH]c(=S)nc-3oc2c1] | 260 | 4.00 (s, 3H), 7.24 (dd, J = 8.86, 2.43 Hz, 1H), 7.88 (d, J = 2.43 Hz, 1H), 8.06 (d, J = 8.86 Hz, 1H), 9.01 (s, 1H), 12.62 (s, 1H) |
| 9 | 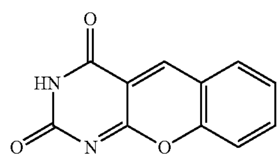 [SMILES: O=c1nc2oc3ccccc3cc-2c(=O)[nH]1] | 214 | 7.56 (ddd, J = 8.30, 7.60, 1.00 Hz, 1H), 7.71 (d, J = 8.30 Hz, 1H), 7.90 (ddd, J = 8.40, 7.30, 1.50 Hz, 1H), 8.09 (dd, J = 8.80, 1.50 Hz, 1H), 8.95 (s, 1H), 11.46 (s, 1H) |
| 10 | 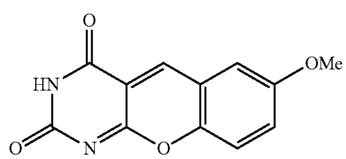 [SMILES: COc1ccc2oc3nc(=O)[nH]c(=O)c-3cc2c1] | 244 | 3.86 (s, 3H), 7.50 (dd, J = 9.12, 3.08 Hz, 1H), 7.65 (d, J = 3.08 Hz, 1H), 7.68 (d, J = 8.00 Hz, 1H), 8.88 (s, 1H), 11.43 (s, 1H) |
| 11 | 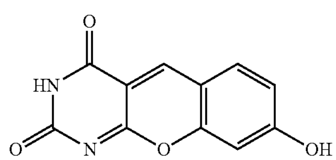 [SMILES: O=c1nc2oc3cc(O)ccc3cc-2c(=O)[nH]1] | 230 | 6.98 (d, J = 2.04 Hz, 1H), 7.00 (dd, J = 8.55, 2.04 Hz, 1H), 7.93 (d, J = 8.60 Hz, 1H), 8.84 (s, 1H), 11.27 (s, 1H), 11.62 (bs, 1H) |
| 12 | 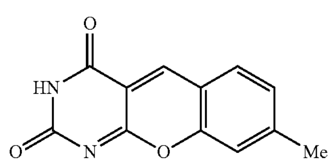 [SMILES: Cc1ccc2cc3c(=O)[nH]c(=O)nc-3oc2c1] | 228 | 2.60 (s, 3H), 7.49 (dd, J = 8.00, 0.85 Hz, 1H), 7.65 (d, J = 0.85 Hz, 1H), 8.05 (d, J = 8.00 Hz, 1H), 9.00 (s, 1H), 11.49 (s, 1H) |
| 13 | 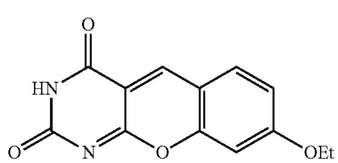 [SMILES: CCOc1ccc2cc3c(=O)[nH]c(=O)nc-3oc2c1] | 258 | 1.32 (t, J = 6.94 Hz, 3H), 4.19 (q, J = 6.94 Hz, 2H), 7.09 (dd, J = 8.78, 2.50 Hz, 1H), 7.25 (d, J = 2.50 Hz, 1H), 7.93 (d, J = 8.78 Hz, 1H), 8.81 (s, 1H), 11.26 (s, 1H) |
| 14 | 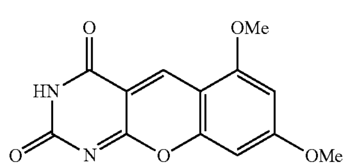 [SMILES: COc1cc(OC)c2cc3c(=O)[nH]c(=O)nc-3oc2c1] | 274 | 3.98 (s, 3H), 4.01 (s, 3H), 6.71 (d, J = 1.67 Hz, 1H), 6.99 (d, J = 1.67 Hz, 1H), 8.61 (s, 1H), 11.30 (s, 1H) |

-continued

| Cmpd. | Structure | MW | 1H NMR, 400 MHz, DMSO-d6 |
|---|---|---|---|
| 15 | 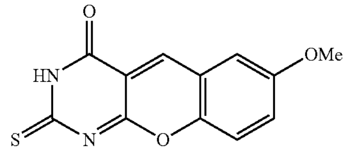 [SMILES: COc1ccc2oc3nc(=S)[nH]c(=O)c-3cc2c1] | 260 | 3.87 (s, 3H), 7.59 (dd, J = 9.13, 3.02 Hz, 1H), 7.68 (d, J = 3.02 Hz, 1H), 7.73 (d, J = 9.13 Hz, 1H), 8.98 (s, 1H), 12.70 (s, 1H) |
| 16 | 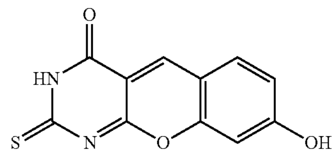 [SMILES: O=c1[nH]c(=S)nc2oc3cc(O)ccc3cc1-2] | 246 | 7.22 (d, J = 2.00 Hz, 1H), 7.27 (dd, J = 8.70, 2.10 Hz, 1H), 8.19 (d, J = 8.80 Hz, 1H), 9.17 (s, 1H), 12.11 (bs, 1H), 12.77 (s, 1H) |
| 17 | 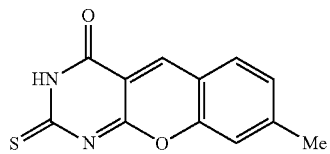 [SMILES: Cc1ccc2cc3c(=O)[nH]c(=S)nc-3oc2c1] | 244 | 2.45 (s, 3H), 7.37 (dd, J = 8.17, 1.00 Hz, 1H), 7.53 (d, J = 1.00 Hz, 1H), 7.92 (d, J = 8.17 Hz, 1H), 8.94 (s, 1H), 12.61 (s, 1H) |
| 18 | 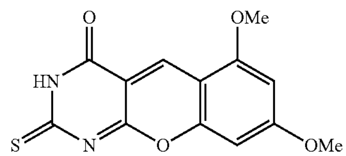 [SMILES: COc1cc(OC)c2cc3c(=O)[nH]c(=S)nc-3oc2c1] | 290 | 3.94 (s, 3H), 3.95 (s, 3H), 6.68 (d, J = 2.01 Hz, 1H), 6.90 (d, J = 2.01 Hz, 1H), 8.60 (s, 1H), 12.53 (s, 1H) |
| 19 | 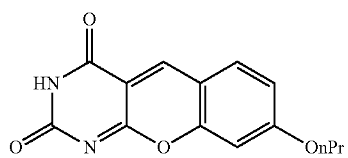 | 272 | 0.81 (t, J = 7.42 Hz, 3H), 1.55-1.63 (m, 2H), 3.97 (t, J = 6.55 Hz, 2H), 6.97 (dd, J = 8.81, 2.40 Hz, 1H), 7.13 (d, J = 2.40 Hz, 1H), 7.81 (d, J = 8.81 Hz, 1H), 8.69 (s, 1H), 11.14 (s, 1H) |
| 20 | 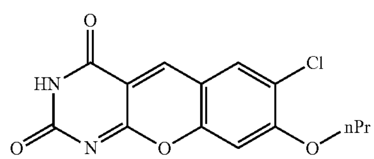 | 307 | 0.96 (t, J = 7.32 Hz, 3H), 1.71-1.80 (m, 2H), 4.19 (t, J = 6.38 Hz, 2H), 7.50 (s, 1H), 8.16 (s, 1H), 8.76 (s, 1H), 11.33 (s, 1H) |
| 21 | 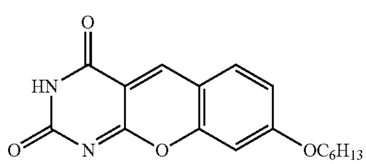 | 314 | 0.87-0.91 (m, 3H), 1.31-1.35 (m, 4H), 1.40-1.45 (m, 2H), 1.74-1.79 (m, 2H), 4.20 (t, J = 6.50 Hz, 2H), 7.16 (dd, J = 8.88, 2.40 Hz, 1H), 7.33 (d, J = 2.40 Hz, 1H), 8.00 (d, J = 8.88 Hz, 1H), 8.89 (s, 1H), 11.33 (s, 1H) |
| 22 | 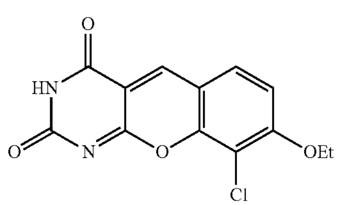 [SMILES: CCOc1ccc2cc3c(=O)[nH]c(=O)nc-3oc2c1Cl] | 293 | 1.43 (t, J = 6.96 Hz, 3H), 4.37 (q, J = 6.96 Hz, 2H), 7.44 (d, J = 8.96 Hz, 1H), 8.05 (d, J = 8.96 Hz, 1H), 8.89 (s, 1H), 11.44 (s, 1H) |
| 23 | 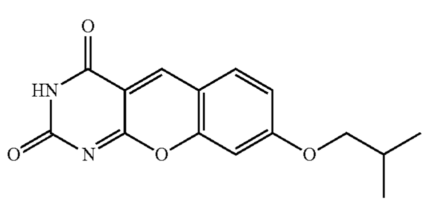 [SMILES: CC(C)COc1ccc2cc3c(=O)[nH]c(=O)nc-3oc2c1] | 286 | 1.12 (s, 3H), 1.14 (s, 3H), 2.15-2.25 (m, 1H), 4.11 (d, J = 6.56 Hz, 2H), 7.29 (dd, J = 8.76, 2.32, Hz, 1H), 7.45 (d, J = 2.24 Hz, 1H), 8.12 (d, J = 8.84 Hz, 1H), 9.01 (s, 1H), 11.45 (s, 1H) |

-continued

| Cmpd. | Structure | MW | 1H NMR, 400 MHz, DMSO-d6 |
|---|---|---|---|
| 24 | 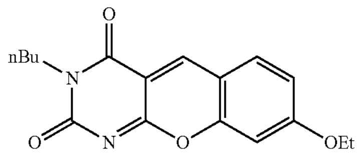 | 314 | 0.92 (t, J = 7.24 Hz, 3H), 1.26-1.33 (m, 2H), 1.40 (t, J = 6.96 Hz, 3H), 1.50-1.57 (m, 2H), 3.84 (t, J = 7.32 Hz, 2H), 4.25 (q, J = 7.00 Hz, 2H), 7.17 (dd, J = 8.76, 2.32, Hz, 1H), 7.34 (d, J = 2.32 Hz, 1H), 8.04 (d, J = 8.84 Hz, 1H), 8.95 (s, 1H) |
| 25 | 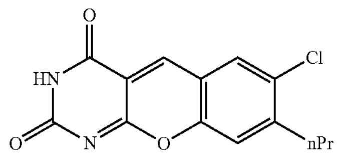 | 291 | 1.05 (t, J = 7.25 Hz, 3H), 1.64-1.70 (m, 2H), 2.81-2.85 (m, 2H), 7.76 (s, 1H), 8.20 (s, 1H), 8.85 (s, 1H), 11.50 (s, 1H) |
| 26 | 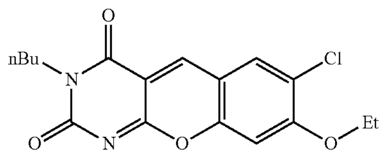 | 349 | 0.86 (t, J = 7.28 Hz, 3H), 1.19-1.28 (m, 2H), 1.36 (t, J = 6.92 Hz, 3H), 1.43-1.50 (m, 2H), 3.76 (q, J = 7.40 Hz, 2H), 4.28 (q, J = 7.00 Hz, 2H), 7.51 (s, 1H), 8.19 (s, 1H), 8.81 (s, 1H) |
| 27 | 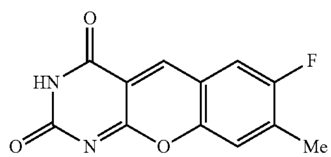 [SMILES: Cc1cc2oc3nc(=O)[nH]c(=O)c-3cc2cc1F] | 246 | 2.43 (d, J = 1.5 Hz, 3H), 7.75 (d, J = 6.17 Hz, 1H), 7.90 (d, J = 9.17 HZ, 1H), 8.87 (s, 1H), 11.47 (s, 47, 1H) |
| 28 | 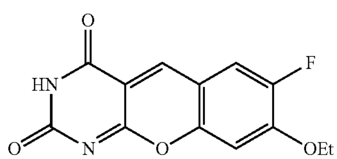 [SMILES: CCOc1cc2oc3nc(=O)[nH]c(=O)c-3cc2cc1F] | 276 | 1.42 (t, J = 6.80 Hz, 3H), 4.28 (q, J = 6.80 Hz, 2H), 7.62 (d, J = 7.05 Hz, 1H), 7.97 (d, J = 10.86 Hz, 1H), 8.83 (s, 1H), 11.38 (s, 1H) |
| 29 | 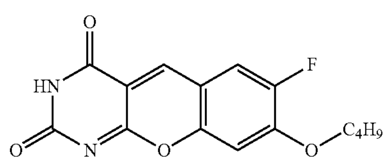 | 304 | 0.96 (t, J = 7.36 Hz, 3H), 1.43-1.49 (m, 2H), 1.76-1.83 (m, 2H), 4.28 (t, J = 6.44 Hz, 2H), 7.63 (d, J = 7.04 Hz, 1H), 7.98 (d, J = 10.85 Hz, 1H), 8.83 (s, 1H), 11.38 (s, 1H) |
| 30 | 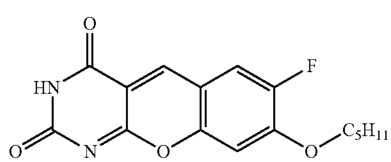 | 318 | 0.93 (t, J = 7.36 Hz, 3H), 1.34-1.44 (m, 4H), 1.77-1.84 (m, 2H), 4.28 (t, J = 6.44 Hz, 2H), 7.62 (d, J = 7.04 Hz, 1H), 7.98 (d, J = 10.85 Hz, 1H), 8.83 (s, 1H), 11.38 (s, 1H) |
| 31 | 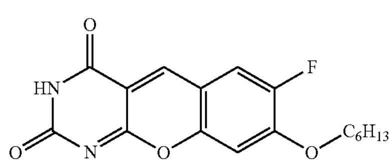 | 332 | 0.87 (t, J = 6.85 Hz, 3H), 1.30-1.35 (m, 4H), 1.39-1.48 (m, 2H), 1.76-1.82 (m, 2H), 4.28 (t, J = 6.50 Hz, 2H), 7.62 (d, J = 7.00 Hz, 1H), 7.98 (d, J = 10.85 Hz, 1H), 8.83 (s, 1H), 11.38 (s, 1H) |
| 32 | 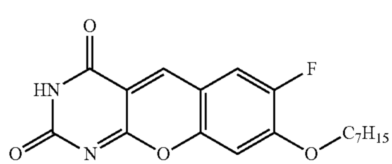 | 346 | 0.86 (t, J = 6.80 Hz, 3H), 1.28-1.30 (m, 4H), 1.32-1.37 (m, 2H), 1.42-1.46 (m, 2H), 1.76-1.83 (m, 2H), 4.27 (t, J = 6.40 Hz, 2H), 7.62 (d, J = 7.00 Hz, 1H), 7.98 (d, J = 10.80 Hz, 1H), 8.83 (s, 1H), 11.38 (s, 1H) |

-continued

| Cmpd. | Structure | MW | 1H NMR, 400 MHz, DMSO-d6 |
|---|---|---|---|
| 33 | 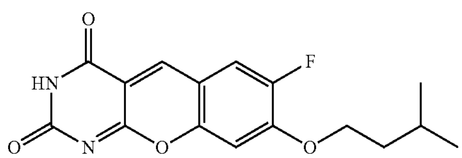 [SMILES: CC(C)CCOc1cc2oc3nc(=O)[nH]c(=O)c-3cc2cc1F] | 318 | 0.95 (s, 3H), 0.97 (s, 3H), 1.68-1.73 (m, 2H), 1.77-1.82 (m, 1H), 4.31 (t, J = 6.60 Hz, 2H), 7.66 (d, J = 7.04 Hz, 1H), 7.97 (d, J = 10.85 Hz, 1H), 8.83 (s, 1H), 11.38 (s, 1H) |
| 34 | 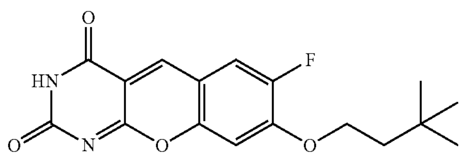 [SMILES: CC(C)(C)CCOc1cc2oc3nc(=O)[nH]c(=O)c-3cc2cc1F] | 332 | 0.99 (s, 9H), 1.75 (t, J = 7.16 2H), 4.33 (t, J = 7.16 Hz, 2H), 7.71 (d, J = 7.04 Hz, 1H), 7.98 (d, J = 10.85 Hz, 1H), 8.83 (s, 1H), 11.38 (s, 1H) |
| 35 | 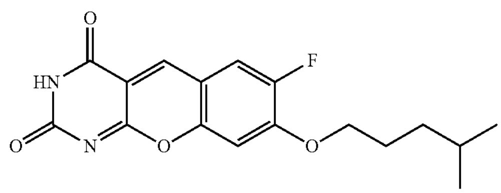 [SMILES: CC(C)CCCOc1cc2oc3nc(=O)[nH]c(=O)c-3cc2cc1F] | 332 | 0.88 (s, 3H), 0.90 (s, 3H), 1.29-1.35 (m, 2H), 1.57-1.64 (m, 1H), 1.76-1.84 (m, 2H), 4.27 (t, J = 6.60 Hz, 2H), 7.61 (d, J = 7.00 Hz, 1H), 7.97 (d, J = 10.85 Hz, 1H), 8.83 (s, 1H), 11.38 (s, 1H) |
| 36 | 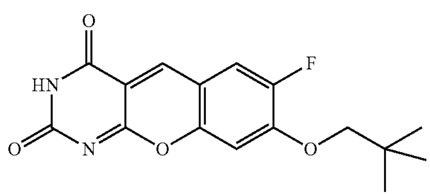 [SMILES: CC(C)(C)COc1cc2oc3nc(=O)[nH]c(=O)c-3cc2cc1F] | 318 | 1.04 (s, 9H), 3.97 (s, 2H), 7.63 (d, J = 7.40 Hz, 1H), 7.99 (d, J = 10.85 Hz, 1H), 8.84 (s, 1H), 11.38 (s, 1H) |
| 37 | 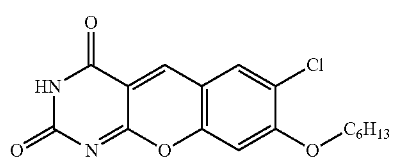 | 349 | 0.83 (t, J = 7.36 Hz, 3H), 1.22.-1.29 (m, 4H), 1.37-1.41 (m, 2H), 4.22 (t, J = 6.40 Hz, 2H), 7.50 (s, 1H), 8.15 (s, 1H), 8.75 (s, 1H), 11.32 (s, 1H) |
| 38 | 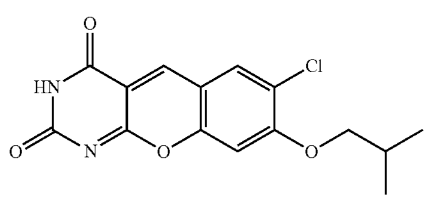 [SMILES: CC(C)COc1cc2oc3nc(=O)[nH]c(=O)c-3cc2cc1Cl] | 321 | 1.02 (s, 3H), 1.04 (s, 3H), 2.09-2.15 (m, 1H), 4.08 (d, J = 6.48 Hz, 2H), 7.56 (s, 1H), 8.23 (s, 1H), 8.83 (s, 1H), 11.40 (s, 1H) |
| 39 | 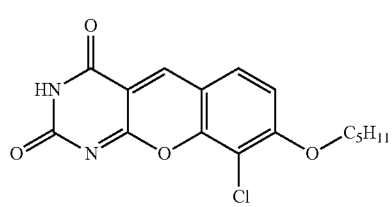 | 335 | 0.91 (t, J = 7.00 Hz, 3H), 1.36-1.47 (m, 4H), 1.77-1.85 (m, 2H), 4.30 (t, J = 6.50 Hz, 2H), 7.45 (d, J = 9.00 Hz, 1H), 8.06 (d, J = 9.00 Hz, 1H), 8.88 (s, 1H), 11.43 (s, 1H) |
| 40 | 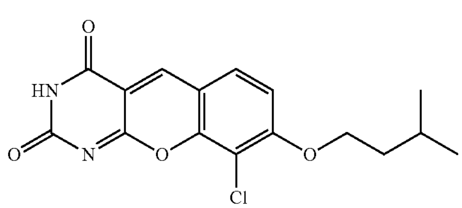 [SMILES: CC(C)CCOc1ccc2cc3c(=O)[nH]c(=O)nc-3oc2c1Cl] | 335 | 0.93 (s, 3H), 0.96 (s, 3H), 1.69-1.74 (m, 2H), 1.81-1.88 (m, 1H), 4.33 (t, J = 6.52 Hz, 2H), 7.48 (d, J = 8.96 Hz, 1H), 8.06 (d, J = 8.96 Hz, 1H), 8.89 (s, 1H), 11.43 (s, 1H) |

-continued

| Cmpd. | Structure | MW | 1H NMR, 400 MHz, DMSO-d6 |
|---|---|---|---|
| 41 | 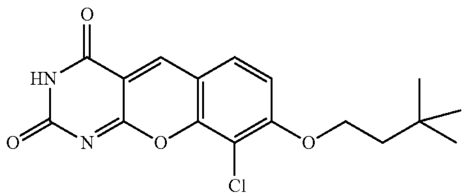 [SMILES: CC(C)(C)CCOc1ccc2cc3c(=O)[nH]c(=O)nc-3oc2c1Cl] | 349 | 1.06 (s, 9H), 1.82 (t, J = 6.90 Hz, 2H), 4.42 (t, J = 6.90 Hz, 2H), 7.59 (d, J = 9.00 Hz, 1H), 8.13 (d, J = 9.00 Hz, 1H), 8.94 (s, 1H), 11.49 (s, 1H) |
| 42 | 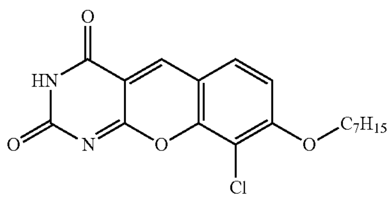 | 363 | 0.86 (t, J = 6.80 Hz, 3H), 1.27-1.30 (m, 4H), 1.32-1.37 (m, 2H), 1.42-1.46 (m, 2H), 1.78-1.83 (m, 2H), 4.30 (t, J = 6.40 Hz, 2H), 7.45 (d, J = 8.96 Hz, 1H), 8.05 (d, J = 8.96 Hz, 1H), 8.89 (s, 1H), 11.43 (s, 1H) |
| 43 | 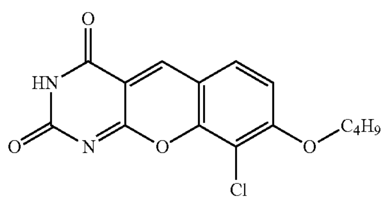 | 321 | 0.96 (t, J = 7.5 Hz, 3H), 1.47-1.52 (m, 2H), 1.76-1.83 (m, 2H), 4.32 (t, J = 6.40 Hz, 2H), 7.46 (d, J = 8.96 Hz, 1H), 8.06 (d, J = 8.96 Hz, 1H), 8.89 (s, 1H), 11.43 (s, 1H) |
| 44 | 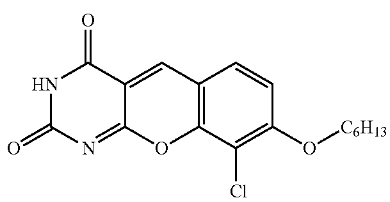 | 349 | 0.88 (t, J = 7.01 Hz, 3H), 1.29-1.36 (m, 4H), 1.45-1.49 (m, 2H), 1.77-1.83 (m, 2H), 4.30 (t, J = 6.40 Hz, 2H), 7.45 (d, J = 8.96 Hz, 1H), 8.05 (d, J = 8.96 Hz, 1H), 8.89 (s, 1H), 11.43 (s, 1H) |
| 45 | 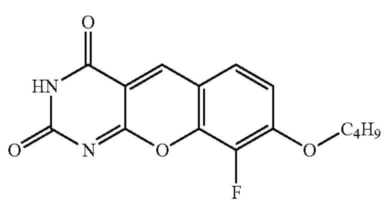 | 304 | 1.01 (t, J = 6.80 Hz, 3H), 1.47-1.57 (m, 2H), 1.83-1.88 (m, 2H), 4.35 (d, t = 6.50 Hz, 2H), 7.52 (dd, J = 7.2 Hz, 8.8 Hz, 1H), 7.96 (dd, J = 1.8 hz, 9.0 Hz, 1H), 8.96 (d, J = 1.40 Hz, 1H), 11.51 (s, 1H) |
| 46 | 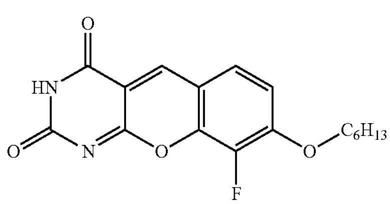 | 332 | 0.87 (t, J = 6.80 Hz, 3H), 1.30-1.35 (m, 4H), 1.39-1.48 (m, 2H), 1.76-1.83 (m, 2H), 4.28 (t, J = 6.50 Hz, 2H), 7.46 (dd, J = 7.2 Hz, 8.8 Hz, 1H), 7.90 (dd, J = 1.8 hz, 9.0 Hz, 1H), 8.89 (d, J = 1.40 Hz, 1H), 11.45 (s, 1H) |
| 47 | 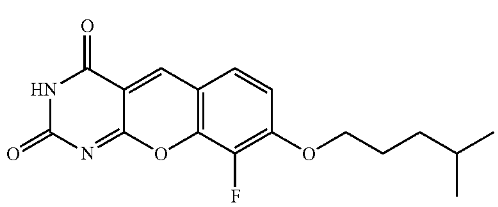 [SMILES: CC(C)CCCOc1ccc2cc3c(=O)[nH]c(=O)nc-3oc2c1F] | 332 | 0.88 (s, 3H), 0.90 (s, 3H), 1.30-1.36 (m, 2H), 1.56-1.63 (m, 1H), 1.76-1.84 (m, 2H), 4.28 (t, J = 6.60 Hz, 2H), 7.46 (dd, J = 7.2 Hz, 8.8 Hz, 1H), 7.90 (dd, J = 1.8 hz, 9.0 Hz, 1H), 8.89 (d, J = 1.40 Hz, 1H), 11.45 (s, 1H) |

| Cmpd. | Structure | MW | 1H NMR, 400 MHz, DMSO-d6 |
|---|---|---|---|
| 48 | 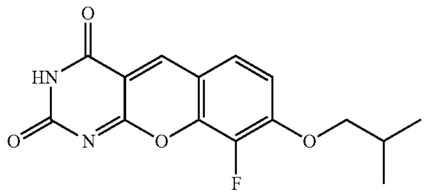 [SMILES: CC(C)COc1ccc2cc3c(=O)[nH]c(=O)nc-3oc2c1F] | 304 | 1.01 (s, 3H), 1.03 (s, 3H), 2.07-2.17 (m, 1H), 4.07 (d, J = 6.60 Hz, 2H), 7.46 (dd, J = 7.2 Hz, 8.8 Hz, 1H), 7.90 (dd, J = 1.8 hz, 9.0 Hz), 8.90 (d, J = 1.54 Hz, 1H), 11.45 (s, 1H) |
| 49 | 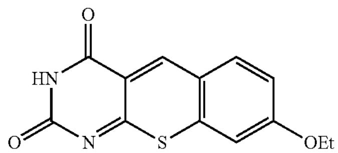 | 274 | 1.39 (t, J = 6.96 Hz, 3H), 4.25 (q, J = 6.97 Hz, 2H), 7.25 (dd, J = 8.84 Hz, 2.40 Hz, 1H), 7.63 (d, J = 2.40 Hz, 1H0, 8.24 (d, J = 8.84 Hz, 1H), 8.82 (s, 1H), 11.33 (s, 1H) |
| 50 | 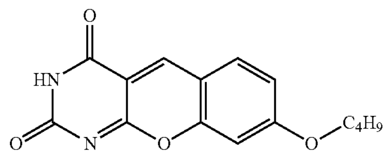 | 286 | 0.91 (t, J = 7.42 Hz, 3H), 1.46-1.53 (m, 2H), 1.72-1.79 (m, 2H), 4.20 (t, J = 6.48 Hz, 2H), 7.16 (dd, J = 8.80 Hz, 2.20 Hz, 1H), 7.33 (d, J = 2.20 Hz, 1H), 7.99 (d, J = 8.84 Hz, 1H), 8.88 (s, 1H), 11.32 (s, 1H) |
| 51 | 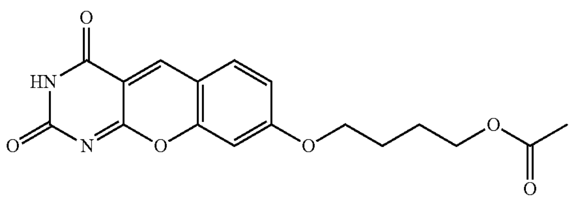 [SMILES: CC(=O)OCCCCOc1ccc2cc3c(=O)[nH]c(=O)nc-3oc2c1] | 344 | 1.73-1.77 (m, 2H), 1.78-1.85 (m, 2H), 2.01 (s, 3H), 4.06 (t, J = 6.40 Hz, 2H) 4.23 (t, J = 6.08 Hz, 2H), 7.17 (dd, J = 8.84 Hz, 2.20 Hz, 1H), 7.33 (d, J = 2.20 Hz, 1H), 8.00 (d, J = 8.84 Hz, 1H), 8.89 (s, 1H), 11.32 (s, 1H) |
| 52 | 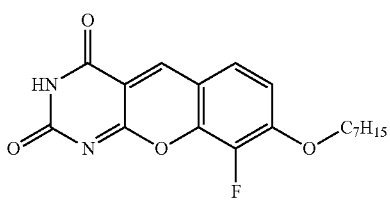 | 346.35 | 0.88 (t, J = 6.40 Hz, 3H), 1.26-1.38 (m, 6H), 1.40-1.47 (m, 2H), 1.77-1.84 (m, 2H), 4.29 (t, J = 6.30 Hz, 2H), 7.46 (dd, J = 7.2 Hz, 8.8 Hz, 1H), 7.89 (dd, J = 1.8 hz, 9.0 Hz), 8.90 (d, J = 1.40 Hz, 1H), 11.45 (s, 1H) |
| 53 | 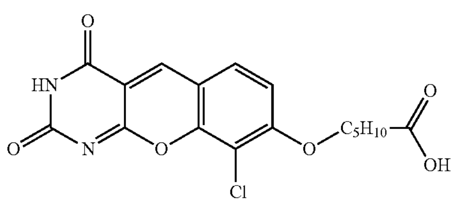 | 378.76 | 1.46-1.51 (m, 2H), 1.56-1.63 (m, 2H), 1.79-1.91 (m, 2H), 2.22-2.27 (m, 2H), 4.31 (t, J = 6.28 Hz, 2H), 7.45 (d, J = 8.96 Hz, 1H), 8.05 (d, J = 8.96 Hz, 1H), 8.89 (s, 1H), 11.43 (s, 1H), 12.02 (bs, 1H) |
| 54 | 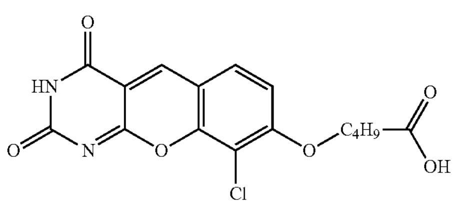 | 364.74 | 1.66-1.74 (m, 2H), 1.80-1.86 (m, 2H), 2.33 (t, J = 7.40 Hz, 2H), 4.32 (t, J = 6.16 Hz, 2H), 7.45 (d, J = 8.96 Hz, 1H), 8.05 (d, J = 8.96 Hz, 1H), 8.89 (s, 1H), 11.43 (s, 1H), 12.07 (bs, 1H) |
| 55 | 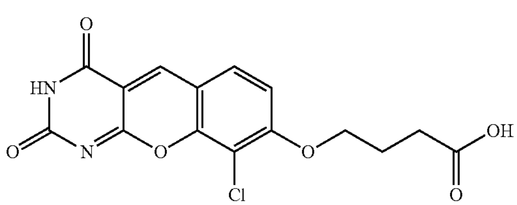 [SMILES: O=C(O)CCCOc1ccc2cc3c(=O)[nH]c(=O)nc-3oc2c1Cl] | 350.71 | 2.01-2.08 (m, 2H), 2.46 (t, J = 7.26 Hz, 2H), 4.33 (t, J = 6.26 Hz, 2H), 7.45 (d, J = 8.91 Hz, 1H), 8.05 (d, J = 8.91 Hz, 1H), 8.89 (s, 1H), 11.44 (s, 1H), 12.22 (bs, 1H) |

-continued

| Cmpd. | Structure | MW | 1H NMR, 400 MHz, DMSO-d6 |
|---|---|---|---|
| 56 | 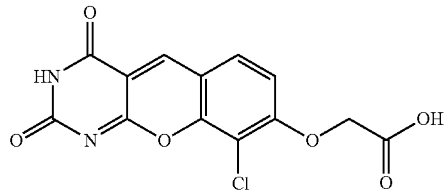 [SMILES: O=C(O)COc1ccc2cc3c(=O)[nH]c(=O)nc-3oc2c1Cl] | 322.66 | 5.10 (s, 2H), 7.36 (d, J = 9.00 Hz, 1H), 8.02 (d, J = 9.00 Hz, 1H), 8.87 (s, 1H), 11.45 (s, 1H), 12.02 (bs, 1H) |
| 57 | 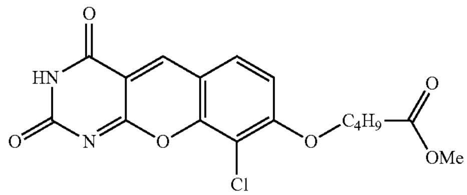 | 378.76 | 1.70-1.77 (m, 2H), 1.81-1.87 (m, 2H), 2.43 (t, J = 7.40 Hz, 2H), 3.60 (s, 3H), 4.32 (t, J = 6.10 Hz, 2H), 7.44 (d, J = 8.96 Hz, 1H), 8.05 (d, J = 8.96 Hz, 1H), 8.89 (s, 1H), 11.43 (s, 1H) |
| 58 | 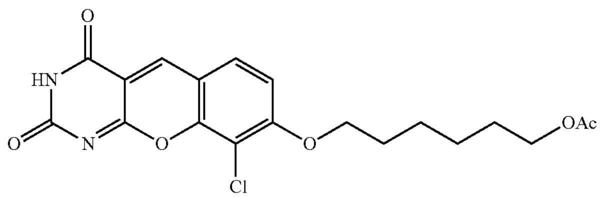 [SMILES: CC(=O)OCCCCCCOc1ccc2cc3c(=O)[nH]c(=O)nc-3oc2c1Cl] | 406.82 | 1.36-1.43 (m, 2H), 1.45-1.1.52 (m, 2H), 1.57-1.62 (m, 2H), 1.78-1.85 (m, 2H), 2.00 (s, 3H), 4.00 (t, J = 6.62 Hz, 2H), 4.31 (t, J = 6.30 Hz, 2H), 7.45 (d, J = 8.96 Hz, 1H), 8.05 (d, J = 8.96 Hz, 1H), 8.89 (s, 1H), 11.43 (s, 1H) |
| 59 | 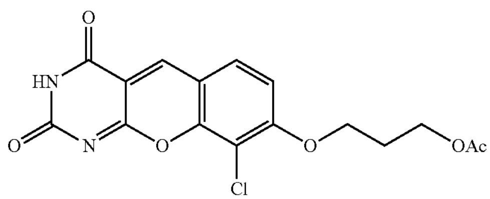 [SMILES: CC(=O)OCCCOc1ccc2cc3c(=O)[nH]c(=O)nc-3oc2c1Cl] | 364.74 | 2.02 (s, 3H), 2.11-2.18 (m, 2H), 4.21 (t, J = 6.38 Hz, 2H), 4.38 (t, J = 6.10 Hz, 2H), 7.46 (d, J = 8.96 Hz, 1H), 8.06 (d, J = 8.96 Hz, 1H), 8.89 (s, 1H), 11.44 (s, 1H) |
| 60 | 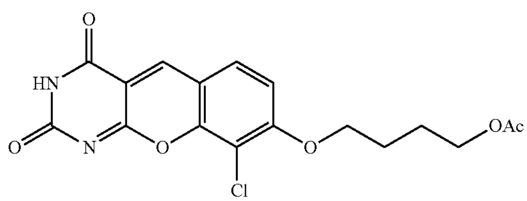 [SMILES: CC(=O)OCCCCOc1ccc2cc3c(=O)[nH]c(=O)nc-3oc2c1Cl] | 378.76 | 1.75-1.82 (m, 2H), 1.84-1.89 (m, 2H), 2.01 (s, 3H), 4.09 (t, J = 6.45 Hz, 2H), 4.31 (t, J = 6.04 Hz, 2H), 7.45 (d, J = 8.96 Hz, 1H), 8.06 (d, J = 8.96 Hz, 1H), 8.89 (s, 1H), 11.44 (s, 1H) |
| 61 | 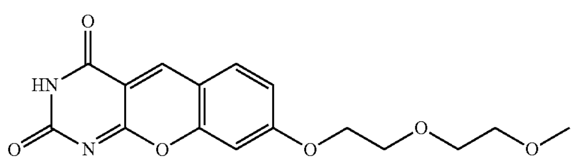 [SMILES: COCCOCCOc1ccc2cc3c(=O)[nH]c(=O)nc-3oc2c1] | 332.31 | 3.25 (s, 3H), 3.44-3.48 (m, 2H), 3.58-3.62 (m, 2H), 3.78-3.81 (m, 2H), 4.32-4.36 (m 2H), 7.18 (dd, J = 8.72, 2.52 Hz, 1H), 7.35 (d, J = 2.52 Hz, 1H), 8.00 (d, J = 8.84 Hz, 1H), 8.88 (s, 1H), 11.33 (s, 1H) |
| 62 | 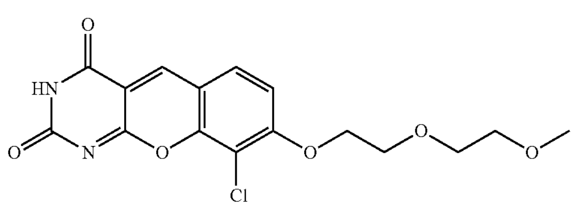 [SMILES: COCCOCCOc1ccc2cc3c(=O)[nH]c(=O)nc-3oc2c1Cl] | 366.75 | 3.25 (s, 3H), 3.47 (t, J = 4.72 Hz, 2H), 3.65 (t, J = 4.72 Hz, 2H), 3.85 (t, J = 4.33 Hz, 2H), 4.44 (t, J = 4.33 Hz, 2H), 7.46 (d, J = 8.82 Hz, 1H), 8.05 (d, J = 8.82 Hz, 1H), 8.89 (s, 1H), 11.44 (s, 1H) |
| 63 | 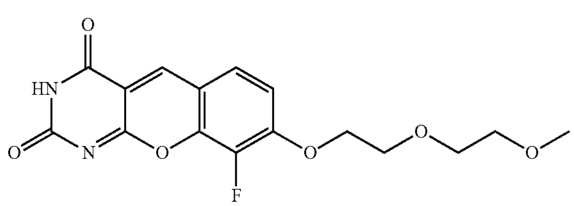 [SMILES: COCCOCCOc1ccc2cc3c(=O)[nH]c(=O)nc-3oc2c1F] | 350.3 | 3.24 (s, 3H), 3.47 (t, J = 4.72 Hz, 2H), 3.65 (t, J = 4.70 Hz, 2H), 3.86 (t, J = 4.36 Hz, 2H), 4.42 (t, J = 4.36 Hz, 2H), 7.46 (dd, J = 7.2 Hz, 8.90 Hz, 1H), 7.89 (dd, J = 1.8 Hz, 9.0 Hz, 1H), 8.90 (d, J = 1.40 Hz, 1H), 11.45 (s, 1H) |

| Cmpd. | Structure | MW | 1H NMR, 400 MHz, DMSO-d6 |
|---|---|---|---|
| 64 | 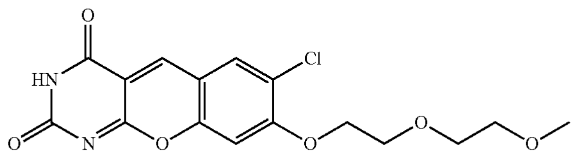 [SMILES: COCCOCCOc1cc2oc3nc(=O)[nH]c(=O)c-3cc2cc1Cl] | 366.75 | 3.25 (s, 3H), 3.49 (t, J = 4.72 Hz, 2H), 3.66 (t, J = 4.74 Hz, 2H), 3.86 (t, J = 4.40 Hz, 2H), 4.45 (t, J = 4.33 Hz, 2H), 7.53 (s, 1H), 8.17 (s, 1H), 8.88 (s, 1H), 11.43 (s, 1H) |
| 65 | 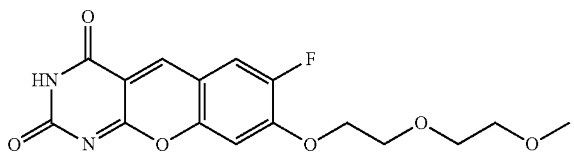 | 350.3 | 3.24 (s, 3H), 3.46 (t, J = 4.72 Hz, 2H), 3.65 (t, J = 4.66 Hz, 2H), 3.86 (t, J = 4.36 Hz, 2H), 4.44 (t, J = 4.36 Hz, 2H), 7.62 (d, J = 7.00 Hz, 1H), 7.98 (d, J = 10.80 Hz, 1H), 8.90 (s, 1H), 11.40 (s, 1H) |
| 66 | 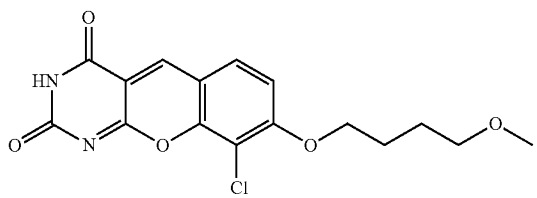 [SMILES: COCCCCOc1ccc2cc3c(=O)[nH]c(=O)nc-3oc2c1Cl] | 350.75 | 1.67-1.73 (m, 2H), 1.82-1.89 (m, 2H), 3.25 (s, 3H), 3.40 (t, J = 6.30 Hz, 2H), 4.33 (t, J = 6.30 Hz, 2H), 7.45 (d, J = 8.95 Hz, 1H), 8.08 (d, J = 8.95 Hz, 1H), 8.89 (s, 1H), 11.43 (s, 1H) |
| 67 | 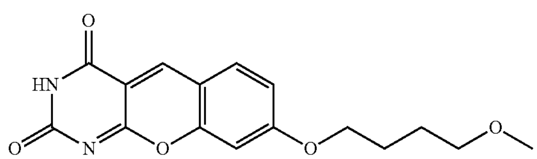 [SMILES: COCCCCOc1ccc2cc3c(=O)[nH]c(=O)nc-3oc2c1] | 316.31 | 1.65-1.70 (m, 2H), 1.77-1.83 (m, 2H), 3.25 (s, 3H), 3.38 (t, J = 6.37 Hz, 2H), 4.22 (t, J = 6.37 Hz, 2H), 7.16 (dd, J = 8.72, 2.26 Hz, 1H), 7.32 (d, J = 2.26 Hz, 1H), 8.00 (d, J = 8.72 Hz, 1H), 8.88 (s, 1H), 11.32 (s, 1H) |
| 68 | 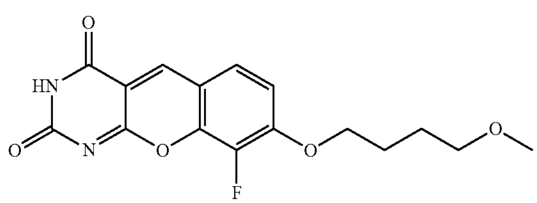 [SMILES: COCCCCOc1ccc2cc3c(=O)[nH]c(=O)nc-3oc2c1F] | 334.3 | 1.66-1.71 (m, 2H), 1.81-1.89 (m, 2H), 3.24 (s, 3H), 3.40 (t, J = 6.36 Hz, 2H), 4.34 (t, J = 6.36 Hz, 2H), 7.45 (dd, J = 7.2 Hz, 8.8 Hz, 1H), 7.89 (dd, J = 1.8 hz, 9.0 Hz), 8.89 (d, J = 1.40 Hz, 1H), 11.45 (s, 1H) |
| 69 | 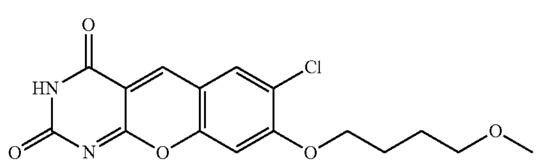 | 350.75 | 1.67-1.74 (m, 2H), 1.82-1.88 (m, 2H), 3.25 (s, 3H), 3.42 (t, J = 6.30 Hz, 2H), 4.32 (t, J = 6.30 Hz, 2H), 7.50 (s, 1H), 8.15 (s, 1H), 8.86 (s, 1H), 11.43 (s, 1H) |
| 70 | 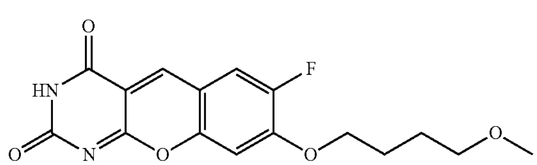 | 334.3 | 1.67-1.75 (m, 2H), 1.82-1.88 (m, 2H), 3.24 (s, 3H), 3.43 (t, J = 6.33 Hz, 2H), 4.32 (t, J = 6.30 Hz, 2H), 7.65 (d, J = 7.04 Hz, 1H), 7.98 (d, J = 10.86 Hz, 1H), 8.84 (s, 1H), 11.40 (s, 1H) |
| 71 | 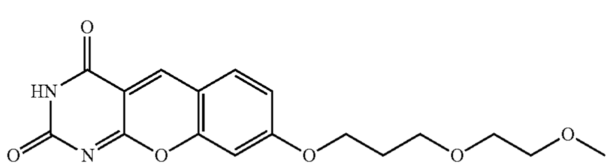 [SMILES: COCCOCCCOc1ccc2cc3c(=O)[nH]c(=O)nc-3oc2c1] | 346.33 | 2.02-2.08 (m, 2H), 3.23 (s, 3H), 3.43-3.45 (m, 2H), 3.50-3.56 (m, 2H), 3.60 (t, J = 6.20 Hz, 2H), 4.36 (t, J = 6.20 Hz, 2H), 7.17 (dd, J = 8.72, 2.24 Hz, 1H), 7.33 (d, J = 2.24 Hz, 1H), 8.00 (d, J = 8.72 Hz, 1H), 8.89 (s, 1H), 11.34 (s, 1H) |

-continued

| Cmpd. | Structure | MW | 1H NMR, 400 MHz, DMSO-d6 |
|---|---|---|---|
| 72 | 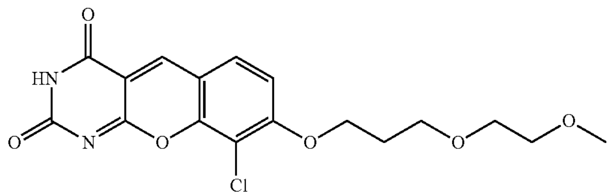 [SMILES: COCCOCCCOc1ccc2cc3c(=O)[nH]c(=O)nc-3oc2c1Cl] | 380.78 | 2.02-2.09 (m, 2H), 3.22 (s, 3H), 3.43-3.45 (m, 2H), 3.50-3.54 (m, 2H), 3.60 (t, J = 6.12 Hz, 2H), 4.36 (t, J = 6.12 Hz, 2H), 7.46 (d, J = 8.92 Hz, 1H), 8.05 (d, J = 8.82 Hz, 1H), 8.89 (s, 1H), 11.44 (s, 1H) |
| 73 | 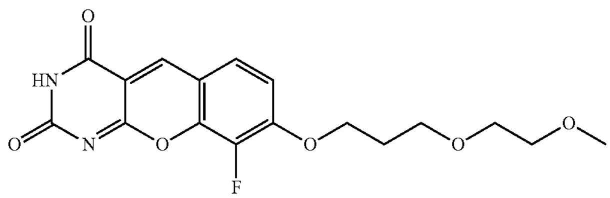 [SMILES: COCCOCCCOc1ccc2cc3c(=O)[nH]c(=O)nc-3oc2c1F] | 364.33 | 2.03-2.10 (m, 2H), 3.24 (s, 3H), 3.41-3.45 (m, 2H), 3.50-3.54 (m, 2H), 3.60 (t, J = 6.18 Hz, 2H), 4.38 (t, J = 6.18 Hz, 2H), 7.45 (dd, J = 7.2 Hz, 8.8 Hz, 1H), 7.88 (dd, J = 1.8 hz, 9.0 Hz), 8.89 (d, J = 1.40 Hz, 1H), 11.42 (s, 1H) |
| 74 | 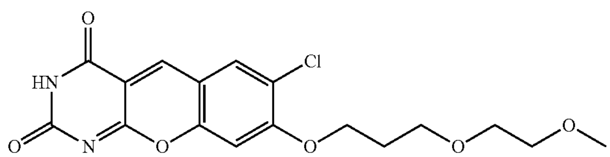 | 380.78 | 2.03-2.09 (m, 2H), 3.23 (s, 3H), 3.43-3.48 (m, 2H), 3.50-3.56 (m, 2H), 3.60 (t, J = 6.18 Hz, 2H), 4.34 (t, J = 6.18 Hz, 2H), 7.52 (s, 1H), 8.18 (s, 1H), 8.86 (s, 1H), 11.35 (s, 1H) |
| 75 | 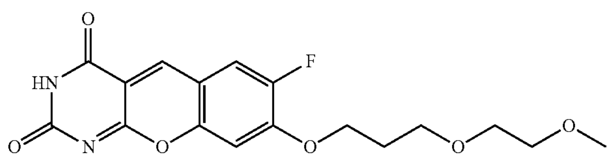 [SMILES: COCCOCCCOc1cc2oc3nc(=O)[nH]c(=O)c-3cc2cc1F] | 364.33 | 2.00-2.08 (m, 2H), 3.24 (s, 3H), 3.43-3.46 (m, 2H), 3.51-3.54 (m, 2H), 3.57 (t, J = 6.25 Hz, 2H), 4.34 (t, J = 6.12 Hz, 2H), 7.64 (d, J = 7.00 Hz, 1H), 7.98 (d, J = 10.71 Hz, 1H), 8.84 (s, 1H), 11.39 (s, 1H) |

Example 3

Materials and Methods

Fluorescence Polarization (FP) Assay

To identify direct NF-κB inhibitors, a fluorescence polarization (FP) screening assay was developed using c-Rel homodimer and CD28 response element (CD28RE) in the promoter region of the IL-2 gene. 5'-fluorescein-labeled duplex CD28RE oligonucleotide probe (10 nM) was mixed with Rel protein (128 nM) in reaction buffer (20 mM Tris (pH7.5), 100 mM NaCl, 0.5 ug/ml polydIdC, 1% NP-40, 0.1% BSA). 20 µl of the mixture was added to each well of a 384-well plate, compound of interest was added (25 µM), and plates were incubated for 30 minutes at room temperature. The anisotropy value of each reaction well was measured using Fusion™ Universal Microplate Analyzer (Perkin Elmer, PE). A series of titration experiments were performed to optimize c-Rel protein and FITC-CD28RE probe concentrations to be used in the FP assay. The representative data for 10 nM and 0.33 nM are shown in FIG. 1A and FIG. 1D, respectively. FIG. 1B shows results from cold competition with specific and non-specific oligos. FIG. 1C shows the distribution of FP signals in a representative 384-well plate.

For the 10 nM and 0.33 nM FP assays shown in FIG. 1A and FIG. 1D, respectively, the maximal Signal to Background (S/B) ratio was in the range of 8-11, indicating a robust assay. The background value for DNA probe alone was ~20 mP and the signal for c-Rel-CD28RE reaction was ~200 mP.

Electrophoretic Mobility Shift Assay (EMSA)

DNA binding reaction (20 µL) was carried out in 1×DNA Binding Buffer (10 mM Tris, 40 mM NaCl, 1 mM EDTA, 4% glycerol) with 10 nM c-Rel protein and 0.5 ng phosphor-labeled CD28RE oligonucleotide for 10 minutes at room temperature in 96-well plates. Test compounds, in serial dilutions, were added into each well, and further incubated for 15 minutes before loading onto native 5% polyacrylamide gel. Electrophoresis proceeded for 2.5 hours at 160V. Radioactive signals were quantified using Phospho-Imager. $IC_{50}$ of compounds of example 1 to 75 were determined by quantifying the intensity of Rel/NF-κB inhibition in EMSA using phospho-imager. An example of EMSA data of the present invention is shown for compound 6 in FIG. 2.

NF-κB GFP Assay

NFκB/Jurkat/GFP transcriptional reporter cell line was obtained from SBI System Biosciences. NF-κB/Jurkat/GFP™ Reporter cells ($5\times10^5$ cells) were plated at a concentration of 1 million cells/ml into each well of a 24-well plate. TNF-α (5 ng/ml) was added. Compounds were added via serial dilutions to corresponding wells. After 24 hours, 100 µl of the cells were transferred to a well of a Costar® UV plate (96 well, No lid, w/UV Transparent Flat Bottom, Corning, N.Y., Cat #3635) and the intensity of GFP fluorescence was measured (Excitation 485+/−20, Emission 528+/−20) in a Synergy™ HT Multi-Detection Microplate Reader (BioTech, Winooski, Vt.). The intensities of GFP measured were plotted against the amount of TNF-α.

Pharmacokinetic Study of Compounds in CD-1 Mice

The study duration was two weeks, including acclimation and in-life portions. Three male mice were studied per compound. 5 mg/kg of the compound of interest was administered intravenously via the tail vein in a single dose. Body weight was determined before the first dose. The dosage vehicle was comprised of 100% PEG 400 and 2 meq NaOH. Blood samples were collected at 0.0833, 0.25, 0.5, 2, 4, and 8 hours post-dose. Plasma was generated from blood with K2EDTA as the anticoagulant.

Example 4

EMSA and NF-κB GFP Assay Results

| Compound | EMSA IC50 (µM) | NF-KB GFP IC50 (µM) |
|---|---|---|
| 1 | <2 | <30 |
| 2 | <2 | <30 |
| 3 | <2 | <30 |
| 4 | <2 | <30 |
| 5 | <2 | <30 |
| 6 | <1 | <10 |
| 7 | <2 | <30 |
| 8 | <0.5 | <30 |
| 9 | <5 | <20 |
| 10 | <1 | <30 |
| 11 | <1 | <20 |
| 12 | <1 | 7 |
| 13 | <1 | 9 |
| 14 | <1 | 8.2 |
| 15 | <0.5 | <30 |
| 16 | <0.5 | <30 |
| 17 | <0.5 | <30 |
| 18 | <0.5 | 10 |
| 19 | <1 | <5 |
| 20 | <1 | <5 |
| 21 | <1 | <5 |
| 22 | <1 | <10 |
| 23 | <1 | <5 |
| 24 | <1 | <30 |
| 25 | <1 | <30 |
| 26 | <1 | <30 |
| 27 | <0.5 | <5 |
| 28 | <0.5 | <5 |
| 29 | <0.5 | <5 |
| 30 | <0.5 | <10 |
| 31 | <0.5 | <5 |
| 32 | <0.5 | <5 |
| 33 | <0.5 | <3 |
| 34 | <0.5 | 10 |
| 35 | <1 | <10 |
| 36 | <0.5 | <10 |
| 37 | <0.5 | <20 |
| 38 | <0.5 | <20 |
| 39 | <0.5 | <3 |
| 40 | <0.5 | 5 |
| 41 | <0.5 | <10 |
| 42 | <0.5 | <10 |
| 43 | <0.5 | <3 |
| 44 | <0.5 | <3 |
| 45 | <0.5 | <5 |
| 46 | <0.5 | <5 |
| 47 | <1 | <5 |
| 48 | <0.5 | <5 |
| 49 | <1 | <5 |
| 50 | <1 | <5 |
| 51 | <1 | <5 |
| 52 | <0.5 | <5 |
| 53 | <5 | <20 |
| 54 | <5 | <20 |
| 55 | <5 | <20 |
| 56 | <5 | <20 |
| 57 | <5 | <20 |
| 58 | <5 | <20 |
| 59 | <5 | <20 |
| 60 | <5 | <20 |
| 61 | <1 | <5 |
| 62 | <1 | <5 |
| 63 | <1 | <5 |
| 64 | <1 | <5 |
| 65 | <1 | <5 |
| 66 | <1 | <5 |
| 67 | <1 | <5 |
| 68 | <1 | <5 |
| 69 | <1 | <5 |
| 70 | <1 | <5 |
| 71 | <1 | <5 |
| 72 | <1 | <5 |
| 73 | <1 | <5 |
| 74 | <1 | <5 |
| 75 | <1 | <5 |

Example 5

Pharmacokinetic Analysis

Pharmacokinetic parameters for compounds 13, 20, 26, 42, 44, and 46 are shown in FIGS. 3A-8B, respectively.

Example 6

Potency of IT-848 Against Lung Cancer Patient-Derived, Erlotinib-Sensitive (HCC827), and Erlotinib-Resistant (11H1975) Cell Lines Compounds
Compounds used in the following experiments and examples include:

| Compound | Lot. No. | Purity | M.W. |
|---|---|---|---|
| IT-839 | IT002-025-1 | >95% | 332.33 |
| IT-843 | IT002-011-1 | >95% | 334.75 |
| IT-848 | IT002-110-1 | >95% | 348.78 |
| IT-852 | IT002-047-2 | >95% | 304.27 |
| IT-878 | IT003-060-1 | >95% | 350.75 |

Cell Culture
All cells were maintained at 37° C. with 5% $CO_2$ in the following media: for primary lung adenocarcinoma and squamous cells—Complete Epithelial Cell Medium, Cell Biologics; for HCC827 and H1975 cells—RPMI, 10% FBS, 1% penicillin/streptomycin; and for wild-type fibroblasts—EMEM, 10% FBS, 1% penicillin/streptomycin.
Viability Assay (ATP Assay)
Cell viability was determined using CellTiter-Glo 2.0 (Promega) according to manufacturers' protocols. Briefly, approximately 30,000 cells were seeded into white, clear-bottom 96-well plates (Fisher Scientific). The next day, vehicle, IT-852, IT-848, erlotinib, and a combination of IT-848 and erlotinib were added to cells at the concentrations indicated in FIG. 9 in duplicate and incubated at 37° C. for 24 and 48 hours. At the end of the incubation periods, cells were processed according to manufacturers' protocols and luminescent signals were obtained using the Synergy H1 Hybrid Multi-Mode plate reader (BioTek).
Apoptosis Induction Assay (PARP Assay)
Cell apoptosis activity was measured using PARP/Apoptosis Chemiluminescent assay kits (Trevigen) according to manufacturers' protocols. Approximately 30,000 cells were seeded into white, clear-bottom 96-well assay plates (Fisher Scientific). The next day, vehicle, IT-852, IT-848, erlotinib, and a combination of IT-848 and erlotinib were added to cells at the concentrations indicated in FIG. 9 in duplicate and incubated at 37° C. for 24 and 48 hours. At the end of the incubation periods, cells were processed according to manufacturers' protocols and luminescent signals were obtained using the Synergy H1 Hybrid Multi-Mode plate reader (BioTek).

The experimental design for determining potency of NF-κB inhibitors on NSCLC is shown in FIG. 9.

Results

Figure 12:
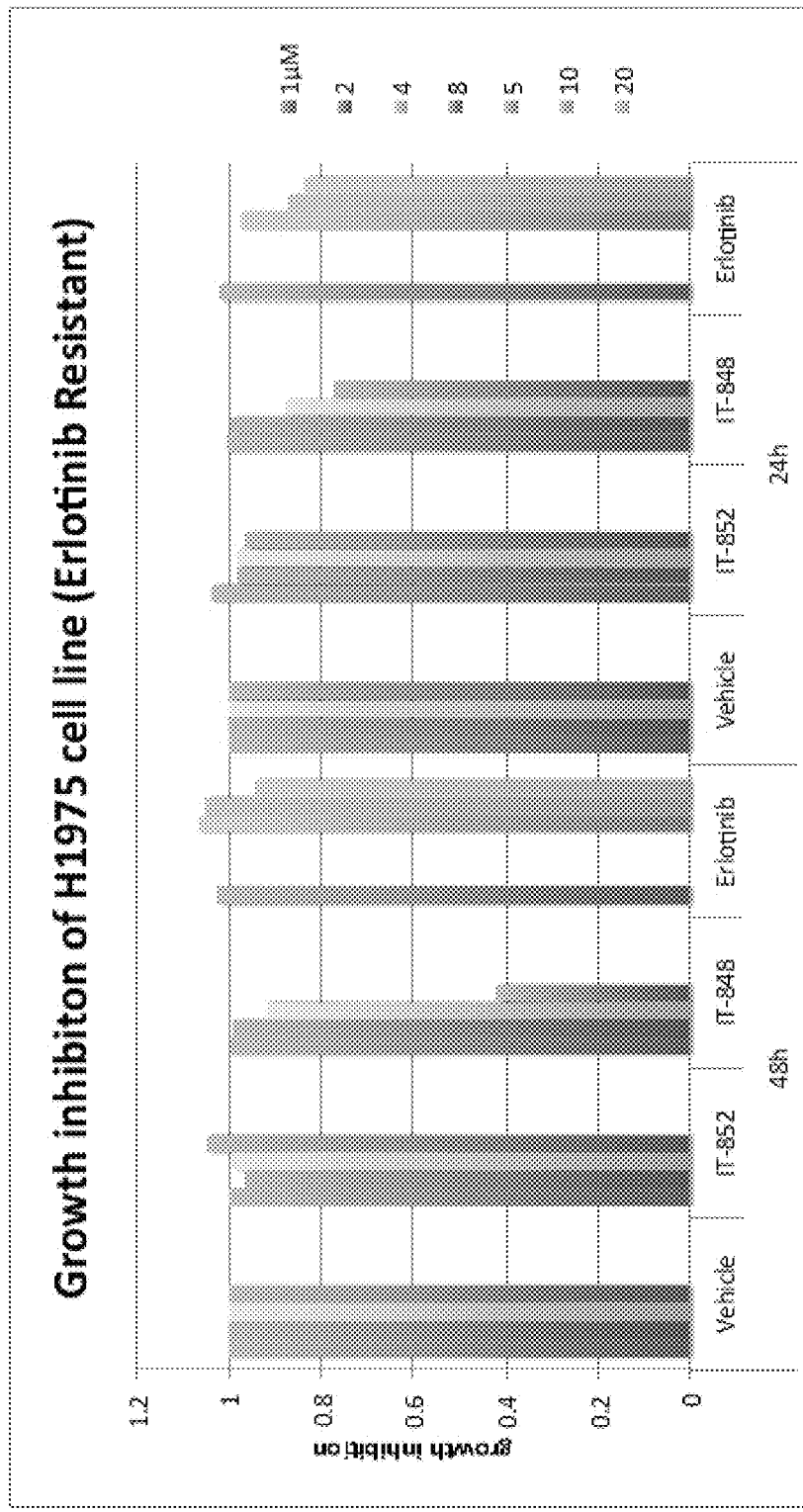
FIG. 12 is a histogram showing growth inhibition of the erlotinib-resistant H1975 cell line exposed to compounds of the present invention at 24 and 48 hours post-treatment. Growth inhibition was detected using CellTiter-Glo 2.0.
Figure 13:
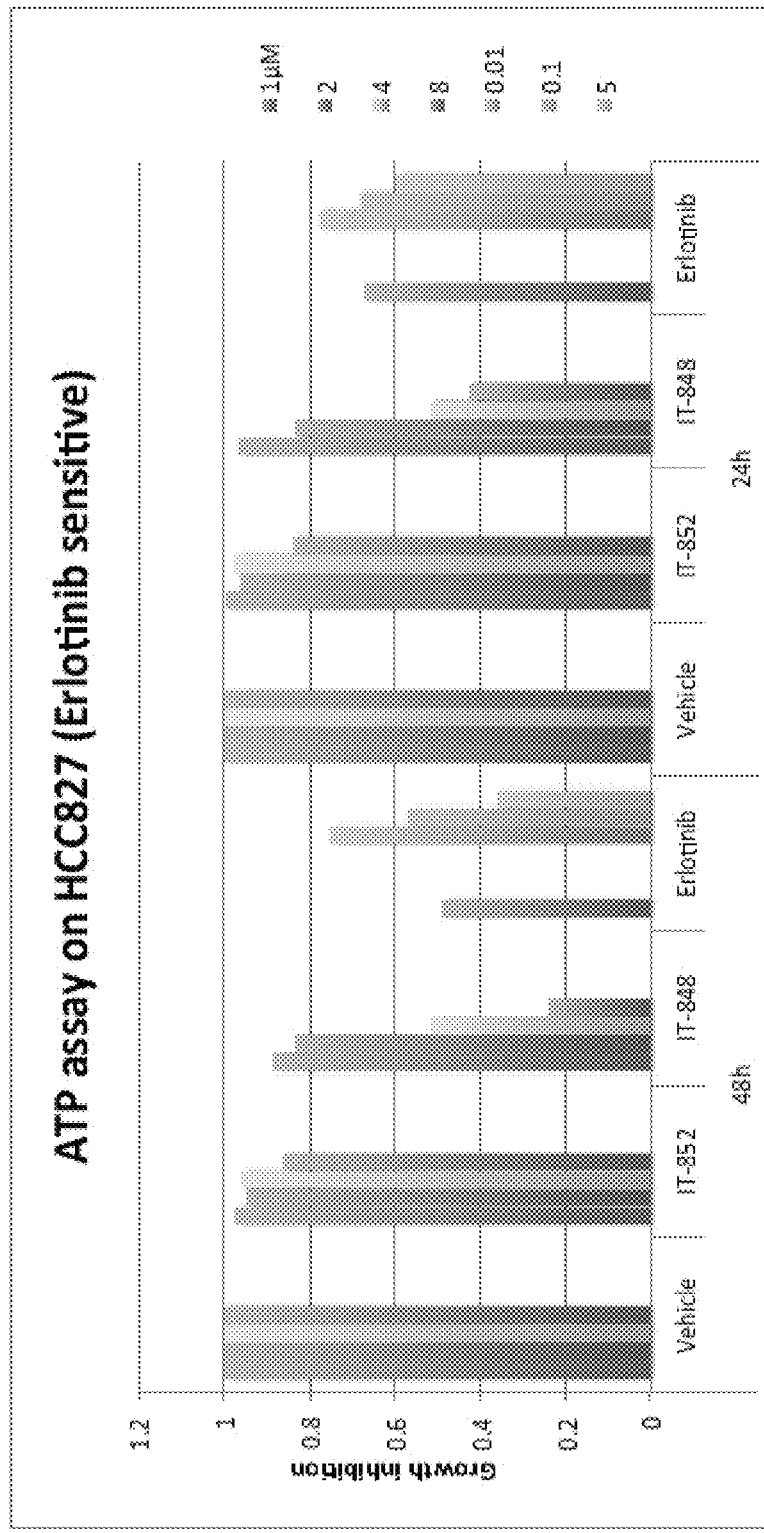
FIG. 13 is a histogram showing growth inhibition of the erlotinib-sensitive HCC827 cell line exposed to compounds of the present invention at 24 and 48 hours post-treatment. Growth inhibition was detected using CellTiter-Glo 2.0.
Figure 15A:
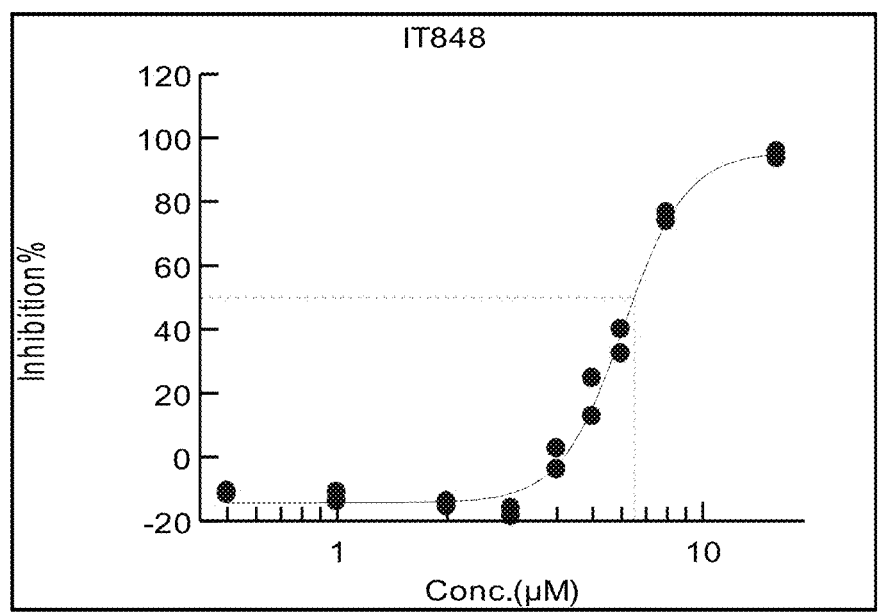
FIGS. 15A-15L are histograms showing growth inhibition of various lung cancer cell lines treated with IT-848 or IT-852.
Figure 15B:
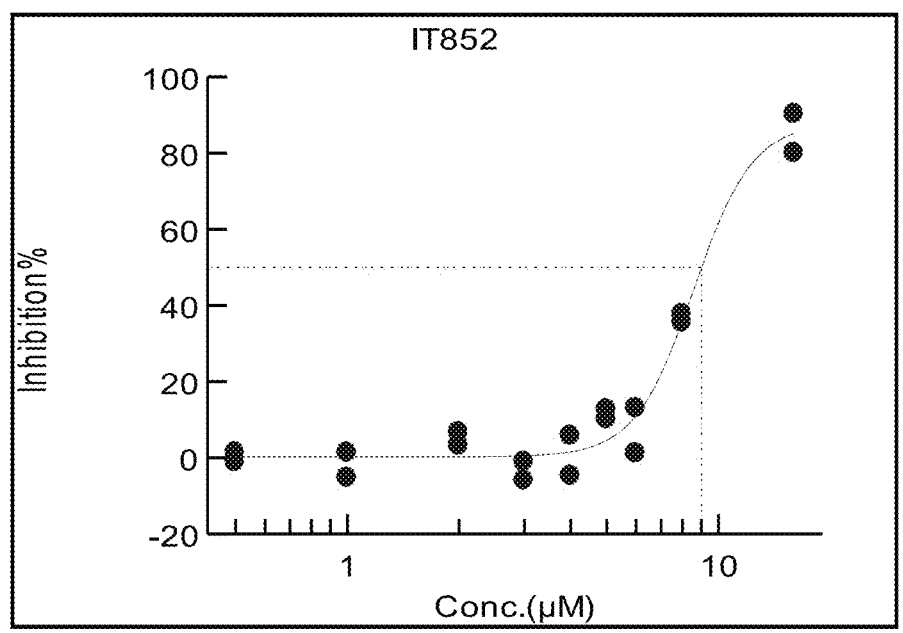
Figure 15C:
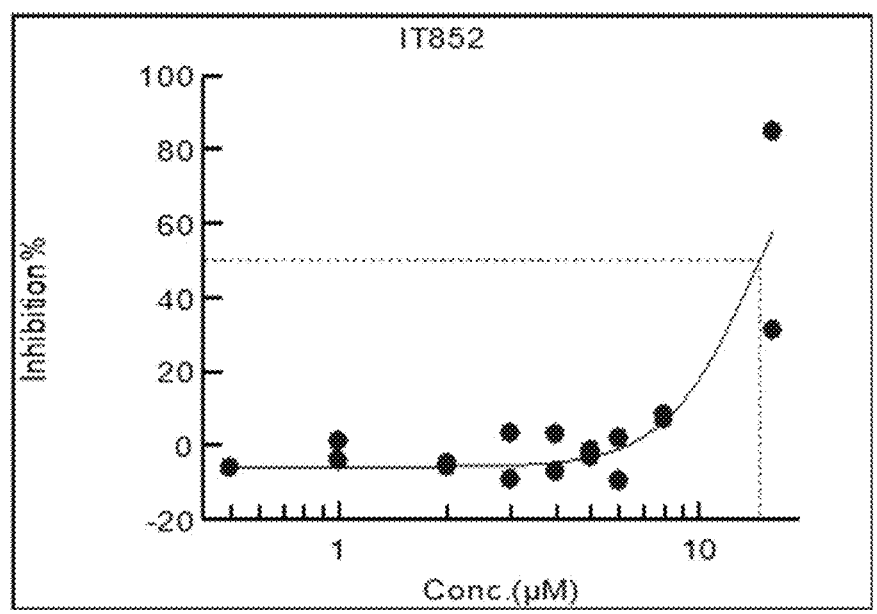
Figure 15D:
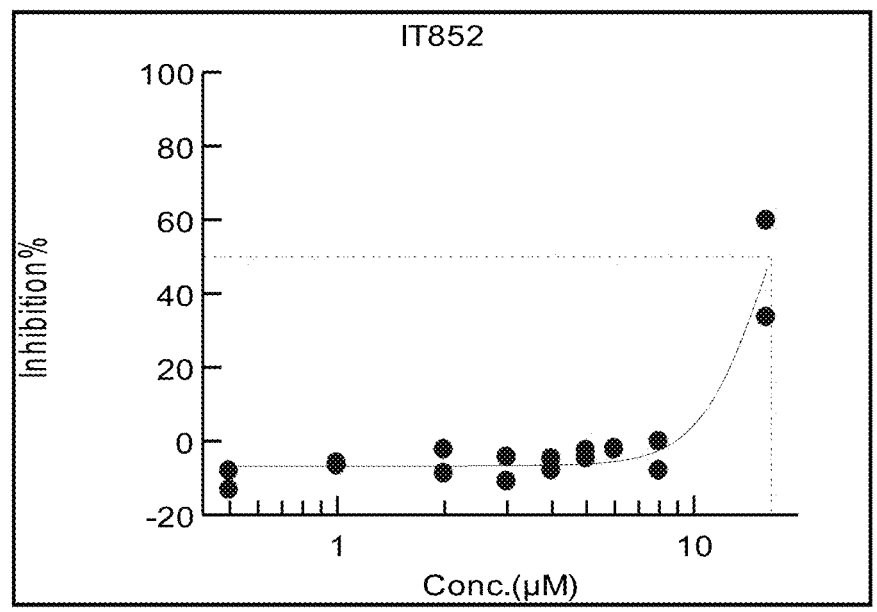
Figure 15E:
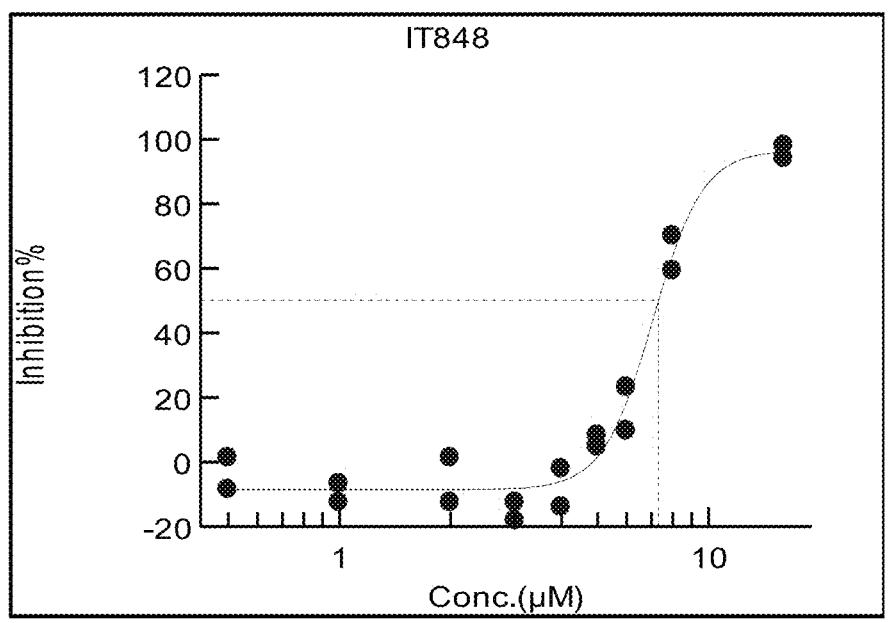
Figure 15F:
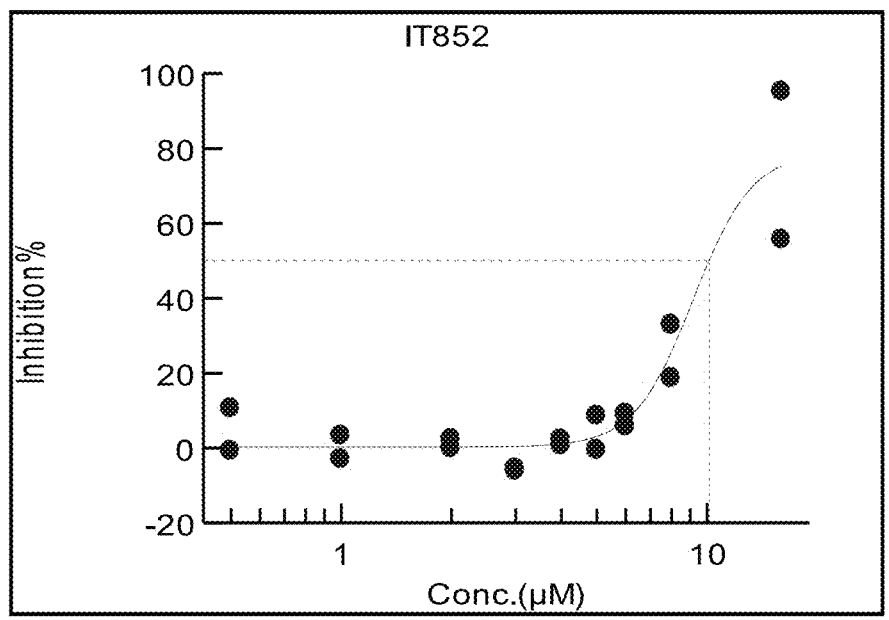
Figure 15G:
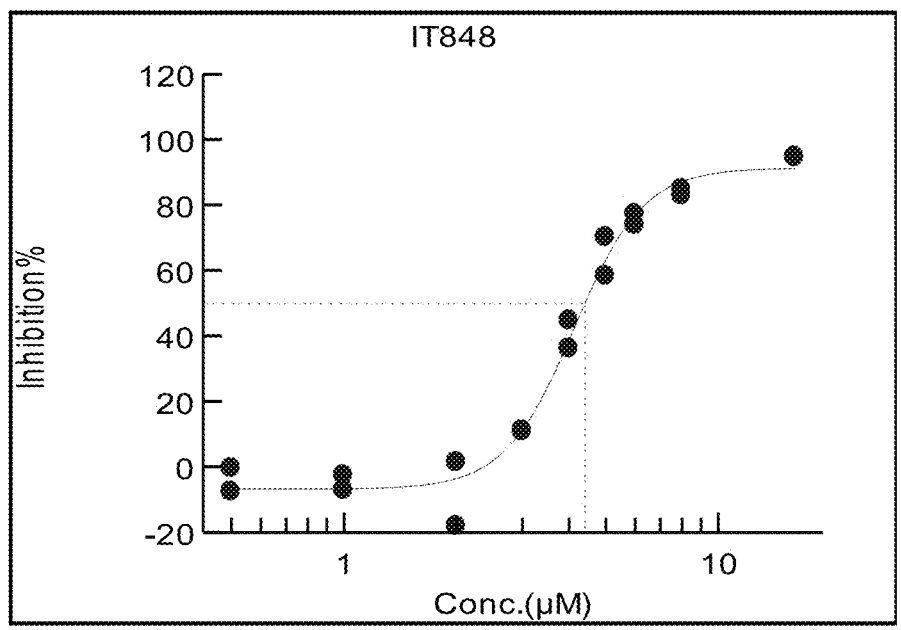
Figure 15H:
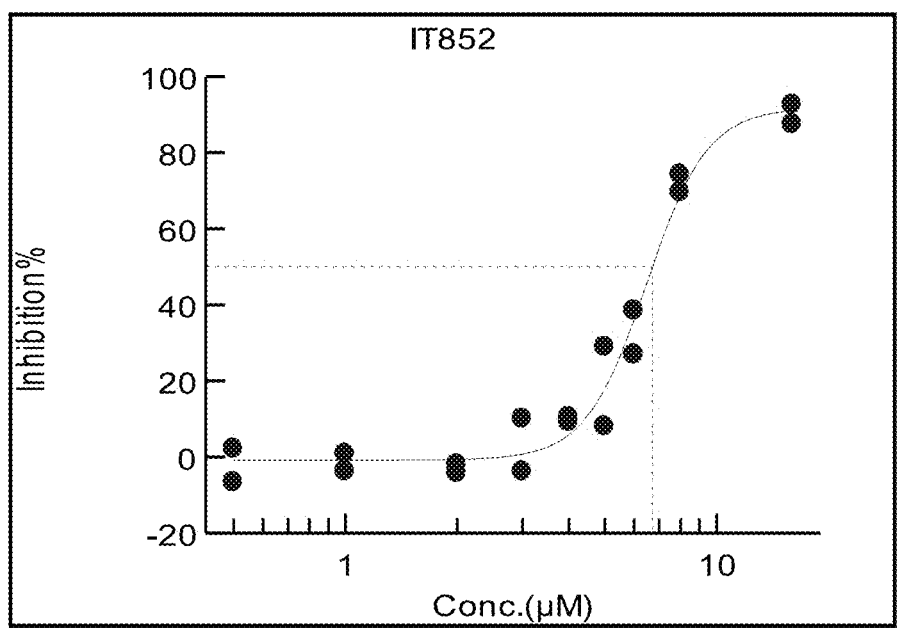
Figure 15I:
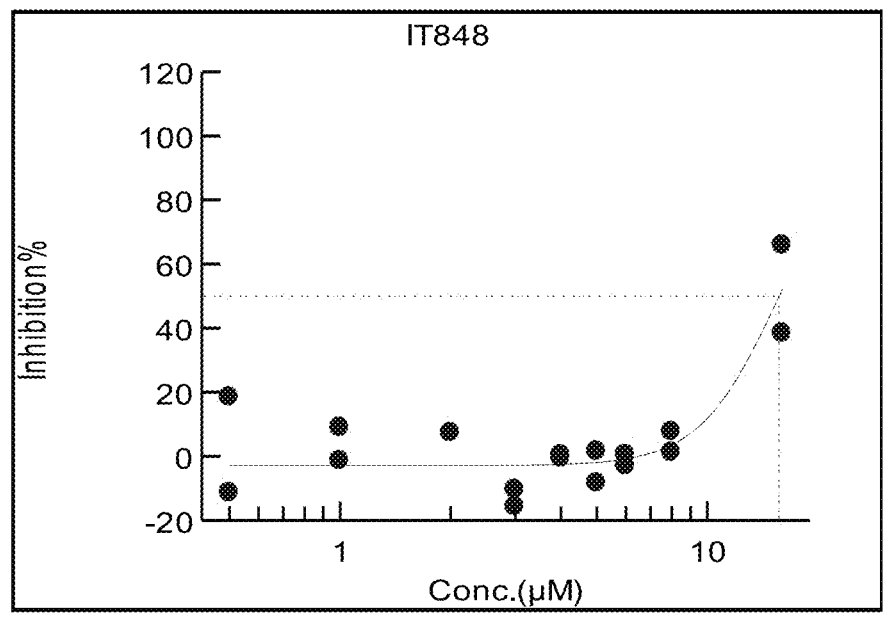
Figure 15J:
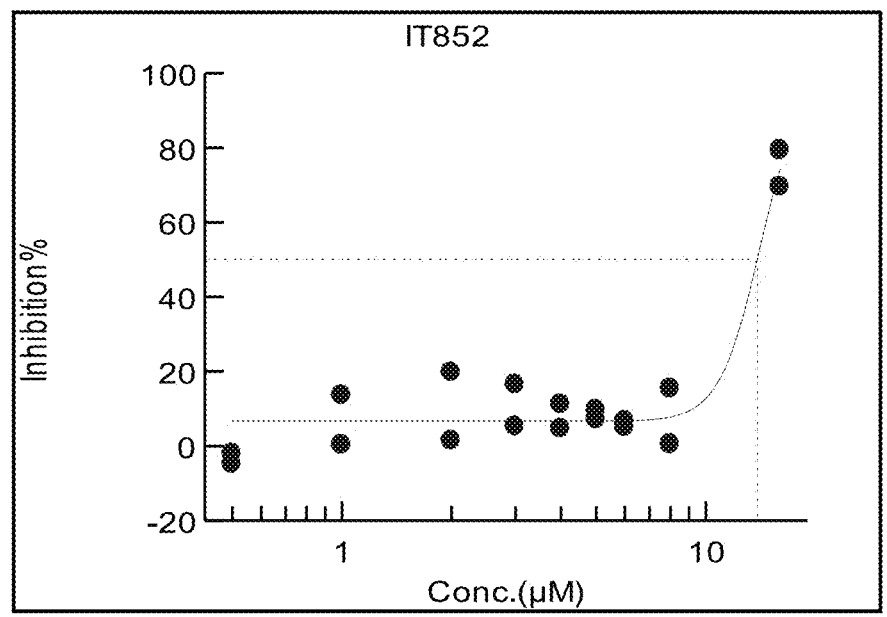
Figure 15K:
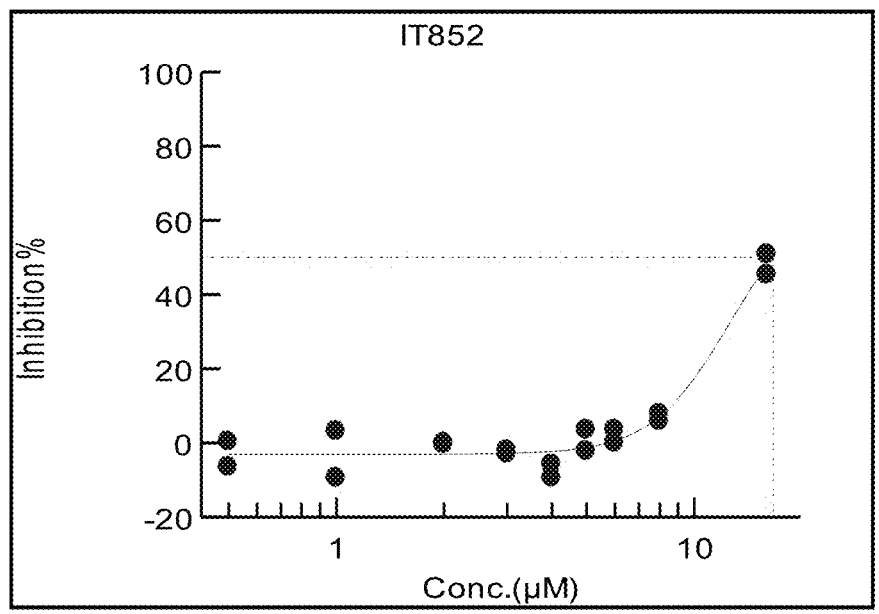
Figure 15L:
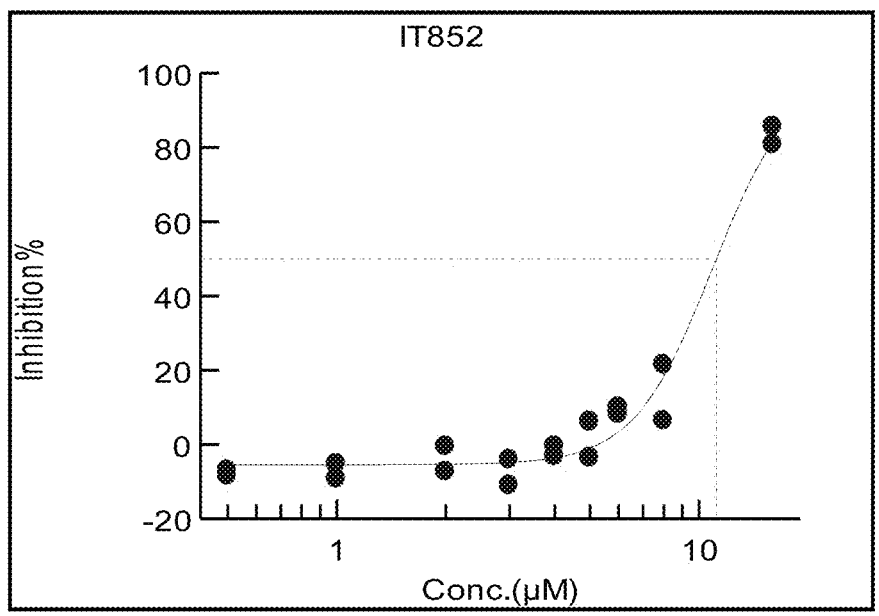

FIG. 10 shows 50% growth inhibition (IG50) and PARP activity inhibition at 24 hours post-treatment with NF-κB inhibitor or reference drug. FIG. 11 shows IG50 and PARP activity inhibition at 48 hours post-treatment with NF-κB inhibitor or reference drug. FIG. 12 shows growth inhibition of the erlotinib-resistant H1975 cell line in the CellTiter-Glo 2.0 assay at both 24 and 48 hours post-treatment with NF-κB inhibitor or reference drug. FIG. 13 shows growth inhibition of the erlotinib-sensitive HCC827 cell line in the CellTiter-Glo 2.0 assay at both 24 and 48 hours post-treatment with NF-κB inhibitor or reference drug.

Example 7

Potency of IT-848 Against a Broad Range of Lung Cancer Cell Lines

Additional experiments were performed as described in Example 6 using the cell lines shown in FIG. 14. Results are shown in FIGS. 15A-15L.

Example 8

Potency of NF-κB Inhibitors Against a Panel of Pancreas, Liver, Colorectal, Breast, and Gastric Cell Lines Various pancreatic, liver, colon, breast, and stomach cancer cell lines were exposed to the NF-κB inhibitors of the present invention, including, for example, IT-839, IT-843, IT-848, and IT-878, and assessed for IG50 in the CellTiter Glo 2.0 assay.

Pancreatic cell lines used include Capan-1, BxPC-3, Mia PaCa2, and PANC-1. Liver cell lines used include, but are not limited to, HepG2, HepB3, and PLC/PRF5. Colon cell lines used include, but are not limited to, HCT116, HT-29, LoVo, SW480, and SW620. Breast cell lines used include, but are not limited to, MCF7, T47D, BT474, and MDA-MB-231. Stomach cell lines used include, but are not limited to, KATO III, MKN 45, and AGS.

Compounds

Compounds used in the following experiments and examples include:

| Compound | Lot. No. | Purity | M.W. |
|---|---|---|---|
| IT-839 | IT002-025-1 | >95% | 332.33 |
| IT-843 | IT002-011-1 | >95% | 334.75 |
| IT-848 | IT002-110-1 | >95% | 348.78 |
| IT-878 | IT003-060-1 | >95% | 350.75 |
| Gemcitabine | S1714 | >95% | 263.2 |
| Sorafenib | S7397 | >95% | 464.82 |
| 5-FU | S1209 | >95% | 130.08 |

Cell Culture

The cells were cultured in an atmosphere of 37° C., 5% $CO_2$ and 95% humidity. All culture media and FBS were purchased from GIBCO, Hyclone or Sigma, USA. The media used for cell culture is described in the table below.

| Tissue Origin | Cell Line | Medium | Seeding Density (Cells/well) | Reference Controls |
|---|---|---|---|---|
| Pancreas | Capan-1 | IMDM + 20% FBS | 2000 | Gemcitabine |
| | MiaPaCa-2 | DMEM + 10% FBS + 2.5% HS | 2000 | |
| | PANC-1 | DMEM + 10% FBS | 2000 | |
| Liver | HepG2 | EMEM + 10% FBS | 2000 | Sorafenib |
| | Hep3B | EMEM + 10% FBS | 2000 | |
| | PLC/PRF/5 | DMEM + 10% FBS | 2000 | |
| Colon | HCT 116 | McCoy's 5a + 10% FBS | 2000 | 5-FU |
| | HT-29 | McCoy's 5a + 10% FBS | 2000 | |
| | LoVo | Ham's F12K + 10% FBS | 2000 | |
| Breast | MCF7 | (MEM + 0.01 mM NEAA) + 10% FBS + 10 ug/ml Insulin | 4000 | Gemcitabine |
| | T47D | RPMI1640 + 10% FBS + 0.2 u/ml Insulin | 3000 | |
| | MDA-MB-231 | L-15(100% air) + 10% FBS | 3000 | |
| Stomach | AGS | Ham's F12K + 10% FBS | 2000 | 5-FU |
| | KATO III | IMDM + 20% FBS | 2000 | |
| | MKN45 | RPMI1640 + 10% FBS | 2000 | |

Day 1: Cell Seeding

The cells were harvested during the logarithmic growth period and counted. Cell concentrations were adjusted to the appropriate number in appropriate medium and 90 μl cell suspensions were added to 96-well plates. When cells were added, the plates were shaken gently to distribute the cells evenly. Cells were incubated at 37° C. and 5% $CO_2$.

Day 2: Compound Treatment

3× serial dilutions of test compound stock solutions with respective solvents were prepared. The stock solutions were diluted with culture medium to generate 10× working solutions of the test compounds. 10 μl of the 10× test compound solutions were added to each well in triplicate for each concentration. Plates were incubated for 72 hours in a humidified incubator at 37° C. and 5% $CO_2$.

Day 5: Plate Reading

CellTiter-Glo (CTG) solution was thawed and equilibrated to room temperature. 50 μl of CTG were added to each well and the contents were mixed for 2 minutes on a plate shaker. Cells were incubated for 10 minutes before luminescence signal was recorded using Envision.

Data Analysis

Cell viability was plotted with GraphPad Prism version 5 and the IG50 was calculated for each cell line. The graphical curves were fitted using a nonlinear regression model with a sigmoidal dose response. IG50 is the concentration of test drug where 100×T/C=50 (the optical density of the test well after a 3-day period of exposure to test drug is T; the control optical density is C).

Results

The results are shown in the table below:

| Cell lines | IT-848 | IT-878 | IT-839 | IT-843 | Sorafenib | 5-FU | Gemcitabine |
|---|---|---|---|---|---|---|---|
| Capan-1 | >16 | >16 | >16 | >16 | | | 0.051 |
| PANC-1 | 9.881 | >16 | 6.93 | 5.536 | | | >16 |
| MIAPACA-2 | >16 | 17.826 | >16 | 10.164 | | | 0.012 |
| PLC/PRF/5 | >16 | >16 | >16 | >16 | 10.756 | | |
| HepG2 | 6.701 | >16 | 10.524 | 3.943 | 5.136 | | |
| Hep3B | 2.428 | 3.448 | 3.348 | 1.419 | 7.493 | | |
| HCT116 | >16 | >16 | >16 | 9.397 | | 5.202 | |
| HT-29 | >16 | >16 | >16 | 6.606 | | 15.858 | |
| LoVo | 5.066 | >16 | 4.339 | 2.887 | | 26.961 | |
| MCF-7 | 5.186 | >16 | >16 | 6.806 | | | >16 |
| MDA-MB-231 | 2.345 | >16 | 2.008 | 2.684 | | | >16 |
| T47D | 6.144 | >16 | >16 | 4.956 | | | >16 |
| AGS | 7.672 | >16 | >16 | 4.444 | | 31.9 | |
| MKN45 | >16 | >16 | >16 | >16 | | 4.721 | |
| KATO III | >16 | >16 | >16 | >16 | | >64 | |

Example 9

Potency of NF-κB Inhibitors Against a Panel of Hepatocellular Carcinoma (HCC) Cell Lines Compounds Compounds used in the following experiments and example include:

| Compound | Lot. No. | M.W. | Purity |
|---|---|---|---|
| IT835 | IT002-023-1 | 332.33 | >95% |
| IT843 | IT002-011-1 | 334.75 | >95% |
| IT845 | IT002-026-1 | 348.78 | >95% |
| IT846 | IT002-028-1 | 362.81 | >95% |
| IT848 | IT002-110-1 | 348.78 | >95% |
| IT855 | IT002-136-2 | 366.75 | >95% |
| IT876 | IT003-026-2 | 378.76 | >95% |
| IT901 | NA | 342.00 | >95% |
| Sorafenib | S7397 | 464.82 | >95% |

Cell Culture

The cells were cultured in an atmosphere of 37° C., 5% CO and 95% humidity. All culture media and FBS were purchased from GIBCO, Hyclone or Sigma, USA. The media used for cell culture is described in the table below.

| Cell Line | Medium | Seeding Density (cells/well) | Reference Controls |
|---|---|---|---|
| Hep G2 | MEM + 10% FBS + 1% NEAA | 2000 | Sorafenib |
| Hep3B | MEM + 10% FBS + 1% NEAA | 2000 | Sorafenib |
| PLC/PRF/5 | DMEM + 10% FBS | 2000 | Sorafenib |
| HUH-7 | DMEM + 10% FBS | 3000 | Sorafenib |
| SNU-878 | RPMI1640 + 10% FBS | 2000 | Sorafenib |
| JHH5 | William's E + 10% FBS + L-Glutamine | 2000 | Sorafenib |
| PBMC | RPMI1640 + 10% FBS | 50000 | Sorafenib |

Following the cell culture protocol and data analysis methods described in Example 8, the following IG50 results (in μM) were observed:

| Compound | HepG2 | Hep3B | PLC/PRF/5 | HUH7 | JHH5 | PBMC | SNU878 |
|---|---|---|---|---|---|---|---|
| IT-848 | 5.836 | 3.509 | >16 | 4.250 | 12.889 | 1.193 | 14.579 |
| IT-855 | >16 | >16 | >16 | >16 | 8.146 | >16 | 9.148 |
| IT-845 | 4.138 | 1.807 | 7.661 | 2.719 | 8.108 | 0.274 | 10.693 |
| IT-846 | 4.273 | 2.336 | 8.512 | 3.386 | >16 | 0.456 | >16 |
| IT-876 | 4.904 | >16 | >16 | 17.695 | 8.499 | 8.672 | >16 |
| IT-901 | 6.483 | 3.905 | 10.605 | 3.821 | 16.444 | 2.901 | 12.896 |
| IT-843 | 4.534 | 3.599 | >16 | 5.158 | 13.261 | 1.088 | >16 |
| IT-835 | >16 | 3.261 | >16 | 5.399 | >16 | 0.985 | >16 |
| Sorafenib | 3.154 | 7.569 | 10.759 | 6.573 | 3.215 | 19.474 | 12.701 |

Example 10

Potency of NF-κB Inhibitors Against a Panel of Hepatocellular Carcinoma (HCC) Cell Lines Compounds Compounds used in the following experiments and example include:

| Compound | Lot. No. | M.W. | Purity |
|---|---|---|---|
| IT845 | IT002-026-1 | 348.78 | >95% |
| IT848 | IT002-110-1 | 348.78 | >95% |
| Sorafenib | S7397 | 464.82 | >95% |

Cell Culture

The cells were cultured in an atmosphere of 37° C., 5% $CO_2$ and 95% humidity. All culture media and FBS were purchased from GIBCO, Hyclone or Sigma, USA. The media used for cell culture is described in the table below.

| Cell Line | Medium | Seeding Density (cells/well) | Reference Controls |
|---|---|---|---|
| Hep G2 | MEM + 10% FBS + 1% NEAA | 2000 | Sorafenib |
| Hep3B | MEM + 10% FBS + 1% NEAA | 2000 | Sorafenib |
| PLC/PRF/5 | DMEM + 10% FBS | 2000 | Sorafenib |
| HUH-7 | DMEM + 10% FBS | 3000 | Sorafenib |
| SNU-878 | RPMI1640 + 10% FBS | 2000 | Sorafenib |
| JHH5 | William's E + 10% FBS + L-Glutamine | 2000 | Sorafenib |
| PBMC | RPMI1640 + 10% FBS | 50000 | Sorafenib |

Following the cell culture protocol and data analysis method described in Example 8, the following IG50 results (in μM) were observed:

| Cell lines | IT-848 (uM) | IT-845 (uM) | Sorafenib (uM) |
|---|---|---|---|
| HepG2 | 9.950 | 6.951 | 4.366 |
| Hep3B | 6.087 | 4.025 | 6.419 |
| PLC/PRF/5 | >16 | 9.217 | 10.145 |
| HUH7 | 7.719 | 6.021 | 5.142 |
| JHH5 | 13.351 | 10.070 | 7.127 |
| PBMC | 3.634 | 2.403 | 14.408 |
| SNU878 | >16 | 9.800 | 10.603 |

Example 11

Potency of NF-κB Inhibitors in Combination with Sorafenib Against a Panel of Hepatocellular Carcinoma (HCC) Cell Lines Following the protocol described in Example 10, the combinations of IT-845+sorafenib and IT-848+sorafenib were tested.

FIGS. 16A-16D indicate the percentage cell viability (%) after treatment with the combination shown at the indicated concentrations.

Example 12

Potency of NF-κB Inhibitors Against a Set of Randomly Selected Patient-Derived Primary Hepatocellular Carcinoma Cells (Sample HCC-01 to HCC-05)

Compounds

Compounds used in the following experiments and examples include:

| Compound | Lot. No. | M.W. | Purity |
|---|---|---|---|
| IT845 | IT002-026-1 | 348.78 | >95% |
| IT848 | IT002-110-1 | 348.78 | >95% |
| Sorafenib | S7397 | 464.82 | >95% |

Primary Cell Preparation

Cells were prepared from human normal liver (for the normal/healthy hepatocyte sample) and liver cancer (for the hepatocellular carcinoma sample) tissue by enzymatic digestion. The cells tested negative for contamination by bacteria, yeast, mold, and mycoplasma. All donors were pre-tested for a blood donation infectious disease panel (ABO/RH, Hepatitis B Surface and Core Antigens, Hepatitis C Virus, HIV1 and 2, Syphilis, Human T Lymphocyte Virus 1 and 2, West Nile Virus and Chagas disease).

Cell Thawing

Cells were stored in liquid nitrogen. For thawing, cryovials were immediately placed in a 37° C. water bath and quickly thawed by gently swirling the vial until there was only a small amount of ice left. Vials were then sprayed with 70% alcohol and transferred to the tissue culture hood. Cells were plated in a flask filled with pre-incubated media for 2-3 hours and media was changed.

Cell Culture

All cells were maintained at 37° C. with 5% $CO_2$ in the supplier-recommended media. HCC cells were cultured in Human Hepatocarcinoma Primary Cell Culture Media with Serum (Celprogen).

ATP Cell Viability Assay

Cells were incubated until ~80% confluent. Cells were then removed from the tissue culture flask using accutase and seeded at a density of approximately ~5,000 cells/well onto collagen-coated 96-well plates (Fisher Scientific). The next day, vehicle, IT-845, IT-848, sorafenib, and combinations thereof were added to cells at the indicated concentrations in triplicate and incubated for 72 hours. Cell viability was determined by the Cell Titer-Glo 2.0 assay kit (Promega) according to manufacturers' instructions using a H1M Synergy plate reader (BioTek).

The following table shows the experimental design (all assays were run in triplicate):

| Compound ID | Concentration [uM] | Patient-Derived HCC sample ID |
|---|---|---|
| IT845 | 1, 2, 4, 8 | HCC-01, HCC-02, |
| IT848 | 1, 2, 4, 8 | HCC-03, HCC-04, |
| Sorafenib | 1, 2, 4, 8 | HCC-05 |
| [IT845 + Sorafenib] | [1 + 1], [1 + 2], [1 + 4]; [2 + 1], [2 + 2], [2 + 4]; [4 + 1], [4 + 2], [4 + 4] | |
| [IT848 + Sorafenib] | [1 + 1], [1 + 2], [1 + 4]; [2 + 1], [2 + 2], [2 + 4]; [4 + 1], [4 + 2], [4 + 4] | |

The following table shows characteristics of the randomly-selected patient-derived HCC samples used in these experiments:

| Sample ID | Patient Description | Cell Passage | Treatment History | Biomarkers |
|---|---|---|---|---|
| HCC-01 | 50 year old, F, Asian, stage 2 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-02 | 58 year old, F, Asian, stage 3 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-03 | 45 year old, M, Asian, stage 2 | 1 | Chemo | Positive for AFP, CDI5s, CD29, CD90, CD151, ESA, ALDH, CEA, CK7, CAM5.2, Mucin, Alpha-I-antitrypsin |
| HCC-04 | 69 year old, F, Asian, stage 4 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-05 | 65 year old, F, Asian, stage 3 | 1 | Chemo, radiation | Positive for AFP, CDI5s, CD29, CD90, CD151, ESA, ALDH, CEA, CK7, CAM5.2, Mucin, Alpha-I-antitrypsin |

Figure 17A:
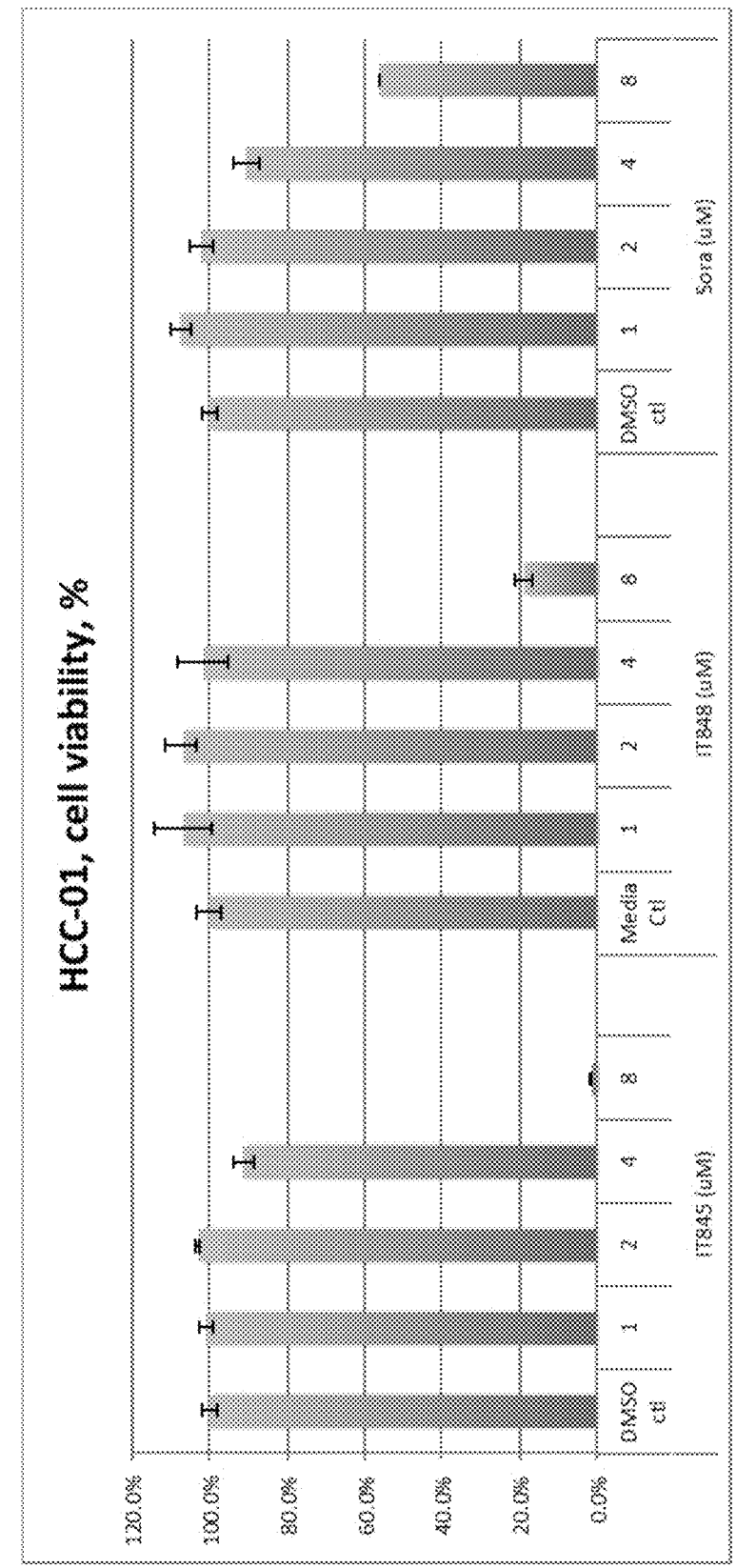
Figure 17B:
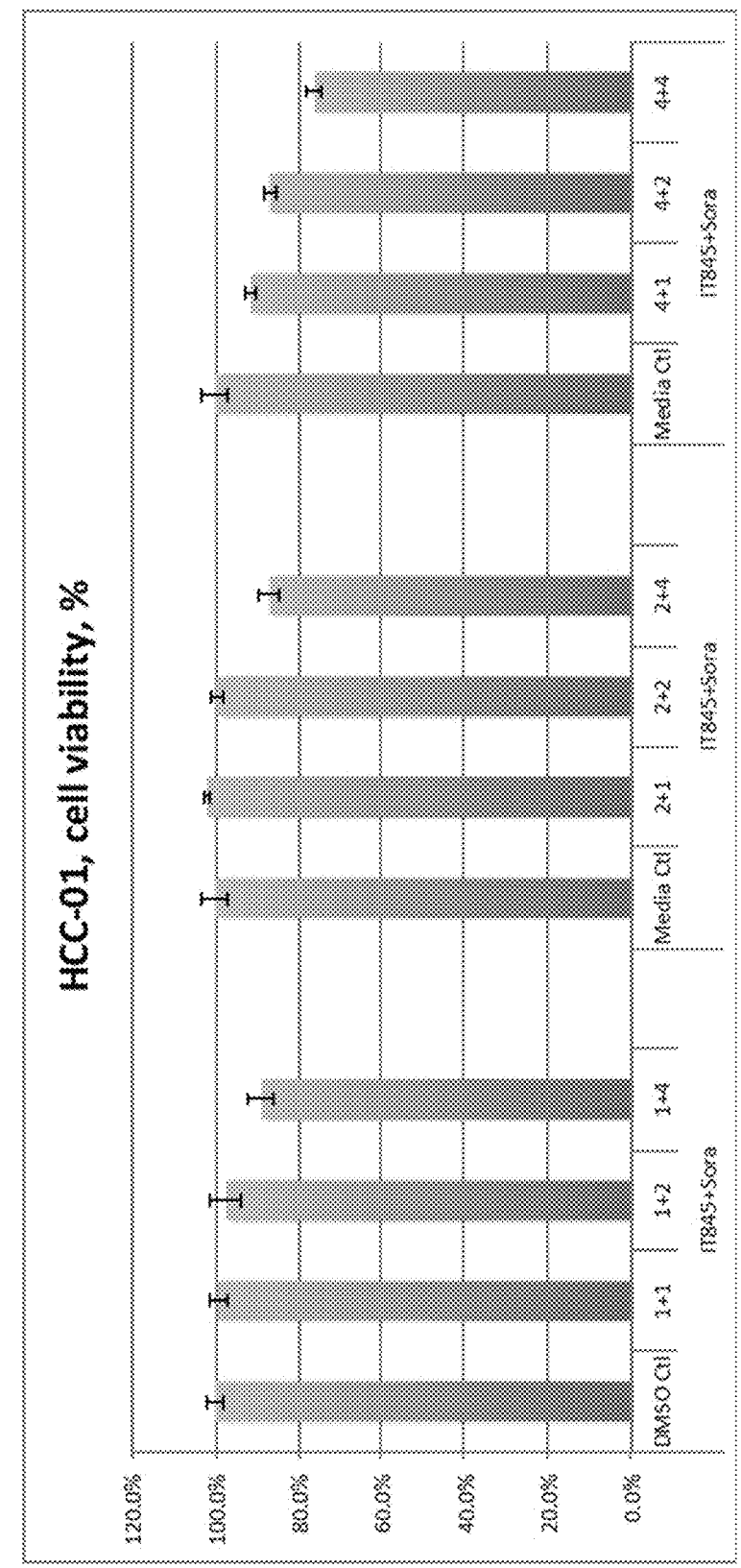
Figure 17C:
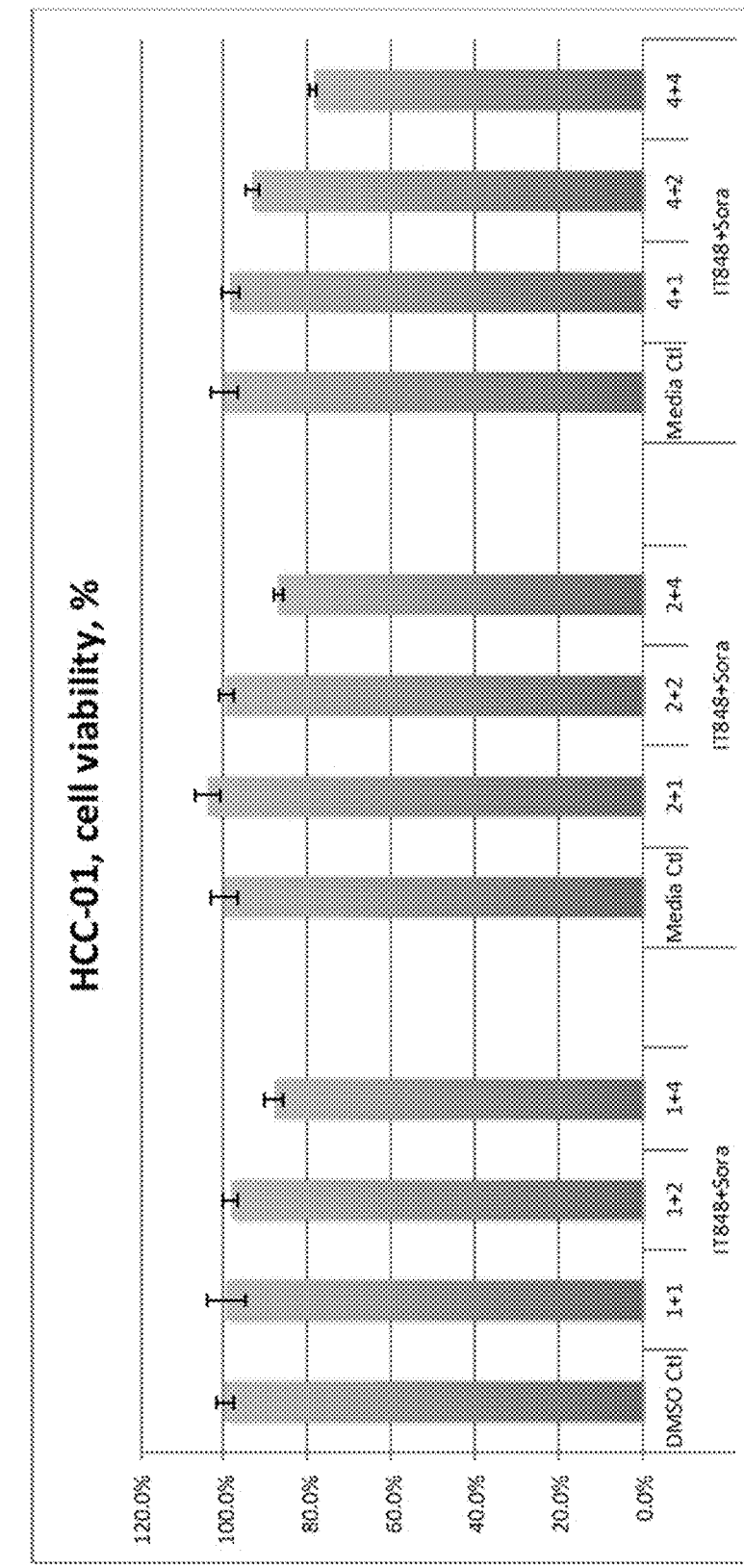
Figure 17D:
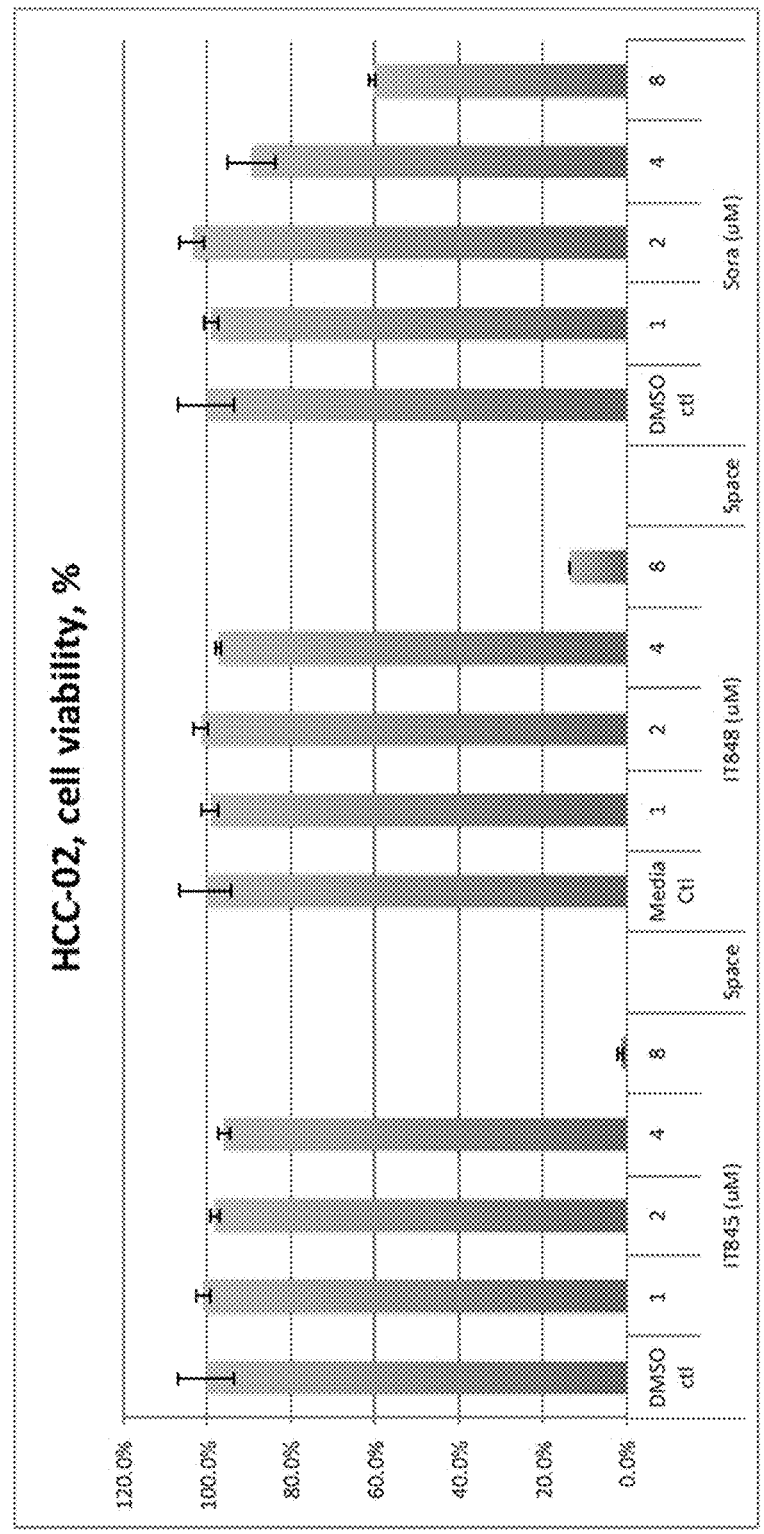
FIGS. 17D-17F: HCC-02 cells.
Figure 17E:
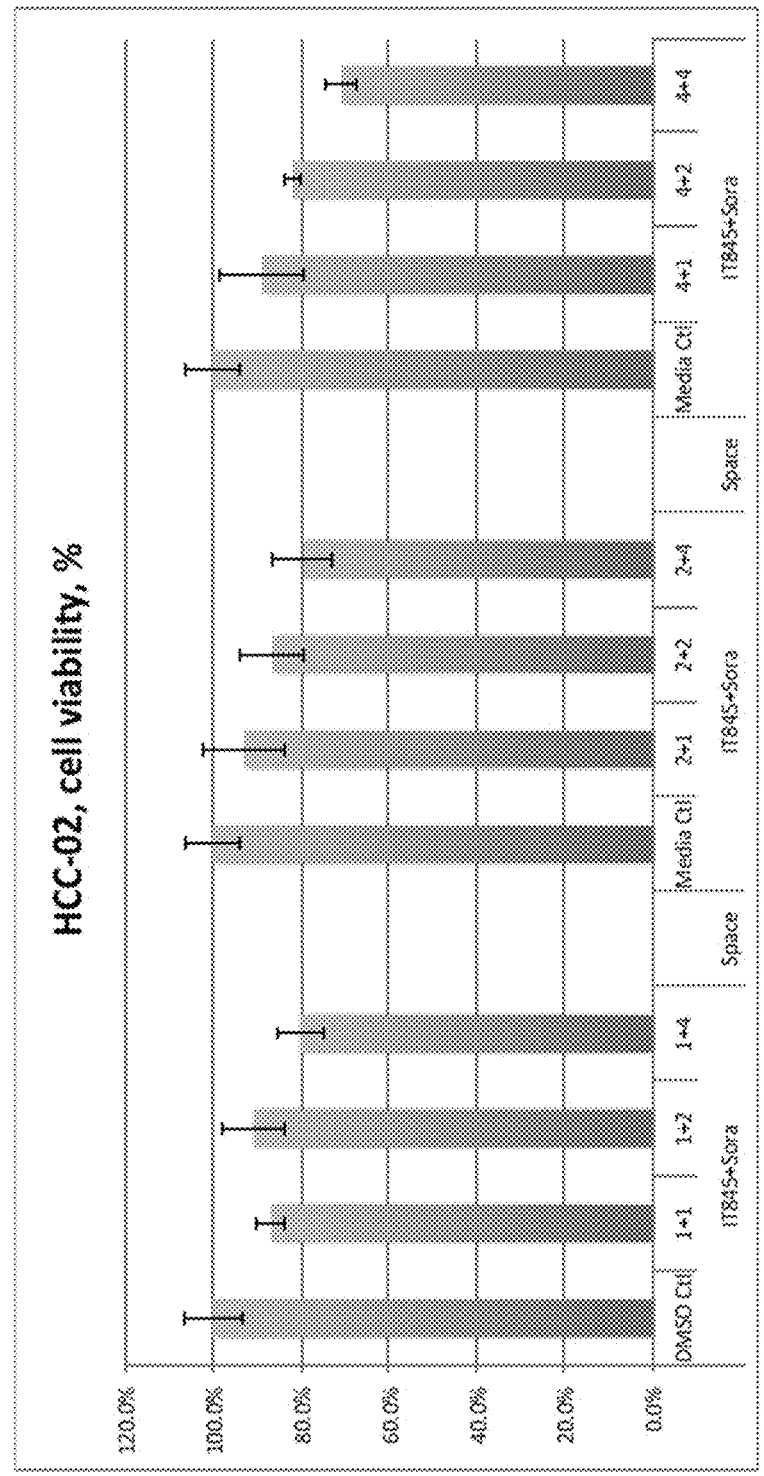
Figure 17F:
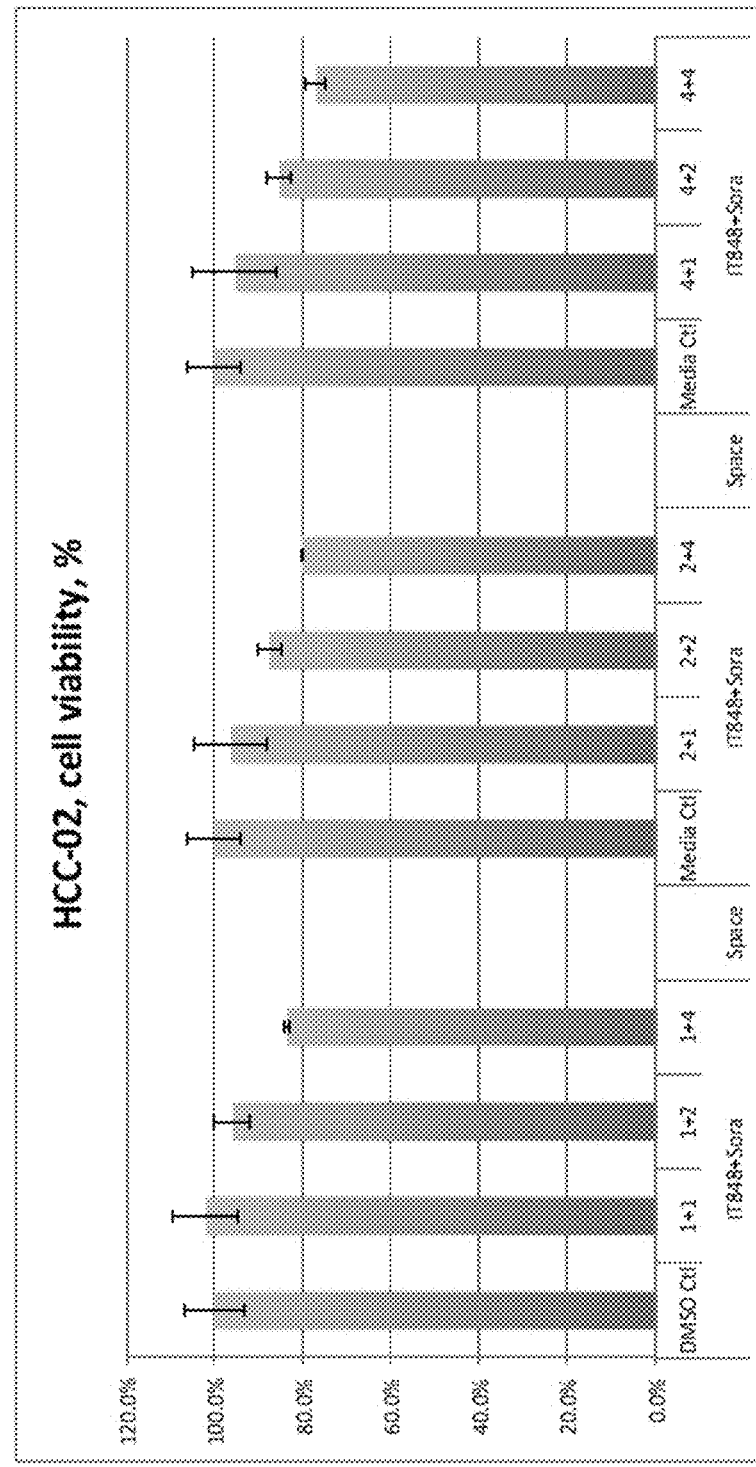
Figure 17G:
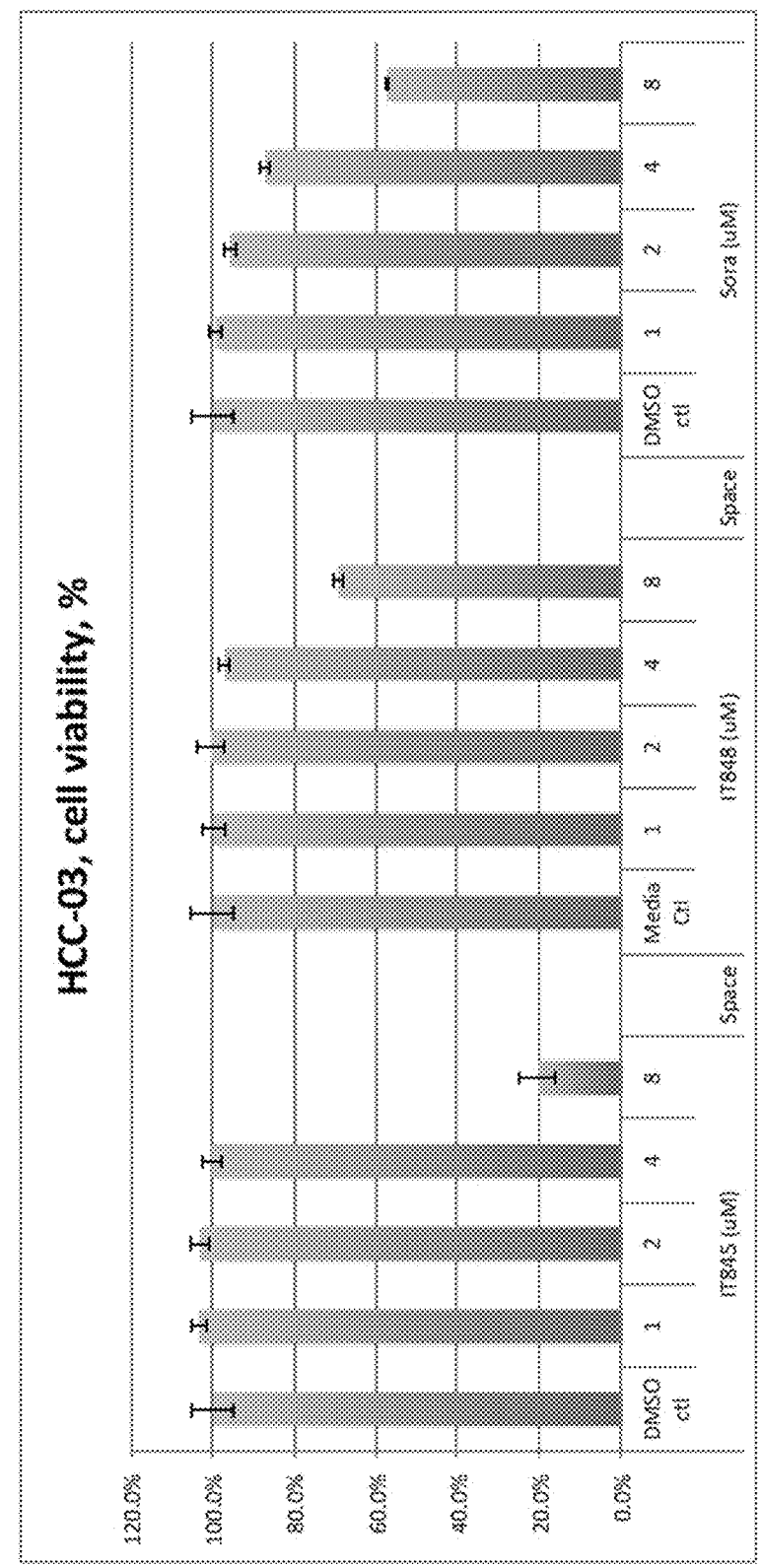
FIGS. 17G-17I: HCC-03 cells.
Figure 17H:
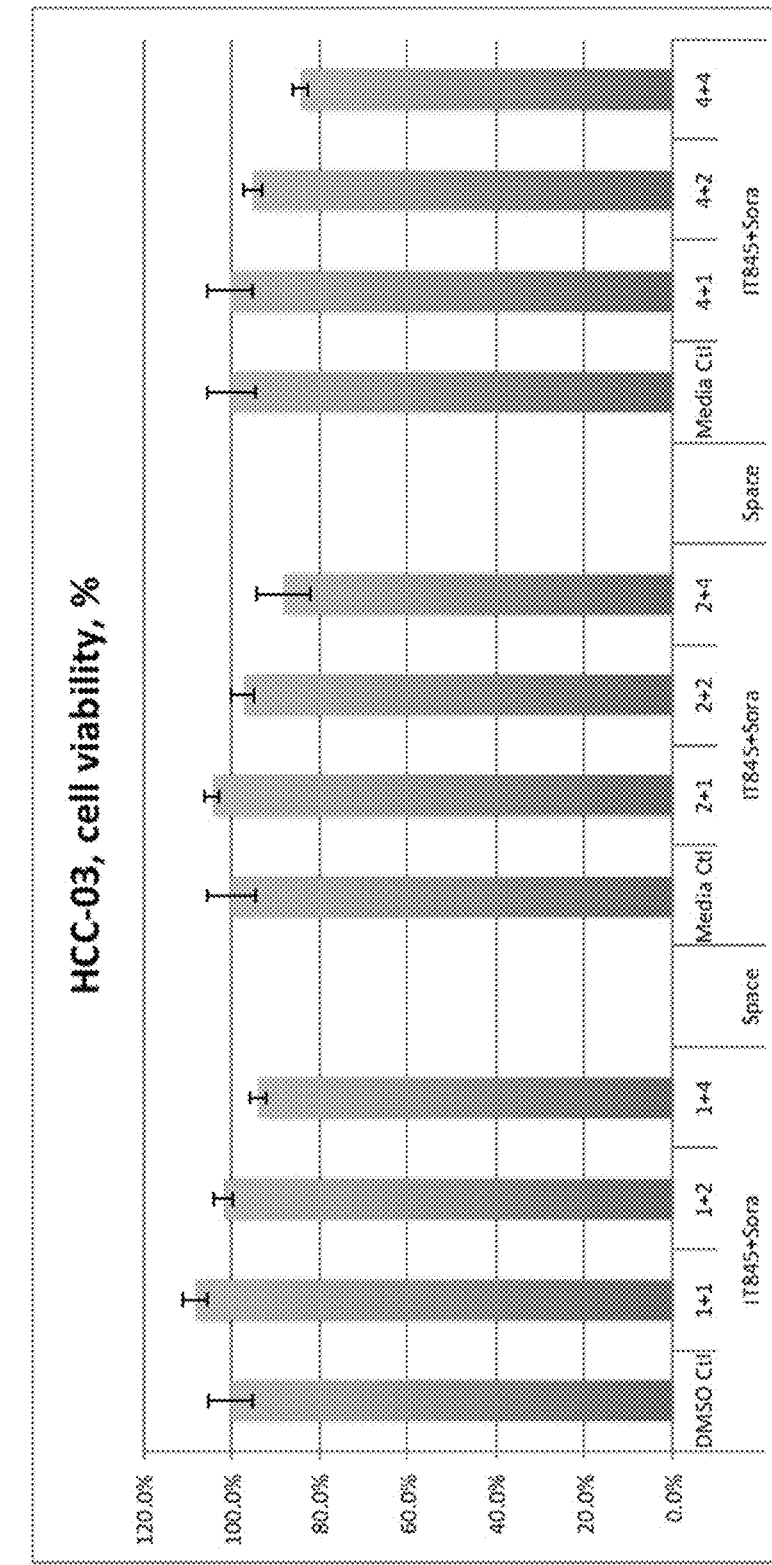
Figure 17I:
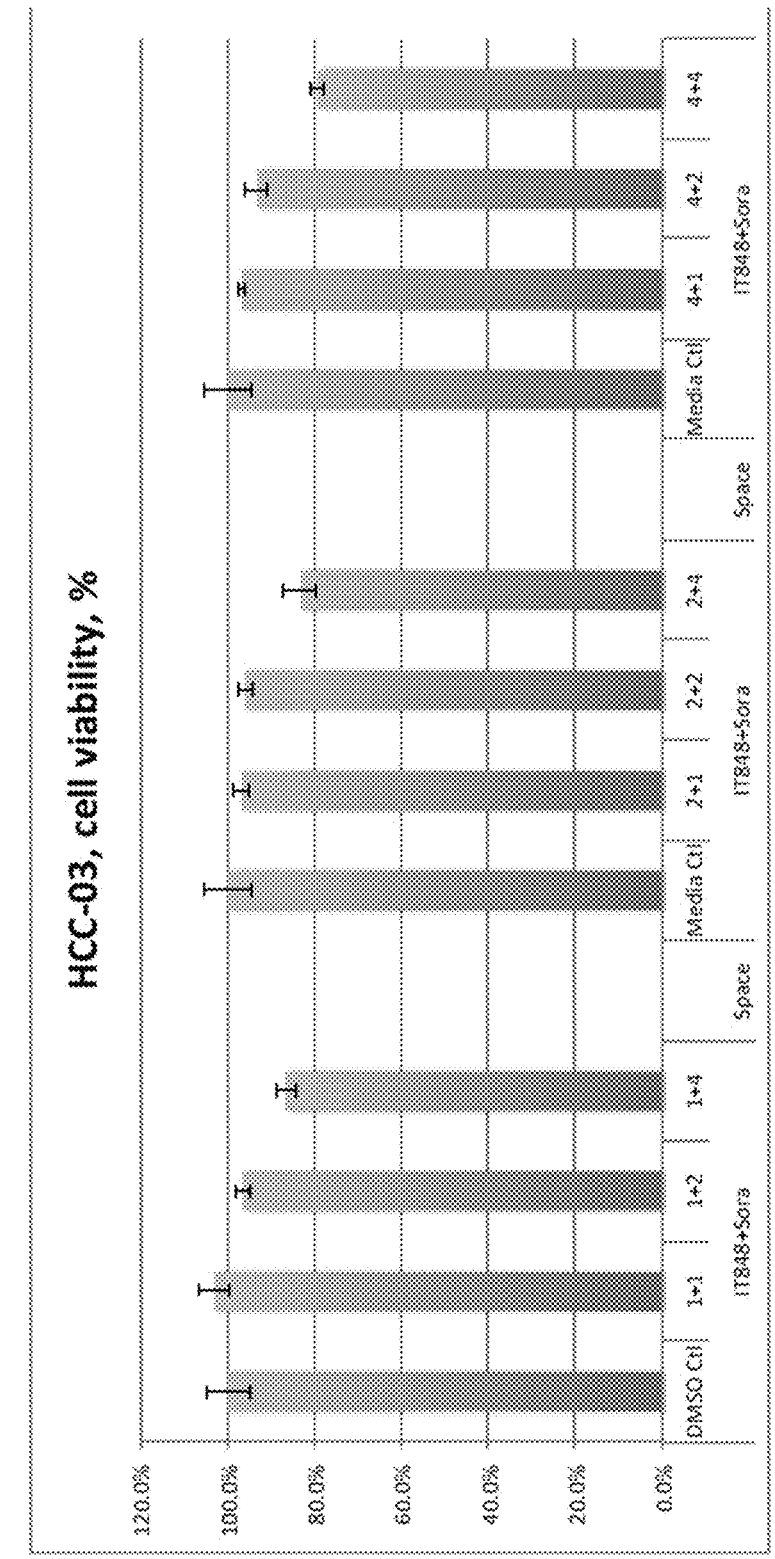
Figure 17J:
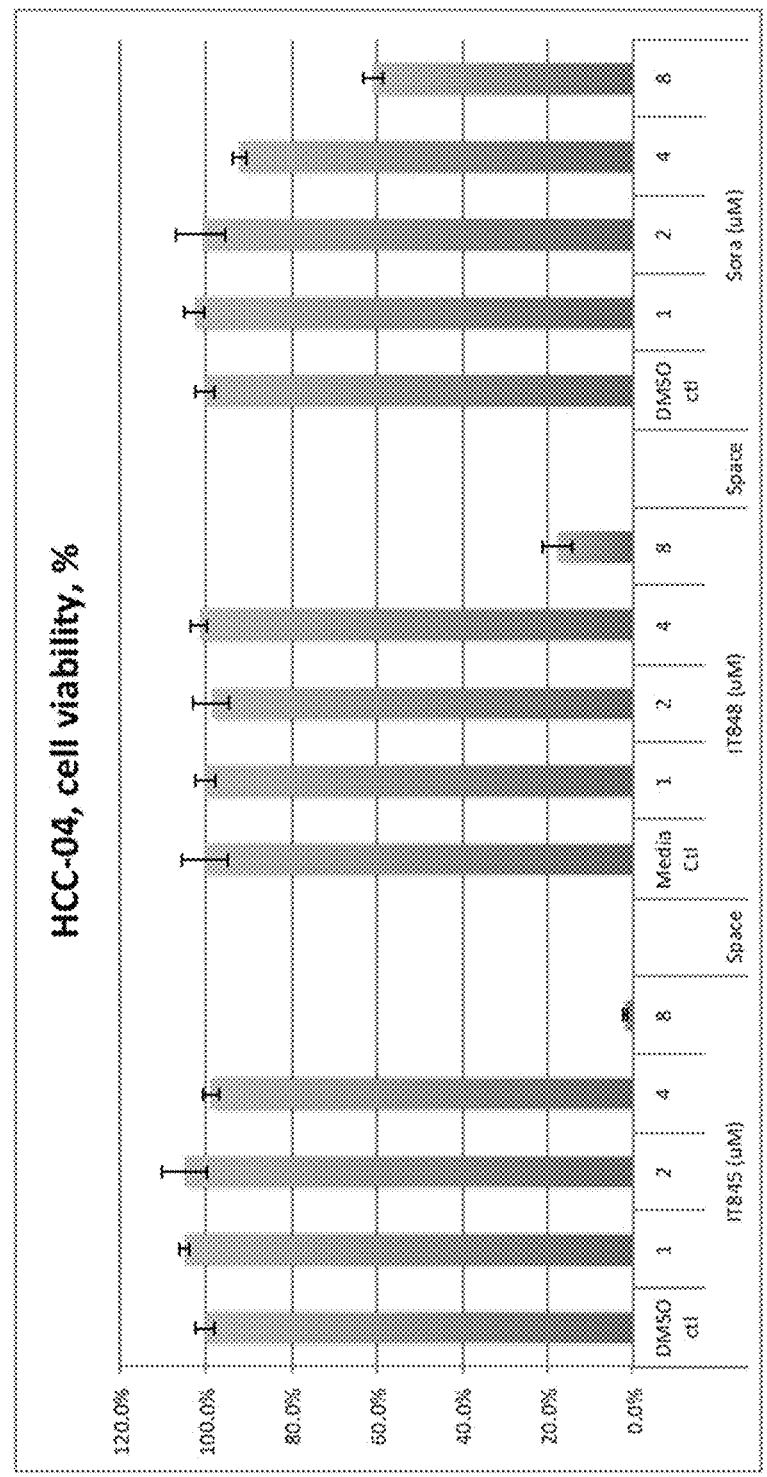
FIGS. 17J-17L: HCC-04 cells.
Figure 17K:
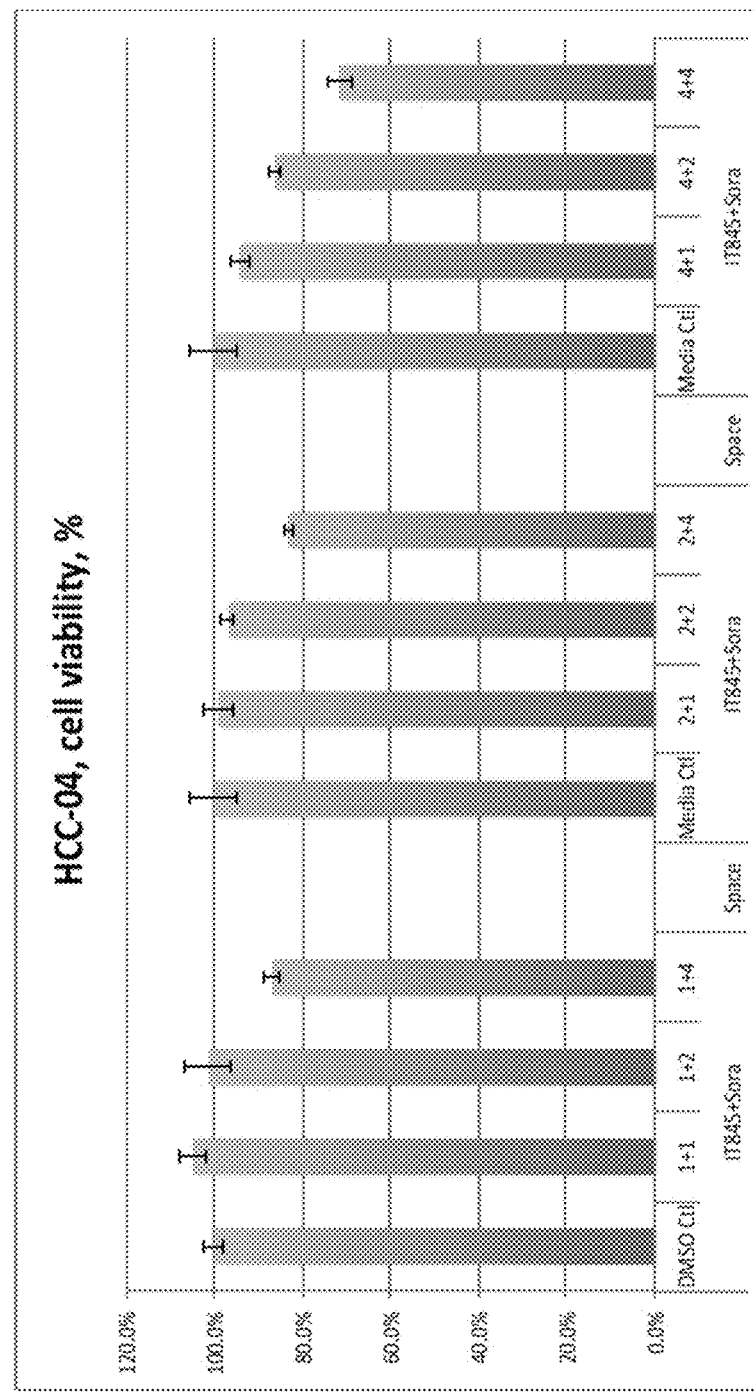
Figure 17L:
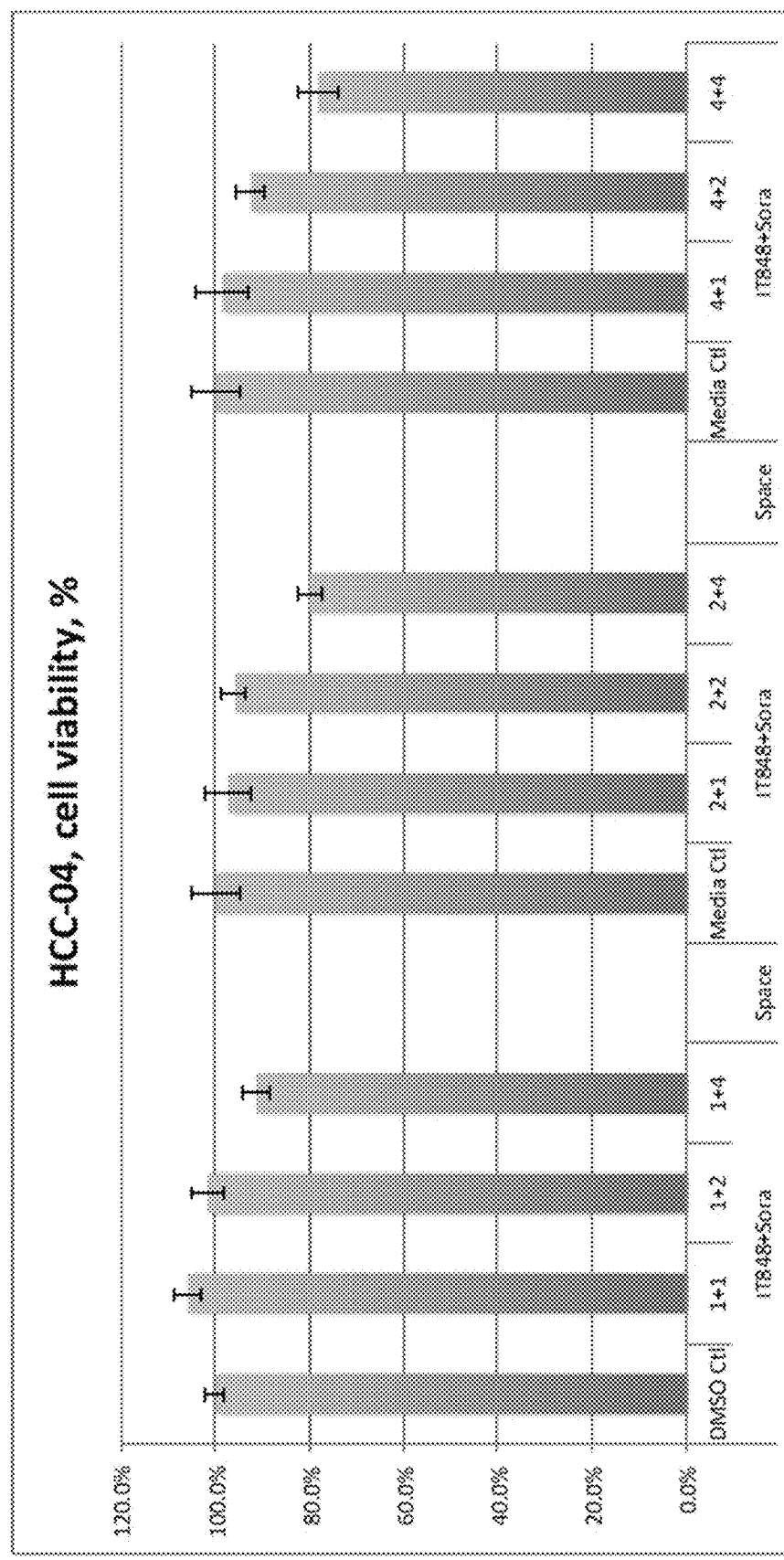
Figure 17M:
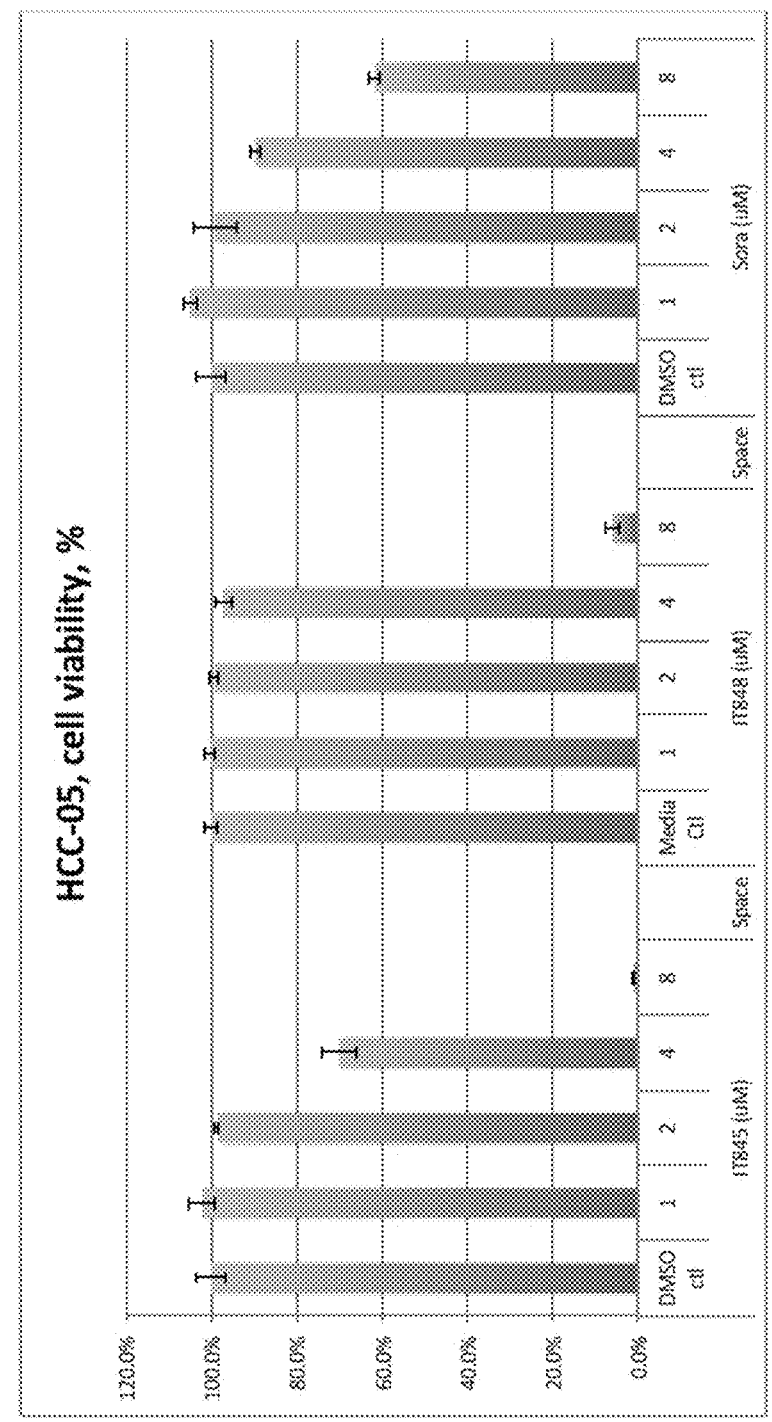
Figure 17N:
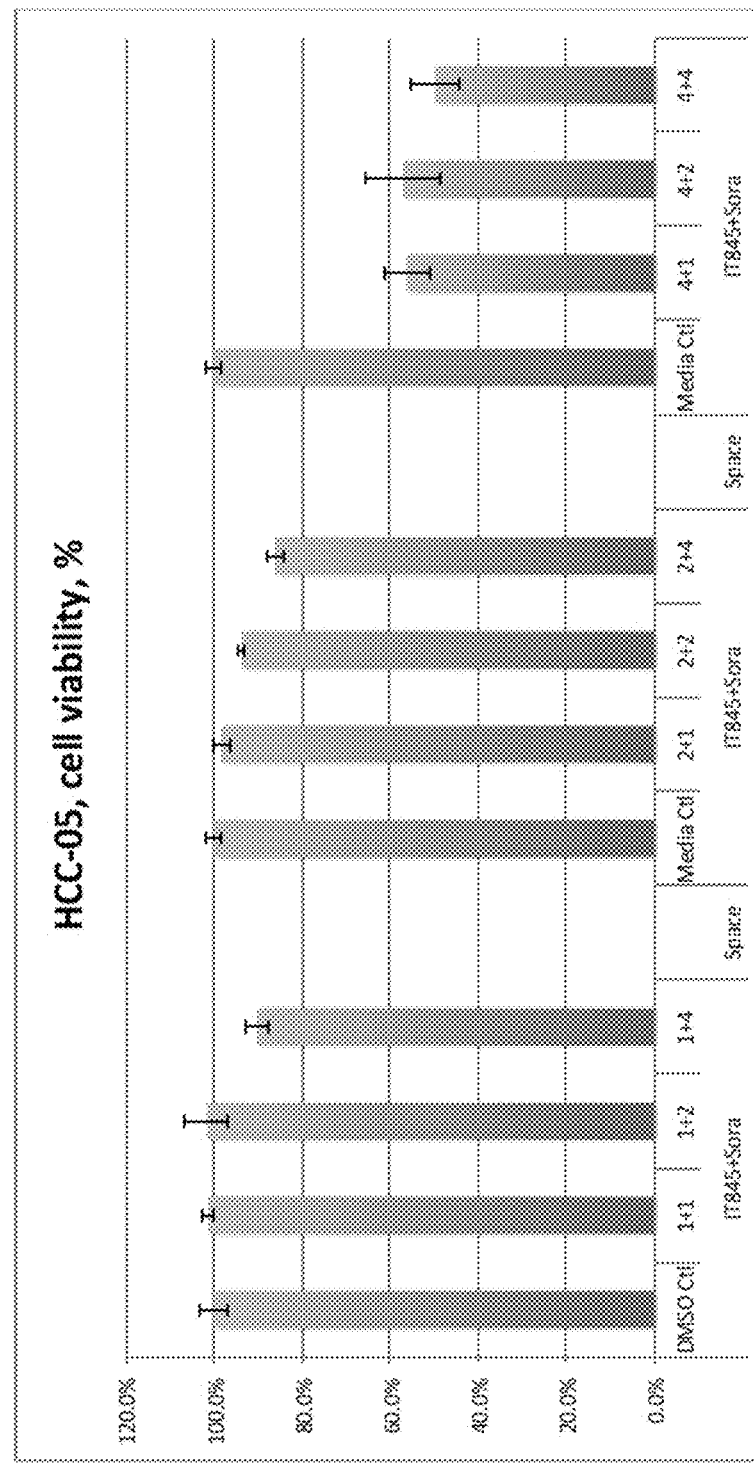
Figure 170:
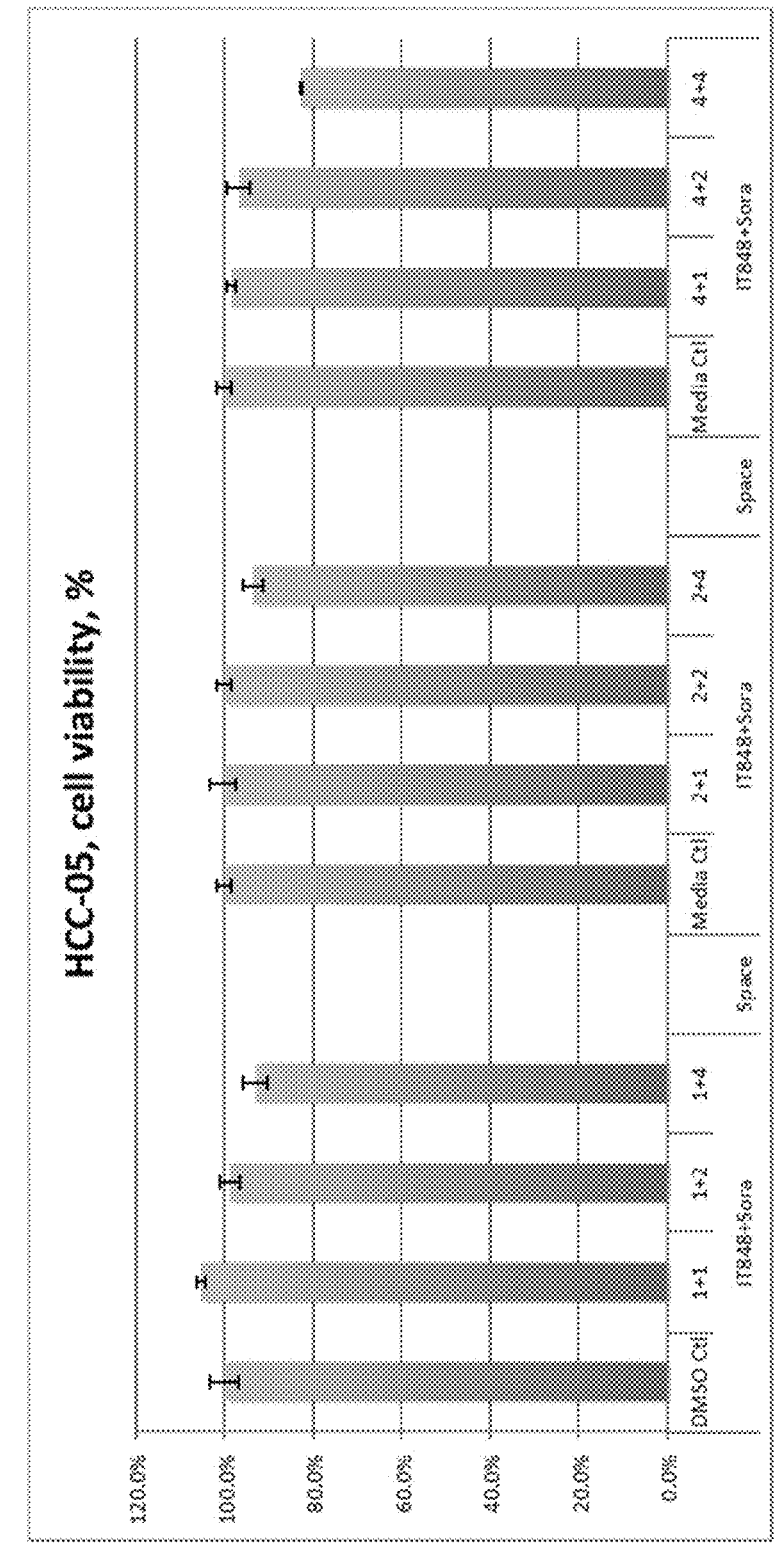

Results from these experiments are shown in FIGS. 17A-17O.

Example 13

Potency of NF-κB Inhibitors Against a Set of Randomly-Selected Patient-Derived Primary Hepatocellular Carcinoma Cells Experiments were performed as described in Example 12, above.

The following table shows the experimental design (all assays were run in triplicate):

| Compound ID | Concentration [uM] | Patient-Derived HCC Sample ID |
|---|---|---|
| IT845 | 2, 4, 6, 8 | HCC-06, HCC-07, |
| IT848 | 2, 4, 6, 8 | HCC-08, HCC-09, |
| Sorafenib | 1, 2, 4, 8 | HCC-10 |
| [IT845 + Sorafenib] | [2 + 1], [2 + 2], [2 + 4]; [4 + 1], [4 + 2], [4 + 4]; [6 + 1], [6 + 2], [6 + 4] | |
| [IT848 + Sorafenib] | [2 + 1], [2 + 2], [2 + 4]; [4 + 1], [4 + 2], [4 + 4]; [6 + 1], [6 + 2], [6 + 4] | |

The following table shows characteristics of the randomly-selected patient-derived HCC samples used in these experiments:

| Sample ID | Patient Description | Cell Passage | Treatment History | Biomarkers |
|---|---|---|---|---|
| HCC-06 | 54 year old, F, Asian, stage 2 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-07 | 52 year old, M, Asian, stage 2 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-08 | 45 year old, M, Asian, stage 3 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-09 | 42 year old, F, Asian, stage 3 | 1 | Chemo, radiation | Positive for AFP, CDI5s, CD29, CD90, CD151, ESA, ALDH, CEA, CK7, CAM5.2, Mucin, Alpha-I-antitrypsin |
| HCC-10 | 48 year old, M, Asian, stage 3 | 1 | Chemo, radiation | Positive for AFP, CDI5s, CD29, CD90, CD151, ESA, ALDH, CEA, CK7, CAM5.2, Mucin, Alpha-I-antitrypsin |

Figure 18A:
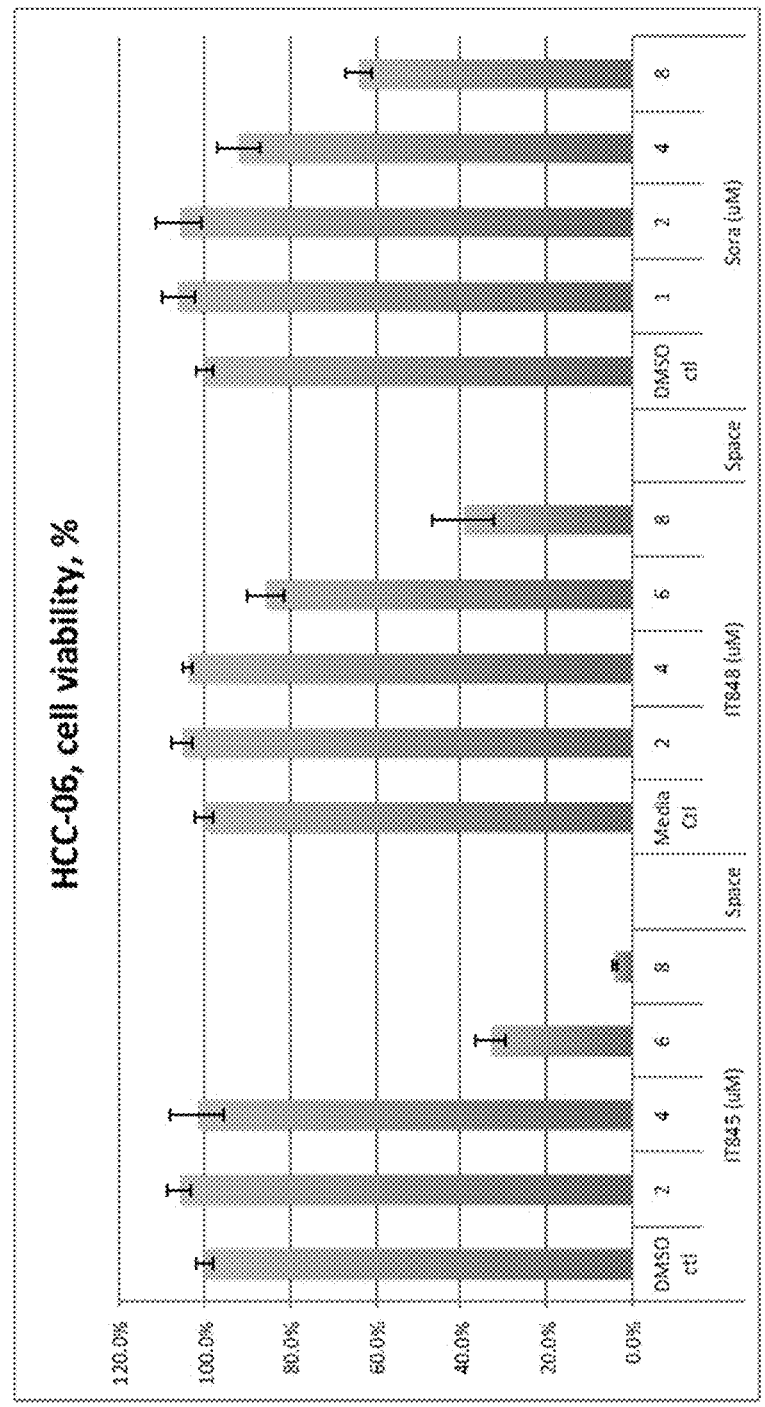
FIGS. 18A-18O are histograms showing the percentage cell viability for various cell types treated with vehicle, IT-845, IT-848, sorafenib, or combinations thereof.
Figure 18B:
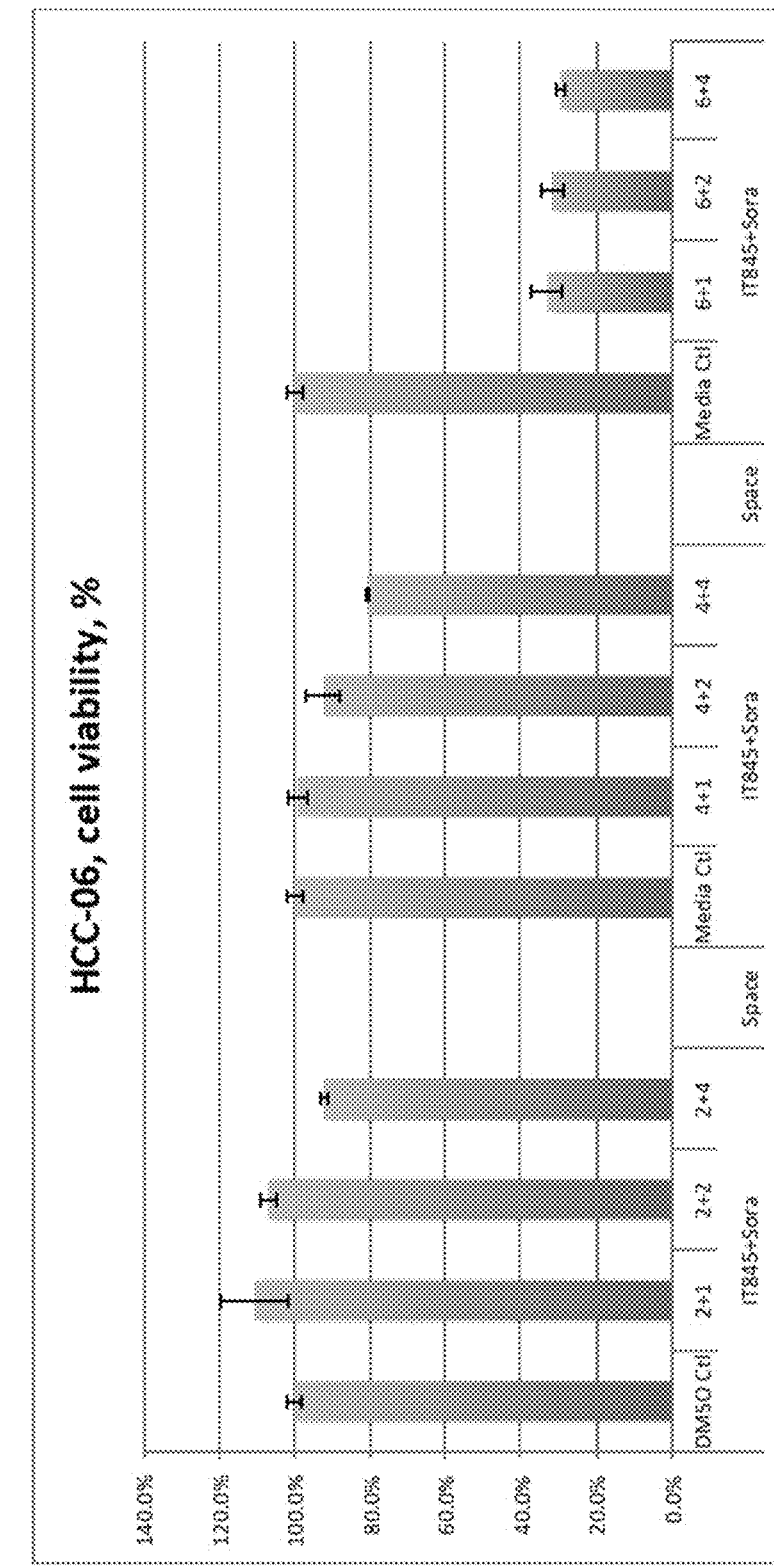
Figure 18C:
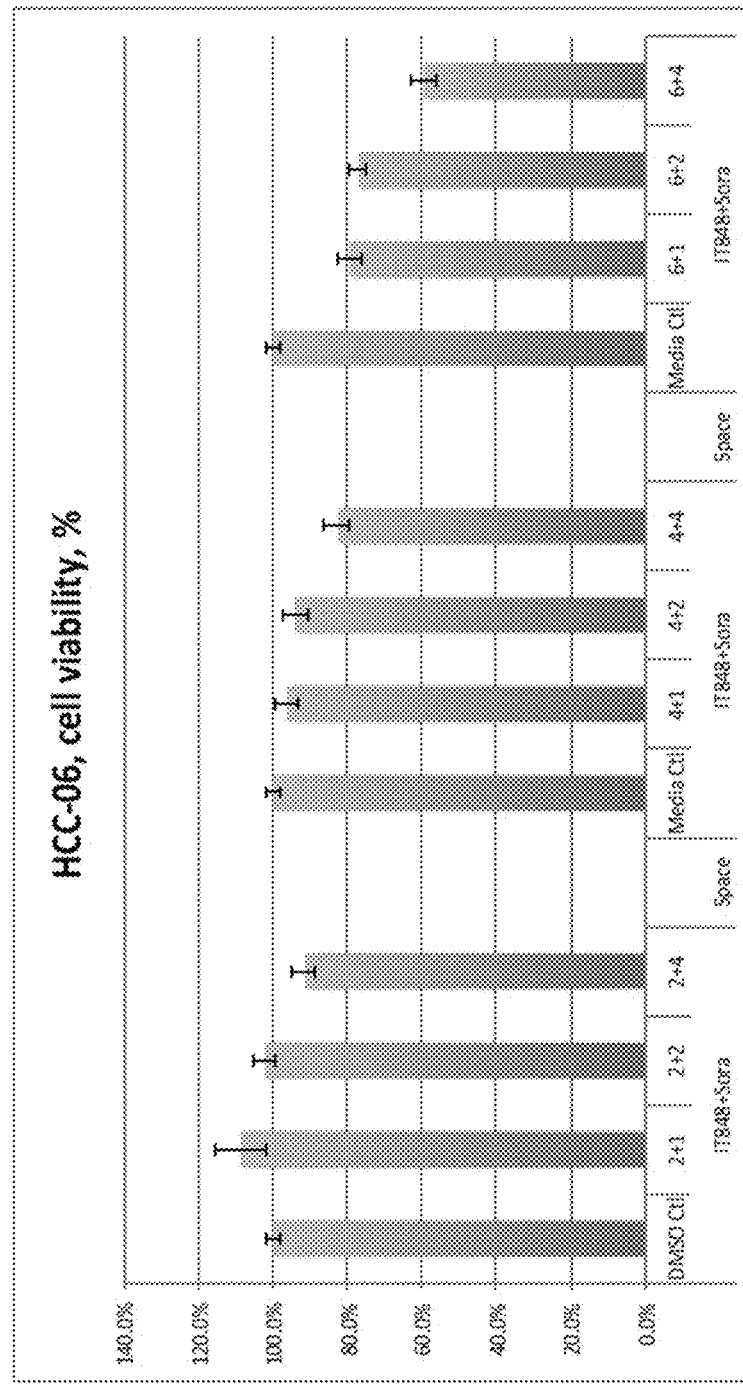
Figure 18D:
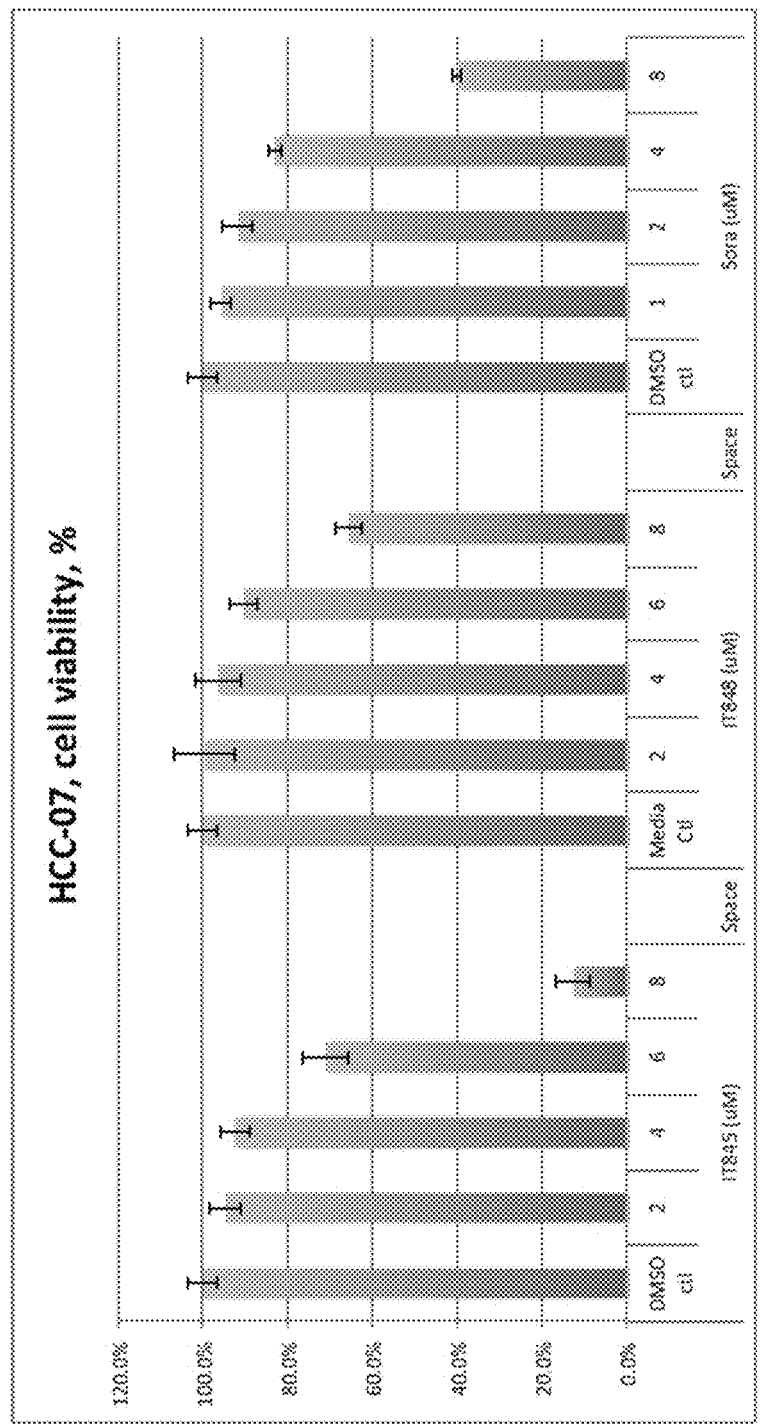
FIGS. 18D-18F: HCC-07 cells.
Figure 18E:
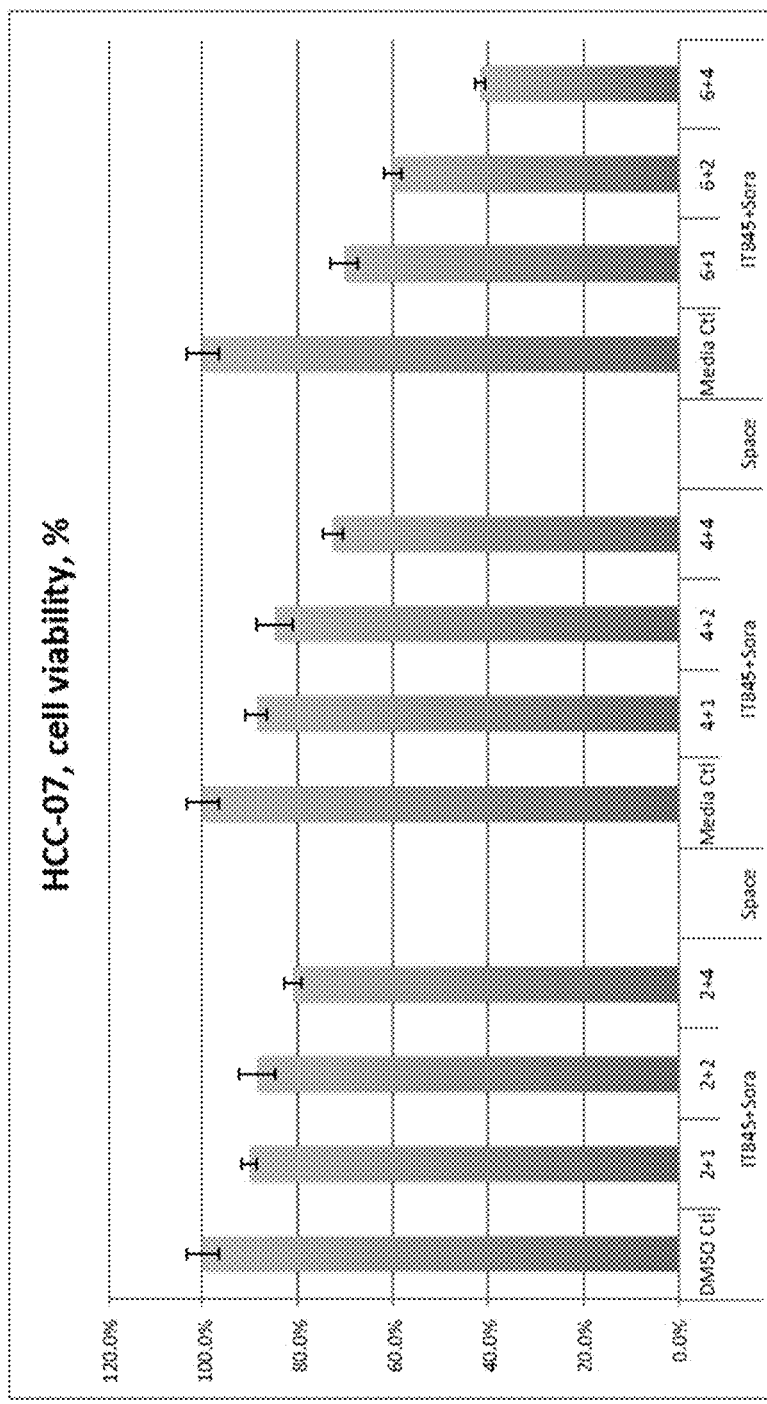
Figure 18F:
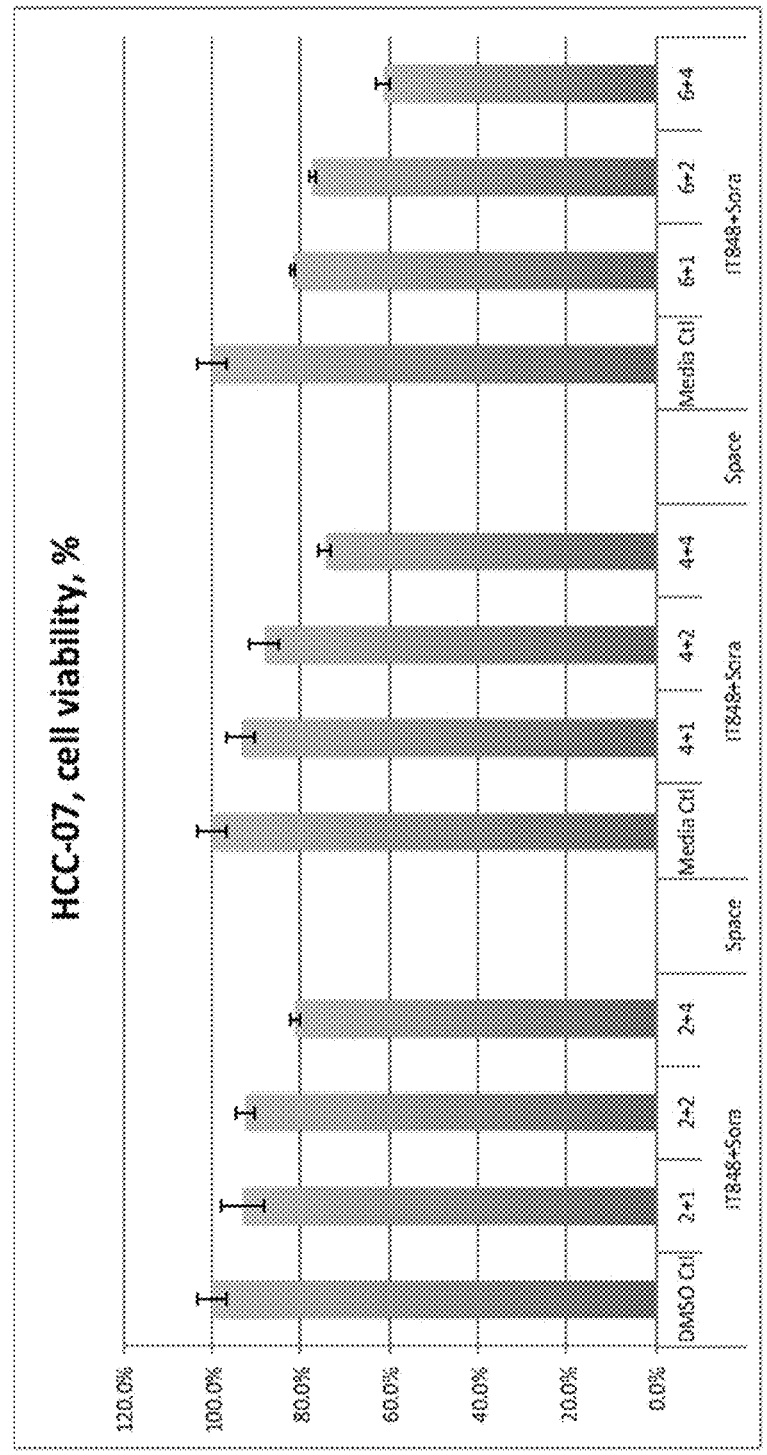
Figure 18G:
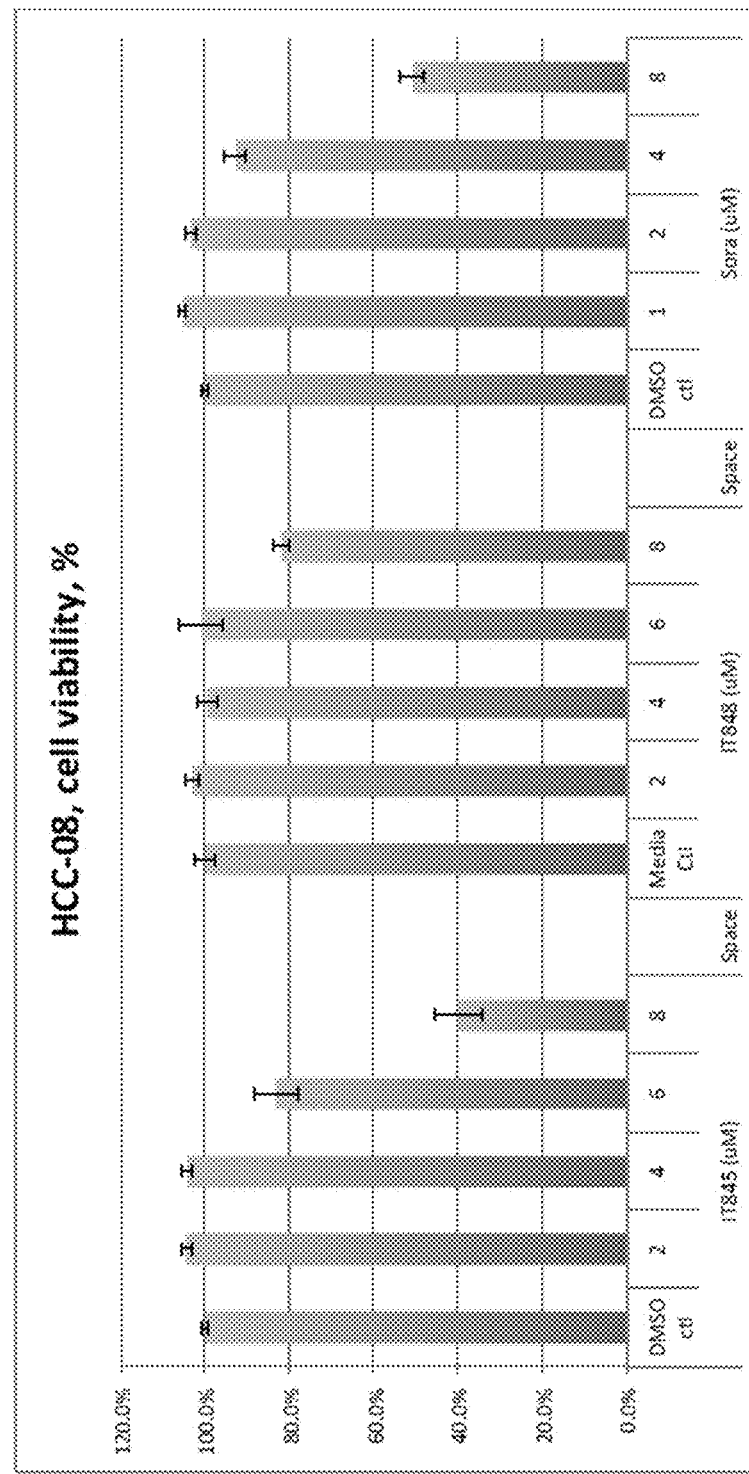
FIGS. 18G-18I: HCC-08 cells.
Figure 18H:
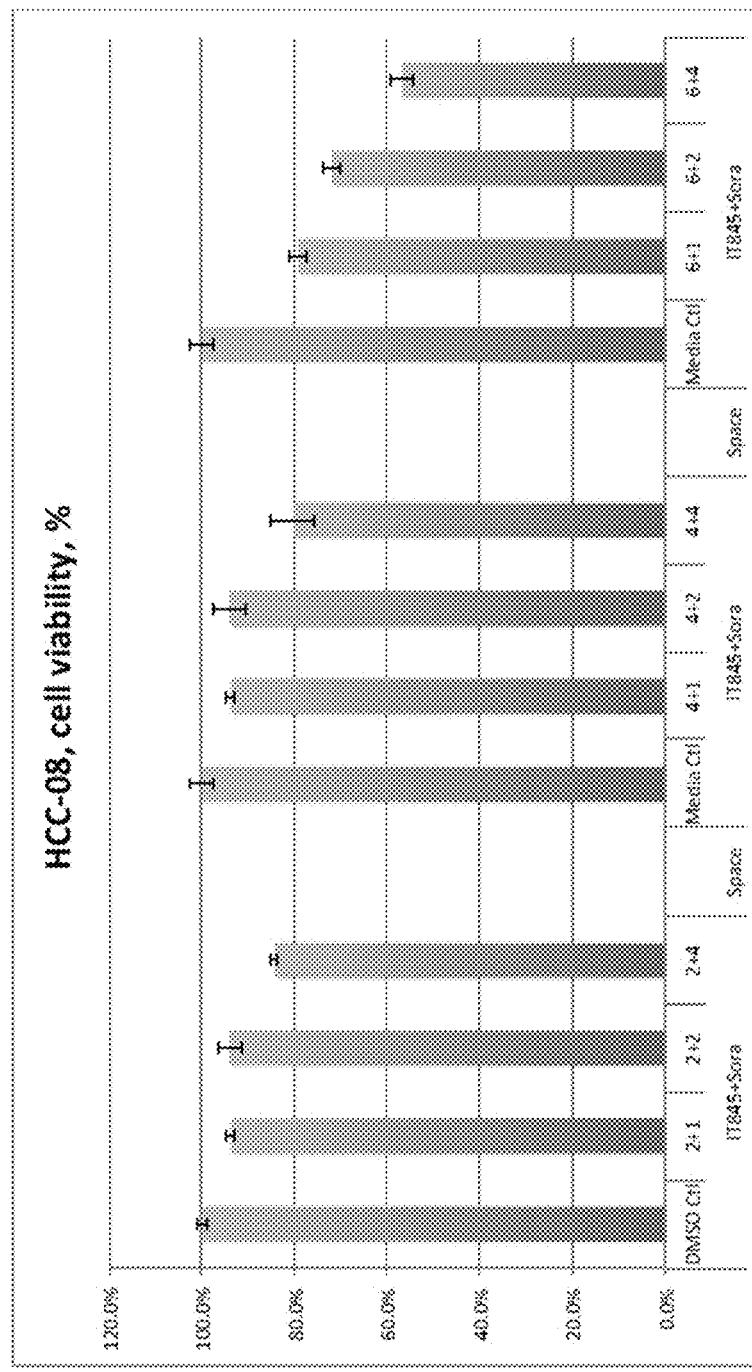
Figure 18I:
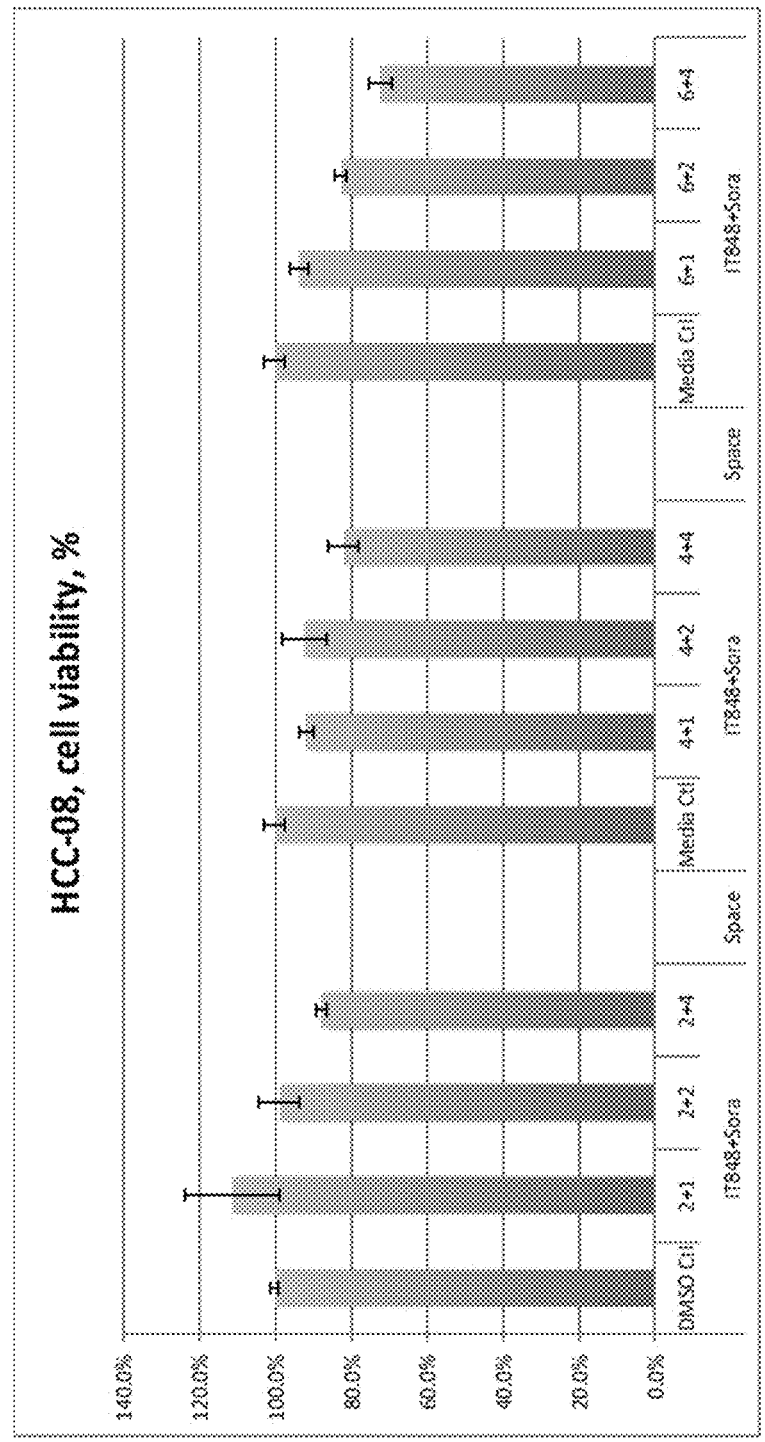
Figure 18J:
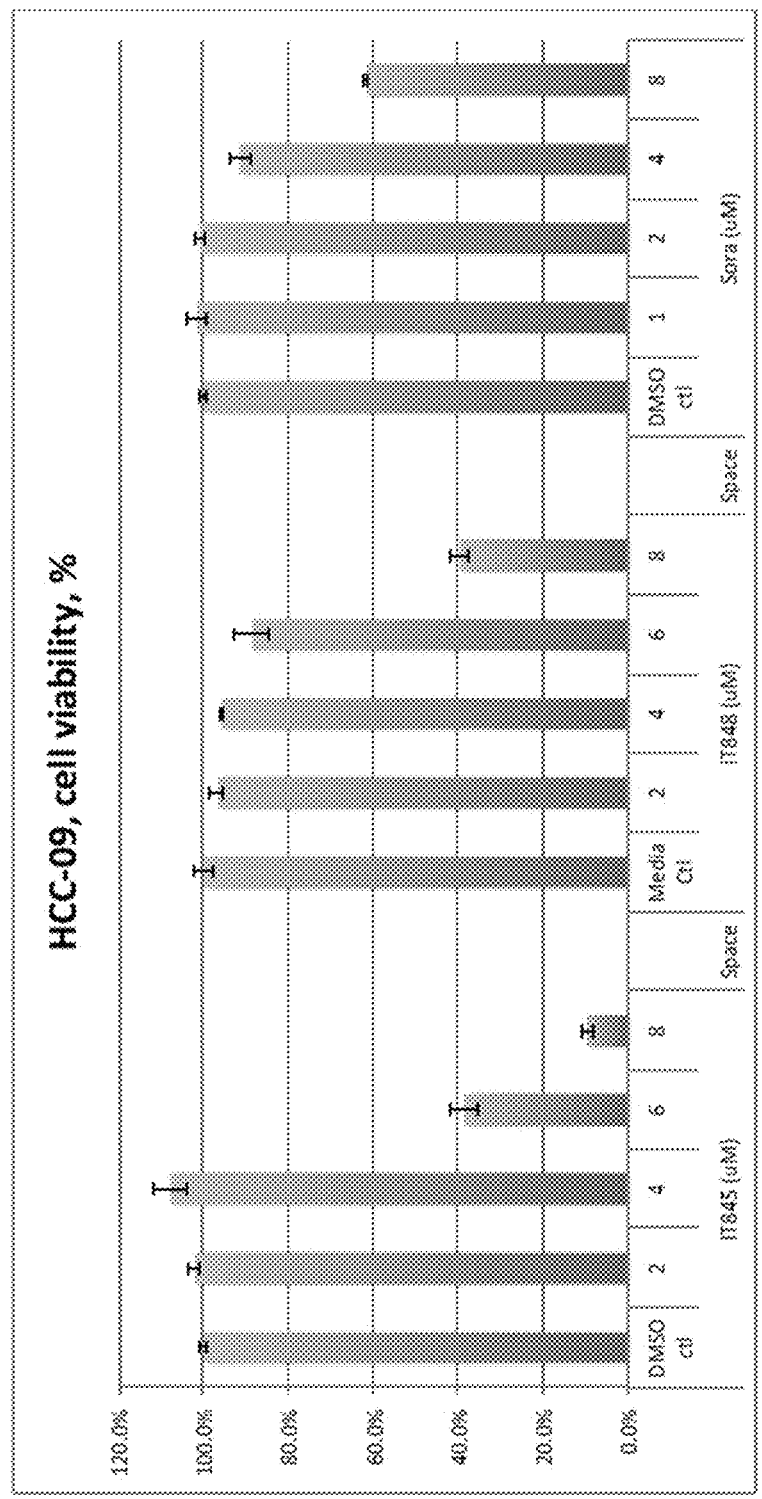
FIGS. 18J-18L: HCC-09 cells.
Figure 18K:
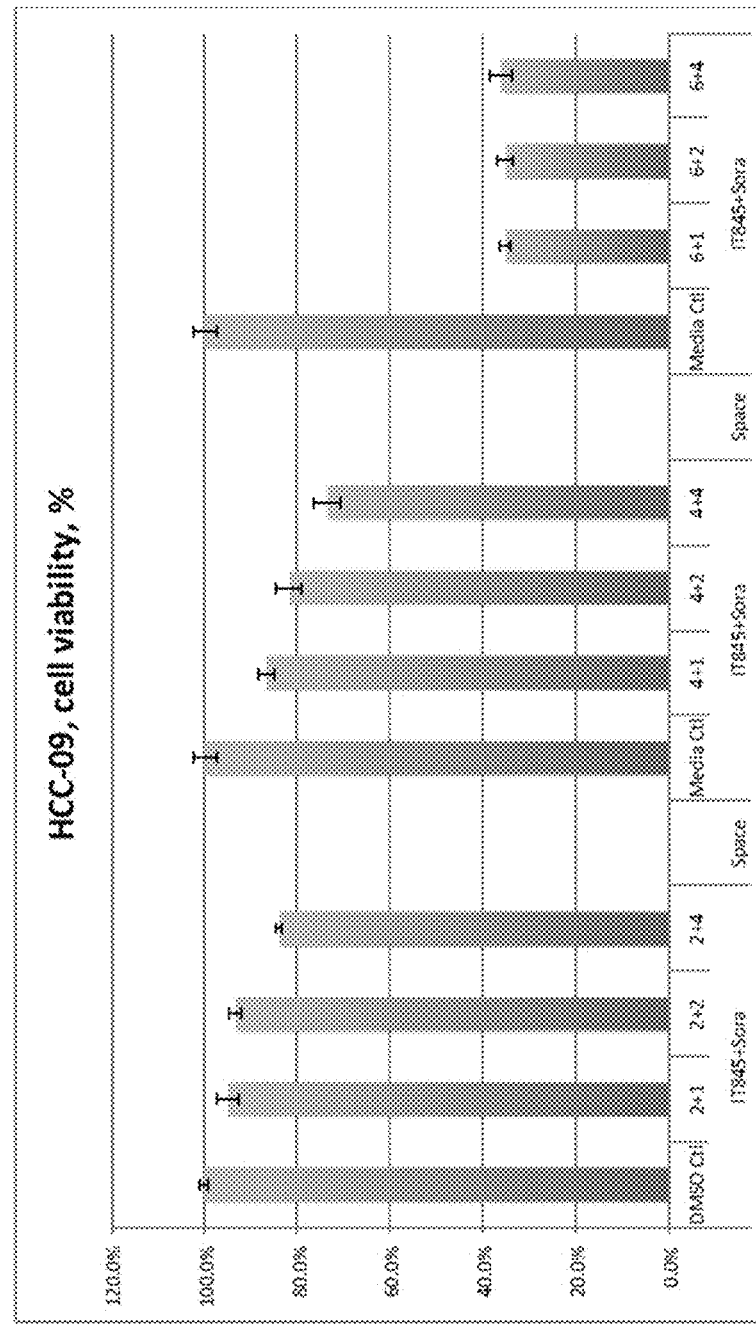
Figure 18L:
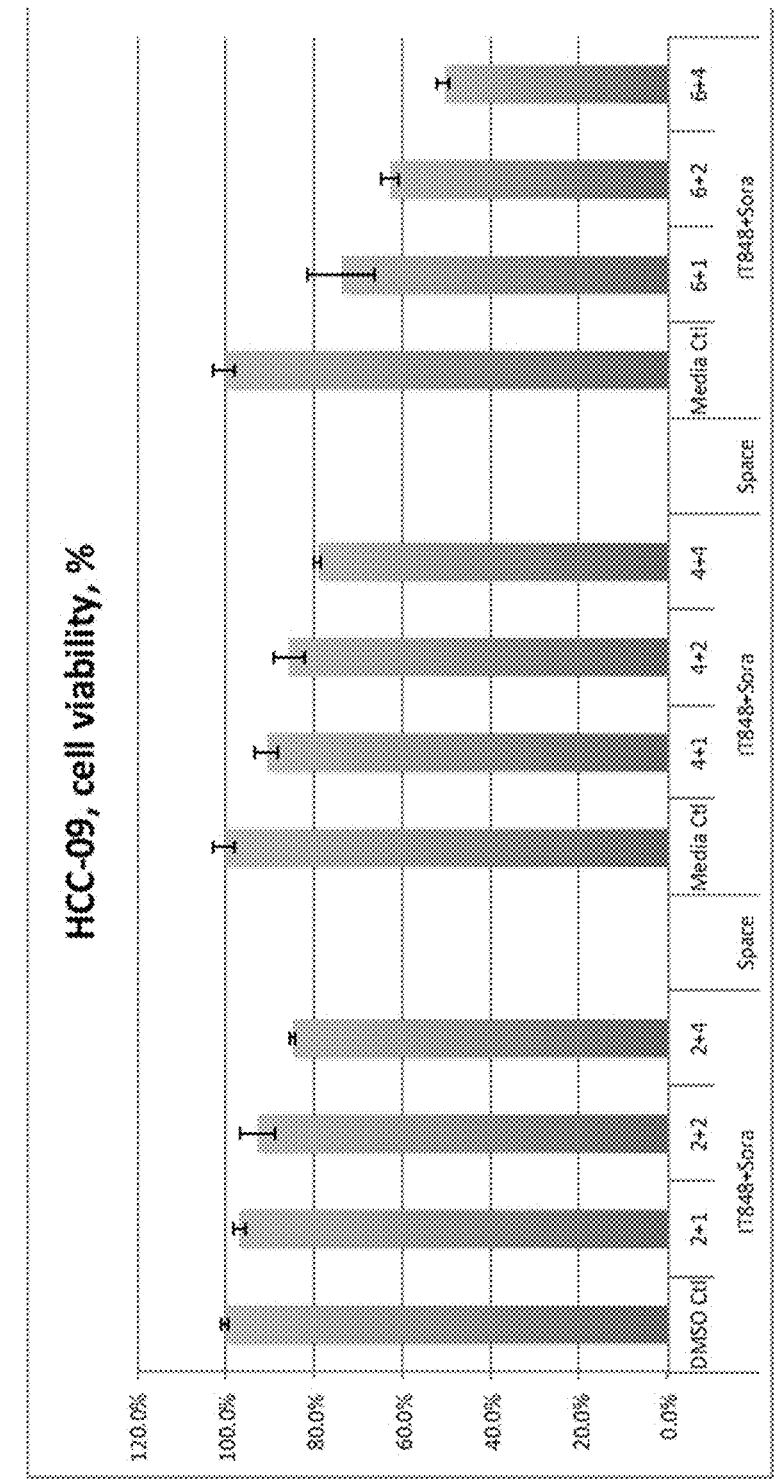
Figure 18M:
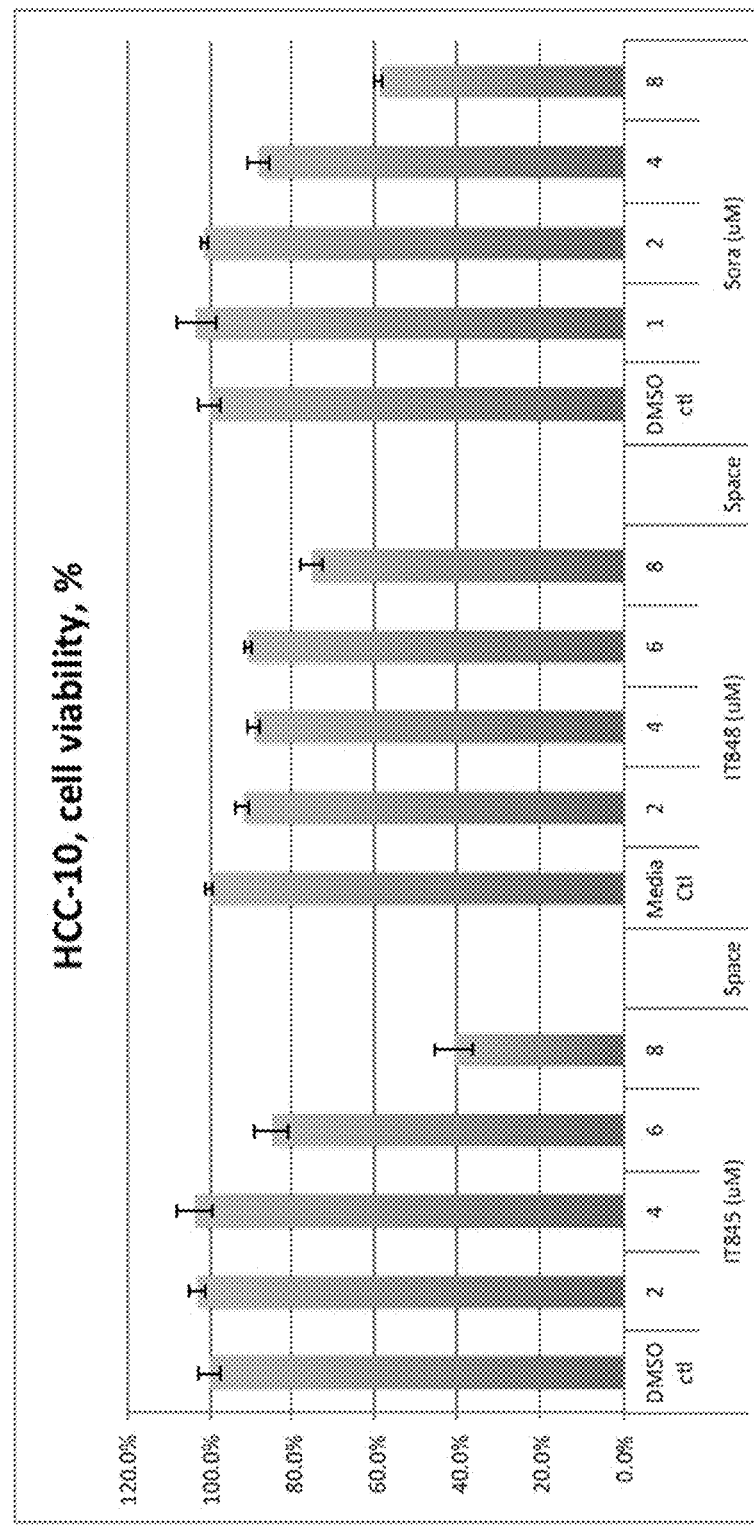
Figure 18N:
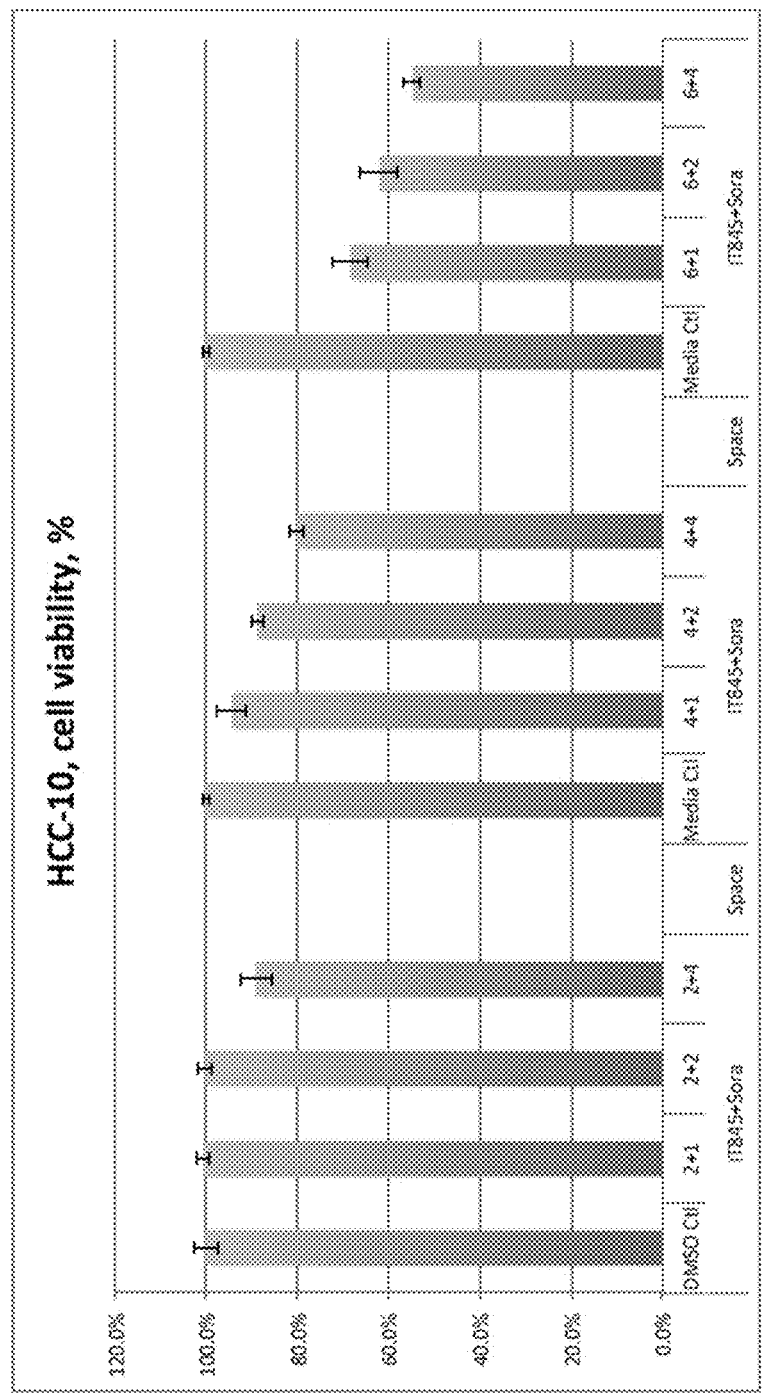
Figure 18O:
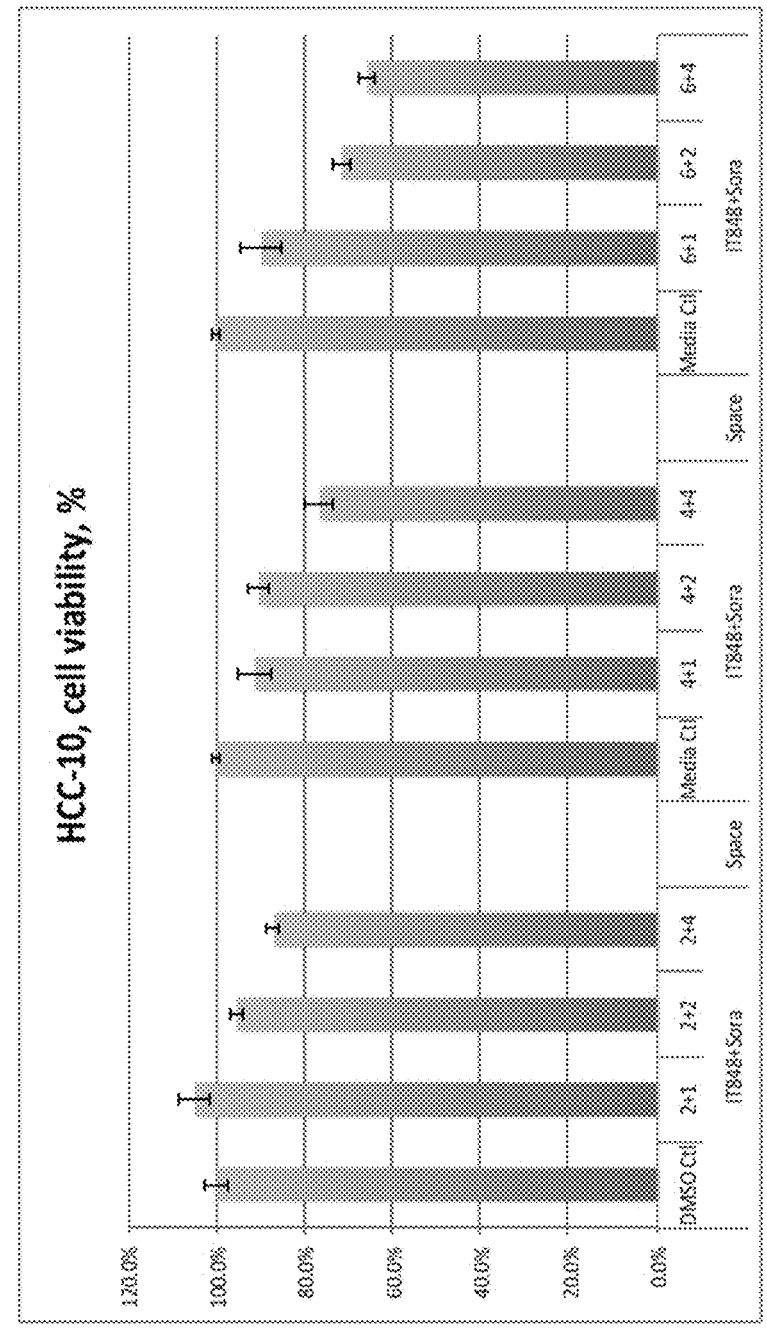
Figure 19A:
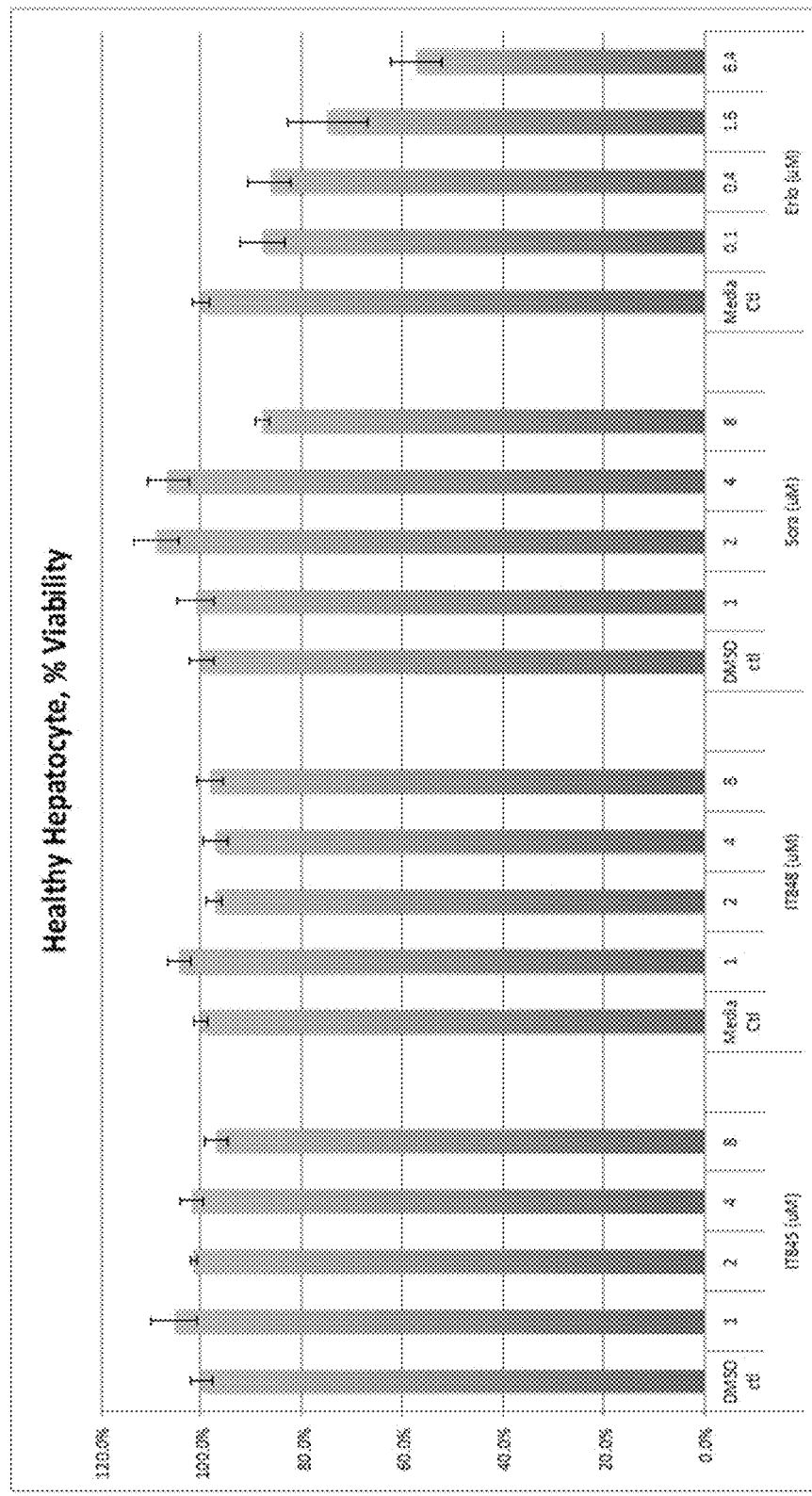
FIGS. 19A-19I are histograms showing percentage cell viability for various cell types treated with vehicle, IT-845, IT-848, sorafenib, erlotinib, or combinations thereof.
Figure 19B:
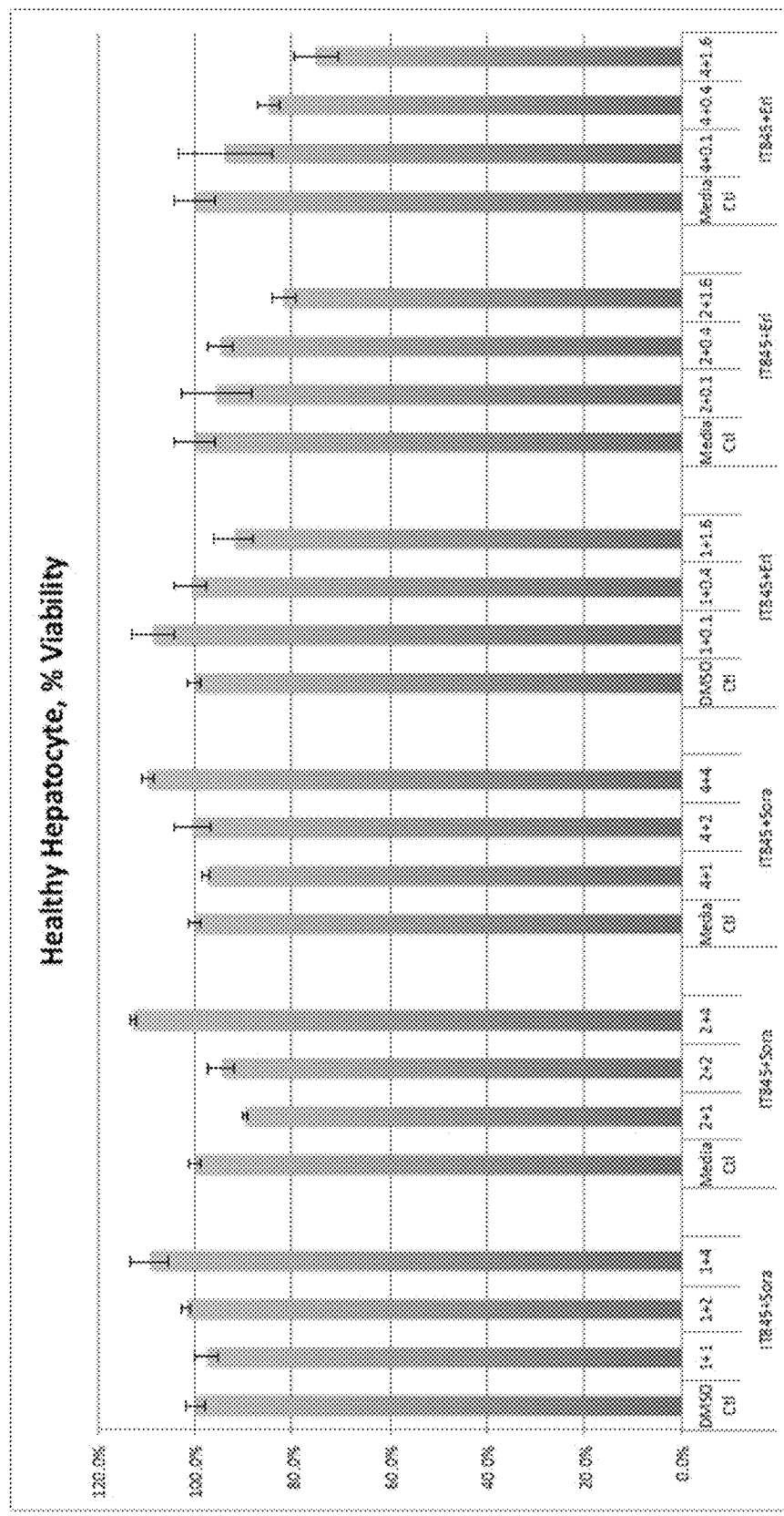
Figure 19C:
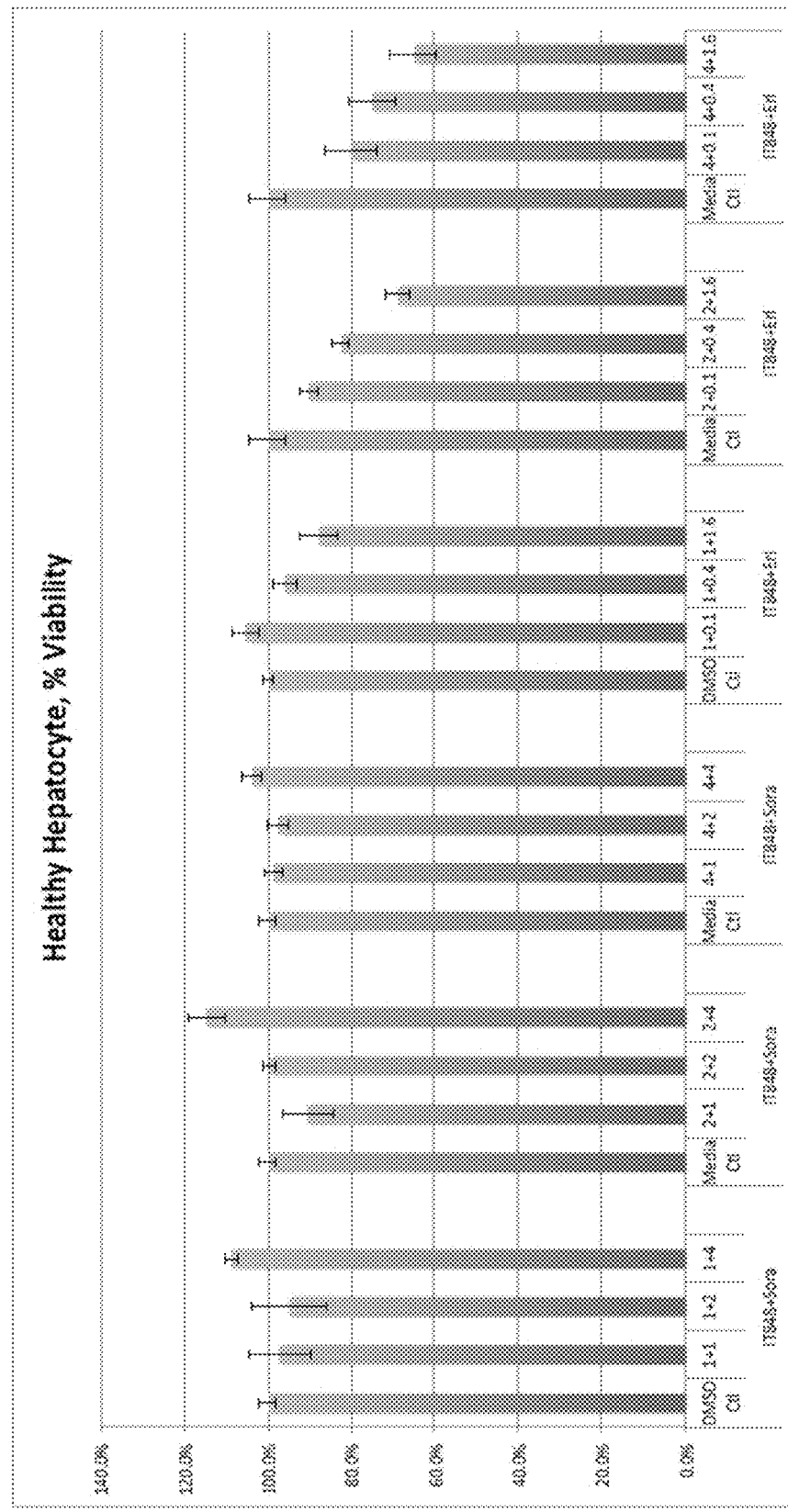
Figure 19D:
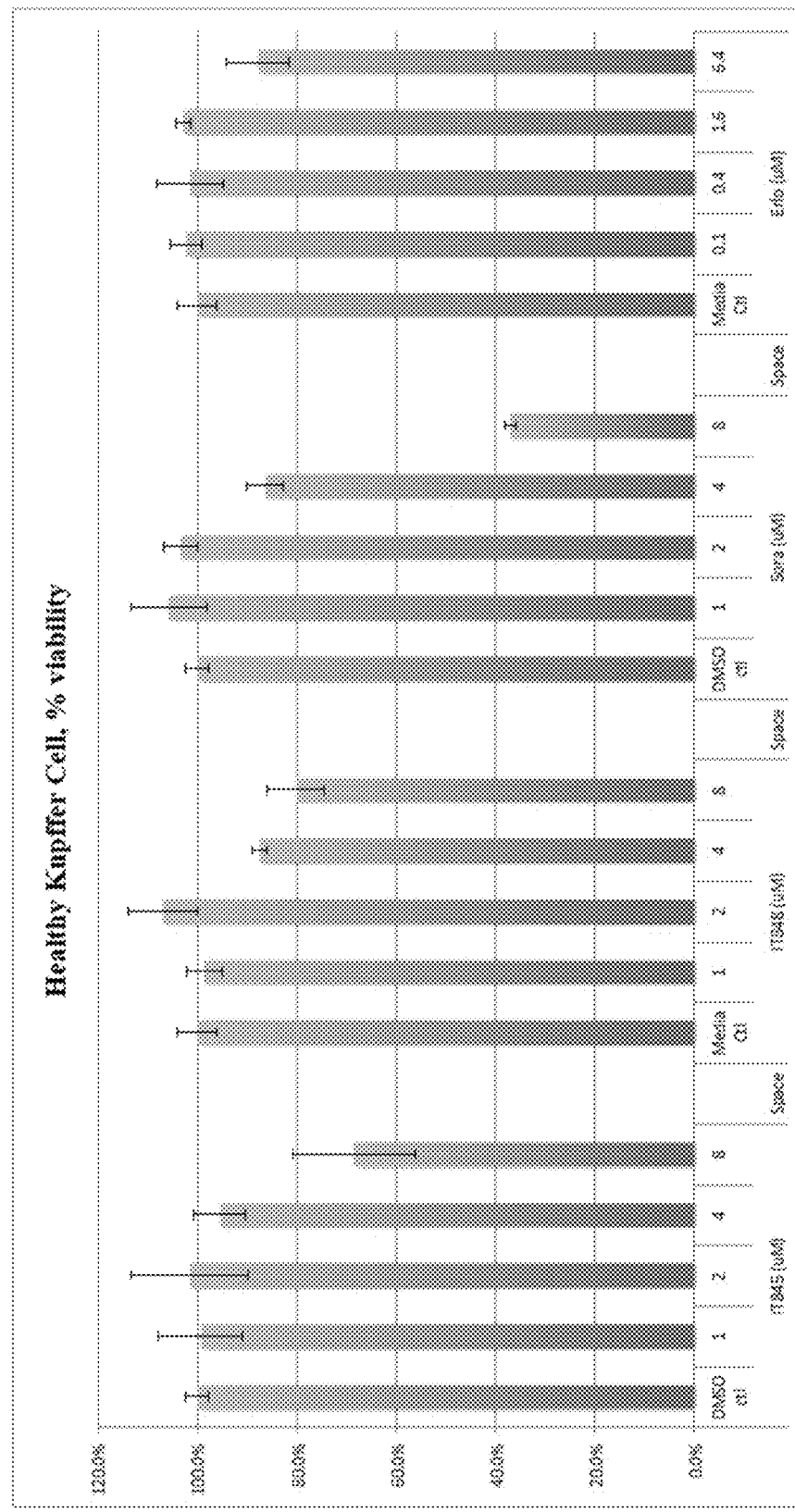
Figure 19E:
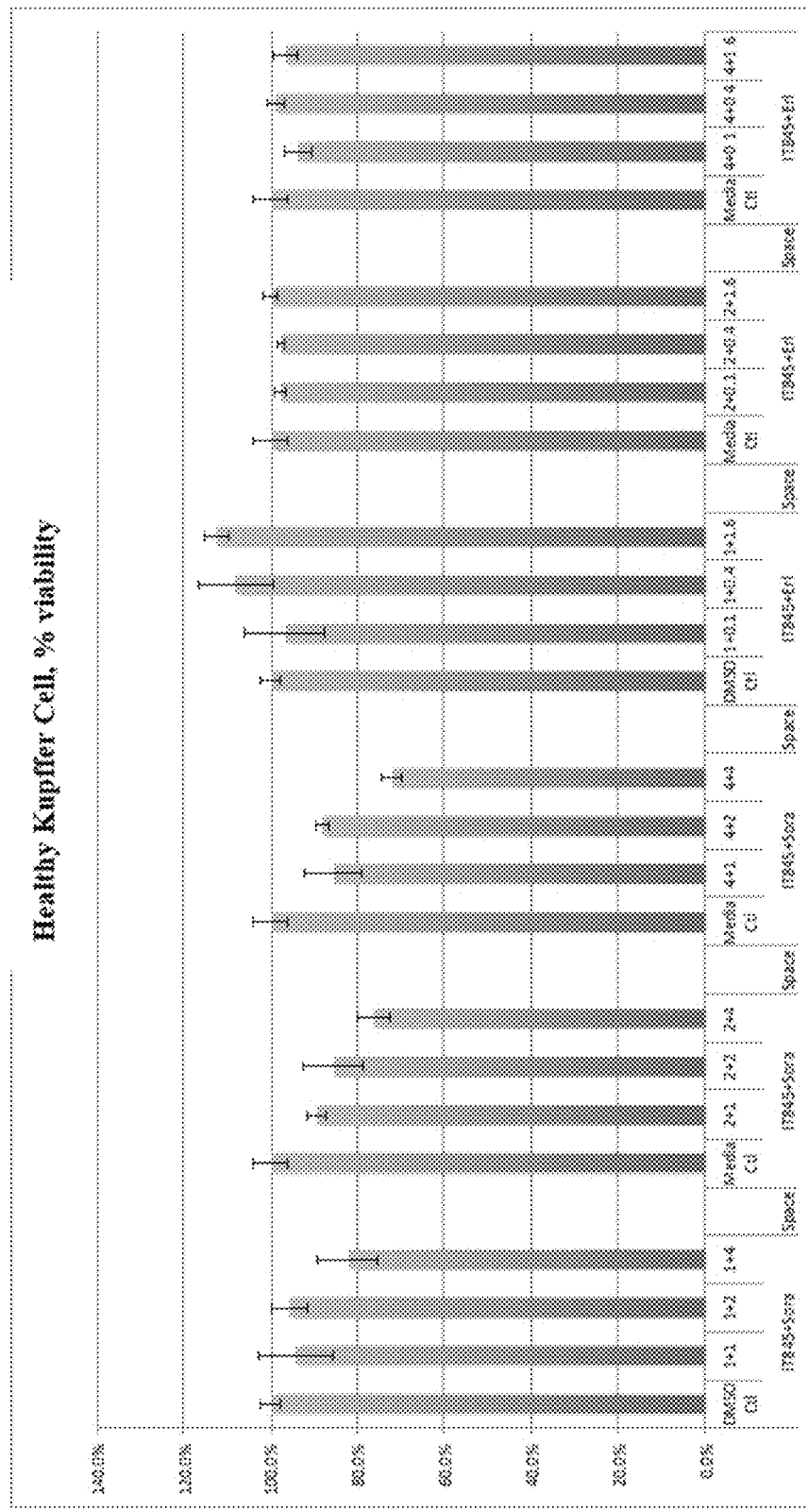
Figure 19F:
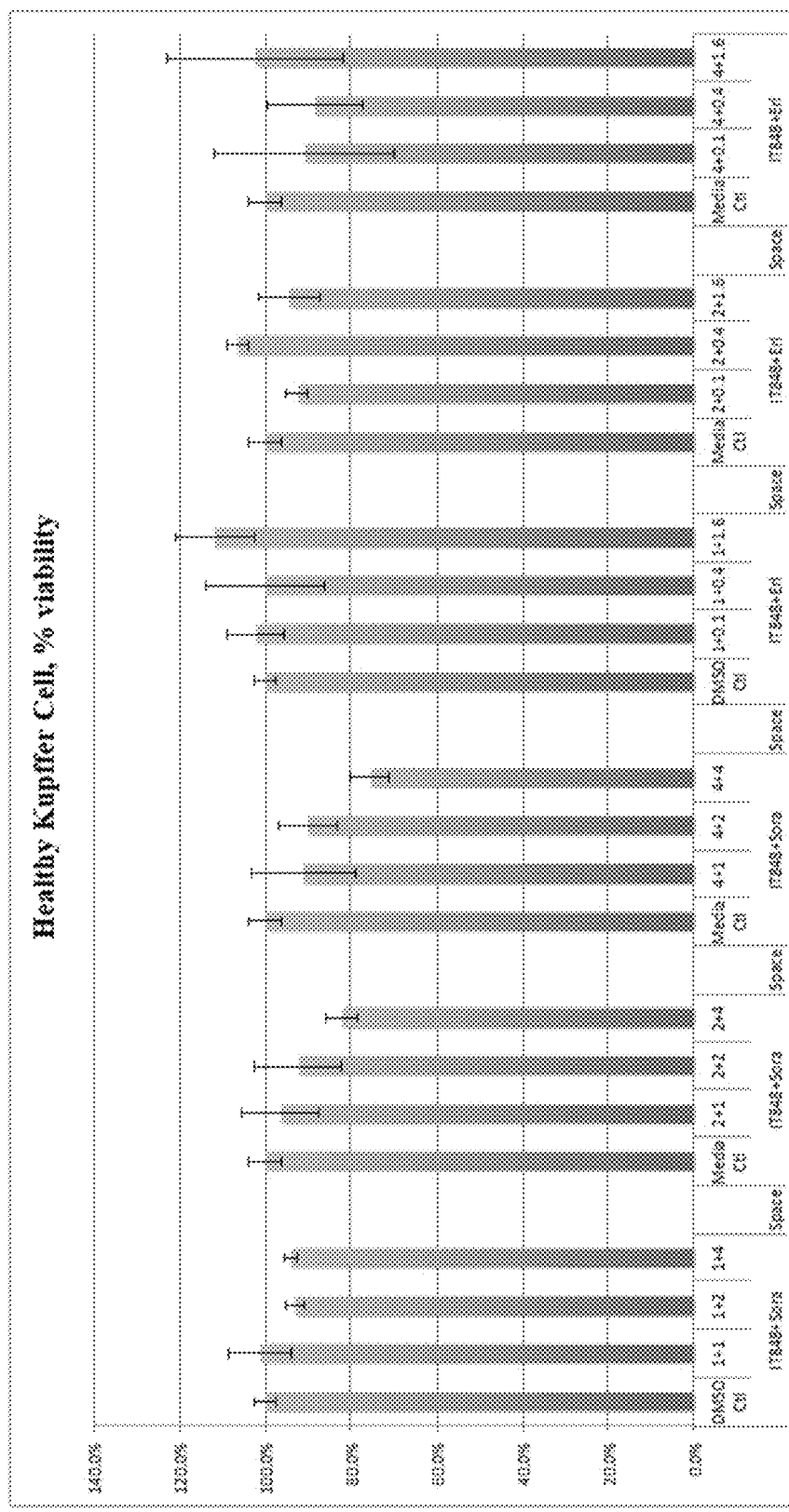
Figure 19G:
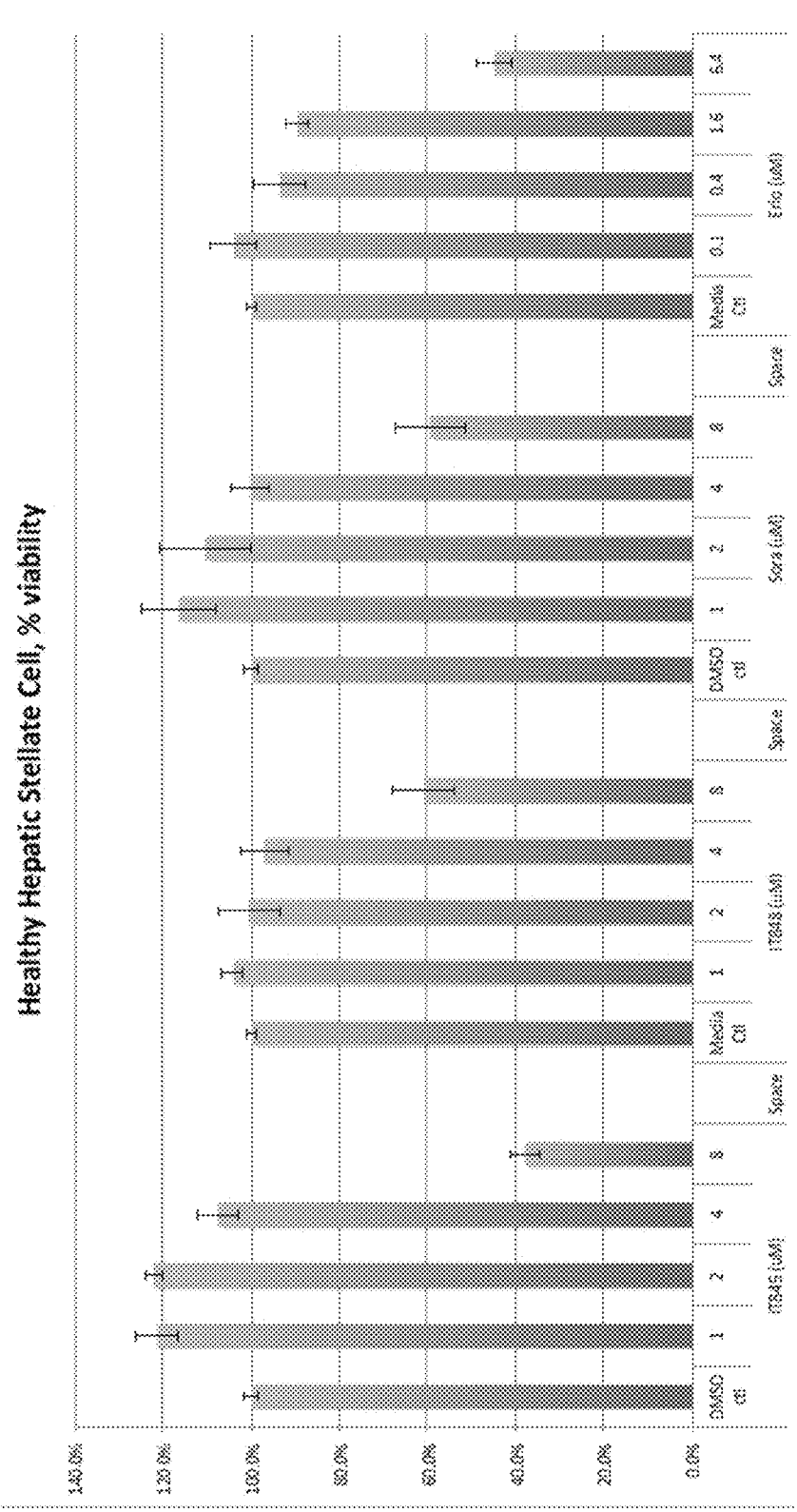
Figure 19H:
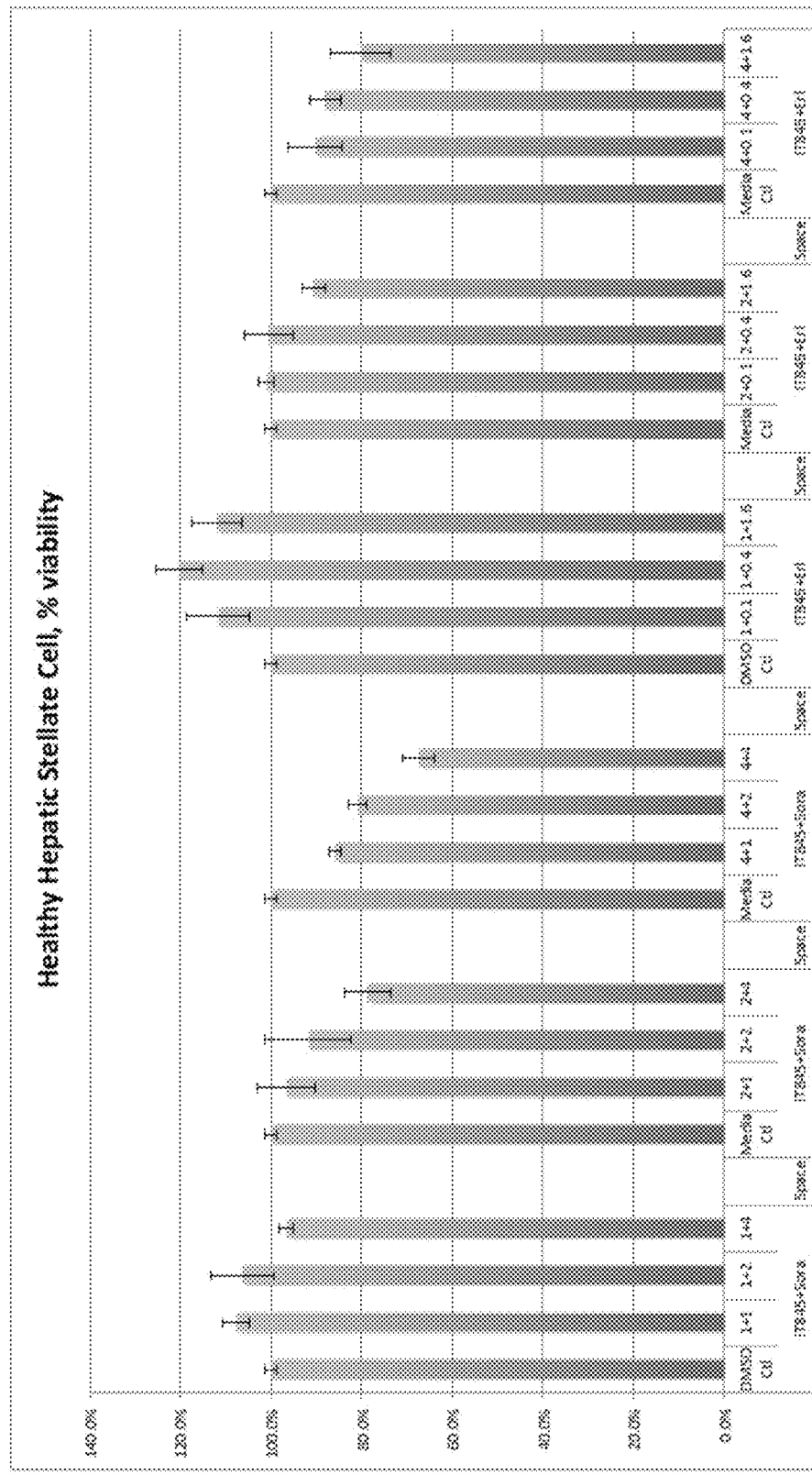
Figure 19I:
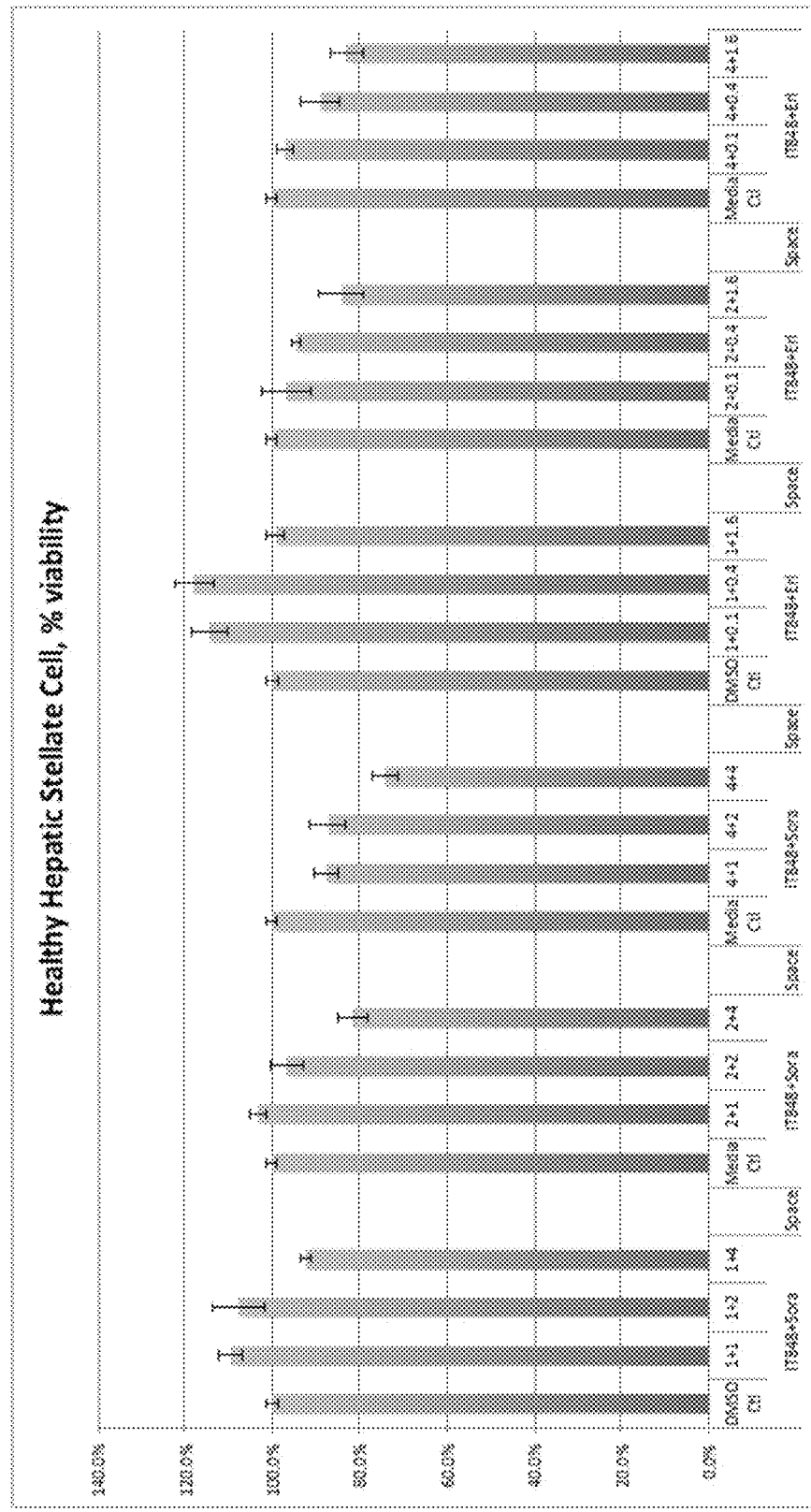

Results from these experiments are shown in FIGS. 18A-18O.

Example 14

Potency of NF-κB Inhibitors Against Normal Liver-Resident Cells

Experiments were performed as described in Example 12, above, except for the aspects relating to cell culture.

Cell Culture

All cells were maintained at 37° C. with 5% $CO_2$ and the supplier-recommended media. Normal human hepatocytes were cultured in InVitroGro Hi Medium (BioIVT), adult human stellate cells were cultured in Stellate Cell Growth Medium (Ixcells Biotech), and human Kupffer cells were cultured in Human Normal Kupffer Cell Culture Complete Media with Serum (Celprogen).

The following table shows the experimental design (all assays were run in triplicate):

| Compound ID | Concentration [uM] | Liver-Resident Cell Sample ID |
|---|---|---|
| IT845 | 1, 2, 4, 8 | Normal hepatocyte from 63 year old Male; |
| IT848 | 1, 2, 4, 8 | Normal Healthy Kupffer cell (KC) from 23 year old caucasian male; |
| Sorafenib | 1, 2, 4, 8 | Normal hepatic stellate cell (HSC) from 25 year old Caucasian male |
| Erlotinib | 0.1, 0.4, 1.6, 6.4 | |
| [IT845 + Sorafenib] | [1 + 1], [1 + 2], [1 + 4]; [2 + 1], [2 + 2], [2 + 4]; [4 + 1], [4 + 2], [4 + 4]; | |
| [IT848 + Sorafenib] | [1 + 1], [1 + 2], [1 + 4]; [2 + 1], [2 + 2], [2 + 4]; [4 + 1], [4 + 2], [4 + 4]; | |
| [IT845 + Erlotinib] | [1 + 0.1], [1 + 0.4], [1 + 1.6]; [2 + 0.1], [2 + 0.4], [2 + 1.6]; [4 + 0.1], [4 + 0.4], [4 + 1.6]; | |
| [IT848 + Erlotinib] | [1 + 0.1], [1 + 0.4], [1 + 1.6]; [2 + 0.1], [2 + 0.4], [2 + 1.6]; [4 + 0.1], [4 + 0.4], [4 + 1.6]; | |

The following table shows characteristics of the normal human hepatocytes used in these experiments:

| Sample ID | Assay (Rate of Formation) | Results (pmol/min/million cells) |
|---|---|---|
| Normal human hepatocyte | ECOD: 7-HC and metabolites (total) | 95.6 |
| | CYP 2C9: 4'-methylhydroxytolbutamide | 52.8 |
| | UGT: 7-hydroxycoumarin glucuronide | 446 |
| | CYP 2C19: 4'-hydroxymephenytoin | 8.78 |
| | ST: 7-hydroxycoumarin sulfate | 46.5 |
| | CYP 2D6: dextrorphan | 1.17 |
| | CYP 1A2: acetaminophen | 24.6 |
| | CYP 2E1: 6-hydroxychlorzoxazone | 18.9 |
| | CYP 2A6: 7-HC and metabolites (total) | 112 |
| | CYP 3A4: 6β-hydroxytestosterone | 82.9 |
| | CYP 2B6: hydroxybupropion | 134 |
| | CYP 3A4: 1-hydroxymidazolam | 65.9 |

Results from these experiments are shown in FIGS. 19A-19I.

Example 15

Potency of NF-κB Inhibitors Against a Set of Randomly-Selected Patient-Derived Primary NSCLC Experiments were performed as described in Example 12, above, except for the aspects relating to cell culture.

Cell Culture

All cells were maintained at 37° C. with 5% $CO_2$ and the supplier-recommended media. NSCLC cells were cultured in Human Lung Cancer Cell Line Complete Media with Serum (Celprogen).

The following tables show the experimental design (all assays were run in triplicate):

| Compound ID | Concentration [uM] | Patient-Derived NSCLC Sample ID |
|---|---|---|
| IT845 | 1, 2, 4, 8 | NSCLC 01 to 04 |
| IT848 | 1, 2, 4, 8 | |
| Erlotinib | 0.1, 0.4, 1.6, 6.4 | |
| [IT845 + Erlotinib] | [1 + 0.1], [1 + 0.4], [1 + 1.6];<br>[2 + 0.1], [2 + 0.4], [2 + 1.6];<br>[4 + 0.1], [4 + 0.4], [4 + 1.6]; | |
| [IT848 + Erlotinib] | [1 + 0.1], [1 + 0.4], [1 + 1.6];<br>[2 + 0.1], [2 + 0.4], [2 + 1.6];<br>[4 + 0.1], [4 + 0.4], [4 + 1.6]; | |
| IT845 | 2, 4, 6, 8 | NSCLC 05 to 10 |
| IT848 | 2, 4, 6, 8 | |
| Erlotinib | 0.1, 0.4, 1.6, 6.4 | |
| [IT845 + Erlotinib] | [2 + 0.1], [2 + 0.4], [2 + 1.6];<br>[4 + 0.1], [4 + 0.4], [4 + 1.6];<br>[6 + 0.1], [6 + 0.4], [6 + 1.6]; | |
| [IT848 + Erlotinib] | [2 + 0.1], [2 + 0.4], [2 + 1.6];<br>[4 + 0.1], [4 + 0.4], [4 + 1.6];<br>[6 + 0.1], [6 + 0.4], [6 + 1.6]; | |

The following table shows characteristics of the randomly-selected patient-derived NSCLC samples used in these experiments:

| Sample ID | Patient Description | Cell Passage | Treatment History | Biomarkers |
|---|---|---|---|---|
| NSCLC-01 | 35 year old, F, Caucasian, stage 3 | 1 | Chemo, radiation | EGFR L858R |
| NSCLC-02 | 45 year old, F, Caucasian, stage 3 | 1 | Chemo, radiation | |
| NSCLC-03 | 55 year old, F, Caucasian, stage 3 | 1 | Chemo, radiation | |
| NSCLC-04 | 35 year old, F, Caucasian, stage 2 | 1 | Chemo, radiation | EGFR L858R |
| NSCLC-05 | 36 year old, F, Caucasian, stage 2 | 1 | Chemo, radiation | |
| NSCLC-06 | 38 year old, M, Caucasian, stage 2 | 1 | Chemo, radiation | |
| NSCLC-07 | 39 year old, M, Caucasian, stage 3 | 1 | Chemo, radiation | |
| NSCLC-08 | 40 year old, M, Caucasian, stage 3 | 1 | Chemo, radiation | EGFR L858R |
| NSCLC-09 | 55 year old, M, Caucasian, stage 3 | 1 | Chemo, radiation | |
| NSCLC-10 | 65 year old, M, Caucasian, stage 2 | 1 | Chemo, radiation | |

Figure 20A:
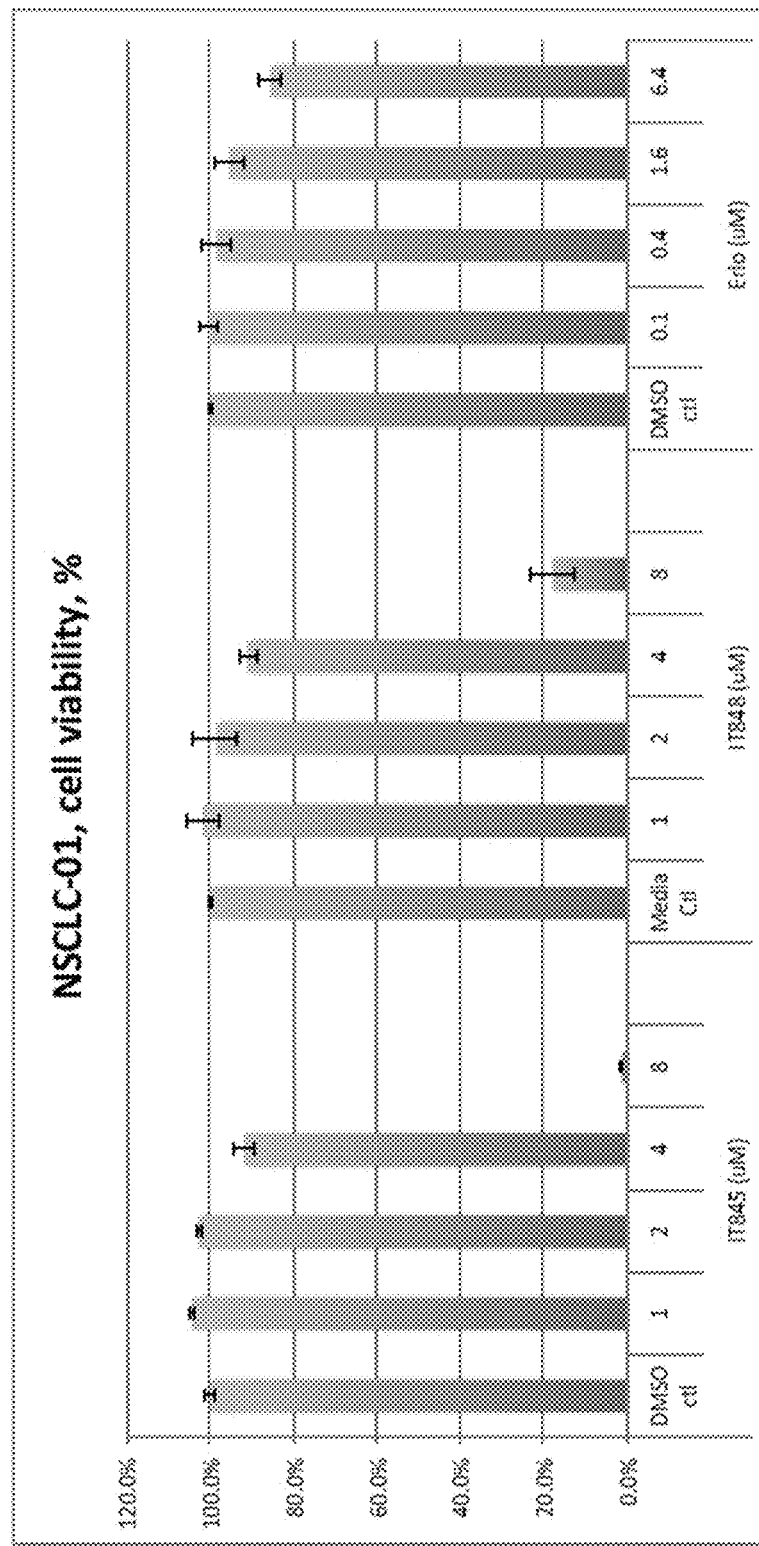
FIGS. 20A-20AD are histograms showing percentage cell viability for various cell types treated with vehicle, IT-845, IT-848, erlotinib, or combinations thereof.
Figure 20B:
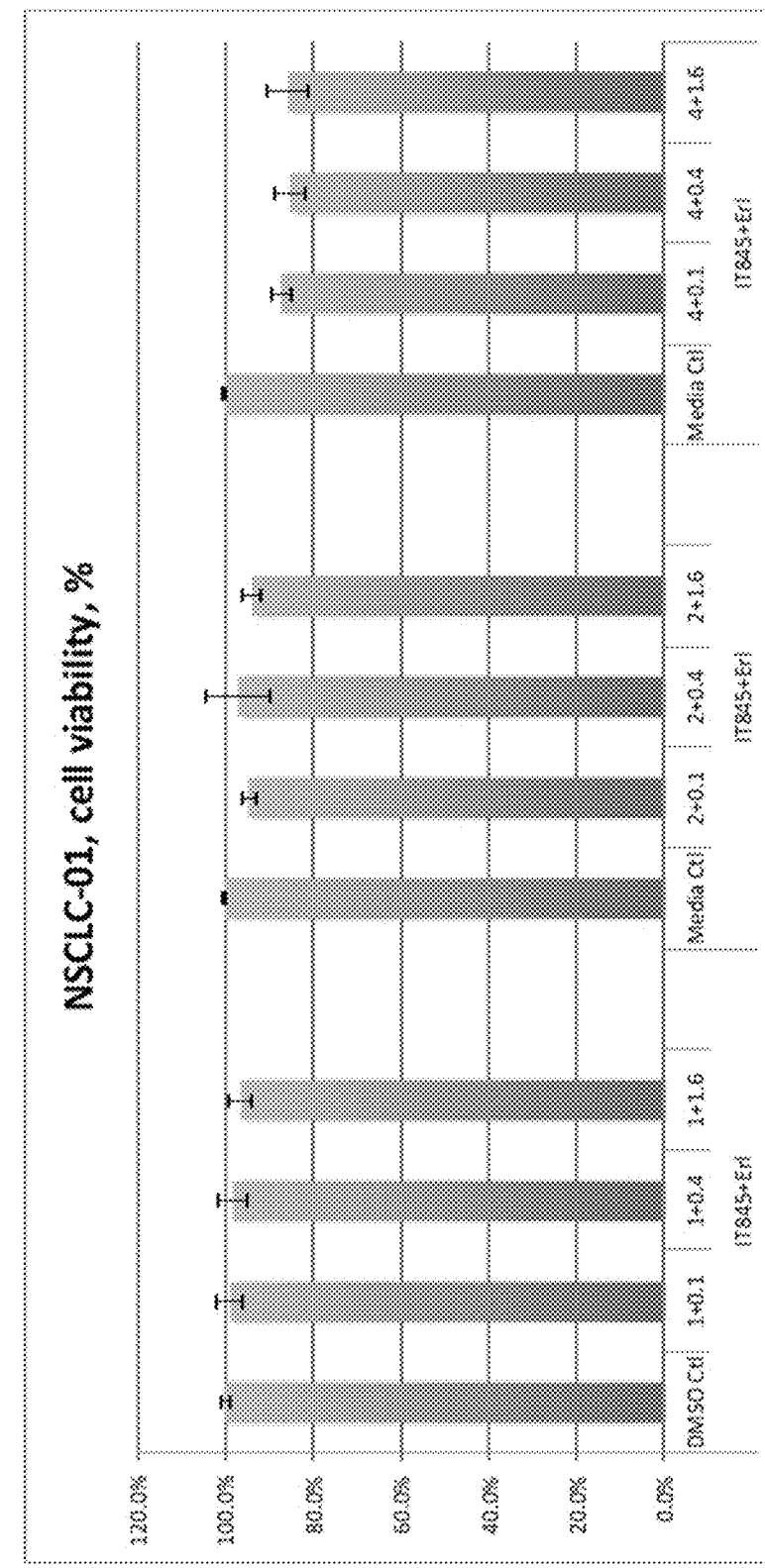
Figure 20C:
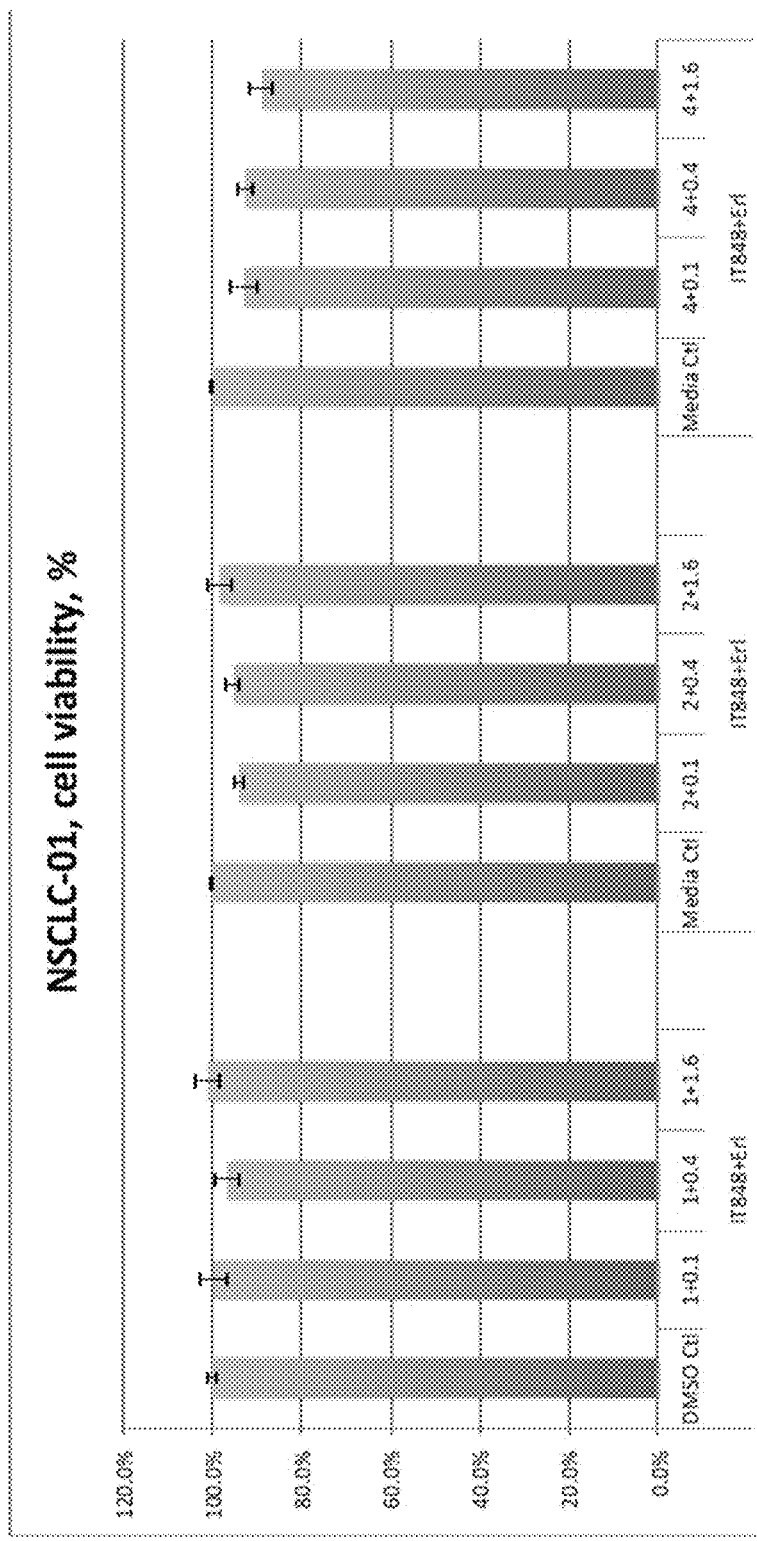
Figure 20D:
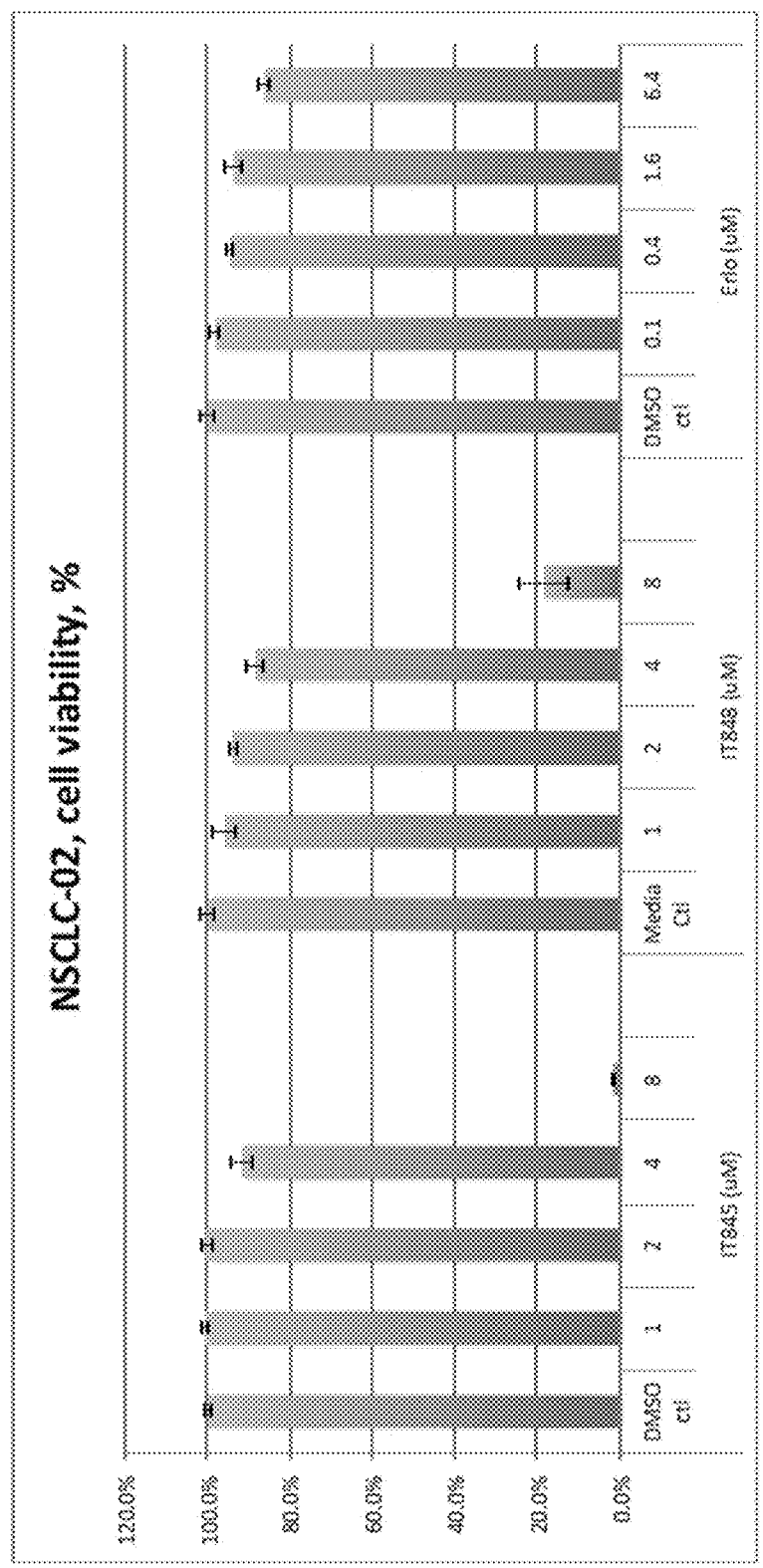
FIGS. 20D-20F: NSCLC-02 cells.
Figure 20E:
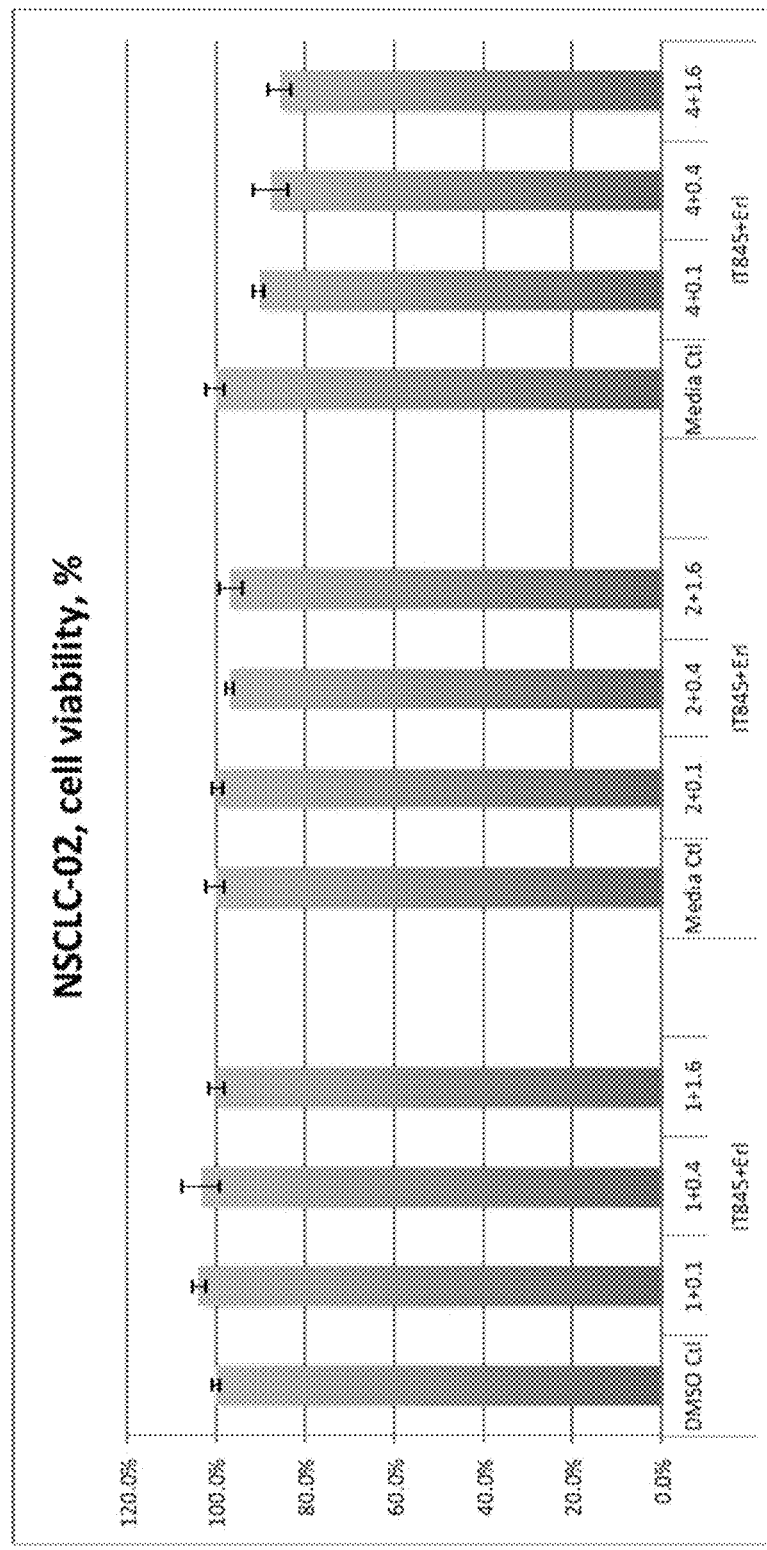
Figure 20F:
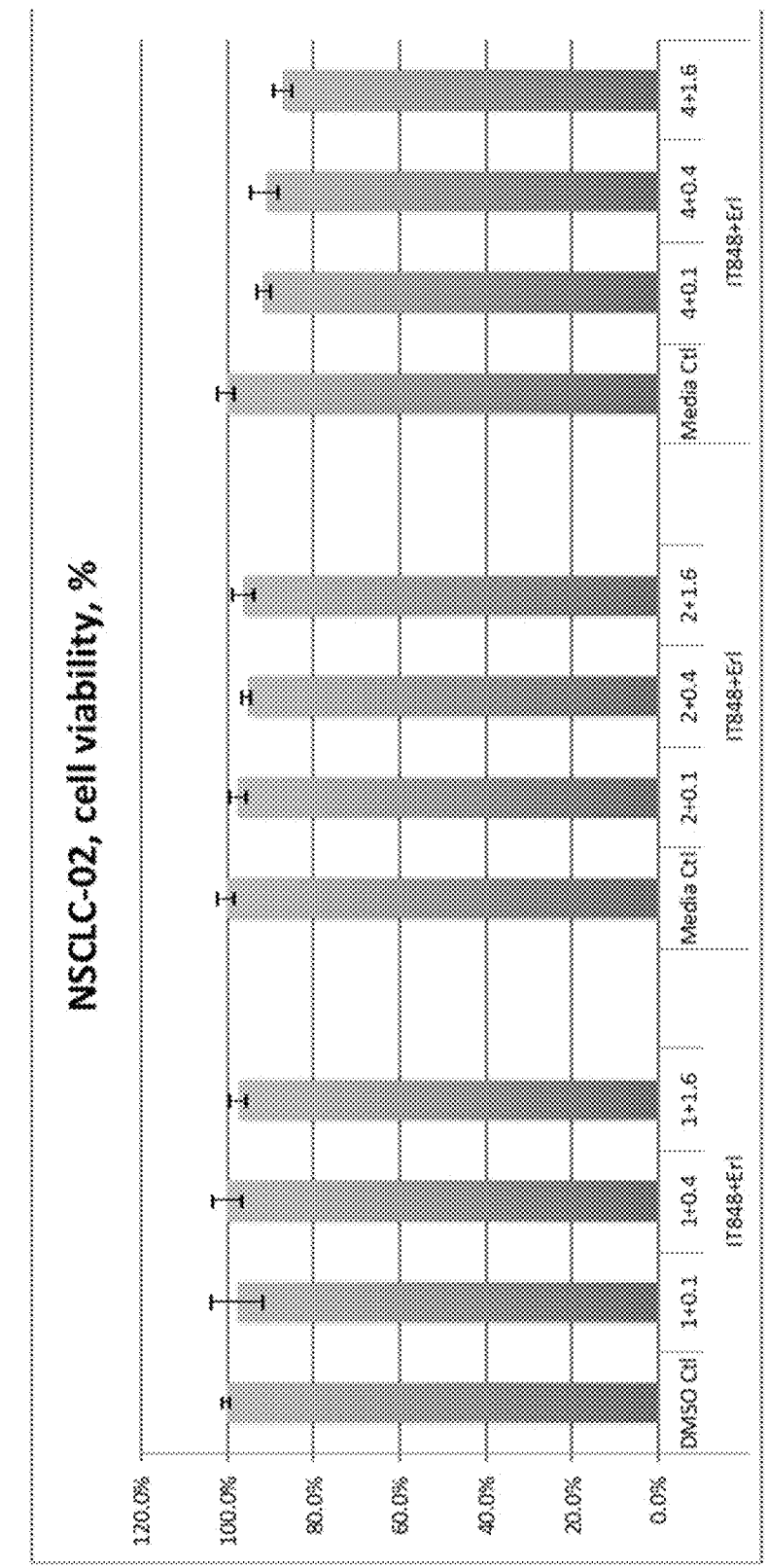
Figure 20G:
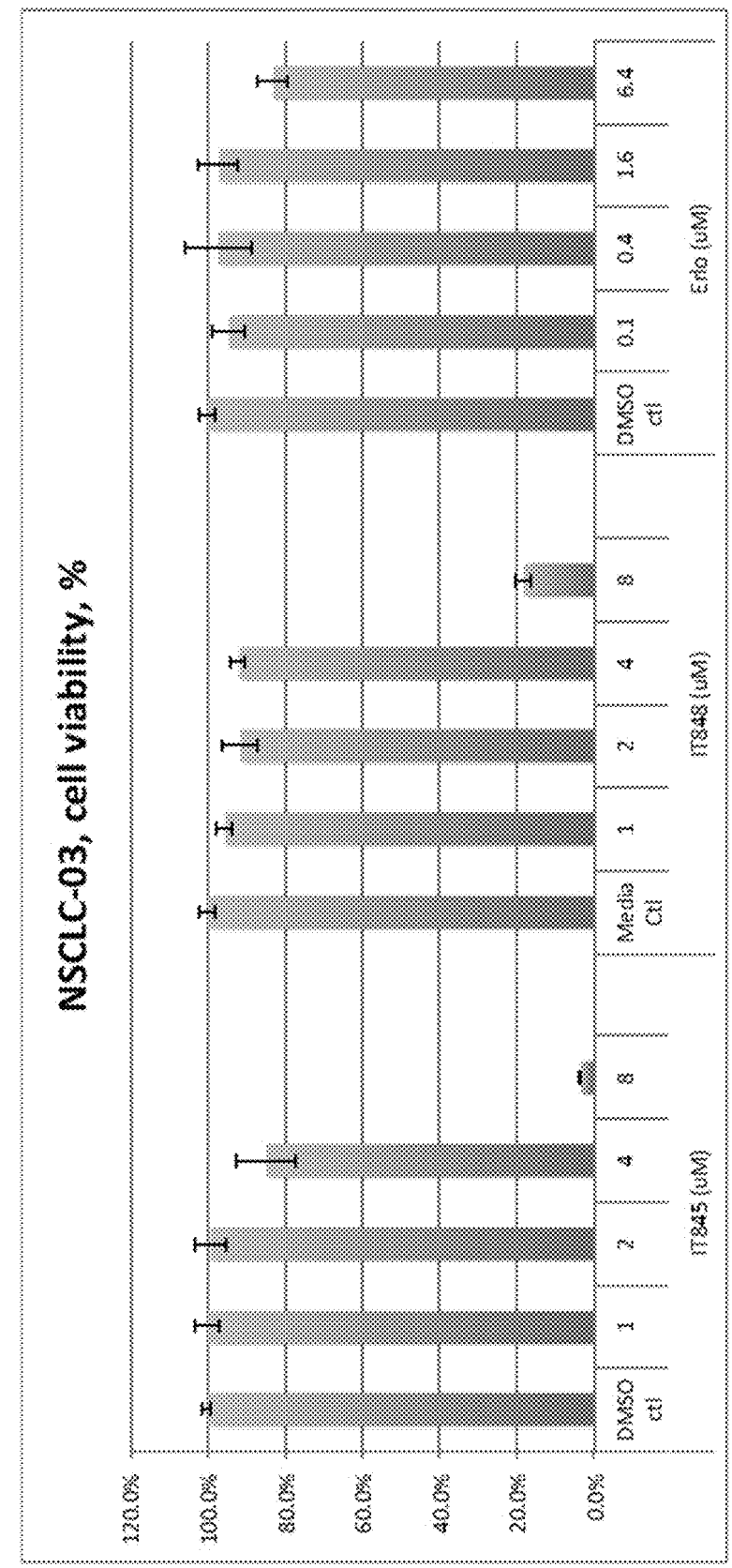
FIGS. 20G-20I: NSCLC-03 cells.
Figure 20H:
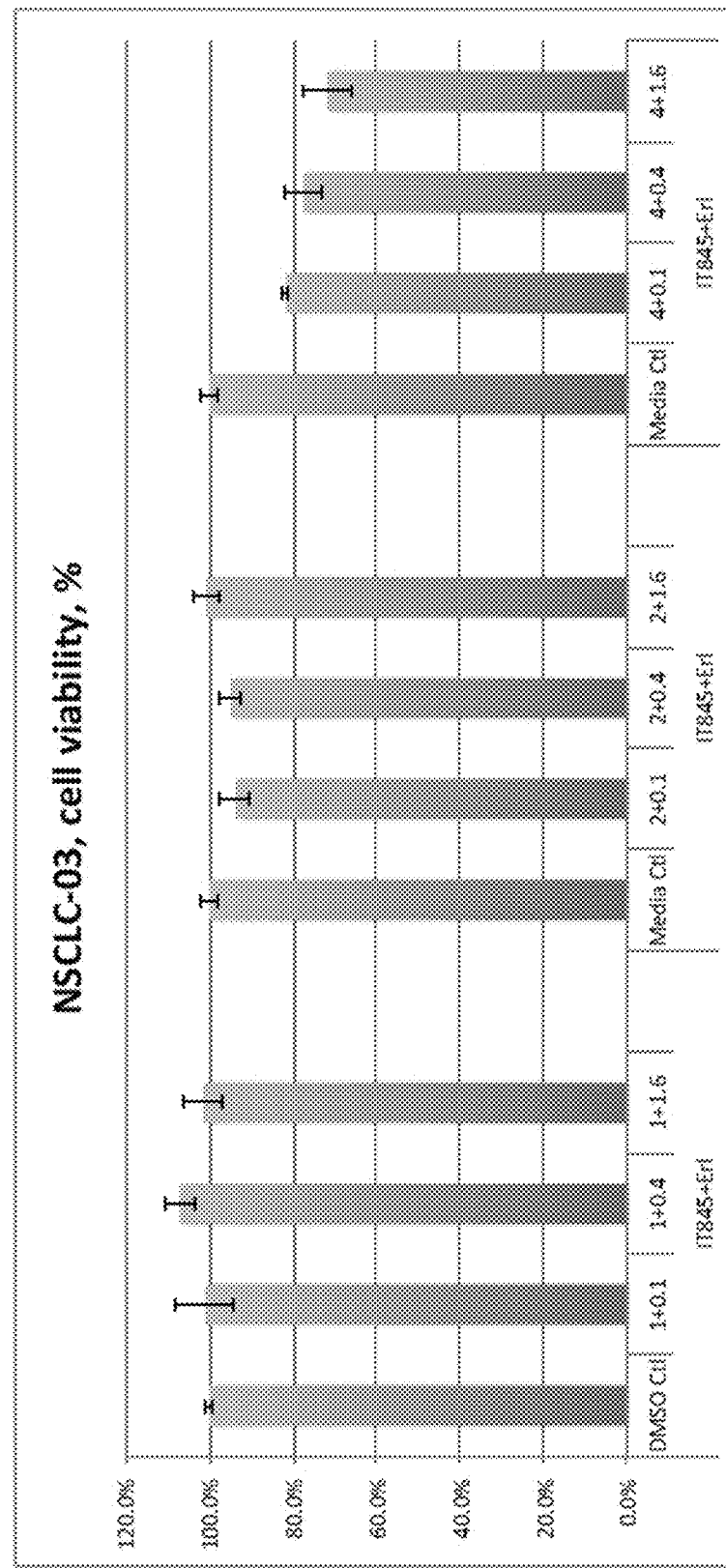
Figure 20I:
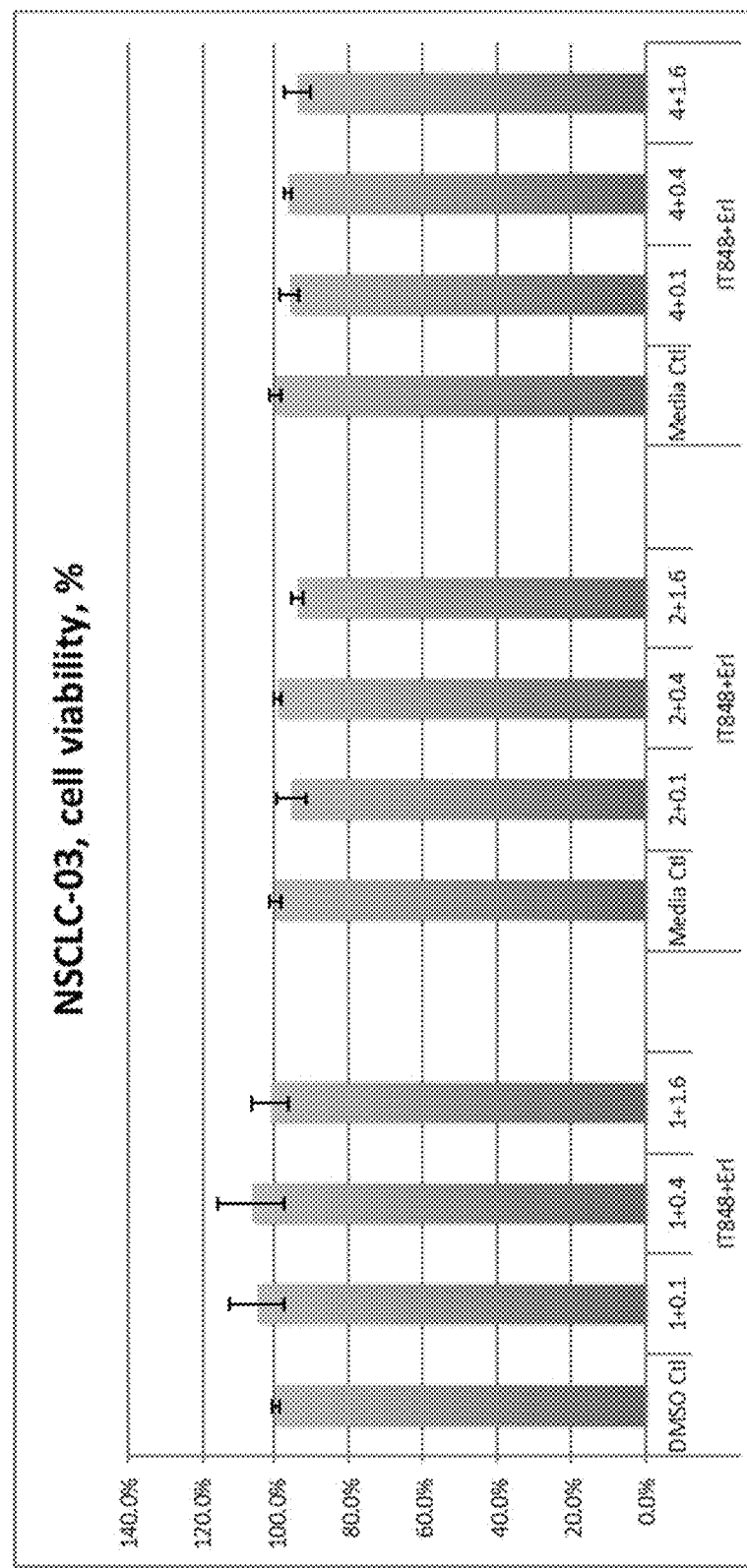
Figure 20J:
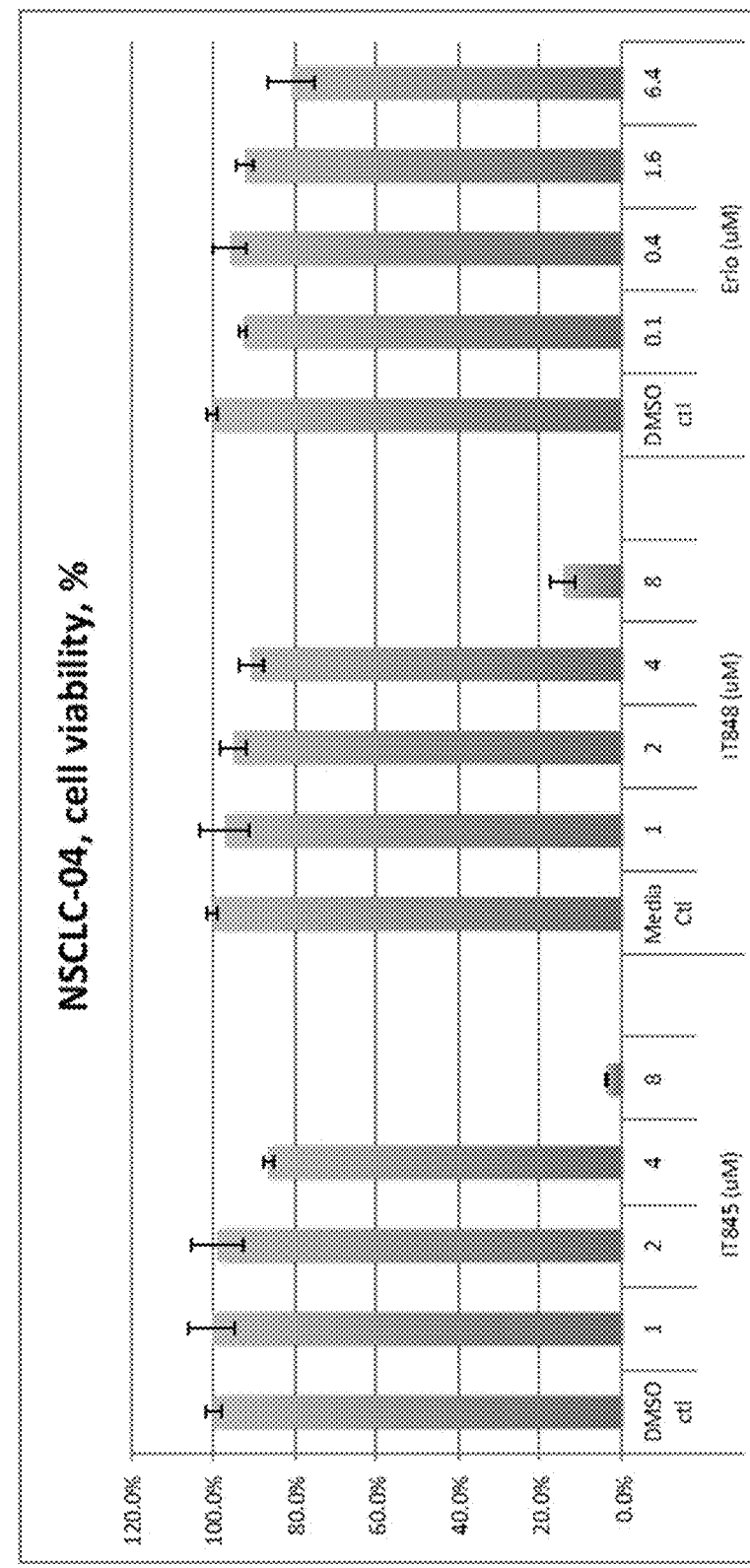
FIGS. 20J-20L: NSCLC-04 cells.
Figure 20K:
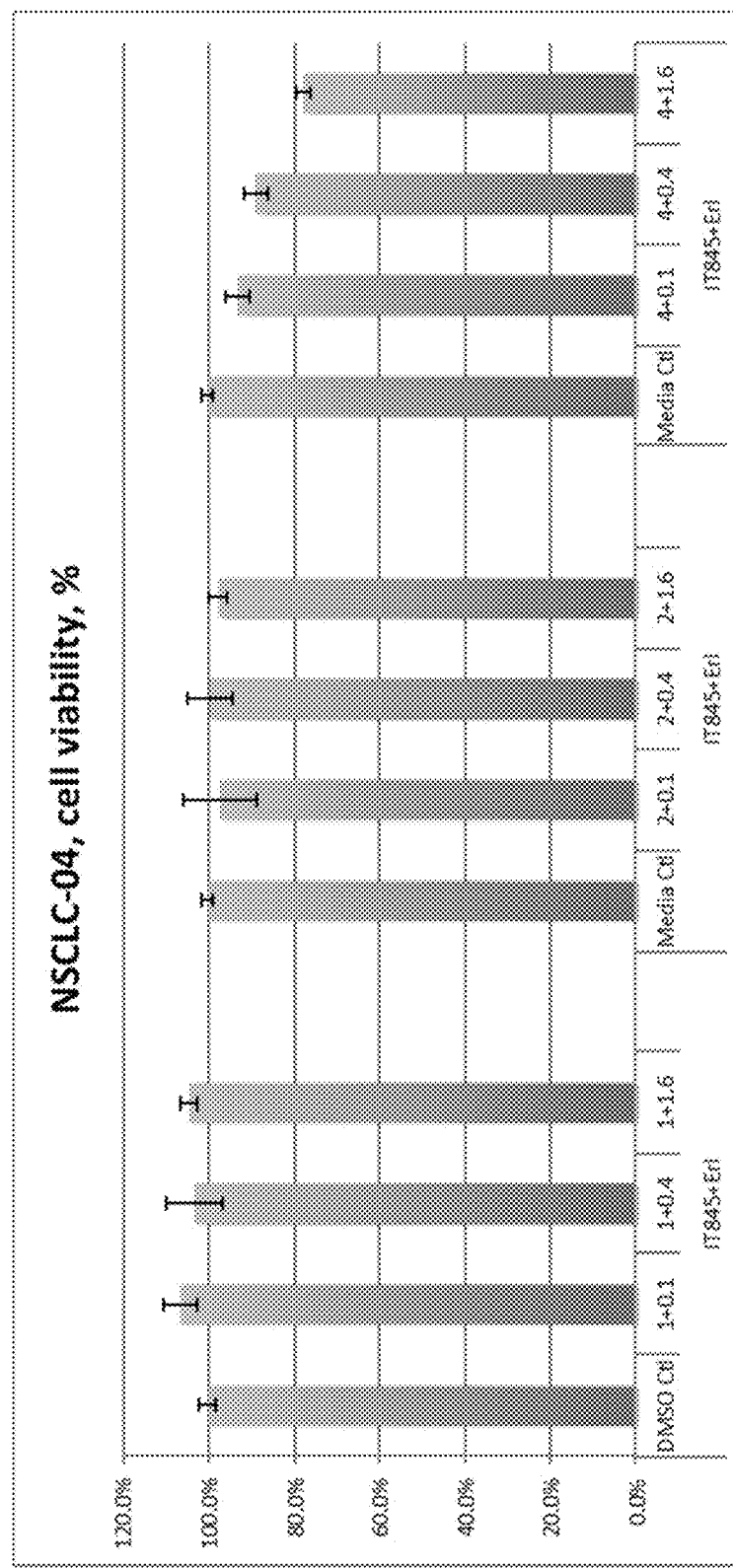
Figure 20L:
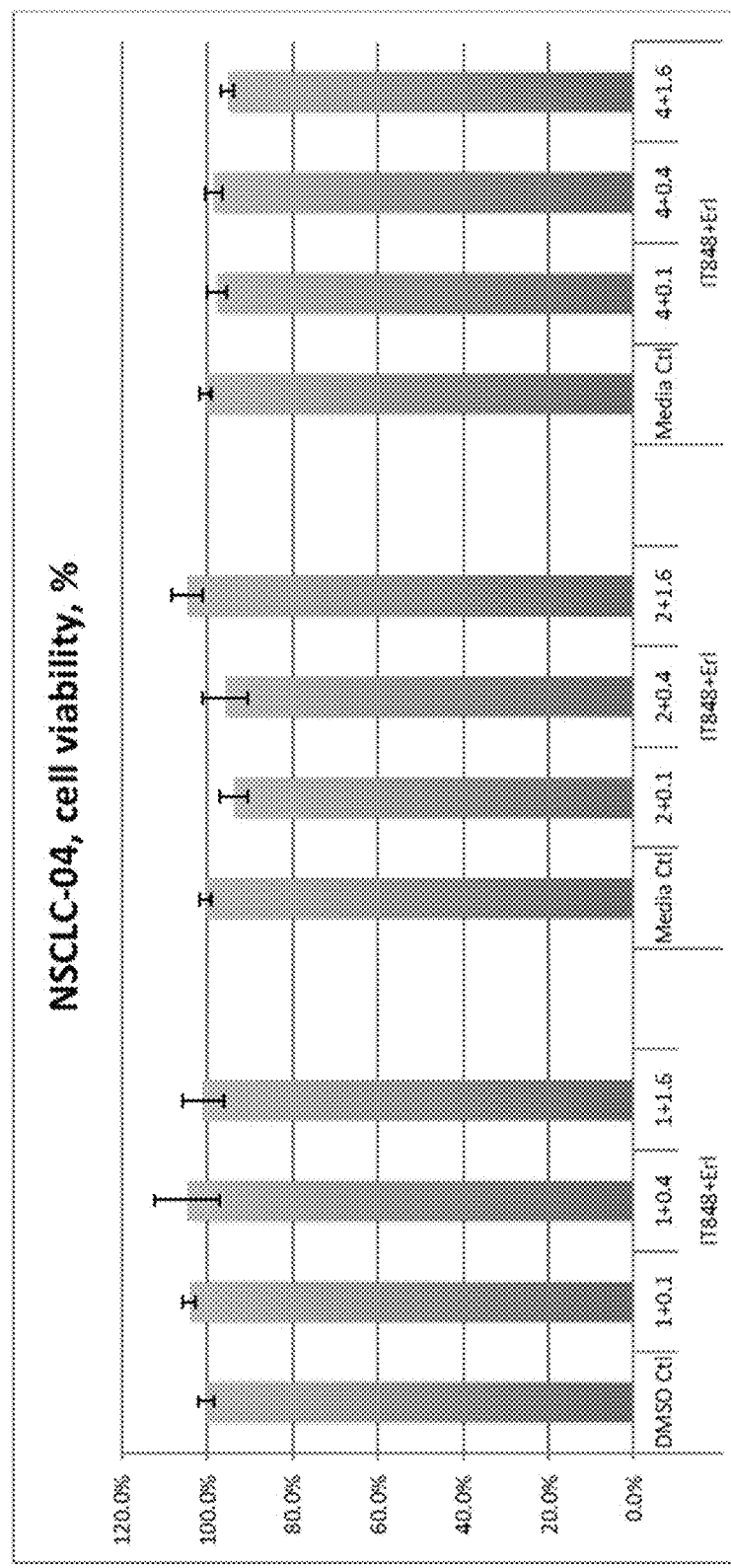
Figure 20M:
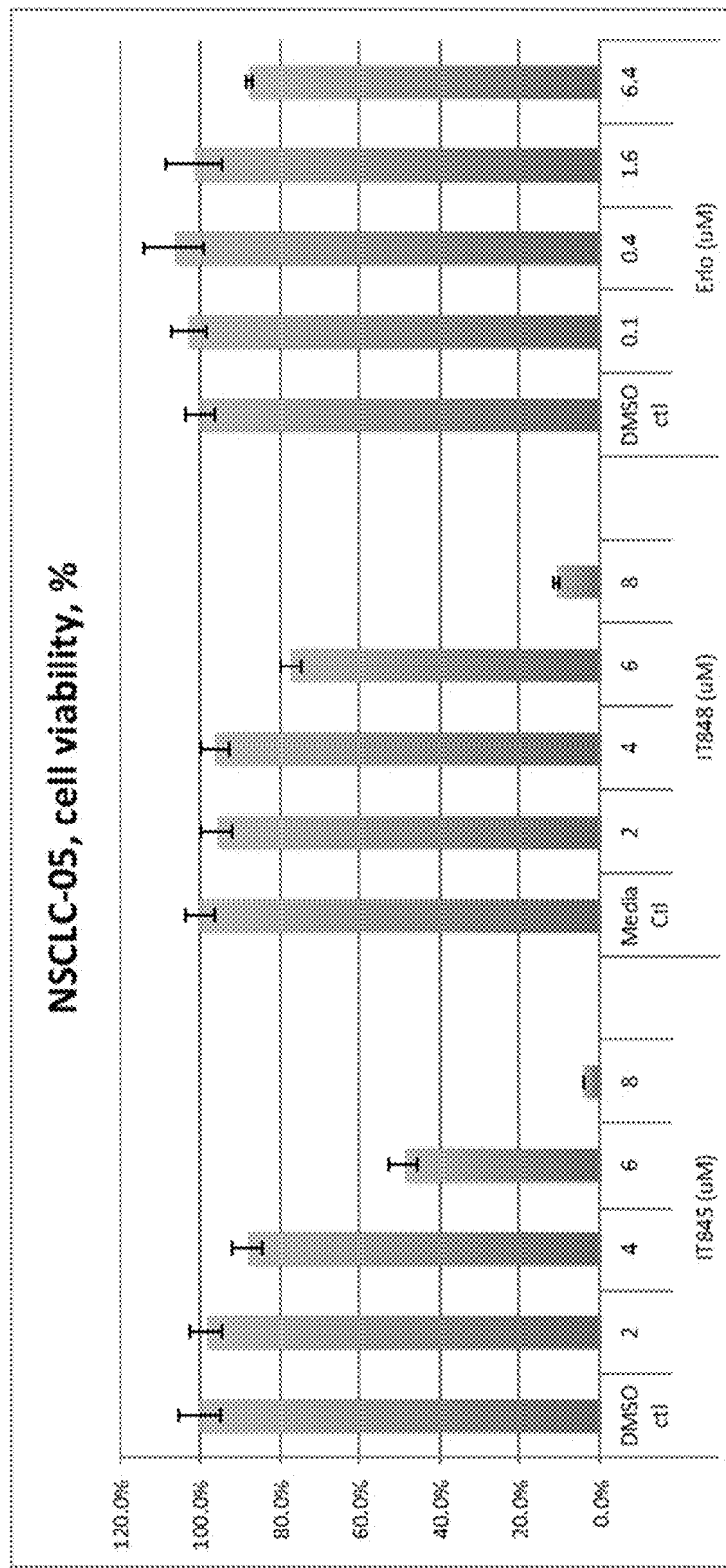
FIGS. 20M-20O: NSCLC-05 cells.
Figure 20N:
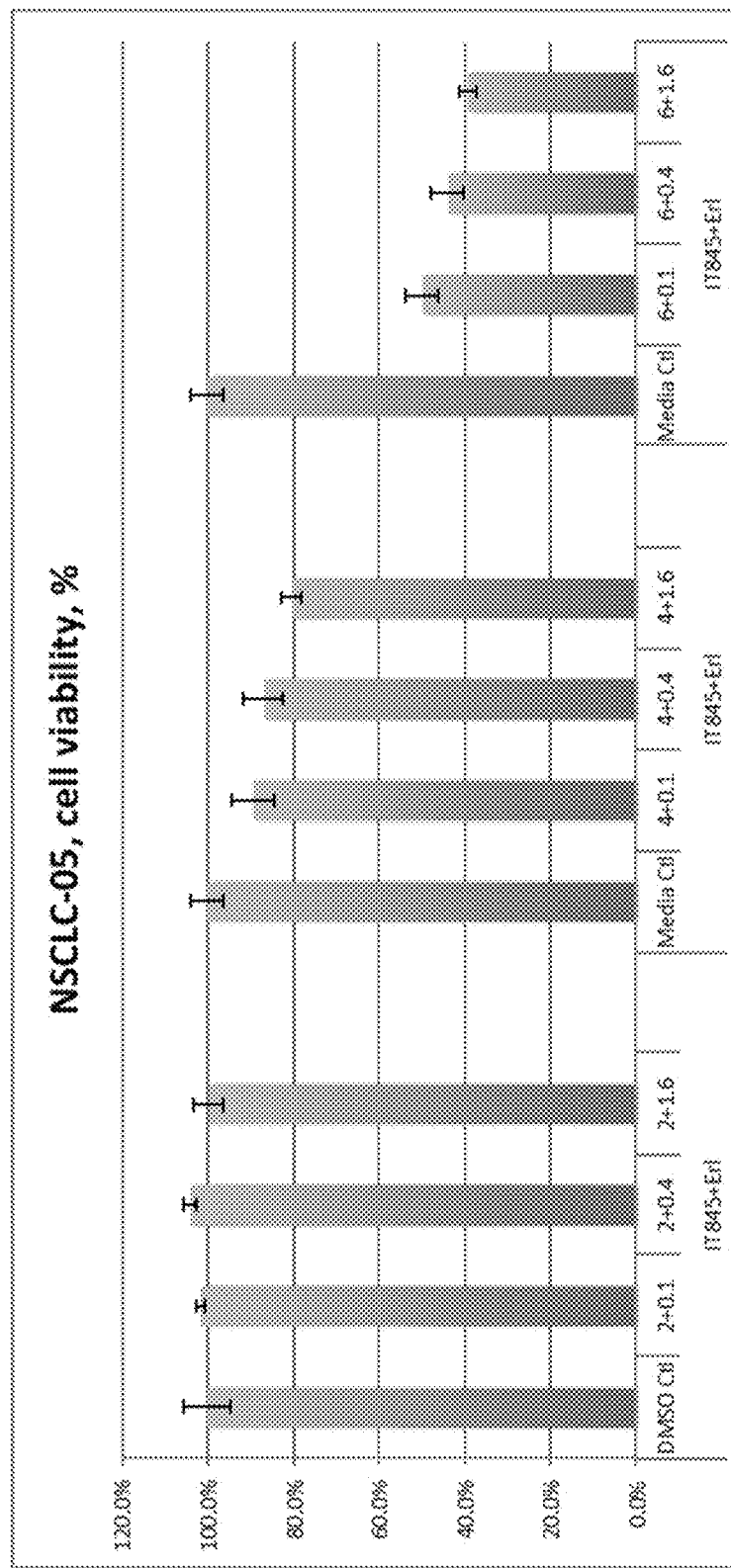
Figure 20O:
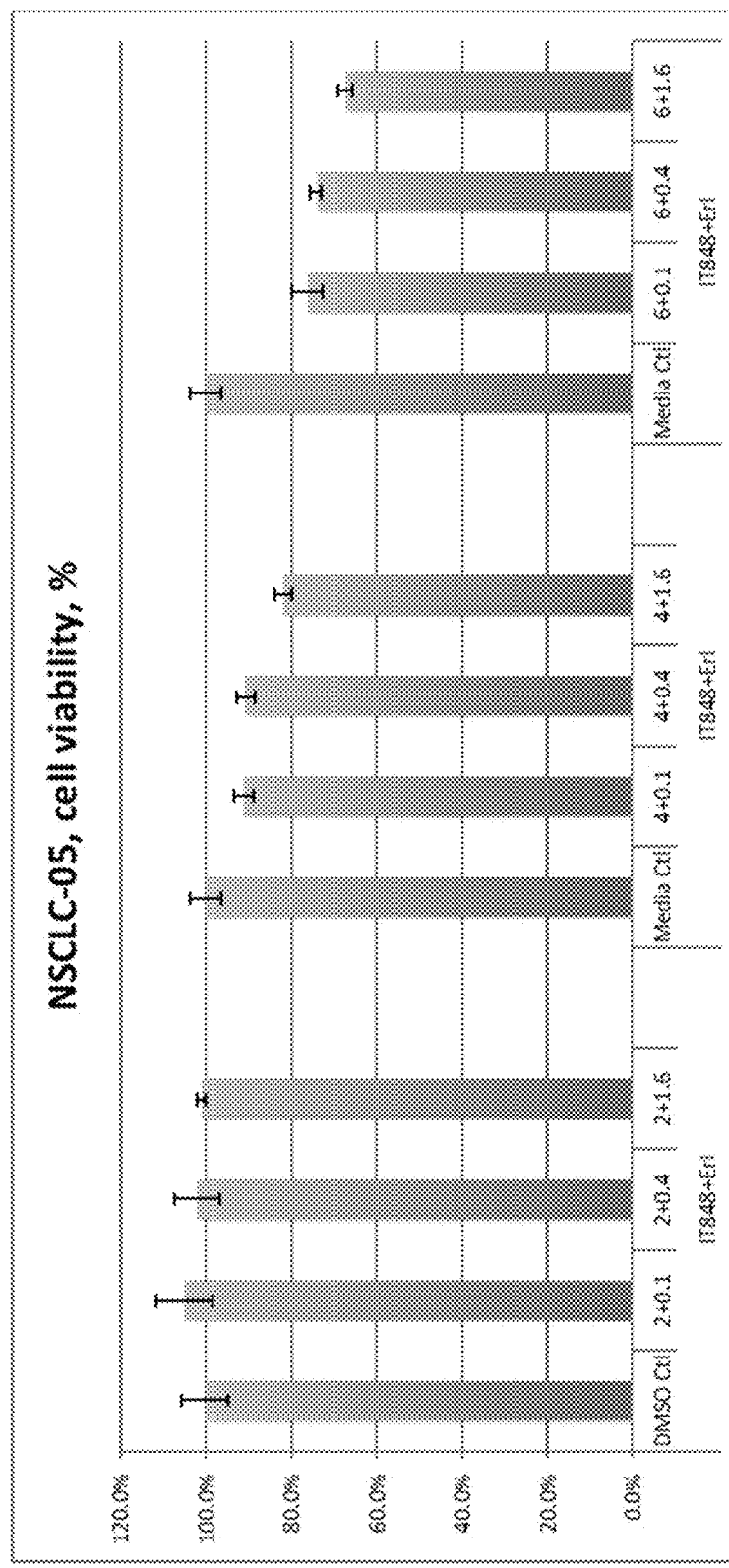
Figure 20P:
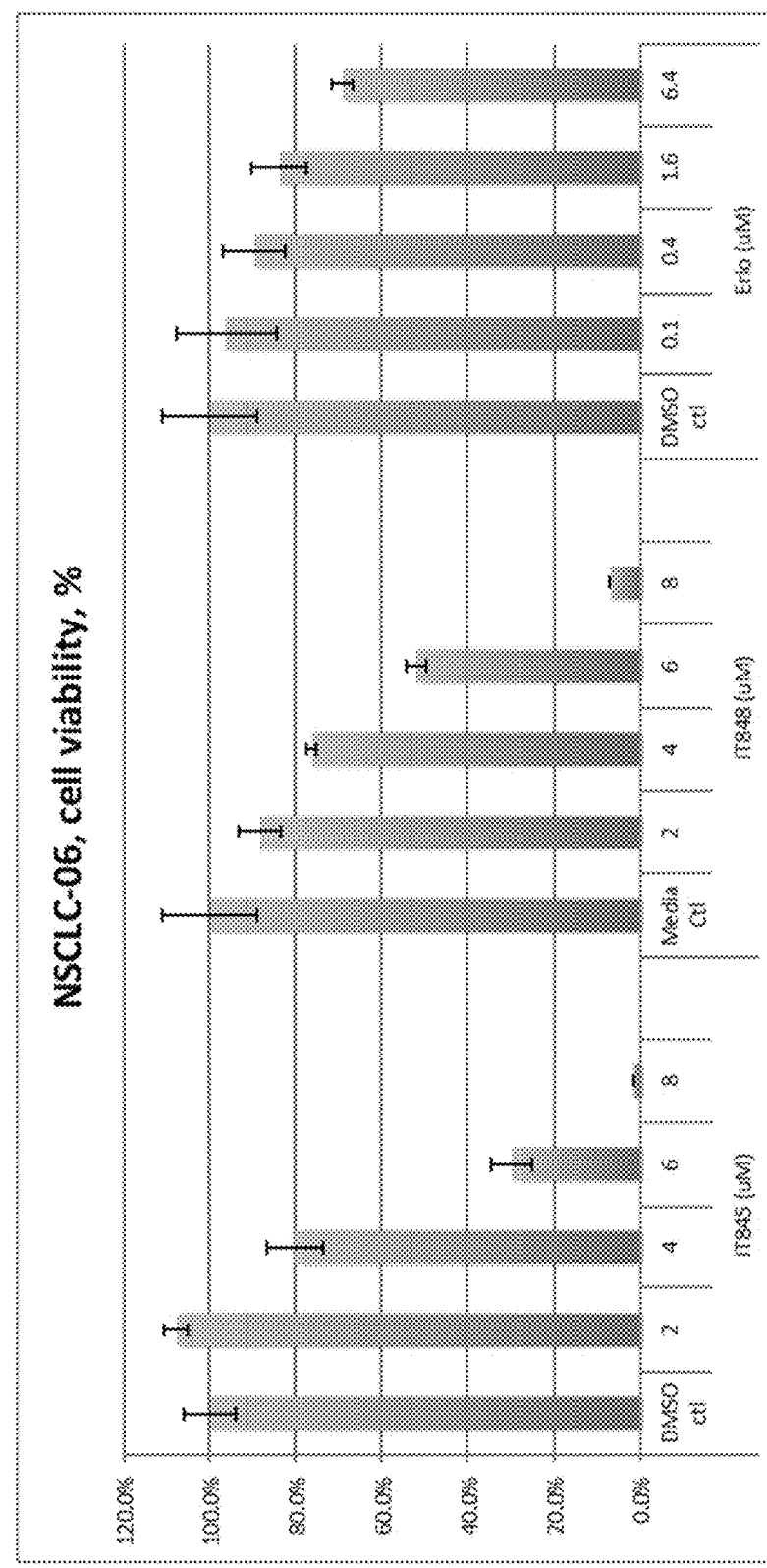
FIGS. 20P-20R: NSCLC-06 cells.
Figure 20Q:
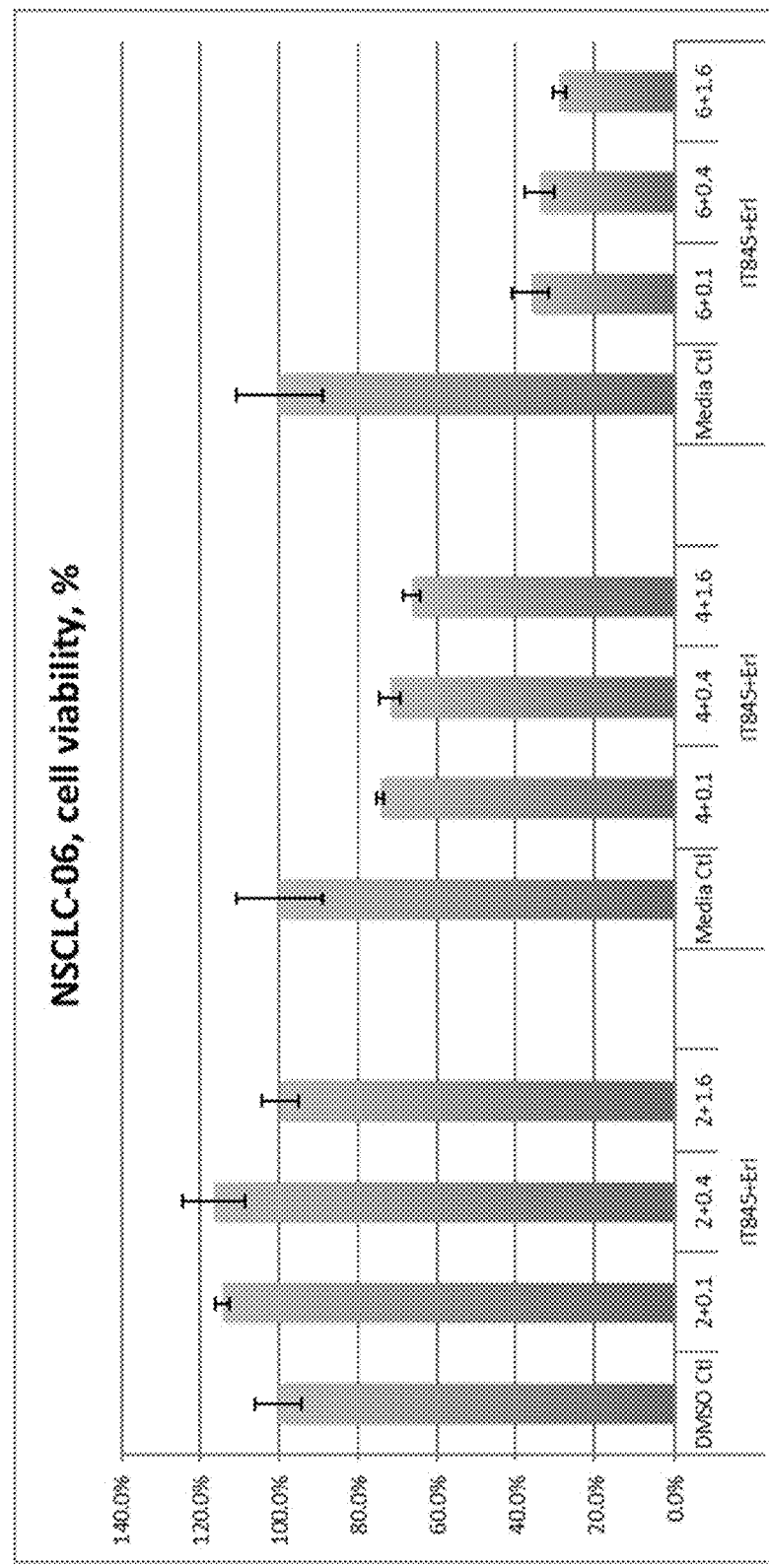
Figure 20R:
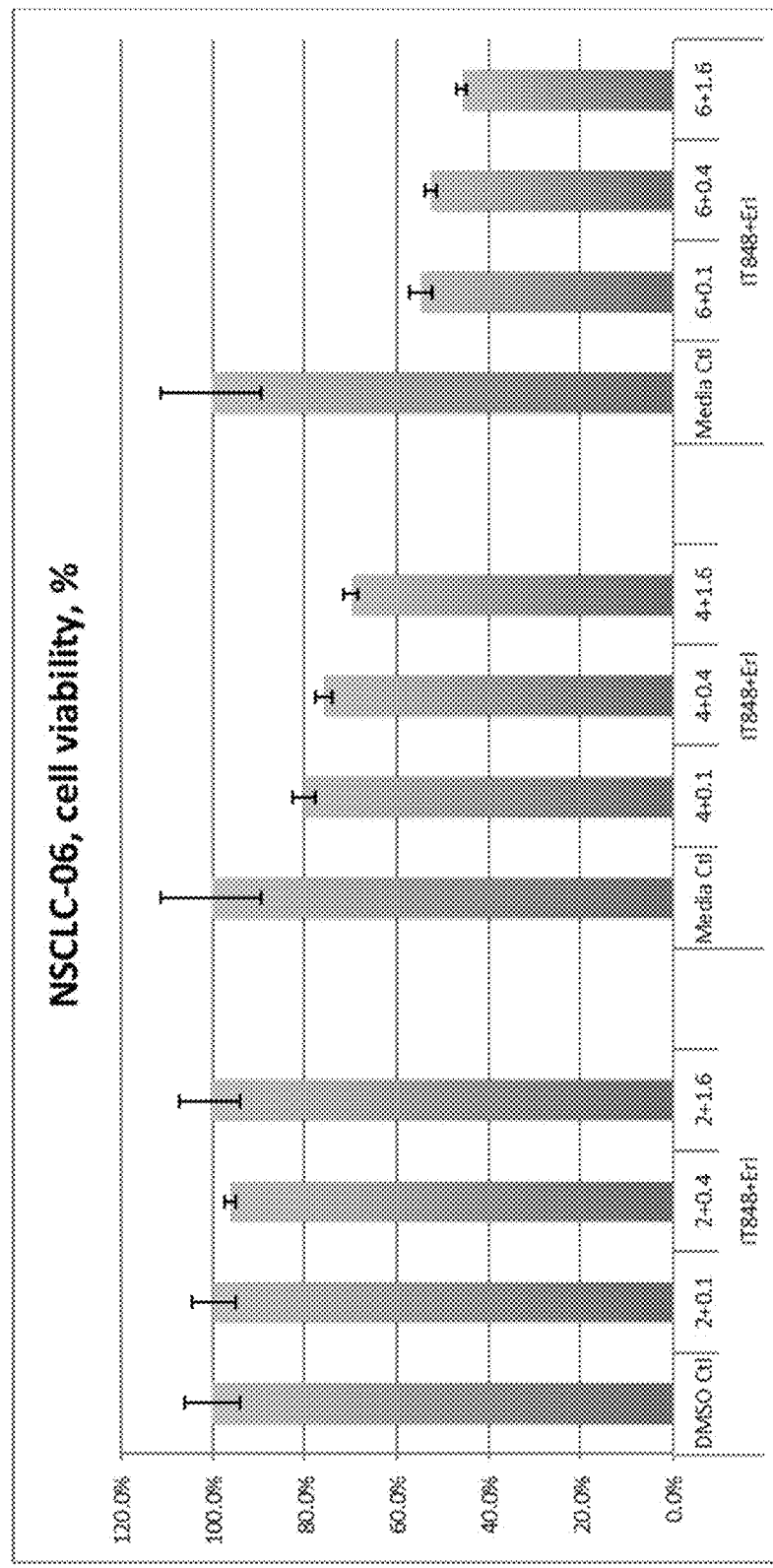
Figure 20S:
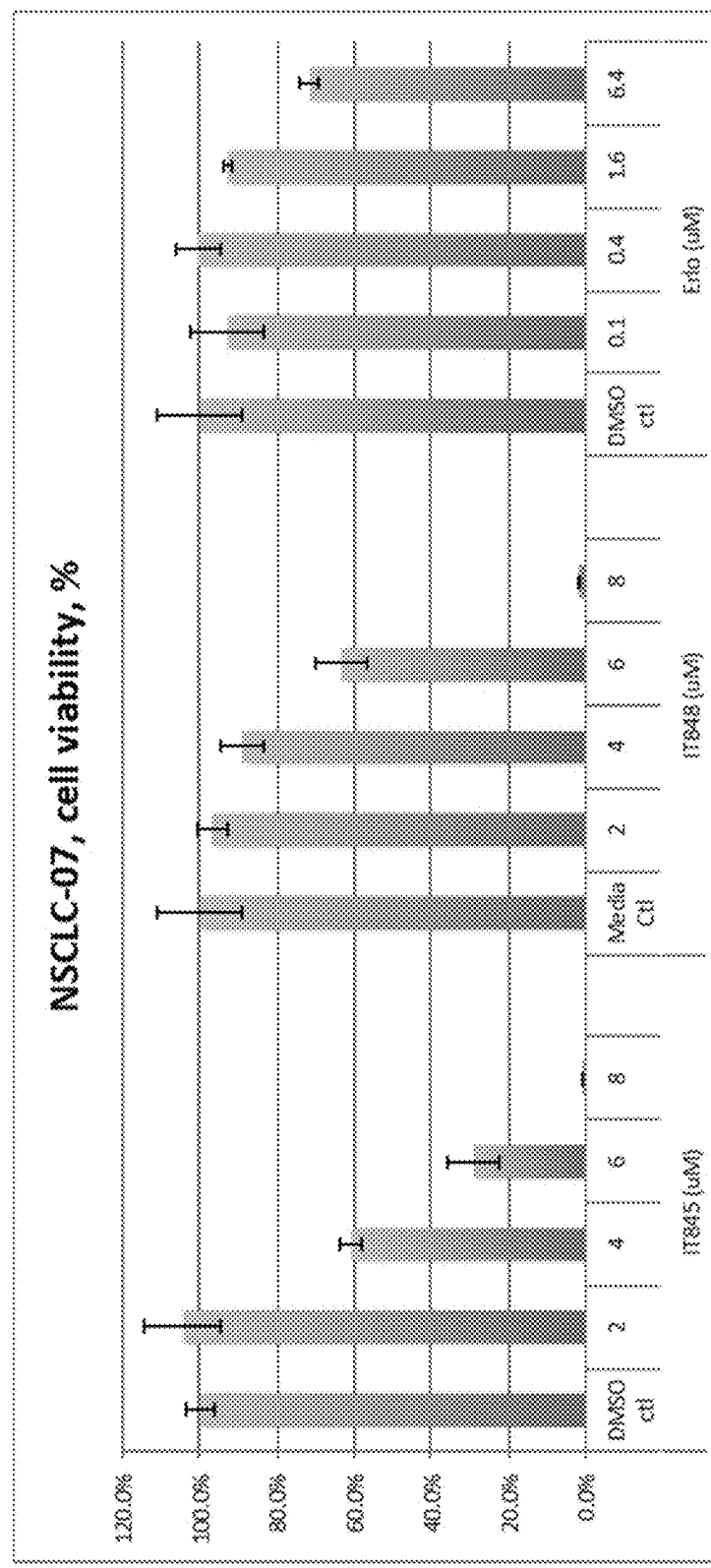
FIGS. 20S-20U: NSCLC-07 cells.
Figure 20T:
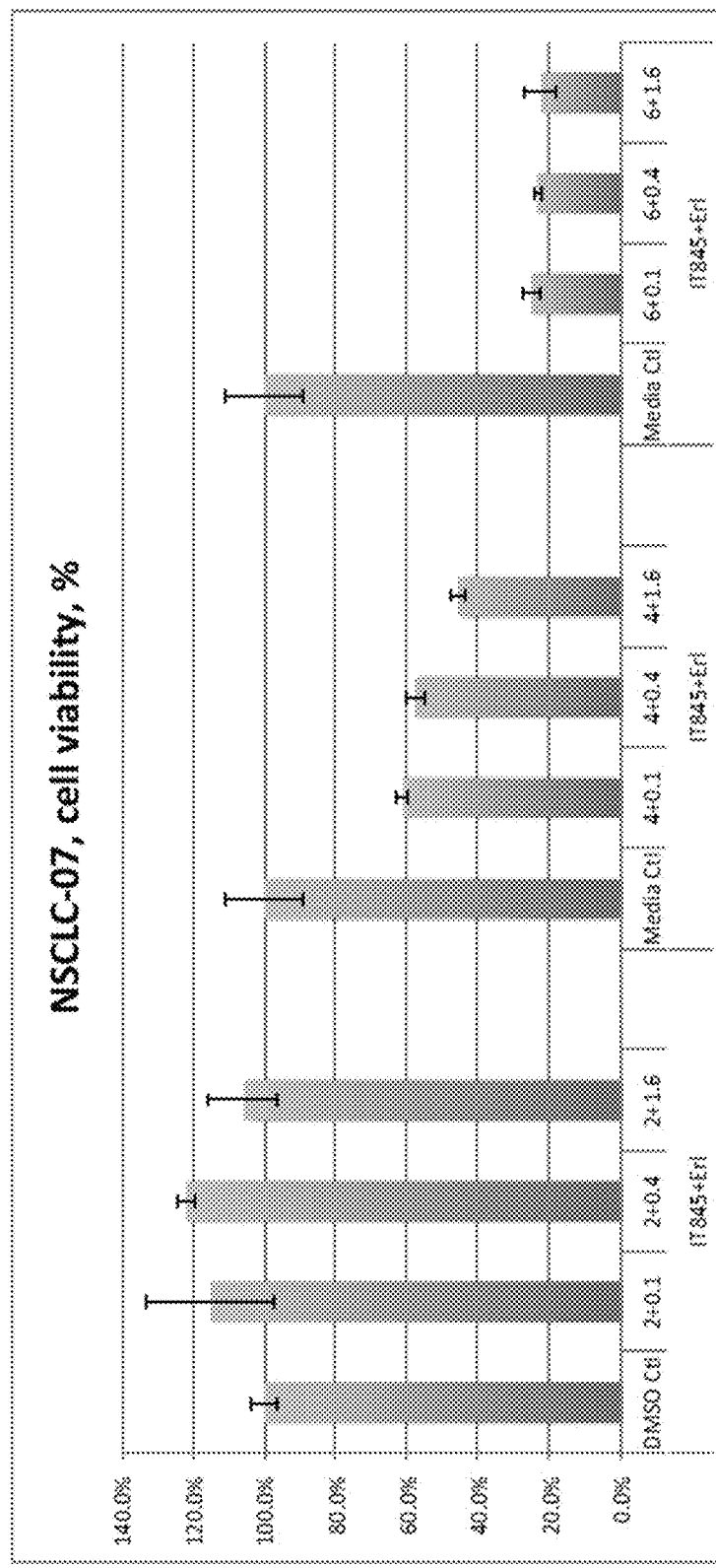
Figure 20U:
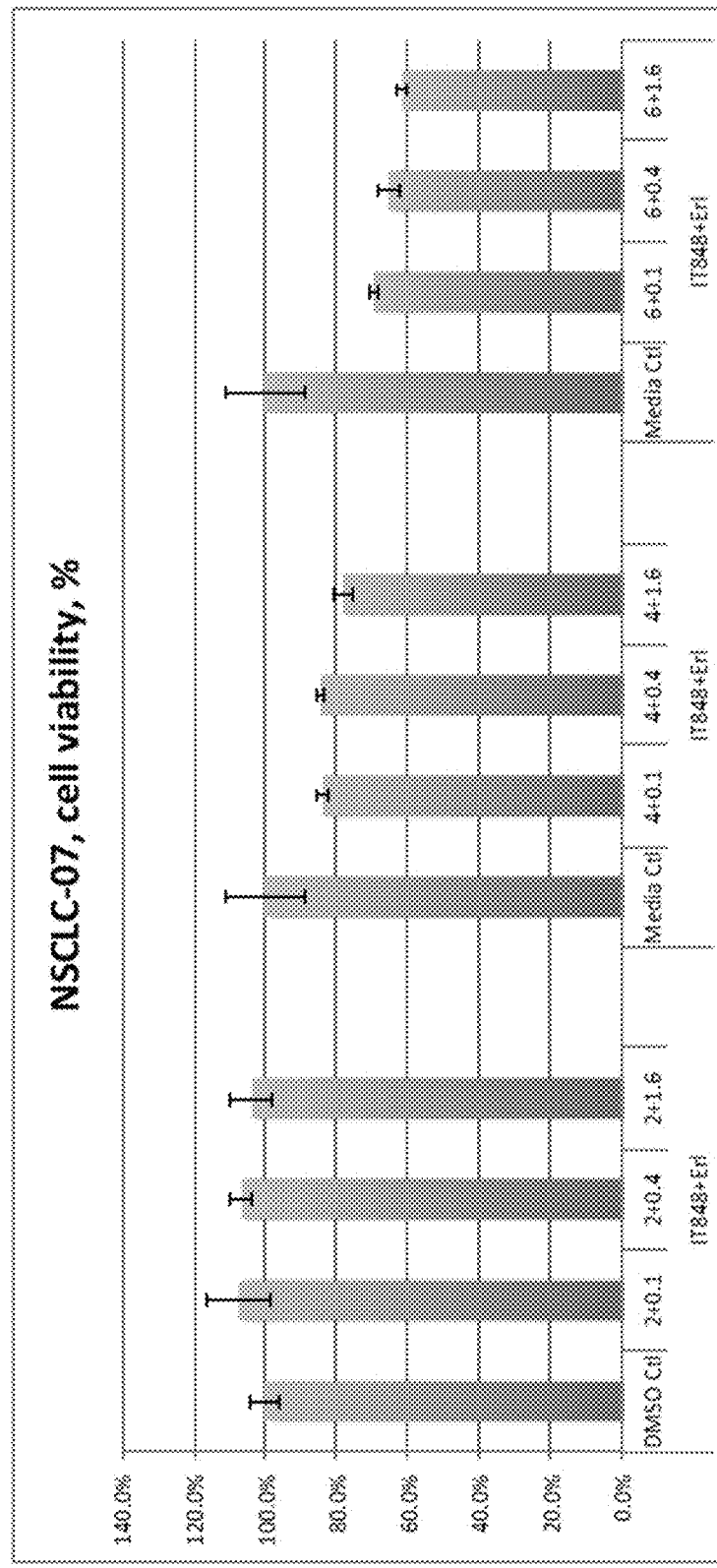
Figure 20V:
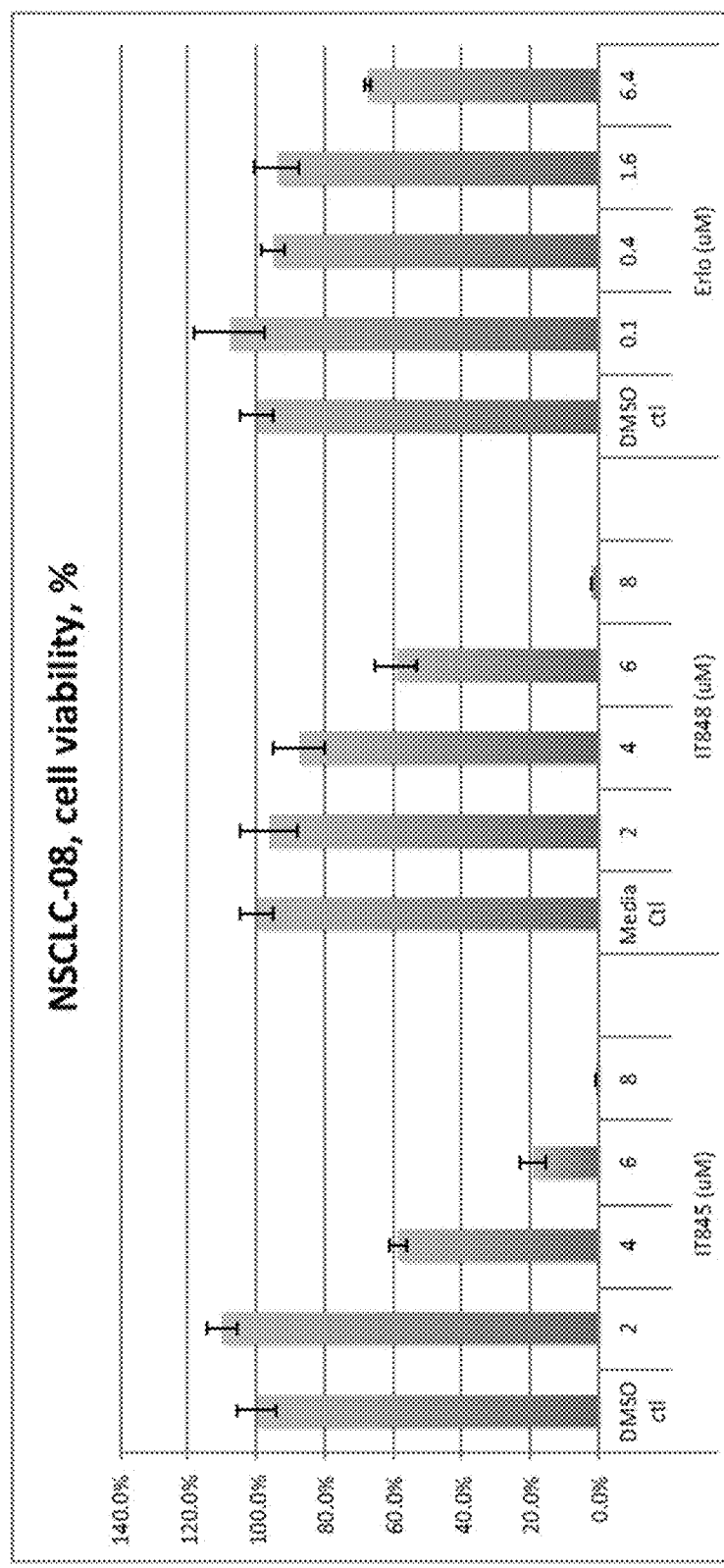
FIGS. 20V-20X: NSCLC-08 cells.
Figure 20W:
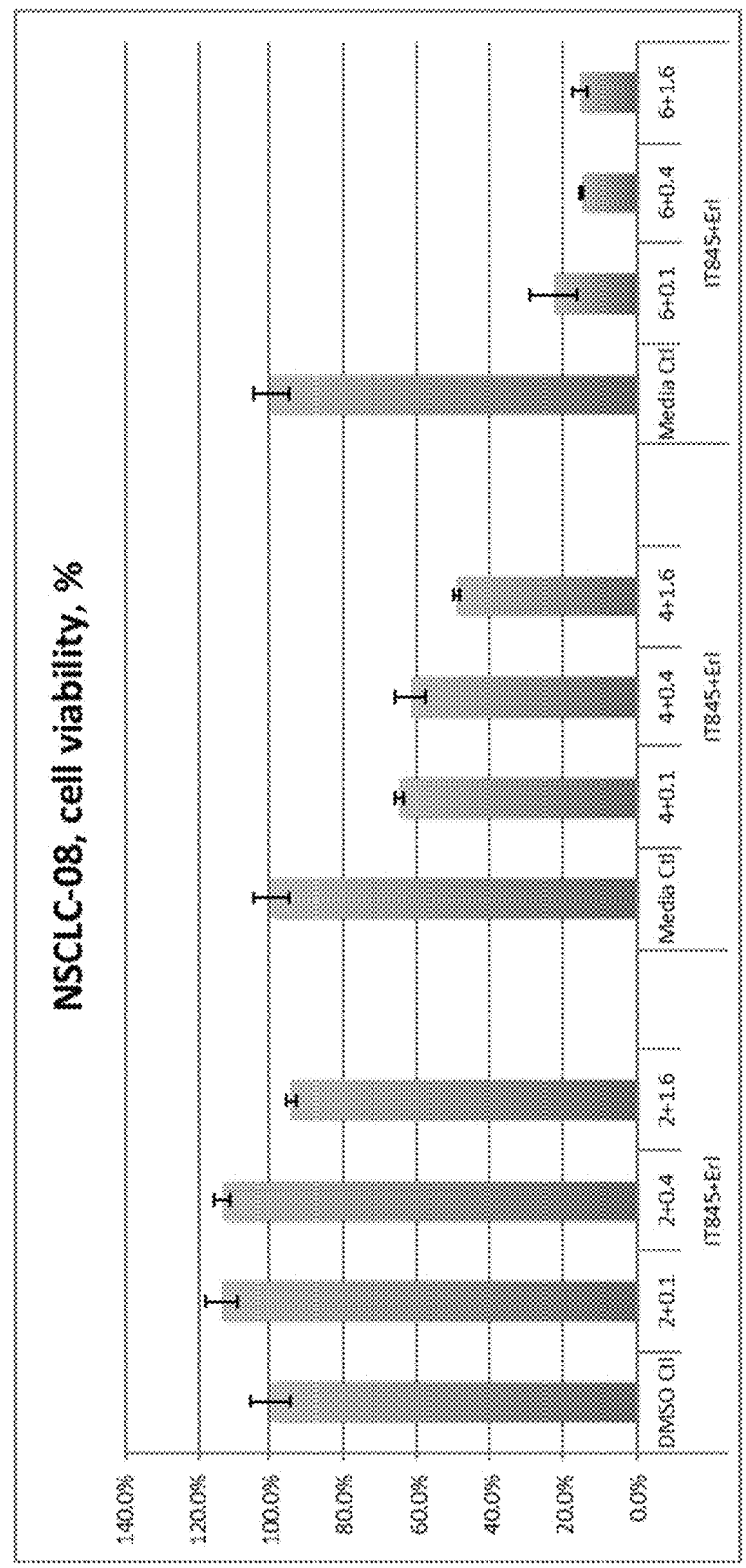
Figure 20X:
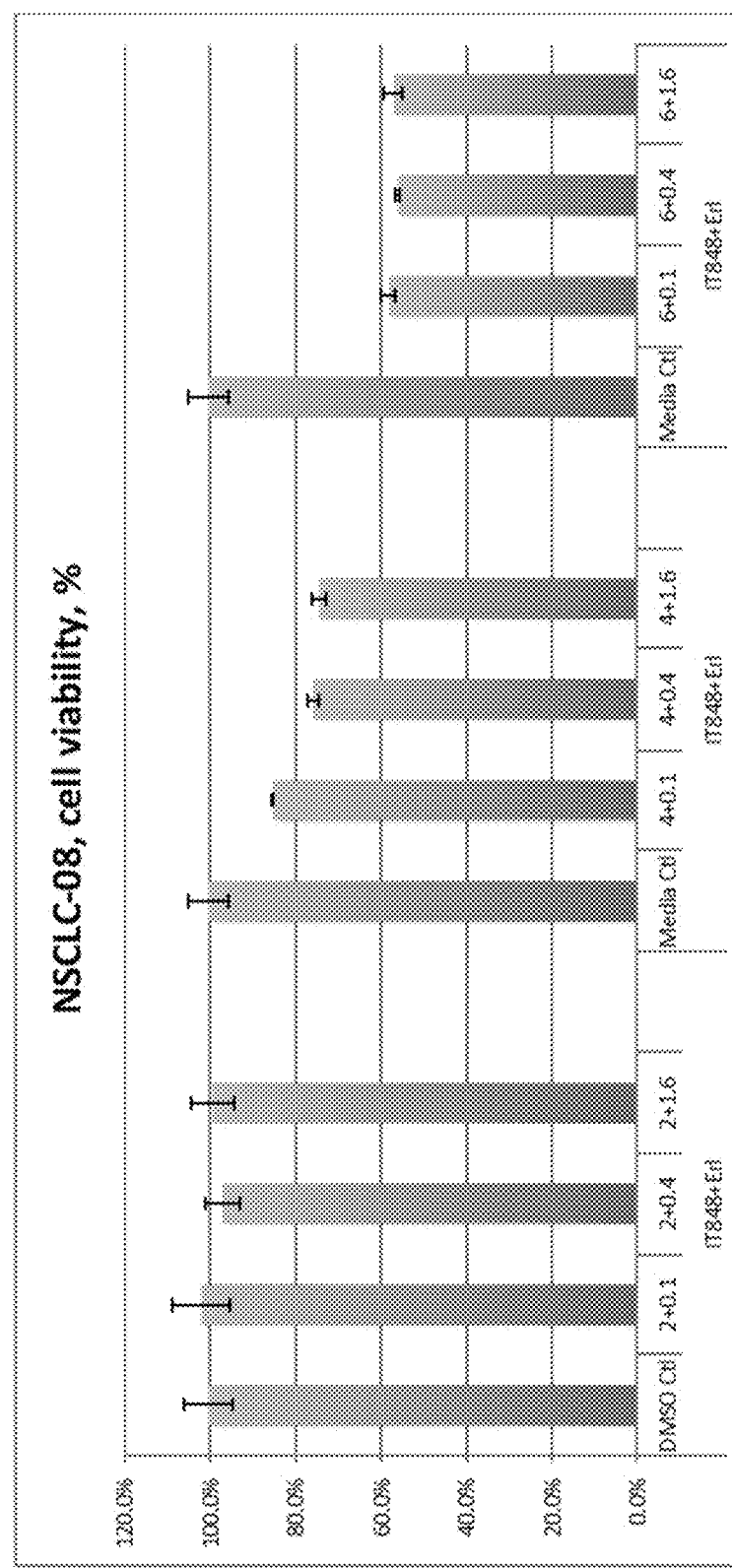
Figure 20Y:
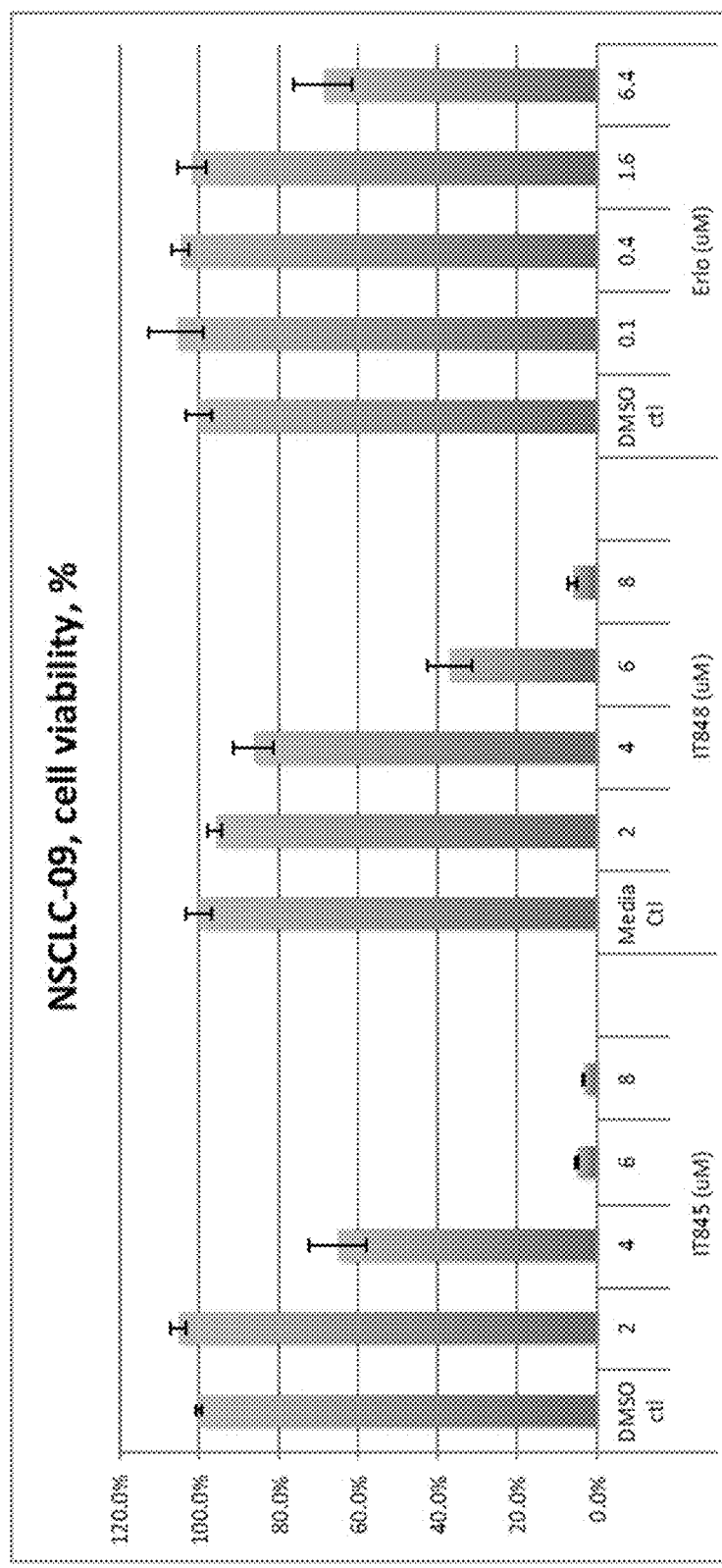
Figure 20Z:
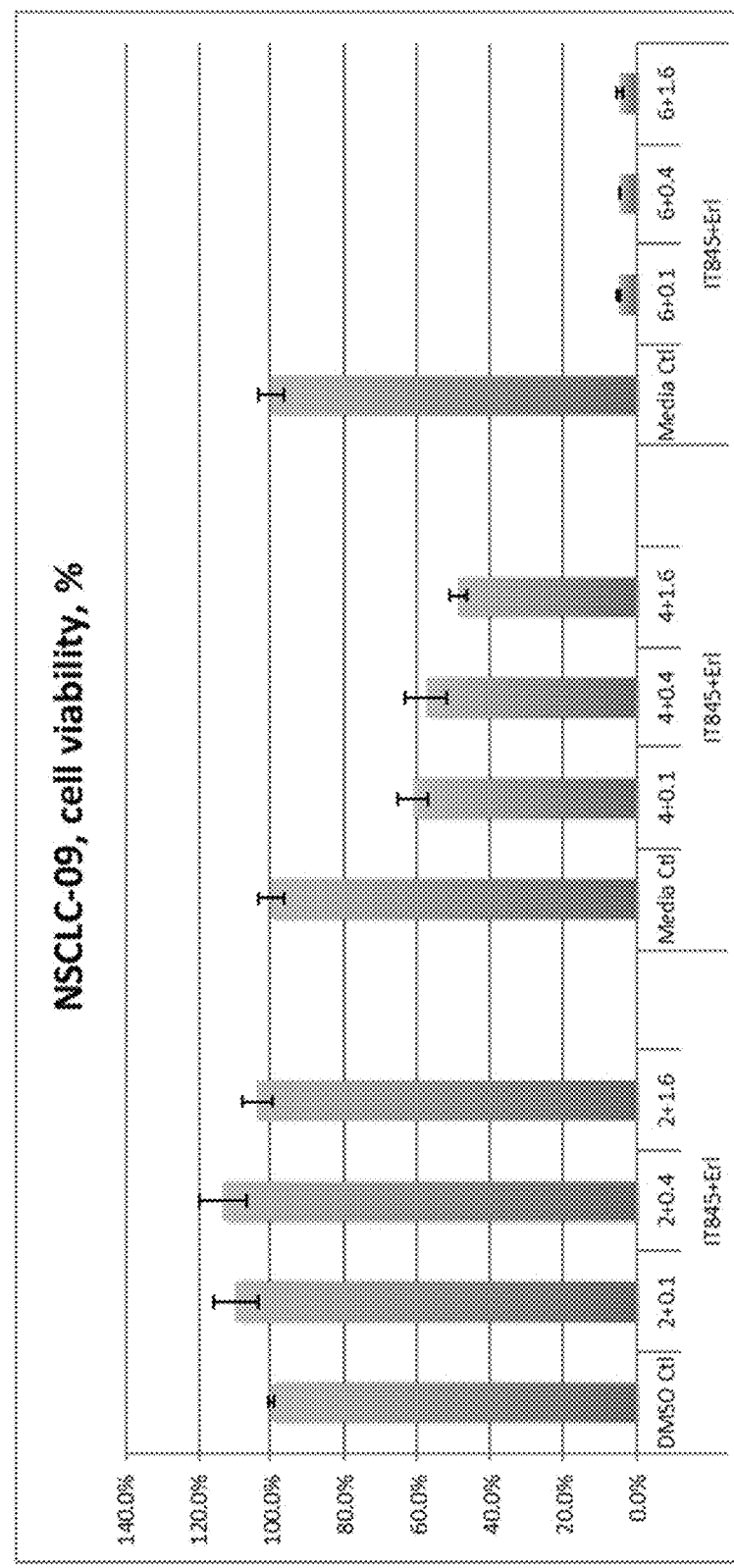
Figure 20A:
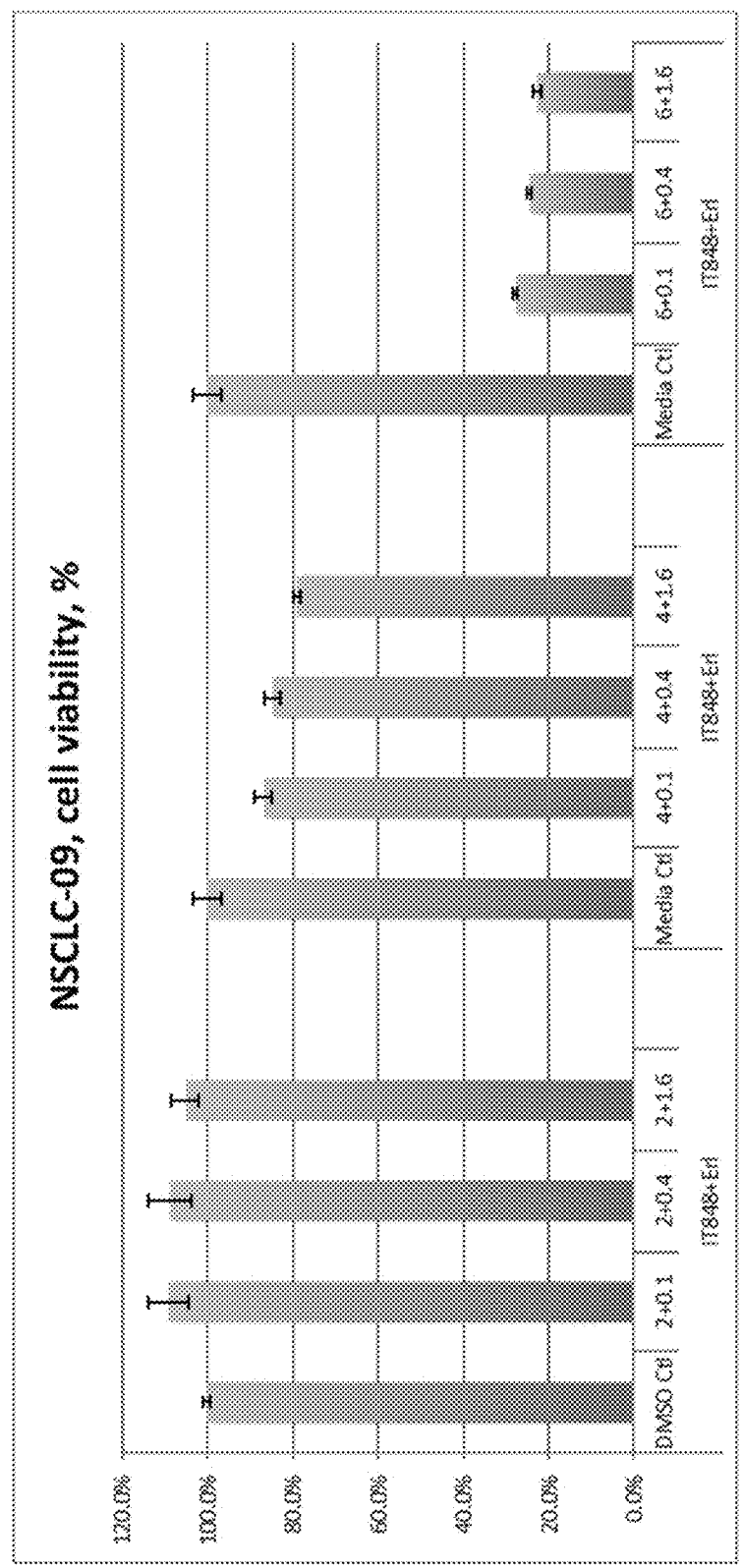
Figure 20A:
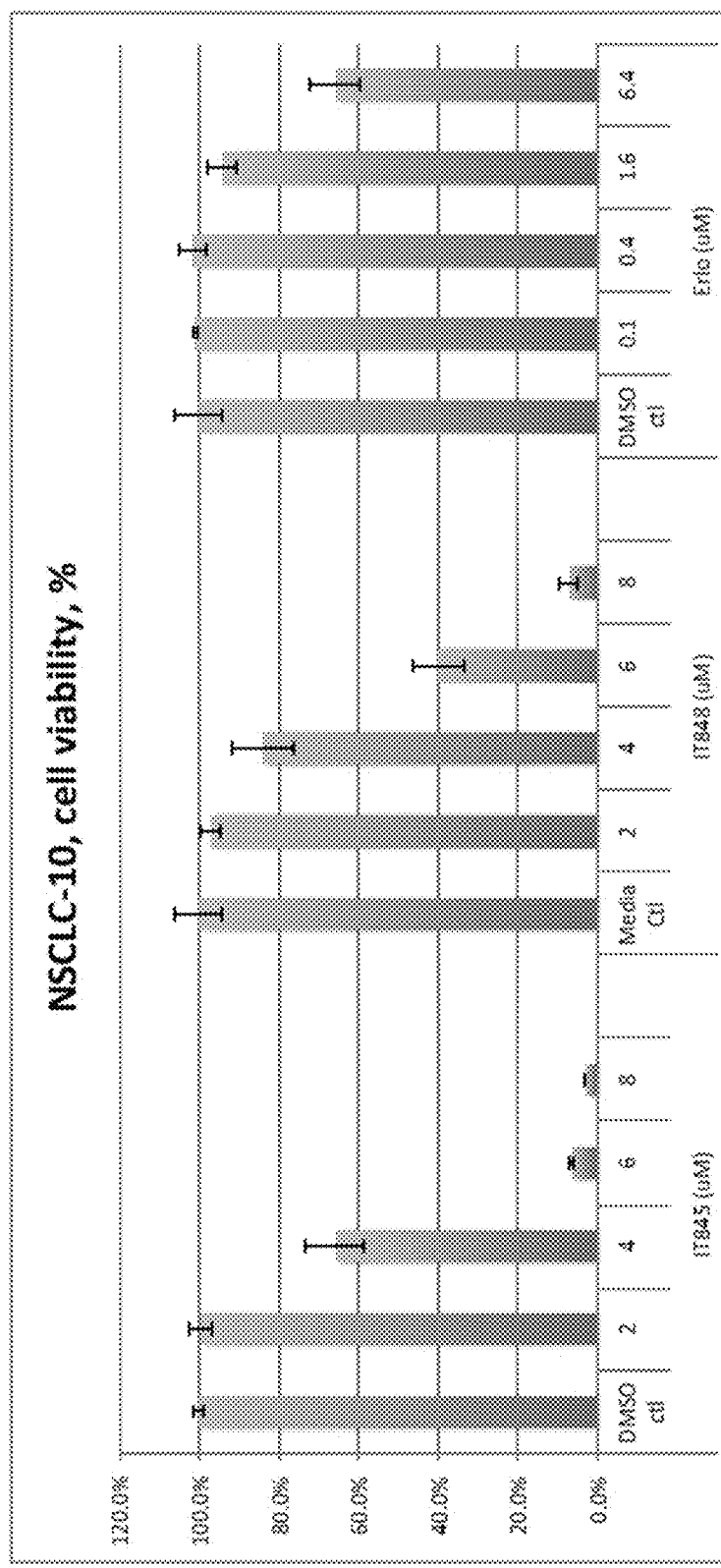
Figure 20A:
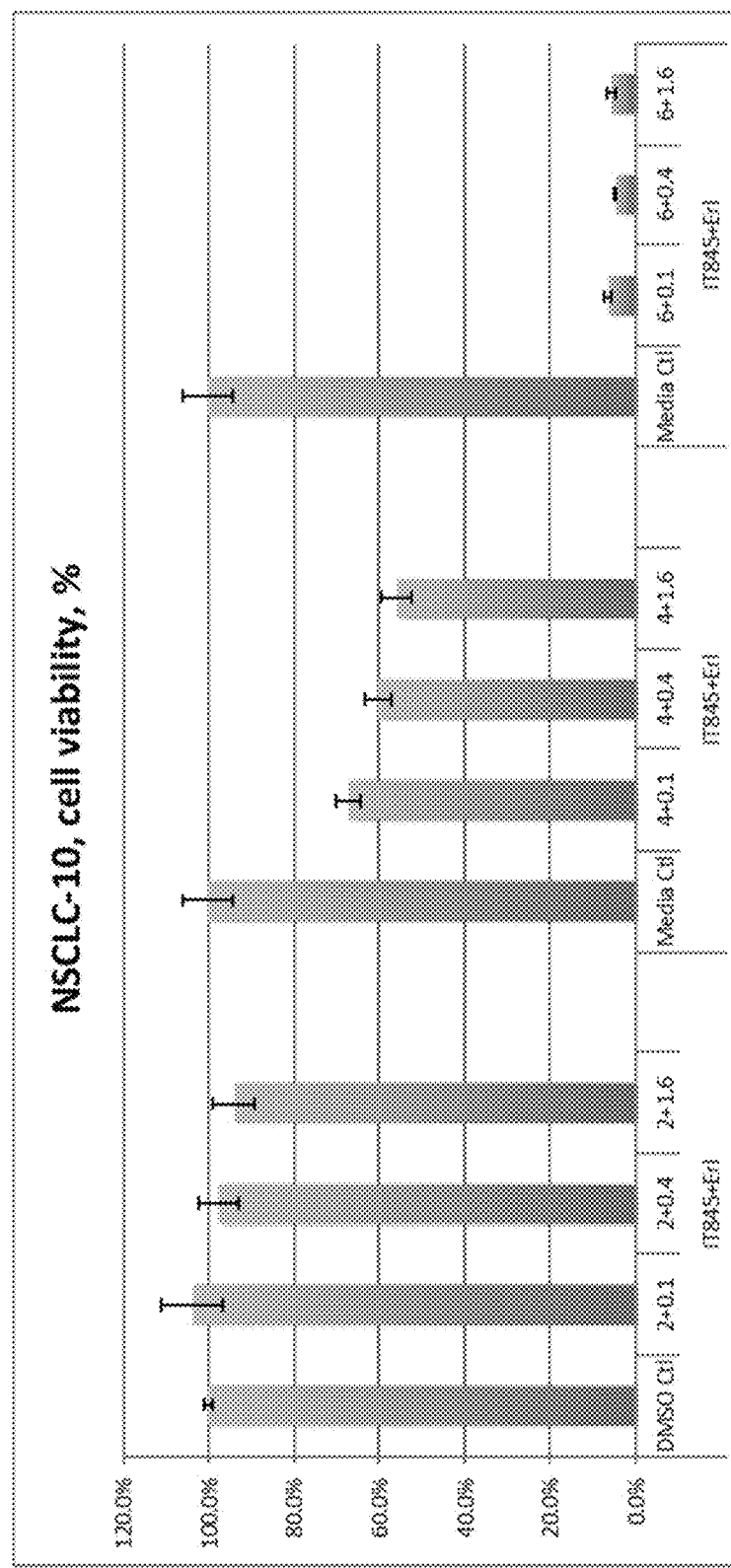
Figure 20A:
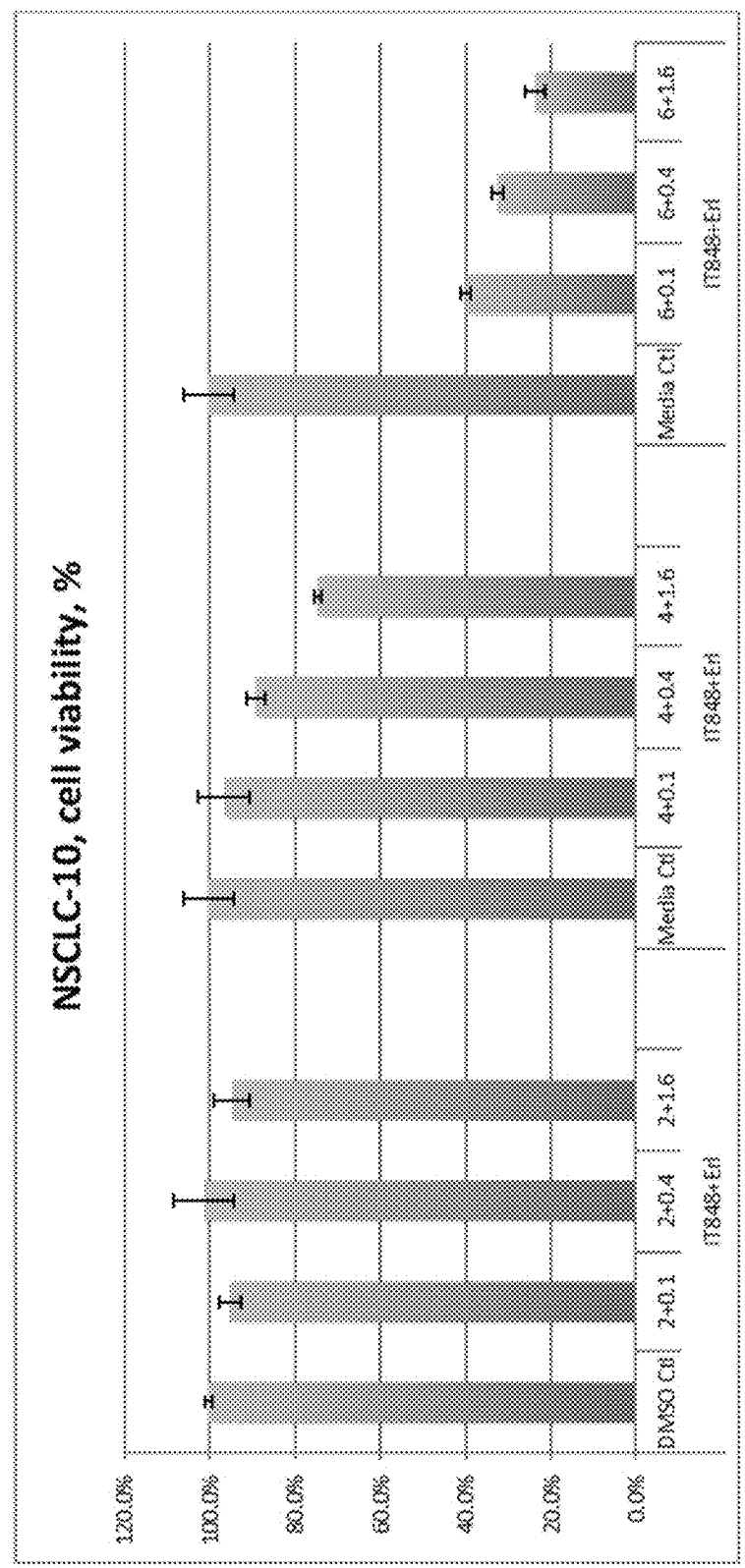

Results from these experiments are shown in FIGS. 20A-20AD.

DOCUMENTS

1. Aly, H. M. and Kamal, M. M. (2012). Efficient one-pot preparation of novel fused chromeno[2,3-d]pyrimidine and pryano[2,3-d]pyrimidine derivatives. *European Journal of Medicinal Chemistry* 47: 18-23.
2. Arora, S., et al. (2013). An undesired effect of chemotherapy: gemcitabine promotes pancreatic cancer cell invasiveness through reactive oxygen species-dependent, nuclear factor κB- and hypoxia-inducible factor 1α-mediated upregulation of CXCR4. *J Biol. Chem.* 288:21197.
3. Barbie, D. A., et al. (2009). Systematic RNA interference reveals that oncogenic KRAS-driven cancers require TBK1. *Nature* 462:108-112.
4. Blakely, C. M., Pazarentzos, E., Olivas, V., Asthana, S., Yan, J. J., Tan, I., Hrustanovic, G., Chan, E., Lin, L., Neel, D. S., Newton, W., Bobb, K. L., Fouts, T. R., Meshulam, J., Gubens, M. A., Jablons, D. M., Johnson, J. R., Bandyopadhyay, S., Krogan, N. J., and Bivona, T. G. (2015). NF-κB-Activating Complex Engaged in Response to EGFR Oncogene Inhibition Drives Tumor Cell Survival and Residual Disease in Lung Cancer. *Cell Reports* 11(1): 98-110.
5. Blythin, D. J., Domalski, M. S., Kim, Y. C., Kuo, J., and Liu, J.-H. (1981). Simple synthetic route to "Oxa-Deaza-Flavins" (2H-[1]-Benzopyrano [2,3-d] Pyrimidine-2,4 (3H)-Diones). *Heterocycles* 16(2): 203-207.
6. Daniluk, J., Liu, Y., Deng, D., Chu, J., Huang, H., Gaiser, S., Cruz-Monserrate, Z., Wang, H., Ji, B., and Logsdon, C. D. (2012). An NF-κB pathway-mediated positive feedback loop amplifies Ras activity to pathological levels in mice. *J Clin Invest* 122(4): 1519-28.
7. Giopanou I, Lilis I, Papaleonidopoulos V, Marazioti A, Spella M, et al. (2015). Comprehensive Evaluation of Nuclear Factor-κB Expression Patterns in Non-Small Cell Lung Cancer. *PLOS ONE* 10(7): e0132527.
8. Jiang, N., Dong, X.-P., Zhang, S.-L., You, Q.-Y., Jiang, X.-T., and Zhao, X.-G. Triptolide reverses the taxol resistance of lung adenocarcinoma by inhibiting the NF-κB signaling pathway and the expression of NF-κB-regulated drug-resistant genes. *Mol Med Rep* 13(1): 153-59.
9. U.S. Pat. No. 4,272,535.
10. International Application No. PCT/US2007/074233.
11. Ouyang, L., et al. (2012). Programmed cell death pathways in cancer: a review of apoptosis, autophagy and programmed necrosis. *Cell Prolif* 45: 487-98.
12. Tait, S. W. G., et al. (2014). Die another way—non-apoptotic mechanisms of cell death. *J Cell Sci* 127:2135-2144.
13. Takeuchi, S., et al. (2015). Chemotherapy-derived inflammatory responses accelerate the formation of immunosuppressive myeloid cells in the tissue microenvironment of human pancreatic cancer. *Cancer Research* 75(13): 2629-40.
14. Wang, W., Abbruzzese, J. L., Evans, D. B., Larry, L., Cleary, K. R., and Chiao, P. J. (1999). The nuclear factor-KB RelA transcription factor is constitutively activated in human pancreatic adenocarcinoma cells. *Clin Cancer Res* 5:119-27.
15. Wu, D., et al. (2015). NF-κB expression and outcomes in solid tumors: A systematic review and meta-analysis. *Medicine* 94(40):1-12.
16. Xie, Y., et al. (2016). Ferroptosis: process and function. *Cell Death and Differentiation* 23:369-79.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for inducing cancer cell death, comprising contacting a cancer cell with an effective amount of a compound having the structure of formula (I):

(I)

wherein:
A, B, C, and D are carbon;
X, Y, and Z are independently selected from the group consisting of oxygen, sulfur, and $NR^a$;
$R_1$, $R_3$ and $R_4$ are independently selected from the group consisting of, hydrogen, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —$OR^a(C=O)R^b$, —$O(C=O)R^a$, —$O(C=O)OR^a$, —$O(C=O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C=O)R^a$, —$S(C=O)OR^a$, —$S(C=O)NR^aR^b$;
$R_2$ is selected from the group consisting of, halogen, $C_{1-9}$ alkyl, $C_{2-9}$ alkenyl, $C_{2-9}$ alkynyl, aryl, heterocyclic, —OH, —$OR^a$, —$OR^aOR^b$, —$OR^aOR^bOR^c$, —$OR^a(C=O)R^b$, —$O(C=O)R^a$, —$O(C=O)OR^a$, —$O(C=O)NR^aR^b$, cyano, nitro, —$CF_3$, —$CHF_2$, —$CH_2F$, —CHO, —COOH, —$COR^a$, —$COOR^a$, —$CONR^aR^b$, —$CONHCONR^aR^b$, —$NR^aR^b$, —$NHCOR^a$, —$NR^bCOR^a$, —CSOH, —$CSR^a$, —$CSOR^a$, —$CSNR^aR^b$, —$CSNHCSNR^aR^b$, —SH, —$SR^a$, —$S(C=O)R^a$, —$S(C=O)OR^a$, —$S(C=O)NR^aR^b$;

or a crystalline form, hydrate, or pharmaceutically acceptable salt thereof,
wherein the cancer cell is selected from the group consisting of lung cancer cell, non-small cell lung cancer (NSCLC) cell, drug-resistant non-small cell lung cancer (NSCLC) cell, and liver cancer cell.

2. The method according to claim 1, wherein the compound is a compound having the structure of formula (I) wherein:
X, Y, and Z are independently selected from the group consisting of oxygen and sulfur;
$R_1$ is selected from the group consisting of —H, —F, —Cl, —OMe, and —OEt;
$R_2$ is selected from the group consisting of —$CH_3$, —OH, —OMe, —OEt, —Me, -Et, -nPr, —O-nPr, —OEtnPr, —$OC_4H_9$, —$OC_5H_{11}$, —$OC_6H_{13}$, —$OC_7H_{15}$, —$OC_nH_{2n}OMe$, —$OC_nH_{2n}OC_mH_{2m}OMe$, —$OC_nH_{2n}OH$, —$OC_nH_{2n}OC_mH_{2m}OH$, —$OC_nH_{2n}OEt$, —$OC_nH_{2n}OC_mH_{2m}OEt$, —O—$C_nH_{2n}COOH$, —O—$C_nH_{2n}CONH2$, —O—$C_nH_{2n}CONHMe$, $R_3$ is selected from the group consisting of —H, —Cl, —Br, —F, and —OMe;
$R_4$ is selected from the group consisting of —H and —OMe;
$R_5$ is selected from the group consisting of —H, —Me, —Et, —Pr, -iPr, -Ph, -iBu, and -nBu; and
$R_6$ is selected from the group consisting of —H and —$CH_3$,
m is 2, 3, 4 or 5;
n is 2, 3, 4, or 5;
or a crystalline form, hydrate, or pharmaceutically acceptable salt thereof.

3. The method according to claim 1, wherein the compound is a compound having the structure of formula (I) wherein:
X, Y, and Z are independently selected from the group consisting of oxygen and sulfur; and
$R_6$ is hydrogen,
or a crystalline form, hydrate, or pharmaceutically acceptable salt thereof.

4. The method according to claim 3, wherein the compound is a compound having the structure of formula (I) wherein:
Z is oxygen;
$R_1$ and $R_3$ are selected from the group consisting of hydrogen, halogen, —CN, and —$CF_3$;
$R_2$ is selected from the group consisting of $C_{1-9}$ alkoxy, —$OC_nH_{2n}OMe$, —$OC_nH_{2n}OC_mH_{2m}OMe$, —$OC_nH_{2n}OH$, —$OC_nH_{2n}OC_mH_{2m}OH$, —$OC_nH_{2n}OEt$, —$OC_nH_{2n}OC_mH_{2m}OEt$, —O—$C_nH_{2n}COOH$, —O—$C_nH_{2n}CONH_2$, —O—$C_nH_{2n}CONHMe$, and —OH;
m is 2, 3, 4 or 5;
n is 2, 3, 4, or 5; and
$R_4$ is selected from the group consisting of hydrogen, $C_{1-9}$ alkoxy and —OH,
or a crystalline form, hydrate, or pharmaceutically acceptable salt thereof.

5. The method according to claim 4, wherein:
X and Y are oxygen; and
$R_4$ is hydrogen,
or a crystalline form, hydrate, or pharmaceutically acceptable salt thereof.

6. The method according to claim 5, wherein the compound is selected from the group consisting of:

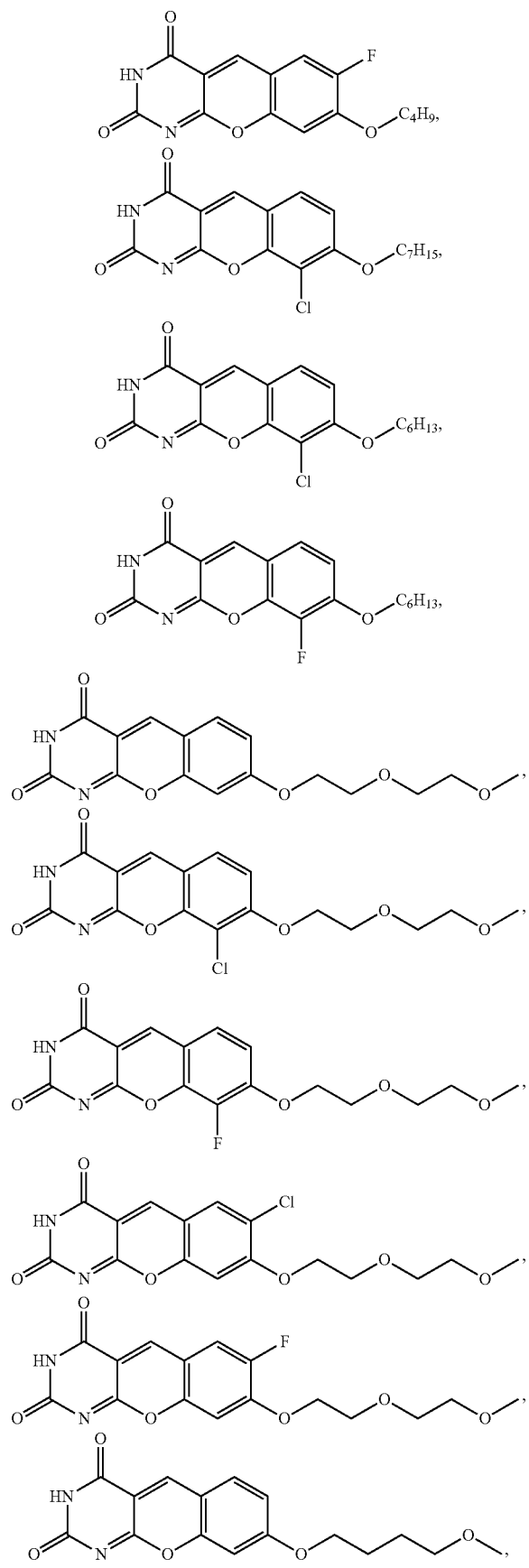
and crystalline forms, hydrates, or pharmaceutically acceptable salts thereof.
7. The method according to claim 1, wherein the effective amount is about 0.01 mg/kg to about 50 mg/kg.
8. A method for inducing cancer cell death, comprising contacting a cancer cell with an effective amount of a compound selected from the group consisting of:

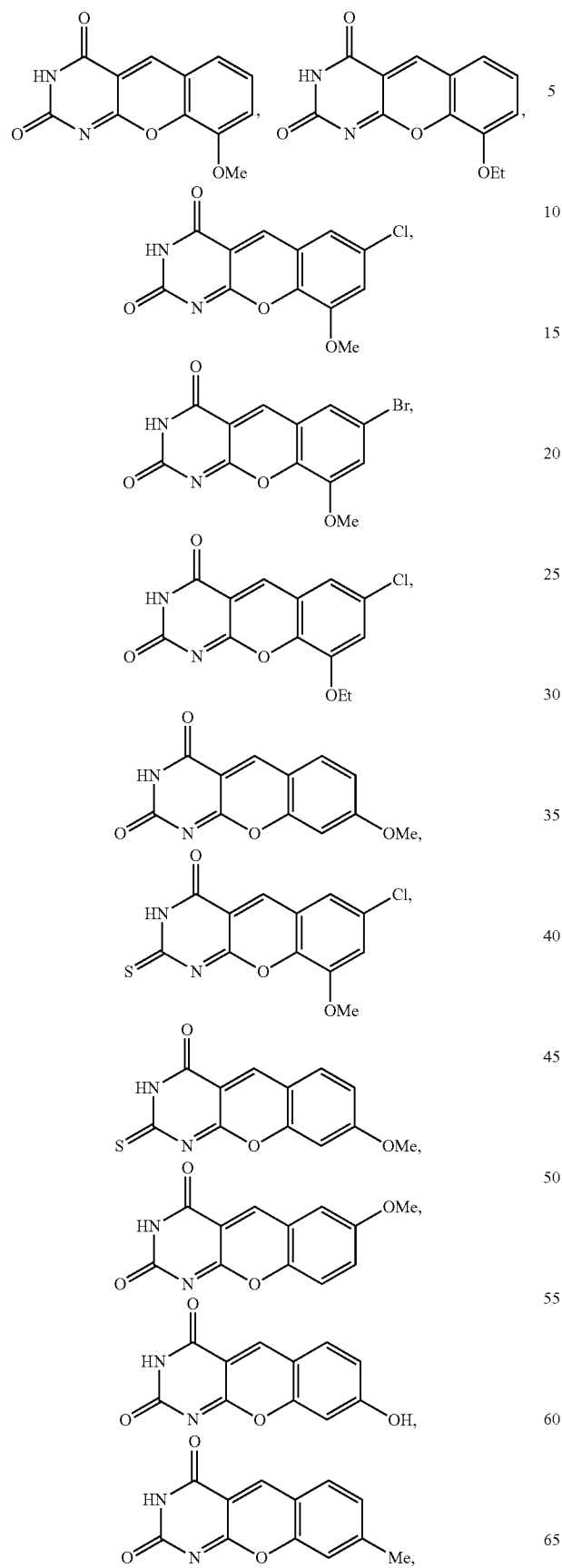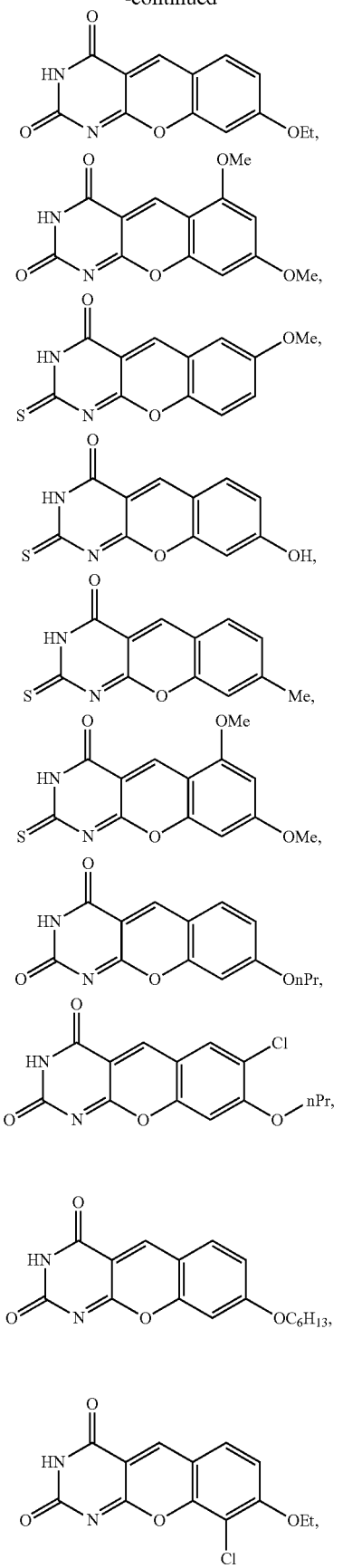

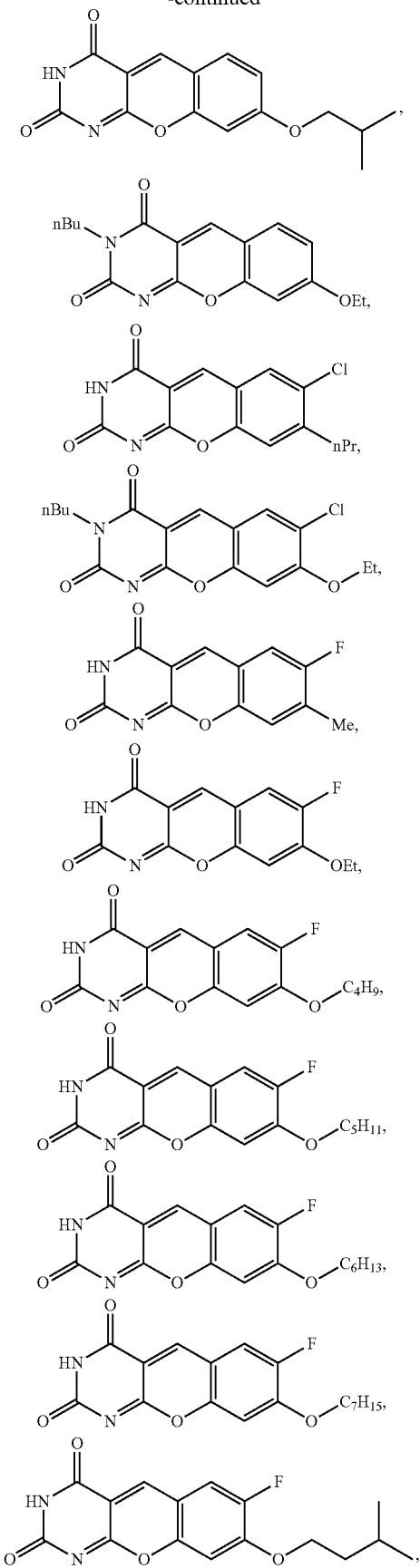
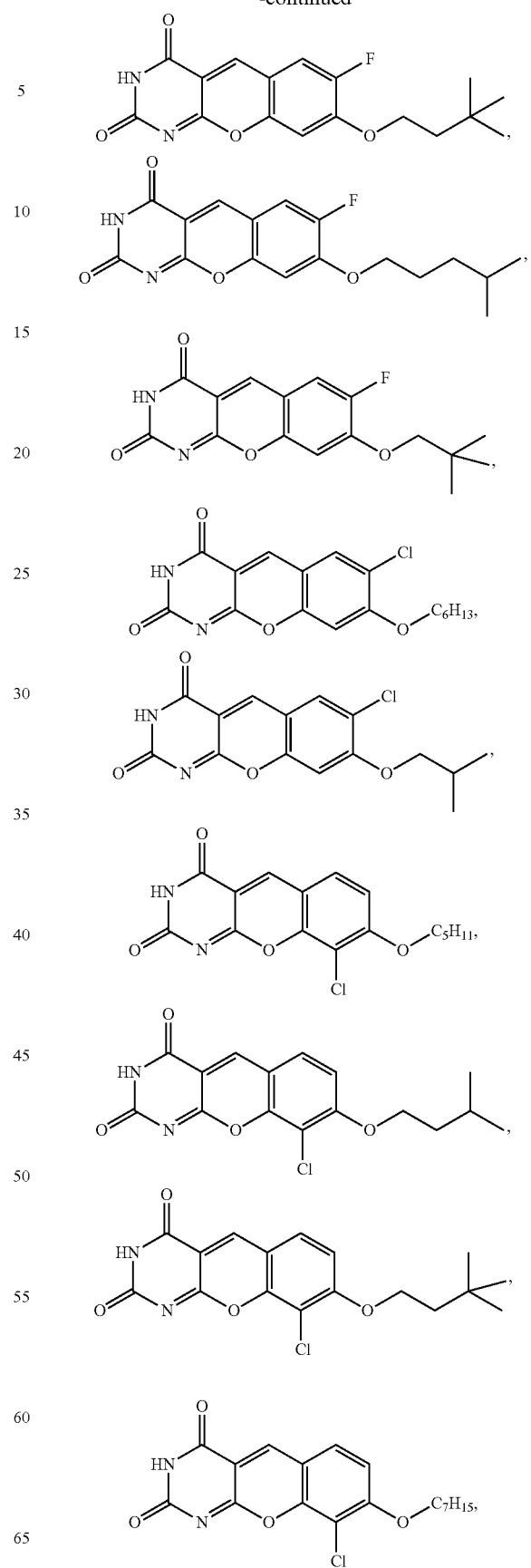

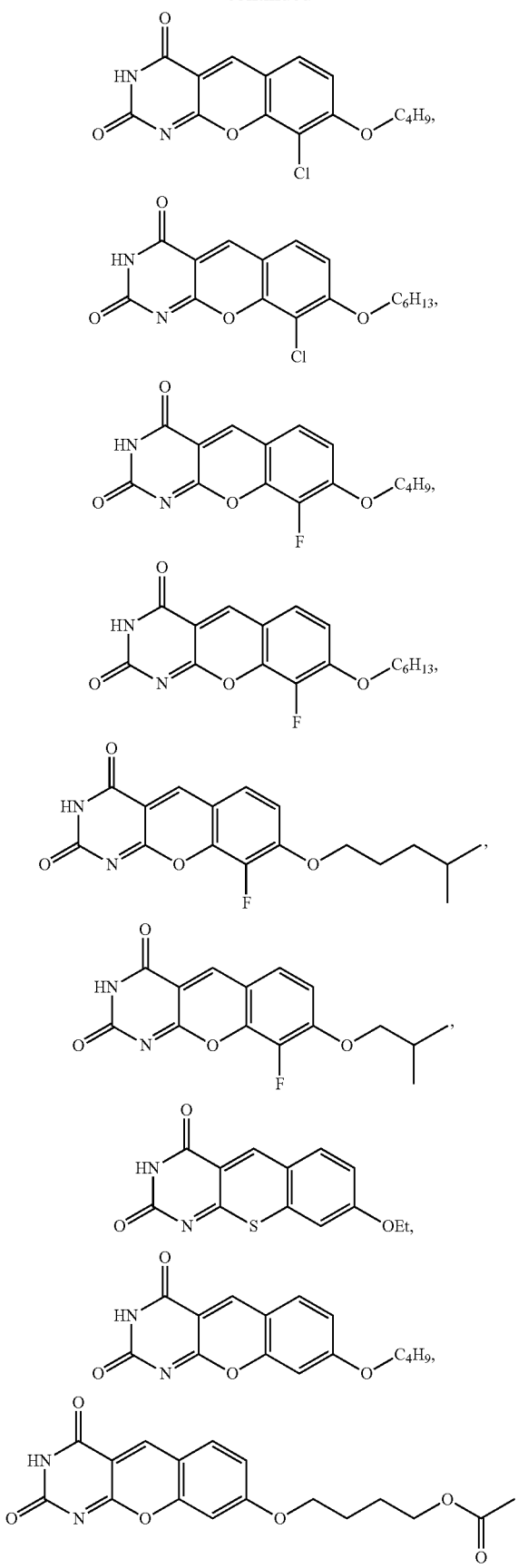
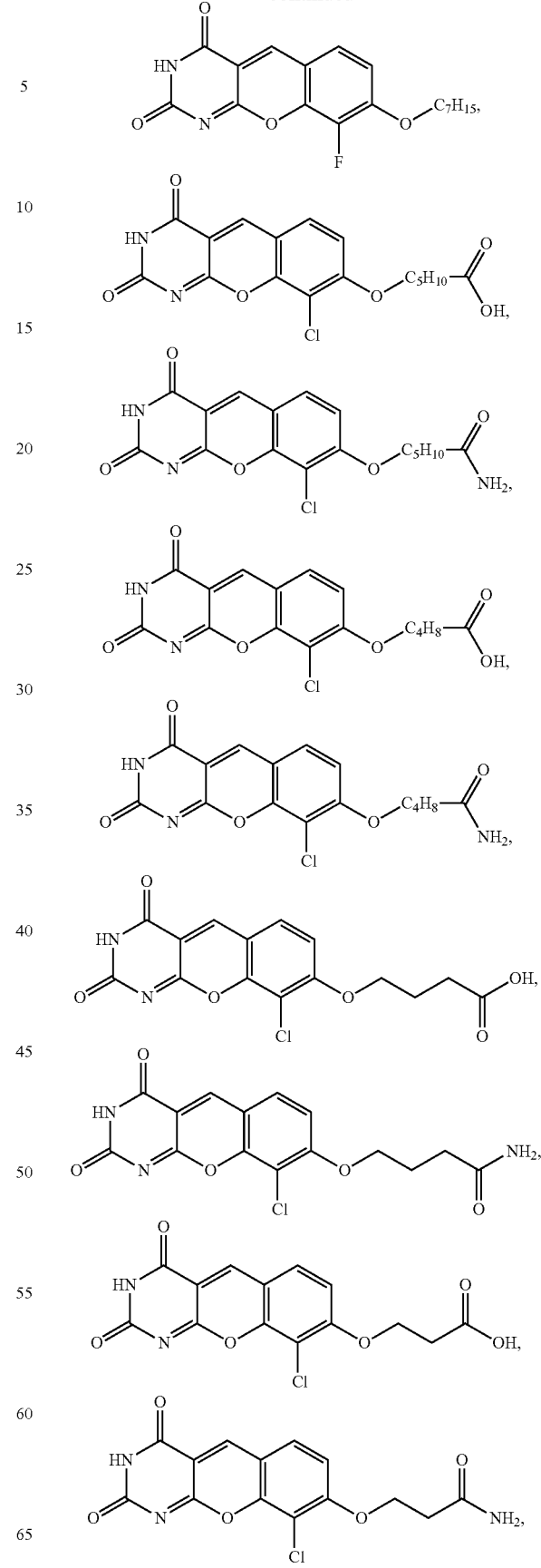

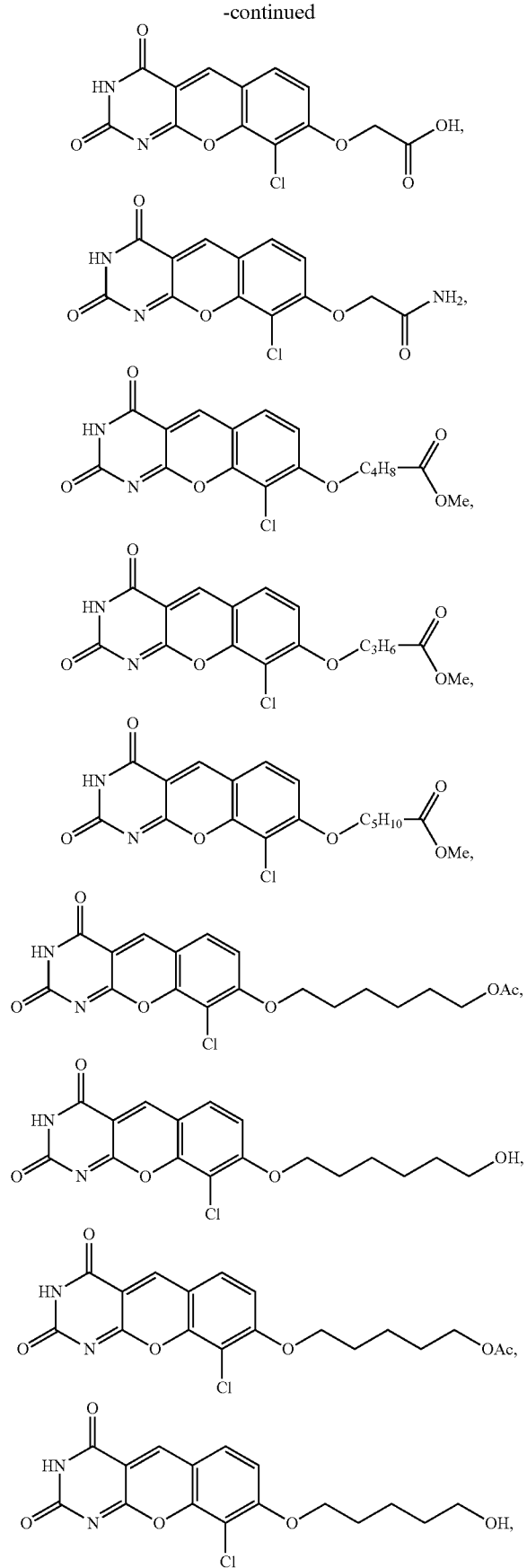
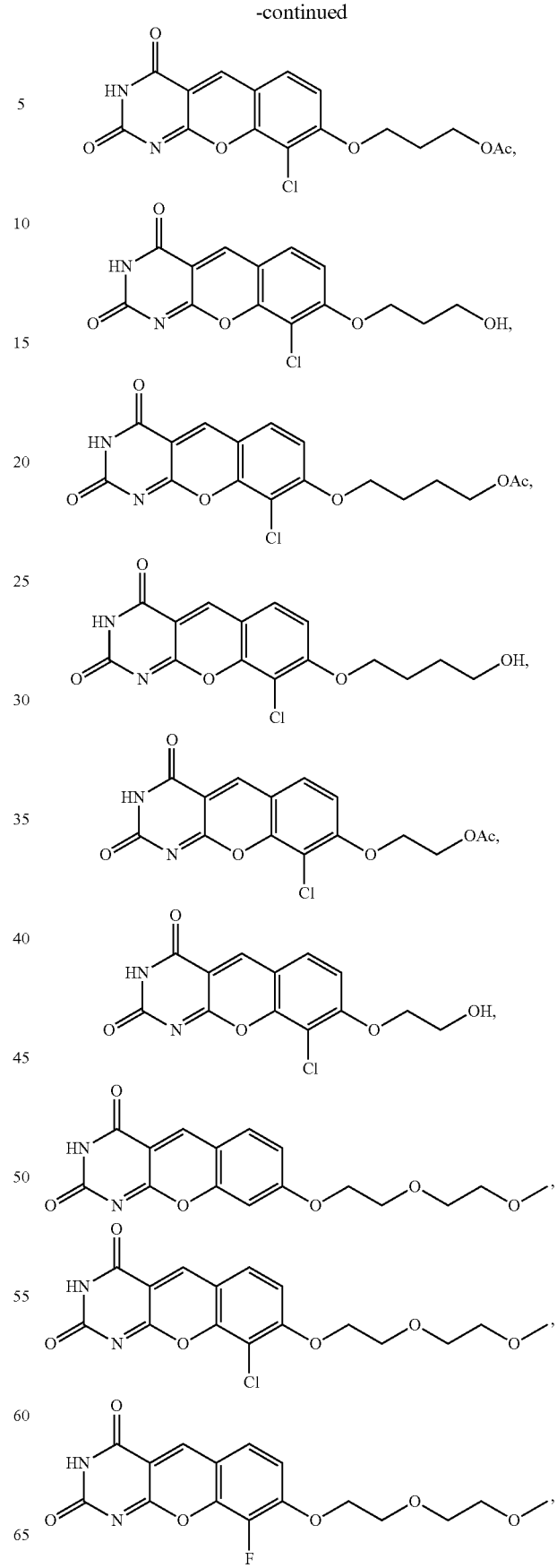

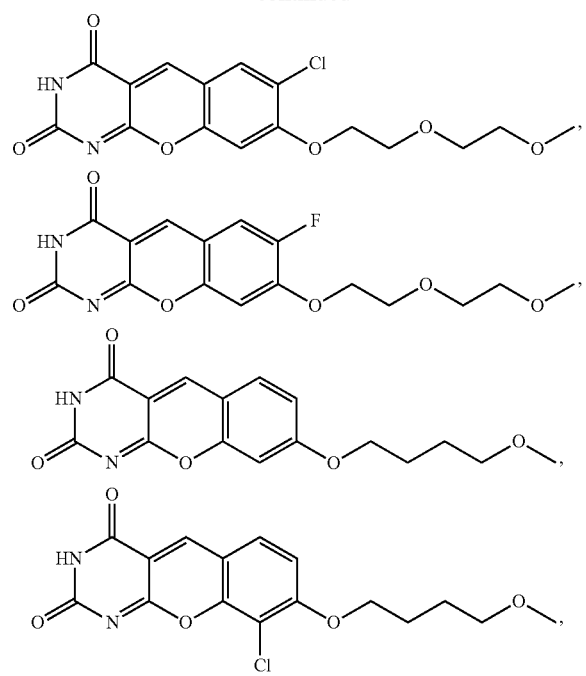

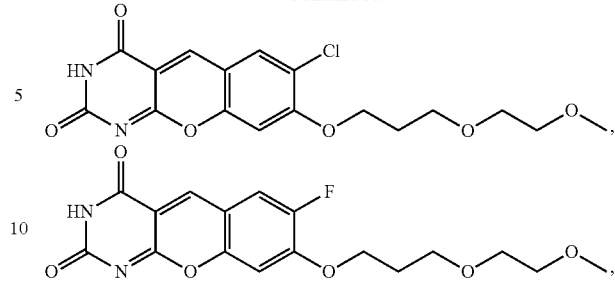

and crystalline forms, hydrates, or pharmaceutically acceptable salts thereof, wherein the cancer cell is selected from the group consisting of lung cancer cell, non-small cell lung cancer (NSCLC) cell, drug-resistant non-small cell lung cancer cell, and liver cancer cell.

9. The method according to claim 8, wherein the effective amount is about 0.01 mg/kg to about 50 mg/kg.

10. A method for inducing cancer cell death, comprising contacting a cancer cell with an effective amount of a compound selected from the group consisting of:

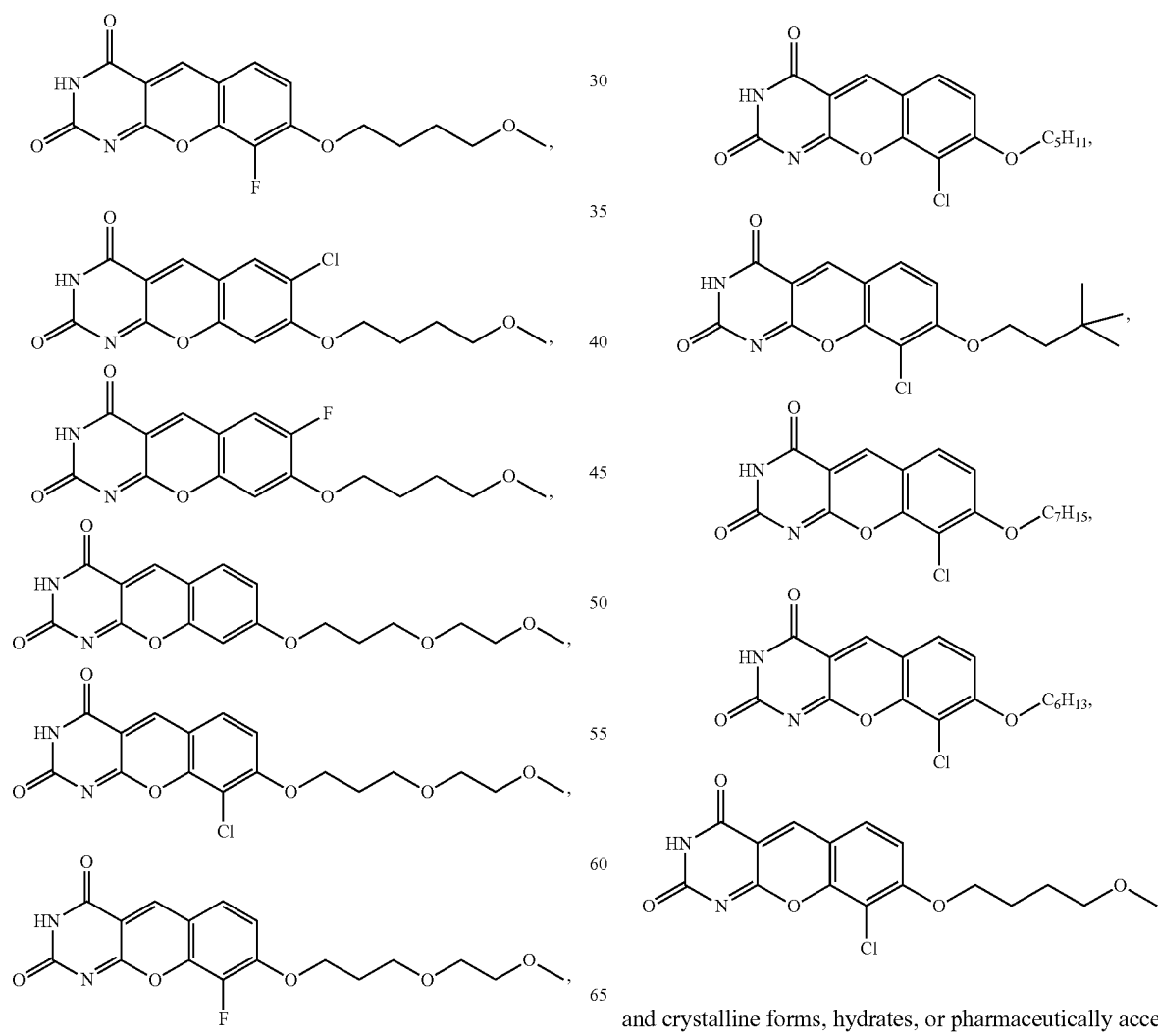

and crystalline forms, hydrates, or pharmaceutically acceptable salts thereof, wherein the cancer cell is selected from the group consisting of lung cancer cell, non-small cell lung cancer (NSCLC) cell, drug-resistant non-small cell lung cancer cell, and liver cancer cell.

11. The method according to claim 10, wherein the effective amount is about 0.01 mg/kg to about 50 mg/kg.

12. The method of claim 1, further comprising contacting the cancer cell with an effective amount of a chemotherapeutic agent or targeted therapeutic agent.

13. The method of claim 8, further comprising contacting the cancer cell with an effective amount of a chemotherapeutic agent or targeted therapeutic agent.

14. The method of claim 10, further comprising contacting the cancer cell with an effective amount of a chemotherapeutic agent or targeted therapeutic agent.

15. The method of claim 1, wherein the compound is a compound having the structure of formula (I) and A, B, C, D, X, Y, Z, $R_1$, $R_2$, $R_3$, $R_4$, $R^a$, $R^b$ and RC have the values as defined in claim 1, or a pharmaceutically acceptable salt thereof.

16. The method of claim 8, wherein the compound is selected from the group consisting of:

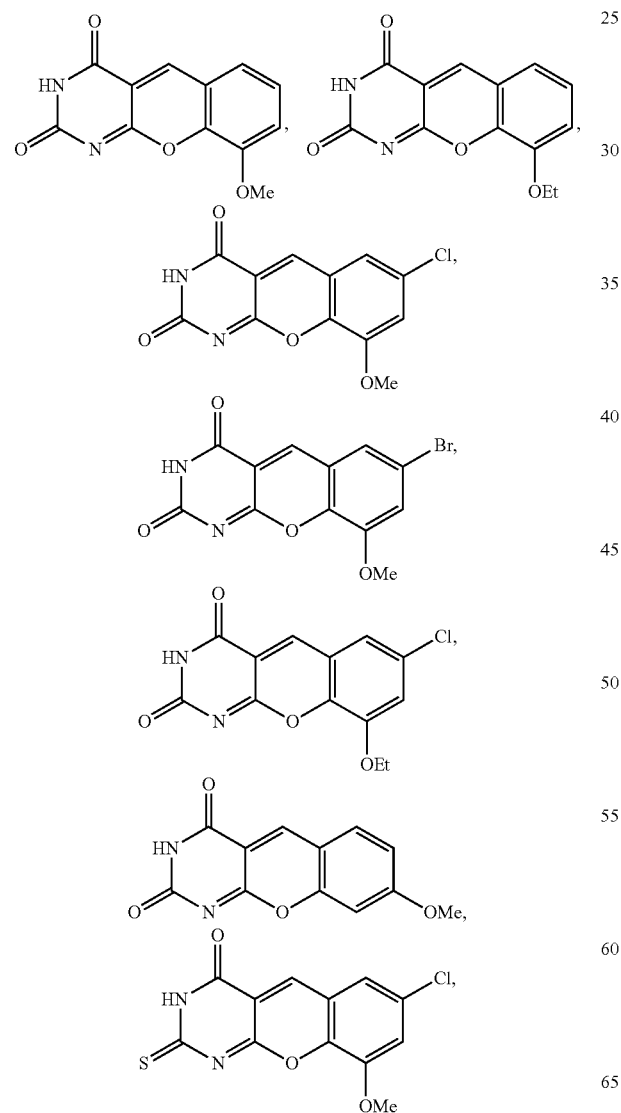

-continued

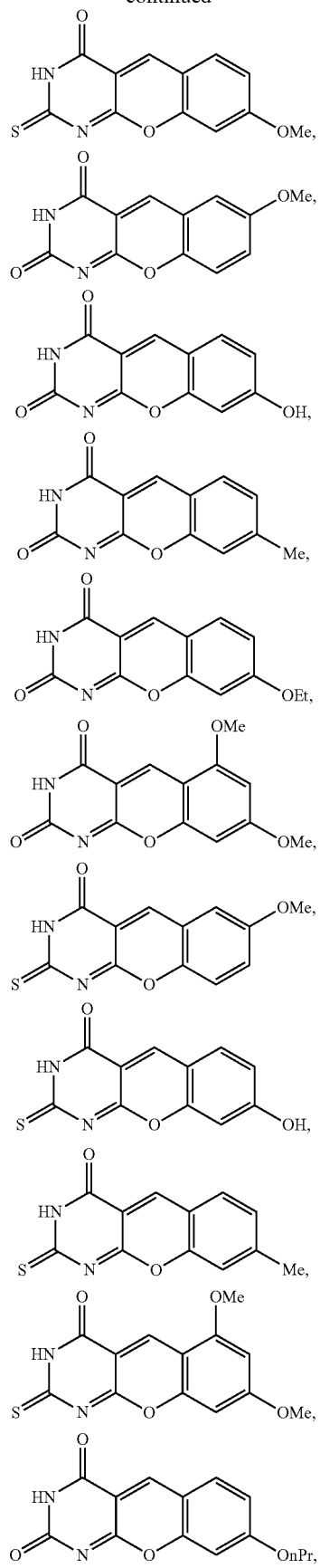

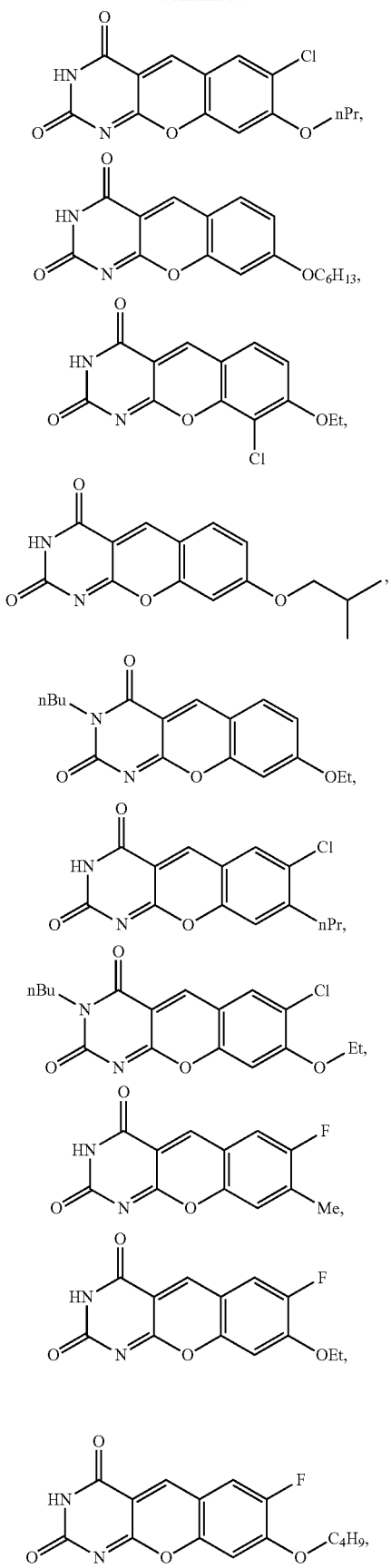
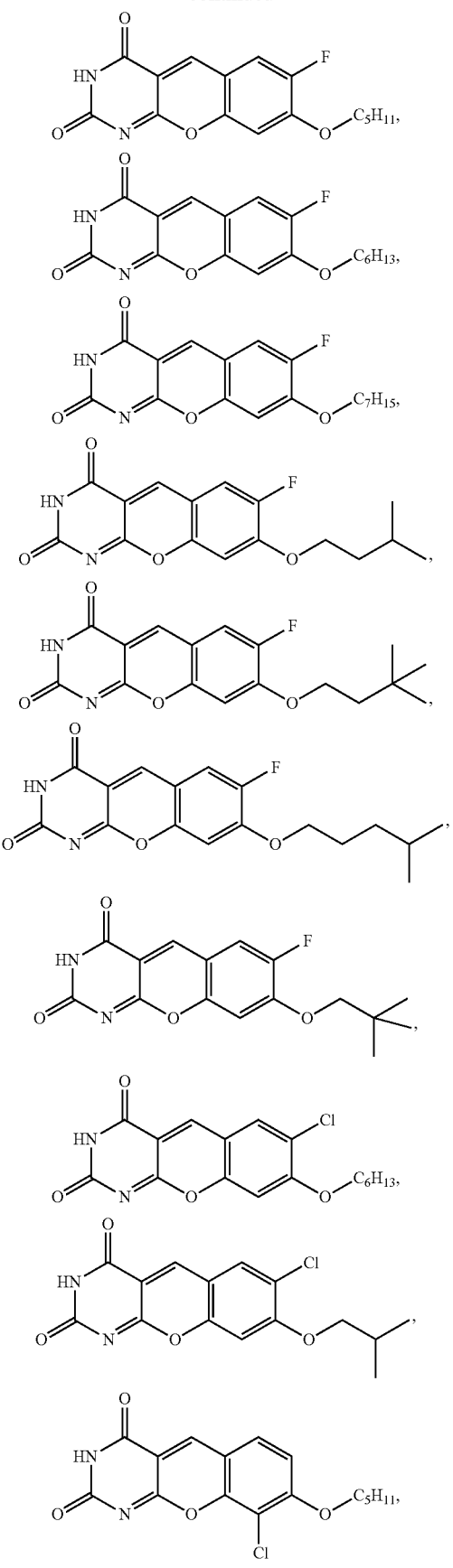

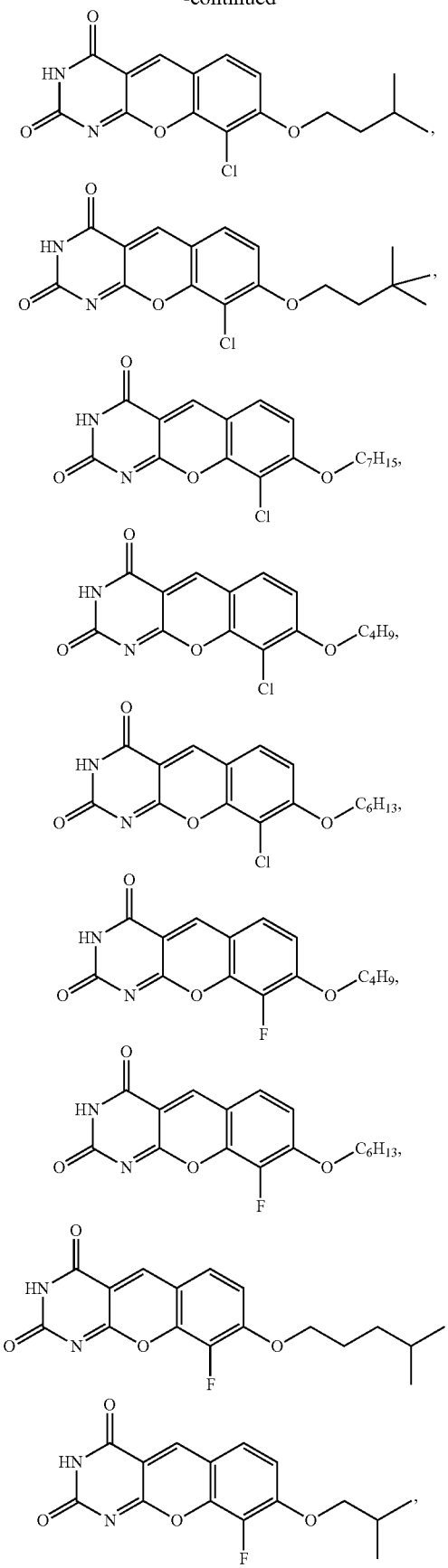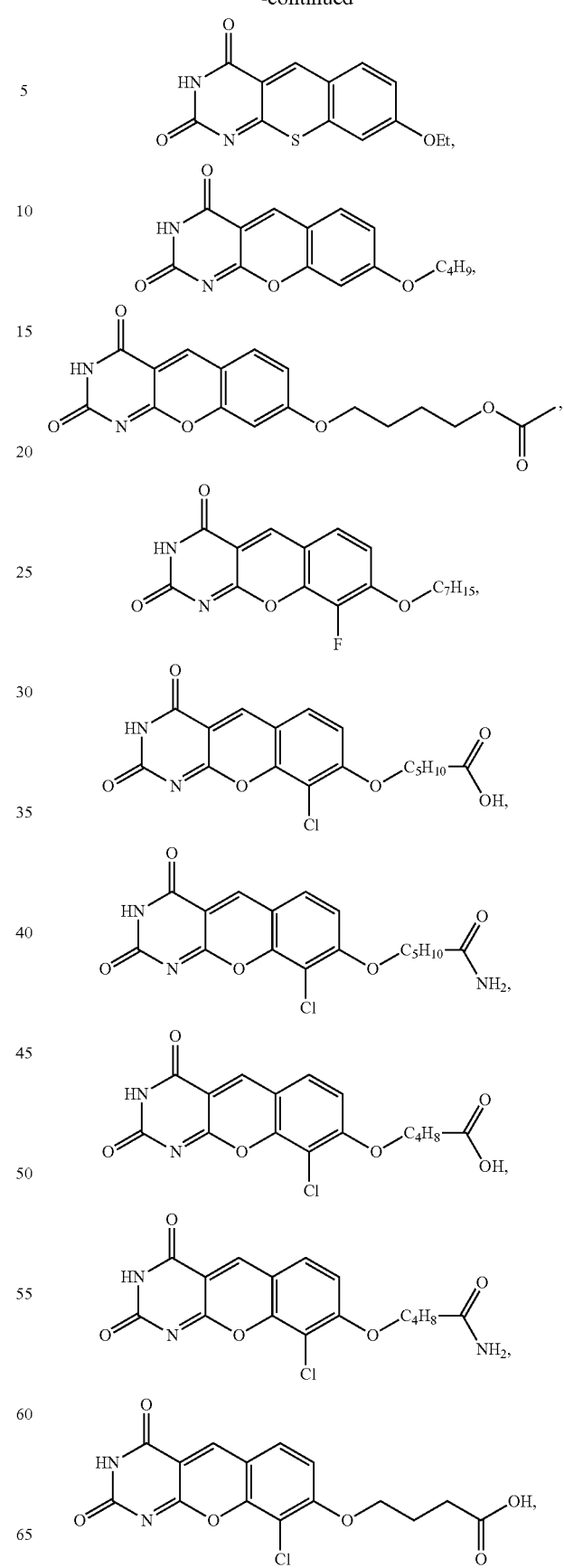

185
-continued
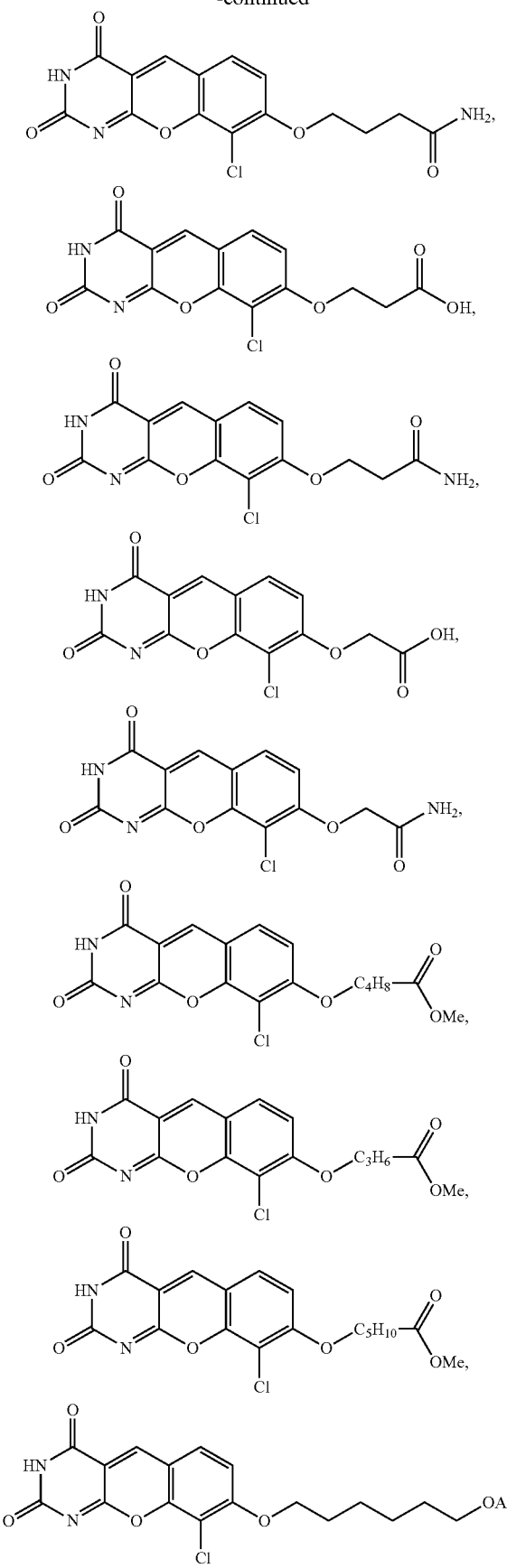
186
-continued
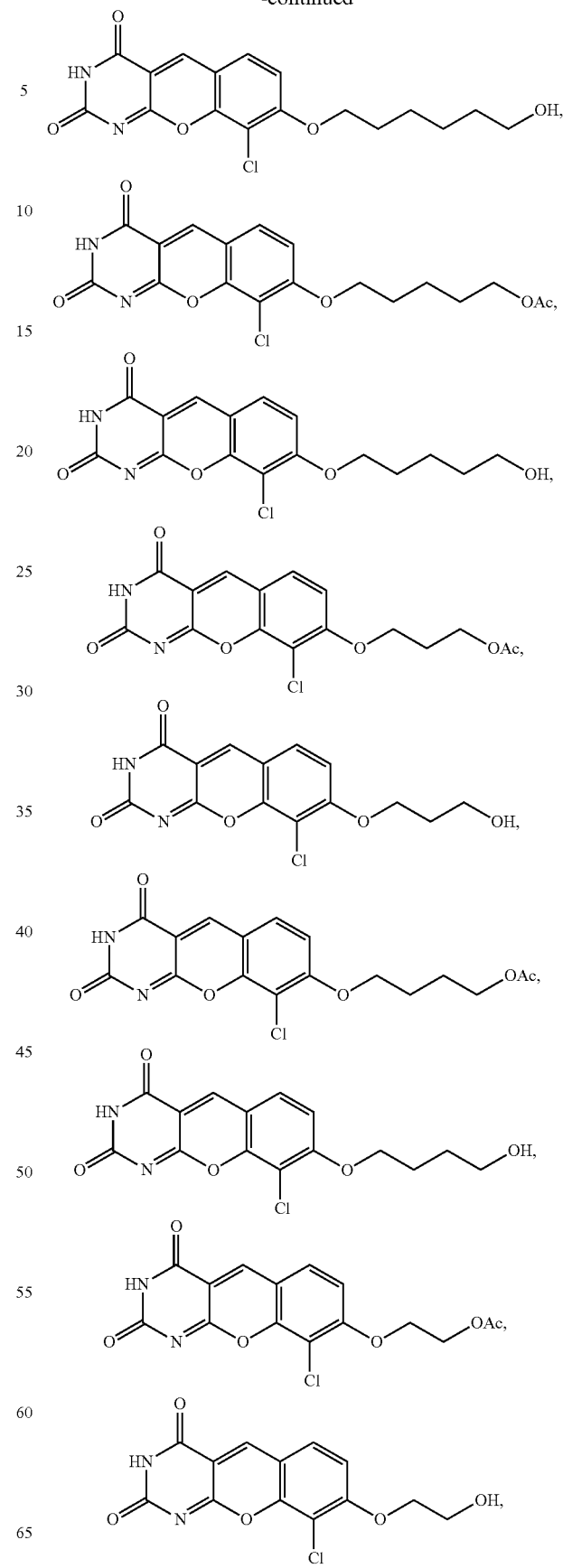

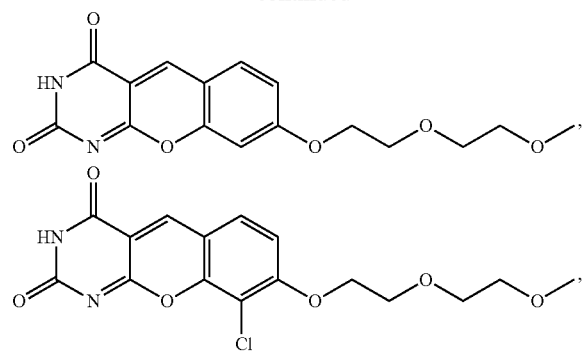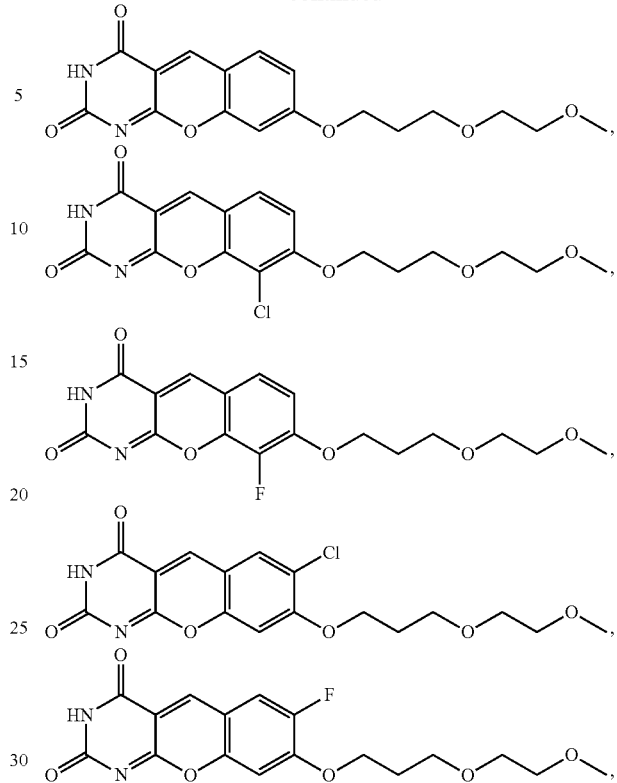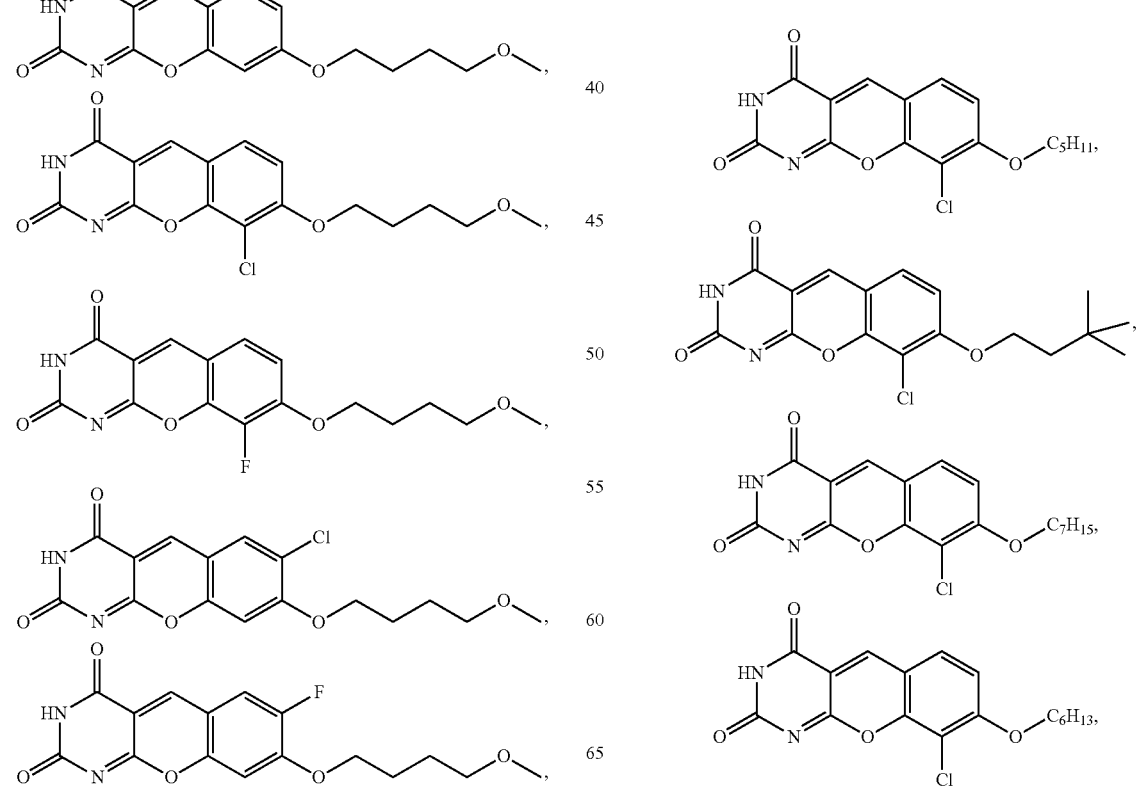
and pharmaceutically acceptable salts thereof.
17. The method of claim 10, wherein the compound is selected from the group consisting of:

-continued
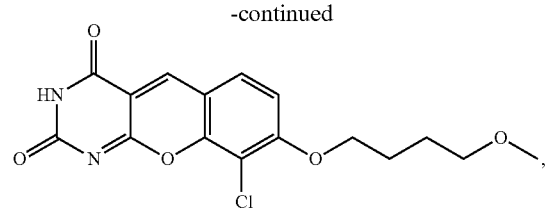
and pharmaceutically acceptable salts thereof.
* * * * *